(12) United States Patent
Singh et al.

(10) Patent No.: US 9,067,897 B2
(45) Date of Patent: Jun. 30, 2015

(54) 2,4-DIAMINOQUINAZOLINES FOR SPINAL MUSCULAR ATROPHY

(75) Inventors: Jasbir Singh, Naperville, IL (US); Mark E. Gurney, Grand Rapids, MI (US)

(73) Assignee: Families of Spinal Muscular Atrophy, Elk Grove Village, IL (US)

( * ) Notice: Subject to any disclaimer, the term of this patent is extended or adjusted under 35 U.S.C. 154(b) by 839 days.

(21) Appl. No.: 13/010,556

(22) Filed: Jan. 20, 2011

(65) Prior Publication Data

US 2011/0112118 A1 May 12, 2011

Related U.S. Application Data

(63) Continuation of application No. 11/147,127, filed on Jun. 7, 2005, now Pat. No. 7,888,366.

(60) Provisional application No. 60/577,844, filed on Jun. 8, 2004.

(51) Int. Cl.
| | |
|---|---|
| *A61K 31/517* | (2006.01) |
| *C07D 239/84* | (2006.01) |
| *A61P 21/00* | (2006.01) |
| *C07D 239/95* | (2006.01) |
| *C07D 401/12* | (2006.01) |
| *C07D 405/12* | (2006.01) |
| *C07D 409/12* | (2006.01) |
| *C07D 413/12* | (2006.01) |
| *C07D 417/12* | (2006.01) |

(52) U.S. Cl.
CPC ............ *C07D 239/95* (2013.01); *C07D 401/12* (2013.01); *C07D 405/12* (2013.01); *C07D 409/12* (2013.01); *C07D 413/12* (2013.01); *C07D 417/12* (2013.01)

(58) Field of Classification Search
USPC ......... 514/266.4, 266.1, 266.2; 544/291, 283, 544/284, 292
See application file for complete search history.

(56) References Cited

U.S. PATENT DOCUMENTS

| | | |
|---|---|---|
| 5,064,833 A | 11/1991 | Ife et al. |
| 5,534,518 A | 7/1996 | Henrie et al. |
| 5,616,718 A | 4/1997 | Henrie et al. |
| 5,760,230 A | 6/1998 | Schohe-Loop et al. |
| 5,874,438 A | 2/1999 | Schohe-Loop et al. |
| 5,874,579 A | 2/1999 | Henrie et al. |
| 6,096,499 A | 8/2000 | Kozlowski et al. |
| 6,204,267 B1 | 3/2001 | Tang et al. |
| 6,248,771 B1 | 6/2001 | Shenoy et al. |
| 6,492,389 B1 | 12/2002 | Huang et al. |

(Continued)

FOREIGN PATENT DOCUMENTS

| | | |
|---|---|---|
| WO | WO94/18980 | 9/1994 |
| WO | WO98/38984 | 9/1998 |

(Continued)

OTHER PUBLICATIONS

Nelson et al., Antimicrobial Agents and Chemotherapy (2002), 46(3), 940 CODEN: AMACCQ; ISSN: 0066-4804.*
Nelson et al., Antimicrobial Agents and Chemotherapy (2001), 45(12), 3293-33.*
Lau et al., Antimicrobial Agents and Chemotherapy (2001), 45(1) pp. 187-195.*
Whitlow et al., J. Med. Chem., 2001, 44 (18), pp. 2928-2932.*
Harris et al. (J'nal Med Chem'1990).*

(Continued)

*Primary Examiner* — Paul V Ward
(74) *Attorney, Agent, or Firm* — Fish & Richardson P.C.

(57) ABSTRACT

2,4-Diaminoquinazolines of formulae I-IV and VI

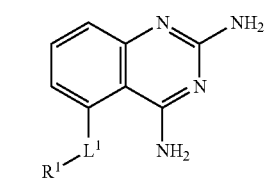

I

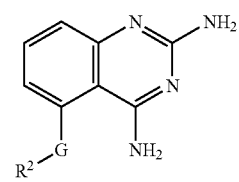

II

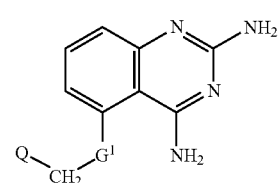

III

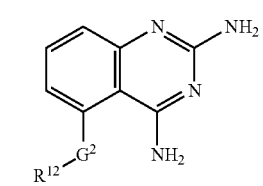

IV

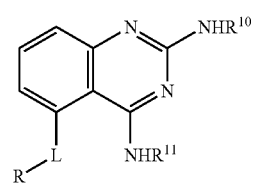

VI are useful for treating spinal muscular atrophy (SMA).

8 Claims, No Drawings

(56) References Cited

U.S. PATENT DOCUMENTS

| | | | |
|---|---|---|---|
| 6,635,651 | B2 | 10/2003 | Uckun et al. |
| 6,911,446 | B2 | 6/2005 | Tang et al. |
| 2005/0065173 | A1 | 3/2005 | Jarecki et al. |
| 2005/0288314 | A1 | 12/2005 | Singh et al. |
| 2009/0042900 | A1 | 2/2009 | Singh et al. |

FOREIGN PATENT DOCUMENTS

| | | |
|---|---|---|
| WO | WO98/50370 | 11/1998 |
| WO | WO00/59884 | 10/2000 |
| WO | WO03/097615 | 11/2003 |
| WO | WO2004/002961 | 1/2004 |
| WO | WO2004/069255 | 8/2004 |
| WO | WO2004/113305 | 12/2004 |
| WO | WO2005/123724 | 12/2005 |

OTHER PUBLICATIONS

Ghose et al., Journal of Medicinal Chemistry (1984), 27(7), 901-14 CODEN: JMCMAR; ISSN: 0022-2623.*

Coats et al., Comparative QSAR of antibacterial dihydrofolate reductase inhibitors QSAR Des. Bioact. Compd. (1984), 71-85. Editor(s): Kuchar, M. Publisher: Prous, Barcelona, Spain. CODEN: 53SIAU.*

Chemical Abstracts 2001: 657149, Ghoda, Keigo et al., "Identification of novel potent inhibitors for ATP-phosphoribosyl transferase using three-dimensional structural database search technique," Quantitative Structure-Activity Relationships, 20(2), 143-147 (2001). Abstract only.

Chemical Abstracts 2002: 146312, Nelson, Richard G. et al., "Dicyclic and tricyclic diaminopyrimidine derivatives as potent inhibitors of *Cryptosporidium parvum* dihydrofolate reductase: structure-activity and structure-selectivity correlations," Antimicrobial Agents and Chemotherapy 46(3), 940(2002). Abstract only.

Amrollahibiyouki at al., "Hydroxymethylation and carbamoylation of di- and tetramethylpyridines using radial substitution (menisci) reactions," Synthetic Communications, 1998, pp. 3817-3825, vol. 28, No. 20.

Andreassi et al., Phenylbutyrate increases SMN expression in vitro: relevance for treatment of spinal muscular atrophy, Eur J Human Genetics, 2004, pp. 59-65, vol. 12.

Appleman et al., "Role of aspartate 27 in the binding of methotrexate to dihydrofolate reductase from *Escherichia coli*," J Biol Chem, 1988, pp. 9187-9198, vol. 263, No. 19.

Brichta et al., "Valproic acid increases the SMN2 protein level: a well-known drug as a potential therapy for spinal muscular atrophy," Human Molecular Genetics, 2003, pp. 2481-2489, vol. 12, No. 9.

Cartegni et al., "Disruption of an SF2/ASF-dependent exonic splicing enhancer in SMN2 causes spinal muscular atrophy in the absence of SMNI," Nautre Genetics, 2002, pp. 377-384, vol. 30, No. 4.

Chang et al., "Treatment of spinal muscular atrophy by sodium butyrate," PNAS, 2001, pp. 9808-9813, vol. 98, No. 17.

Ghose et al., "General distance-geometry three-dimensional receptor model for diverse dihydrofolate reductase inhibitors," J. Med. Chem. 27(7), 901-14 (1984).

Harris et al., "Antifolate and Antibacterial Activities of 5-Substituted 2,4-Diaminoquinazolines," J. Med. Chem. 33, 434-444 (1990).

Jagdmann et al., "Synthesis of 5-(4-substituted benzyl)-2,4-diaminoquinazolines as inhibitors of *Candida albicans* dihydrofolate reductase," Journal of Heterocyclic Chemistry, 1995, pp. 1461-1456, vol. 32, No. 5.

Pitman et al., "Flashflood: A 3D field-based similarity search and alignment method for flexible molecules," J. Comput. Aid. Mol. Des. 15(7), 587-612 (2001).

Remenar et al., "Crystal engineering of novel cocrystals of a triazole drug with 1,4-dicarboxylic acids," J Am Chem Soc, 2003, pp. 8456-8457, vol. 125.

Rosowsky et al., "2,4 Diamino-5-substituted-quinazolines as inhibitors of a human dihydrofolate reductase with a site-directed mutation at position 22 and of the dihydrofolate reductases from pneumocystic carinii and toxoplasma gondii," J. Med. Chem., 38(5), 745-752 (1995).

Sumner et al., "Valproic acid increases SMN levels in spinal muscular atrophy patient cells," Annals of Neurology, 2003, pp. 647-654, vol. 54. No. 5.

Zlokarnik at al.," Quantitation of transcription and clonal selection of single living cells with B-lactamase as reporter," Science, 1998, pp. 84-88, vol. 279.

Zolli-Juran et al., "High throughput screening identifies novel inhibitors of *Escherichia coli* dihydrofolate reductase that are competitive with dihydrofolate," Bioorganic & Medicinal Chemistry Letters, 2003, pp. 2493-2496, vol. 13. No. 15.

International Search Report dated Oct. 29, 2007 in connection with International Patent Application No. PCT/US2007/074971.

International Search Report dated Jun. 6, 2005 in connection with International Patent Application No. PCT/US2005/019753.

Examiner Douglas M. Willis, Restriction Requirement in U.S. Appl. No. 11/832,255, dated Dec. 29, 2008.

Examiner Douglas M. Willis, Non-Final Office Action in U.S. Appl. No. 11/832,255, dated Feb. 23, 2009.

Examiner Douglas M. Willis, Final Office Action in U.S. Appl. No. 11/832,255, dated Oct. 1, 2009.

Fish and Richardson P.C., Response to Final Office Action of Oct. 1, 2009 in U.S. Appl. No. 11/832,255 filed on Jan. 4, 2010.

Examiner Douglas M. Willis, Advisory Action in U.S. Appl. No. 11/832,255, dated Jan. 26, 2010.

Examiner Tamthom Ngo Truong, Restriction Requirement in U.S. Appl. No. 11/147,127, dated Mar. 11, 2008.

Examiner Tamthom Ngo Truong, Non-Final Office Action in U.S. Appl. No. 11/147,127, dated Nov. 25, 2008.

Examiner Tamthom Ngo Truong, Final Office Action in U.S. Appl. No. 11/147,127, dated Sep. 3, 2009.

Examiner Tamthom Ngo Truong, Advisory Action in U.S. Appl. No. 11/147,127, dated Apr. 5, 2010.

Examiner Tamthom Ngo Truong, Notice of Allowance in U.S. Appl. No. 11/147,127, dated Sep. 20, 2010.

* cited by examiner

2,4-DIAMINOQUINAZOLINES FOR SPINAL MUSCULAR ATROPHY

CROSS REFERENCE TO RELATED APPLICATIONS

This application is a continuation of U.S. application Ser. No. 11/147,127 filed Jun. 7, 2005 which claims priority from U.S. Provisional Application 60/577,844 filed Jun. 8, 2004. The entire disclosure of each of these related applications is incorporated herein by reference.

FIELD OF THE INVENTION

The invention relates to a genus of 2,4-diaminoquinazolines that are useful for treating spinal muscular atrophy (SMA).

BACKGROUND

Spinal muscular atrophy (SMA) is a currently untreatable, autosomal recessive genetic disease caused by a deficiency of full-length survival motor neuron (SMN) protein. The symptoms are the result of progressive degeneration of motor neurons in the anterior horn of the spinal cord resulting in weakness and wasting of the voluntary muscles.

Type I (Acute) SMA is also called Werdnig-Hoffmann Disease. SMA type I is evident before birth or within the first few months of life. There may be a reduction in fetal movement in the final months of pregnancy. There is a general weakness in the intercostals and accessory respiratory muscles. The chest may appear concave. Symptoms include floppiness of the limbs and trunk, feeble movements of the arms and legs, swallowing and feeding difficulties, and impaired breathing. Affected children never sit or stand and usually die before the age of 2.

Type II (Chronic) SMA is usually diagnosed by 15 months. Children may have respiratory problems, floppy limbs, decreased or absent deep tendon reflexes, and twitching of arm, leg, or tongue muscles. These children may learn to sit but cannot stand or walk. Life expectancy varies. Feeding and swallowing problems are not usually characteristic of Type II, although in some patients a feeding tube may become necessary. Tongue fasciculations are less often found in children with Type II but a fine tremor in the outstretched fingers is common.

Type III (Mild) SMA, often referred to as Kugelberg-Welander or Juvenile Spinal Muscular Atrophy, is usually diagnosed between 2 and 17 years of age. Symptoms include abnormal manner of walking; difficulty running, climbing steps, or rising from a chair; and slight tremor of the fingers. The patient with Type DI can stand alone and walk; tongue fasciculations are seldom seen. Types I, II and III progress over time, accompanied by deterioration of the patient's condition.

Type IV (Adult Onset) typically begins after age 35. Adult SMA is characterized by insidious onset and very slow progression. The bulbar muscles are rarely affected in Type IV. It is not clear that Type IV SMA is etiologically related to the Type I-III forms. There is a second type of Adult Onset X-Linked SMA, known as Kennedy's Syndrome or Bulbo-Spinal Muscular Atrophy. It occurs only in males, and, unlike the other forms of SMA, it is associated with a mutation in the gene that codes for part of the androgen receptor. The facial and tongue muscles are noticeably affected. The course of the Adult Onset disease is variable, but in general it tends to be slowly progressive or nonprogressive.

Type I, II and III SMA are caused by a mutation in a part of the DNA called the survival motor neuron (SMN1) gene, which normally produces a protein called SMN. Because of their gene mutation, people with SMA make less SMN protein, which results in the loss of motor neurons. SMA symptoms may be improved by increasing the levels of SMN protein. Normally the SMN1 gene provides instructions for making a protein called Survival of Motor Neuron 1. The SMN1 protein helps to assemble the cellular machinery needed to process pre-mRNA. More than 90 percent of individuals with spinal muscular atrophy lack part or all of both copies of the SMN1 gene. A small percentage of people with this condition lack one copy of the SMN1 gene and have a small type of mutation in the remaining copy. About 30 different mutations have been identified. The most frequent of these mutations replaces the amino acid tyrosine with cysteine at position 272 in the SMN1 protein. Other mutations replace amino acids at different positions or produce an abnormally short protein. As a result of these missing or altered genes, cells have a shortage of functional SMN1 protein. It remains unclear why motor neurons are particularly vulnerable to a shortage of this protein. Loss of the SMN1 protein from motor neurons results in the degeneration of these nerve cells, leading to the signs and symptoms of spinal muscular atrophy.

In some cases of spinal muscular atrophy, particularly the milder cases, the SMN1 gene is replaced by an almost identical gene called SMN2. Typically, people who do not have spinal muscular atrophy have two copies of the SMN2 gene. In some affected individuals, however, the SMN2 gene replaces the SMN1 gene, and as a result, the number of SMN2 genes increases from two to three or more (and the number of SMN1 genes decreases). On a limited basis, extra SMN2 genes can help replace the protein needed for the survival of motor neurons. In general, symptoms are less severe and begin later in life in affected individuals with three or more copies of the SMN2 gene. The SMN2 gene provides instructions for making a protein called survival of motor neuron 2. This protein is made in four different versions, but only isoform d is full size and functional and appears to be identical to the SMN1 protein. The other isoforms (a, b, and c) are smaller and may not be fully functional. It appears that only a small amount of the protein made by the SMN2 gene is isoform d. Among individuals with spinal muscular atrophy (who lack functional SMN1 genes), additional copies of the SMN2 gene can modify the course of the disorder. On a limited basis, the extra SMN2 genes can help replace the protein needed for the survival of motor neurons. Spinal muscular atrophy still occurs, however, because most of the proteins produced by SMN2 genes are isoforms a, b, and c, which are smaller than the SMN1 protein and cannot fully compensate for the loss of SMN1 genes. A recent article by Cartegni and Krainer [*Nature Genetics* 30, 377-384 (2002)] suggests that the molecular basis for the failure of the nearly identical gene SMN2 to provide full protection against SMA stems from inefficient recognition of an exonic splicing enhancer by the splicing factor SF2/ASF. Even so, the small amount of full-sized protein produced from three or more copies of the SMN2 gene can delay onset and produce less severe symptoms, as seen in spinal muscular atrophy, types II and III.

One of the first studies on pharmaceutical therapy for spinal muscular atrophy has demonstrated that, in cultured cells, valproic acid increases production of normal protein produced by the SMN2 gene. While preliminary, these studies [Britcha et al. Human Molecular Genetics, 12, 2481-2489 (2003); Sumner et al. *Annals of Neurology*, 54, 647-654 (2003)], suggest that valproic acid or related drugs may be able to halt or even reverse the course of SMA. The study used cultured cells taken from patients with SMA type I, and demonstrated a dose-related increase in gene activity, increasing production of functional SMN protein by 30 to 50 percent. Unfortunately, treatment with valproic acid can lead to liver toxicity, especially in children under 2 years of age, and safe doses of the drug may not be able to increase the amount of SMN protein enough to reduce symptoms of the disease. However, valproic acid belongs to a class of drugs known as histone deacetylase (HDAC) inhibitors, and persons of skill in the art believe that other HDAC inhibitors may be useful for treating SMA. For example, two other HDAC inhibitor, sodium butyrate and phenylbuytreate have also been shown to increase SMN expession [Chang et al. PNAS, 98, 9808-9813 (2001); Andreassi et al. European Journal of Human Genetics, 12, 59-65. The National Institute of Neurological Disorders and Stroke (NINDS) is currently undertaking studies to support this hypothesis.

It would be useful to have compounds that promote SMN2 without the adverse side effects of valproic acid. It would be further useful to have compounds that increase the total SMN1 protein or that alter the splicing to provide increase in Full length to Δ7 SMN transcripts ratio in favor of full length protein or that do both.

SUMMARY OF THE INVENTION

It has now been found that certain 2,4-diaminoquinazolines are useful for treating SMA.

In one aspect, the invention relates to novel 2,4-diaminoquinazoline compounds having formulae I-III

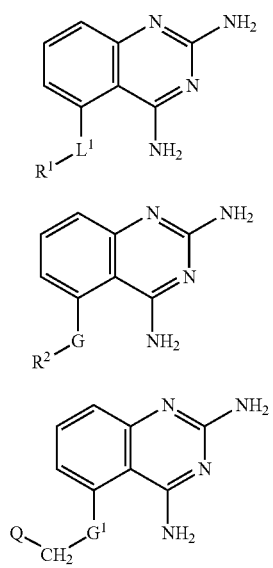

wherein $L^1$ is a bond or a linker of empirical formula $C_pH_qN_rO_sS_t$ in which
p is 2-20;
q is 0-40;
r is 0-3;
s is 0-6;
t is 0-2;
$R^1$ is selected from the group consisting of cycloalkyl, aryl, fused cycloalkylaryl, heterocyclyl, heteroaryl, substituted cycloalkyl, substituted aryl, substituted fused cycloalkylaryl, substituted heterocyclyl, and substituted heteroaryl;

G is selected from the group consisting of —$NR^6$—, —$CH_2$—, —$SO_2$— and —$CH_2O$—;
$G^1$ is selected from the group consisting of —O—, —$NR^6$—, —S— and —$OCH(CH_3)$—;
$R^2$ is selected from the group consisting of cycloalkyl, aryl, fused cycloalkylaryl, heterocyclyl, and heteroaryl; substituted cycloalkyl, substituted aryl, substituted fused cycloalkylaryl, substituted heterocyclyl, and substituted heteroaryl with the proviso that when G is —$CH_2$— then $R^2$ is other than phenyl or substituted phenyl;
$R^6$ is hydrogen or $C_1$-$C_6$ alkyl; and
Q is selected from the group consisting of —$CH_2OCH_3$, —$CH_2OCH_2CH=CH_2$, $C_6$-$C_{20}$ hydrocarbon, heterocyclyl, and heteroaryl; substituted $C_6$-$C_{20}$ hydrocarbon, substituted heterocyclyl, and substituted heteroaryl; and —$CH(OH)Ar_2$, wherein Ar is phenyl or substituted phenyl, with the proviso that when $G^1$ is —O— or —S—, then Q is other than 4-chlorophenyl.

The invention also includes pharmaceutically acceptable salts thereof, in any stereoisomeric or tauromeric form, and mixtures of any such compounds in any ratio.

In a second aspect, the invention relates to compounds having formula IV. These compounds are also useful in the treatment of SMA:

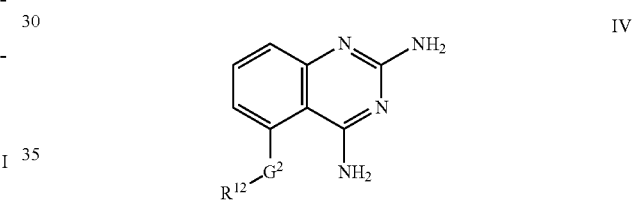

wherein $G^2$ is selected from the group consisting of —O—, —S—, and —NH—; and
$R^{12}$ is selected from the group consisting of $C_7$-$C_{10}$ polycyclic hydrocarbon, substituted $C_2$-$C_{10}$ polycyclic hydrocarbon, and

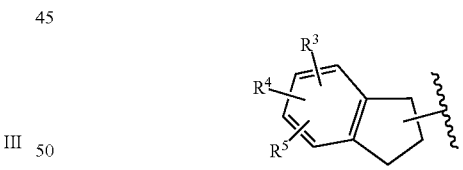

wherein the wavy line indicates the point of attachment, and wherein one or more carbon atoms in the cyclopentyl ring is optionally replaced by a heteroatom independently selected from the group consisting of N, O, and S; and
$R^3$, $R^4$ and $R^5$ are independently selected from the group consisting of hydrogen, halogen, $C_1$-$C_6$ alkyl, $C_1$-$C_6$ alkoxy, haloalkyl, hydroxy, carboxy, $C_1$-$C_6$ alkoxycarbonyl, carboxamido, cyano, formyl, nitro, amino, $C_1$-$C_6$ alkylamino, $C_1$-$C_6$ dialkylamino, mercapto, $C_1$-$C_6$ alkylthio, $C_1$-$C_6$ alkylsulfoxide, $C_1$-$C_6$ alkylsulfone, $C_1$-$C_6$ acylamino, amidino, phenyl, benzyl, phenoxy and benzyloxy, with the proviso that at least one of $R^3$, $R^4$, and $R^5$ must be other than hydrogen;
and pharmaceutically acceptable salts thereof, in any stereoisomeric or tautomeric form, and mixtures of any such compounds in any ratio.

In a third aspect, the invention relates to 2,4-diaminoquinazoline compounds having formula VI:

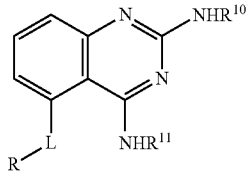

VI wherein L is a linker of empirical formula $C_pH_qN_rO_sS_t$
p is 0-20;
q is 0-40;
r is 0-3;
s is 0-6;
t is 0-2; and
R is selected from the group consisting of cycloalkyl, aryl, fused cycloalkylaryl, heterocyclyl, heteroaryl, $C_3$-$C_{10}$ alkyl and $C_3$-$C_{10}$ oxaalkyl; substituted cycloalkyl, substituted aryl, substituted fused cycloalkylaryl, substituted heterocyclyl, substituted heteroaryl, substituted $C_3$-$C_{10}$ alkyl and substituted $C_3$-$C_{10}$ oxaalkyl; and
$R^{10}$ and $R^{11}$ are chosen independently from H, —$NH_2$, —NH(alkyl), —NHOH, —NHO(alkyl), and acyl, with the proviso that at least one of $R^{10}$ and $R^{11}$ is not H;
and pharmaceutically acceptable salts thereof, in any stereoisomeric or tautomeric form, and mixtures of any such compounds in any ratio.

In a fourth aspect, the invention relates to a method of treating SMA by administering to a patient a therapeutically effective amount of a 2,4-diaminoquinazoline compound of formula I-IV or VI.

In a fifth aspect, the invention also relates to a method of treating SMA by administering to a patient a therapeutically effective amount of a 2,4-diaminoquinazoline compound of formula V:

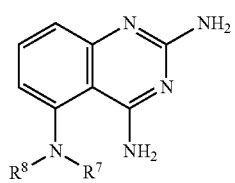

V wherein
$R^7$ and $R^8$ are $C_1$-$C_6$ alkyl, or taken together with the nitrogen to which they are attached $R^7$ and $R^8$ form a three to eight-membered ring, which may be monocyclic or part of a bicyclic ring system; and pharmaceutically acceptable salts thereof, in any stereoisomeric or tautomeric form, and mixtures of any such compounds in any ratio.

In a sixth aspect, the invention relates to pharmaceutical compositions containing a pharmaceutically acceptable, carrier and a compound of formula I-IV or VI useful for treating SMA.

DETAILED DESCRIPTION OF THE INVENTION

As summarized above, the invention relates to novel 2,4-diaminoquinazoline compounds having formulae I-IV and VI, which are useful in the treatment of SMA.

Compounds of formula III include novel ethers, thioethers, and amines. In these 2,4-diaminoquinazolines the substituent at the 5 position is defined as -$G^1$-$CH_2$-Q, wherein $G^1$ is —O—, —$NR^6$—, —S— or —$OCH(CH_3)$—, and $R^6$ is hydrogen or $C_1$-$C_6$ alkyl. In these compounds, residue Q is one of —$CH_2OCH_3$, —$CH_2OCH_2CH$=$CH_2$, $C_6$-$C_{20}$ hydrocarbon, heterocyclyl, and heteroaryl; substituted $C_6$-$C_{20}$ hydrocarbon, substituted heterocyclyl, and substituted heteroaryl; and —$CH(OH)Ar_2$, wherein Ar is substituted or unsubstituted phenyl. Examples of substituted and unsubstituted $C_6$-$C_{20}$ hydrocarbons, include, but are not limited to, substituted and unsubstituted cycloalkyls, cycloalkenyls, aryls, and fused cycloalkylaryls. In some embodiments of formula III, $G^1$ is —O— or —S—. However, it should be noted that when $G^1$ is —O— or —S—, then Q must be other than 4-chlorophenyl.

Compounds of formula II include 2,4-diaminoquinazolines in which the substituent at the 5 position is defined as -G-$R^2$. In this genus, G is —$NR^6$—, —$CH_2$—, —$SO_2$— or —$CH_2O$—, and $R^2$ is cycloalkyl, aryl, fused cycloalkylaryl, heterocyclyl, and heteroaryl; substituted cycloalkyl, substituted aryl, substituted fused cycloalkylaryl, substituted heterocyclyl, or substituted heteroaryl. However, when G is —$CH_2$— then $R^2$ must be other than phenyl or substituted phenyl.

Genus I includes 2,4-diaminoquinazolines in which the substituent at the 5 position is defined as -$L^1$-$R^1$. $L^1$ links substituent $R^1$ to the diaminoquinazoline structure. $R^1$ is selected from the group consisting of cycloalkyl, aryl, fused cycloalkylaryl, heterocyclyl, heteroaryl, substituted cycloalkyl, substituted aryl, substituted fused cycloalkylaryl, substituted heterocyclyl, and substituted heteroaryl. In some embodiments, $L^1$ is simply a bond. In other embodiments, $L^1$ is a linker of empirical formula $C_pH_qN_rO_sS_t$ in which p is 2-20; q is 0-40; r is 0-3; s is 0-6; and t is 0-2. Furthermore, in some embodiments, $L^1$ has the empirical formula —$C_{2-7}H_{4-15}O_{1-3}$—. Examples include, but $L^1$ is not limited to, —$O(CH_2)_2$—; —$(CH_2)_2O$—; —$O(CH_2)_3$—; —$CH(CH_3)O$—; —$OCH(CH_3)$—; —$CH_2CH_2$—; —$O(CH_2)_6CH_3$—, —$OCH(CH_2CH_3)$—; —$CH(CH_2OH)O$—; —CH($CH_2OCH_3$)O—; —OCH(tBu)-; OCH($C_6H_5$)—; $OCH_2CH$(OH)—; —$O(CH_3)_2$—; —$OCH(CH_2OH)$—; —OCH($CH_2OCH_3$)—; —$OCH_2CH(OCH_3)$—; —$OCH(COOH)$—; —$OCH_2CH(CH_2OCH_2OCH_3)$—; —$OCH_2CH(CH_2OH)$—; —OCH($CH_2OCH_2OCH_3$)—; —OCH($CH_2CH_2CH_3$)—; —$OCH_2CH(OCH_2OCH_3)$—; —C≡C—

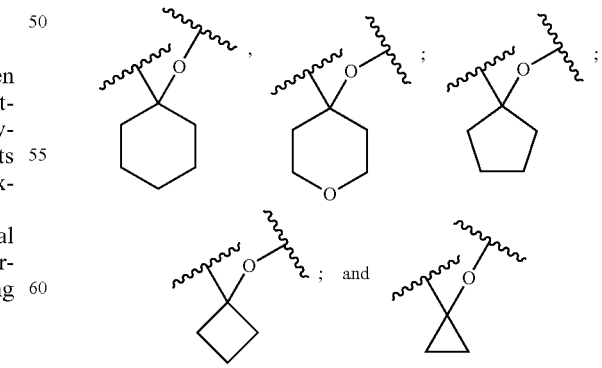

wherein the wavy lines indicate the points of attachment. In some of these embodiments, $R^1$ is selected from the group consisting of phenyl, halophenyl.

Genus IV includes ethers, thioethers, and amines. In these compounds, the substituent at position 5 is defined as -$G^2$-$R^{12}$. $G^2$ is —O—, —S—, or —NH—. In some embodiments, $R^{12}$ is $C_7$-$C_{10}$ polycyclic hydrocarbon or substituted $C_7$-$C_{10}$ polycyclic hydrocarbon, such as substituted and unsubstituted adamantyl and norbornyl. In other embodiments, $R^{12}$ is an indanyl residue having the following structure:

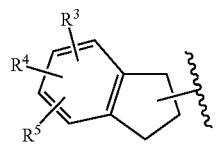

wherein the wavy line indicates the point of attachment. However, it should be noted that in some embodiments, one or more carbon atoms in the cyclopentyl ring of the above-depicted indanyl residue may optionally replaced by a heteroatom, such as N, O, or S. $R^3$, $R^4$ and $R^5$ are independently selected from the group consisting of hydrogen, halogen, $C_1$-$C_6$ alkyl, $C_1$-$C_6$ alkoxy, haloalkyl, hydroxy, carboxy, $C_1$-$C_6$ alkoxycarbonyl, carboxamido, cyano, formyl, nitro, amino, $C_1$-$C_6$ alkylamino, $C_1$-$C_6$ dialkylamino, mercapto, $C_1$-$C_6$ alkylthio, $C_1$-$C_6$ alkylsulfoxide, $C_1$-$C_6$ alkylsulfone, $C_1$-$C_6$ acylamino, amidino, phenyl, benzyl, phenoxy and benzyloxy. However, at least one of $R^3$, $R^4$, and $R^5$ must be other than hydrogen. In some embodiments, $R^3$, $R^4$ and $R^5$ are independently selected from the group consisting of hydrogen, halogen, $C_1$-$C_6$ alkoxy, $C_1$-$C_6$ alkoxy, and haloalkyl. Again, at least one of $R^3$, $R^4$ and $R^5$ is not hydrogen.

The amino groups at 2 and 4 may be substituted, and 2,4-diaminoquinazolines of formula VI also demonstrate activity. Thus, in formula VI, a hydrogen on one or both of the aminos at the 2 and 4 positions is replaced by —$NH_2$, —NH(alkyl), —NHOH, —NHO(alkyl), or by an acyl group, such as, but not limited to, —(C=O)$CH_3$. Furthermore, in formula VI, the substituent at the 5 position is defined as -L-R. L is a linker of empirical formula $C_pH_qN_rO_sS_t$, wherein p is 0-20; q is 0-40; r is 0-3; s is 0-6; and t is 0-2. R is cycloalkyl, aryl, fused cycloalkylaryl, heterocyclyl, heteroaryl, $C_3$-$C_{10}$ alkyl and $C_3$-$C_{10}$ oxaalkyl; substituted cycloalkyl, substituted aryl, substituted fused cycloalkylaryl, substituted heterocyclyl, substituted heteroaryl, substituted $C_3$-$C_{10}$ alkyl or substituted $C_3$-$C_{10}$ oxaalkyl.

As previously stated, the present invention includes a method for treating SMA by administering to a patient suffering from or disposed to SMA a therapeutically effective amount of a 2,4-diaminoquinazoline compound having formula I-IV or VI.

In addition, the invention envisions the use of any and all compounds of formula V in the method of treatment.

Owing to the requirements of patent law, and having nothing whatever to do with the scope of the inventors' conception of the invention, some compounds within the genera of formulae I-IV and VI appear from a preliminary search of the literature ineligible to be claimed (as compounds) because they are known. It may be found upon examination that additional species and genera not presently excluded are not patentable to the inventors in this application. In such an event, the exclusion of species and genera in applicants' claims are to be considered artifacts of patent prosecution and not reflective of the inventors' concept or description of their invention, which, as it relates to compounds, encompasses all members of the genera I-IV and VI that are novel, unobvious and whose synthesis is enabled by the description below in combination with the knowledge of the skilled artisan.

Definitions

Throughout this specification the terms and substituents retain their definitions.

A comprehensive list of abbreviations utilized by organic chemists (i.e. persons of ordinary skill in the art) appears in the first issue of each volume of the *Journal of Organic Chemistry*. The list, which is typically presented in a table entitled "Standard List of Abbreviations" is incorporated herein by reference.

Alkyl is intended to include linear, branched, or cyclic hydrocarbon structures and combinations thereof. Lower alkyl refers to alkyl groups of from 1 to 6 carbon atoms. Examples of lower alkyl groups include methyl, ethyl, propyl, isopropyl, butyl, s- and t-butyl and the like. Preferred alkyl groups are those of $C_{20}$ or below. Cycloalkyl is a subset of alkyl and includes cyclic hydrocarbon groups having from 3 to 8 carbon atoms, as well as polycyclic hydrocarbons having 7 to 10 carbon atoms. Examples of cycloalkyl groups include c-propyl, c-butyl, c-pentyl, and the like. Examples of $C_7$ to $C_{10}$ polycyclic hydrocarbons include ring systems such as norbornyl and adamantyl.

$C_1$ to $C_{20}$ Hydrocarbon includes alkyl, cycloalkyl, cycloalkenyl, alkenyl, alkynyl, aryl and combinations thereof. Examples include phenethyl, cyclohexylmethyl, camphoryl and naphthylethyl Examples of cycloalkenyls include cyclohexenyl, nobomenyl, and the like.

Alkoxy or alkoxyl refers to groups of from 1 to 8 carbon atoms of a straight, branched, cyclic configuration and combinations thereof attached to the parent structure through an oxygen. Examples include methoxy, ethoxy, propoxy, isopropoxy, cyclopropyloxy, cyclohexyloxy and the like. Loweralkoxy refers to groups containing one to four carbons.

Oxaalkyl refers to alkyl residues in which one or more carbons has been replaced by oxygen. Examples include methoxypropoxy, 3,6,9-trioxadecyl and the like.

Acyl refers to groups of from 1 to 8 carbon atoms of a straight, branched, cyclic configuration, saturated, unsaturated and aromatic and combinations thereof, attached to the parent structure through a carbonyl functionality. One or more carbons in the acyl residue may be replaced by nitrogen, oxygen or sulfur as long as the point of attachment to the parent remains at the carbonyl. Examples include acetyl, benzoyl, propionyl, isobutyryl, t-butoxycarbonyl, benzyloxycarbonyl and the like. Lower-acyl refers to groups containing one to four carbons.

Aryl and heteroaryl mean a 5- or 6-membered aromatic or heteroaromatic ring containing 0-3 heteroatoms selected from O, N, or S; a bicyclic 9- or 10-membered aromatic or heteroaromatic ring system containing 0-3 heteroatoms selected from O, N, or S; or a tricyclic 13- or 14-membered aromatic or heteroaromatic ring system containing 0-3 heteroatoms selected from O, N, or S. The aromatic 6- to 14-membered carbocyclic rings include, e.g., benzene, naphthalene, indane, tetralin, and fluorene and the 5- to 10-membered aromatic heterocyclic rings include, e.g., imidazole, pyridine, indole, thiophene, benzopyranone, thiazole, furan, benzimidazole, quinoline, isoquinoline, quinoxaline, pyrimidine, pyrazine, tetrazole and pyrazole.

Arylalkyl means an alkyl residue attached to an aryl ring. Examples are benzyl, phenethyl and the like. Fused cycloalkylaryl refers to a cycloalkyl residue fused to an aryl ring. Examples are indane and tetrahydronapthalene.

Heteroarylalkyl means an alkyl residue attached to a heteroaryl ring. Examples include, e.g., pyridinylmethyl, pyrimidinylethyl and the like.

Heterocycle means a cycloalkyl or aryl residue in which from one to three carbons is replaced by a heteroatom selected from the group consisting of N, O and S. The nitrogen and sulfur heteroatoms may optionally be oxidized, and the nitrogen heteroatom may optionally be quaternized. Examples of heterocycles that fall within the scope of the invention include pyrrolidine, pyrazole, pyrrole, indole, quinoline, isoquinoline, tetrahydroisoquinoline, benzofuran, benzodioxan, benzodioxole (commonly referred to as methylenedioxyphenyl, when occurring as a substituent), tetrazole, morpholine, thiazole, pyridine, pyridazine, pyrimidine, thiophene, furan, oxazole, oxazoline, isoxazole, dioxane, tetrahydrofuran and the like. It is to be noted that heteroaryl is a subset of heterocycle in which the heterocycle is aromatic. Examples of heterocyclyl residues additionally include piperazinyl, 2-oxopiperazinyl, 2-oxopiperidinyl, 2-oxo-pyrrolidinyl, 2-oxoazepinyl, azepinyl, 4-piperidinyl, pyrazolidinyl, imidazolyl, imidazolinyl, imidazolidinyl, pyrazinyl, oxazolidinyl, isoxazolidinyl, thiazolidinyl, isothiazolyl, quinuclidinyl, isothiazolidinyl, benzimidazolyl, thiadiazolyl, benzopyranyl, benzothiazolyl, tetrahydrofuryl, tetrahydropyranyl, thienyl, benzothienyl, thiamorpholinyl, thiamorpholinylsulfoxide, thiamorpholinylsulfone, oxadiazolyl, triazolyl and tetrahydroquinolinyl.

Substituted alkyl, aryl, cycloalkyl, heterocyclyl, etc. refer to alkyl, aryl, cycloalkyl, or heterocyclyl wherein up to three H atoms in each residue are replaced with halogen, haloalkyl, hydroxy, loweralkoxy, carboxy, carboalkoxy (also referred to as alkoxycarbonyl), carboxamido (also referred to as alkylaminocarbonyl), cyano, carbonyl, nitro, amino, alkylamino, dialkylamino, mercapto, alkylthio, sulfoxide, sulfone, acylamino, amidino, phenyl, benzyl, halobenzyl, heteroaryl, phenoxy, benzyloxy, heteroaryloxy, benzoyl, halobenzoyl, or loweralkylhydroxy.

The term "halogen" means fluorine, chlorine, bromine or iodine.

As used herein, and as would be understood by the person of skill in the art, the recitation of "a compound" is intended to include salts, solvates, co-crystals and inclusion complexes of that compound.

The term "solvate" refers to a compound of Formula I in the solid state, wherein molecules of a suitable solvent are incorporated in the crystal lattice. A suitable solvent for therapeutic administration is physiologically tolerable at the dosage administered. Examples of suitable solvents for therapeutic administration are ethanol and water. When water is the solvent, the solvate is referred to as a hydrate. In general, solvates are formed by dissolving the compound in the appropriate solvent and isolating the solvate by cooling or using an antisolvent. The solvate is typically dried or azeotroped under ambient conditions. Co-crystals are combinations of two or more distinct molecules arranged to create a unique crystal form whose physical properties are different from those of its pure constituents. Pharmaceutical co-crystals have recently become of considerable interest for improving the solubility, formulation and bioavailability of such drugs as itraconazole [see Remenar et al. *J. Am. Chem. Soc.* 125, 8456-8457 (2003)] and fluoxetine. Inclusion complexes are described in *Remington: The Science and Practice of Pharmacy* 19$^{th}$ Ed. (1995) volume 1, page 176-177, which is incorporated herein by reference. The most commonly employed inclusion complexes are those with cyclodextrins, and all cyclodextrin complexes, natural and synthetic, are specifically encompassed within the claims.

The term "pharmaceutically acceptable salt" refers to salts prepared from pharmaceutically acceptable non-toxic acids or bases including inorganic acids and bases and organic acids and bases. When the compounds of the present invention are basic, salts may be prepared from pharmaceutically acceptable non-toxic acids including inorganic and organic acids. Suitable pharmaceutically acceptable acid addition salts for the compounds of the present invention include acetic, benzenesulfonic (besylate), benzoic, camphorsulfonic, citric, ethenesulfonic, fumaric, glucosic, glutamic, hydrobromic, hydrochloric, isethionic, lactic, maleic, malic, mandelic, methanesulfonic, mucic, nitric, pamoic, pantothenic, phosphoric, succinic, sulfuric, tartaric acid, p-toluenesulfonic, and the like. When the compounds contain an acidic side chain, suitable pharmaceutically acceptable base addition salts for the compounds of the present invention include metallic salts made from aluminum, calcium, lithium, magnesium, potassium, sodium and zinc or organic salts made from lysine, N,N'-dibenzylethylenediamine, chloroprocaine, choline, diethanolamine, ethylenediamine, meglumine (N-methylglucamine) and procaine.

As used herein, reference to "treatment" of a patient is intended to include palliation and prophylaxis. The term "method of treating" when used herein means amelioration, prevention or relief from the symptoms and/or effects associated with SMA. The term "preventing" as refers to administering a medicament beforehand to forestall or obtund an attack. The person of ordinary skill in the medical art (to which the present invention is directed) recognizes that the term "prevent" is not an absolute term. In the medical art it is understood to refer to the prophylactic administration of a drug to substantially diminish the likelihood or seriousness of a condition, and this is the sense intended when the term is used herein.

The compounds of the invention may also be broadly protective in other motor neuron disorders, such as primary lateral sclerosis, amyotrophic lateral sclerosis and peripheral motor neuron axonopathy as well as neurodegenerative disorders involving other classes of neurons, such as Huntington's disease, Parkinson's disease and Alzheimer's disease.

Compounds described herein may contain one or more asymmetric centers and may thus give rise to enantiomers, diastereomers, and other stereoisomeric forms that may be defined, in terms of absolute stereochemistry, as (R)— or (S)—. The present invention is meant to include all such possible isomers, as well as their racemic and optically pure forms and mixtures thereof in any range or proportion. Optically active (R)— and (S)— forms may be prepared using chiral synthons or chiral reagents, or resolved using conventional techniques. When the compounds described herein contain olefinic double bonds or other centers of geometric asymmetry, and unless specified otherwise, it is intended that the compounds include both E and Z geometric isomers. The configuration of any carbon-carbon double bond appearing herein is selected for convenience only and is not intended to designate a particular configuration; thus a carbon-carbon double bond depicted arbitrarily herein as trans may be cis, trans, or a mixture of the two in any proportion. Likewise, all polymorphs and tautomeric forms are also intended to be included.

Terminology related to "protecting", "deprotecting" and "protected" functionalities occurs throughout this application. Such terminology is well understood by persons of skill in the art and is used in the context of processes which involve sequential treatment with a series of reagents. In that context, a protecting group refers to a group which is used to mask a functionality during a process step in which it would otherwise react, but in which reaction is undesirable. The protecting group prevents reaction at that step, but may be subsequently removed to expose the original functionality. The removal or "deprotection" occurs after the completion of the reaction or reactions in which the functionality would interfere. Thus, when a sequence of reagents is specified, as it is in the processes of the invention, the person of ordinary skill can readily envision those groups that would be suitable as "protecting groups". Suitable groups for that purpose are discussed in standard textbooks in the field of chemistry, such as *Protective Groups in Organic Synthesis* by T. W. Greene [John Wiley & Sons, New York, 1991], which is incorporated herein by reference.

Generalized synthetic schemes showing the various interrelated processes of the invention are presented below as Schemes 1-14. In general, the compounds of the present invention may be prepared by the methods illustrated in the general reaction schemes as, for example, described below, or by modifications thereof, using readily available starting materials, reagents and conventional synthesis procedures. In these reactions, it is also possible to make use of variants that are in themselves known, but are not mentioned here.

The 2,4-diaminoquinazoline derivative functionalized at the C5 position may be prepared via the general scheme described by Harris et. al. (J. Med. Chem. 1990, 33, 434-444). Alternatively, a more efficient route may be via reaction of an alcohol (primary, secondary or tertiary), an anime (primary or secondary, acyclic or cyclic), or a thiol, represented by G1a, with 2,6 difluorobenzonitrile, providing the intermediate G2, which upon reaction with guanidine carbonate leads to the CS functionalized 2,4-diaminoquinazoline, the desired product G3 (Scheme 1). General reaction scheme 1 yields the desired compounds, which bear a heteroatom at the C5-position of the 2,4-diaminoquinazoline core.

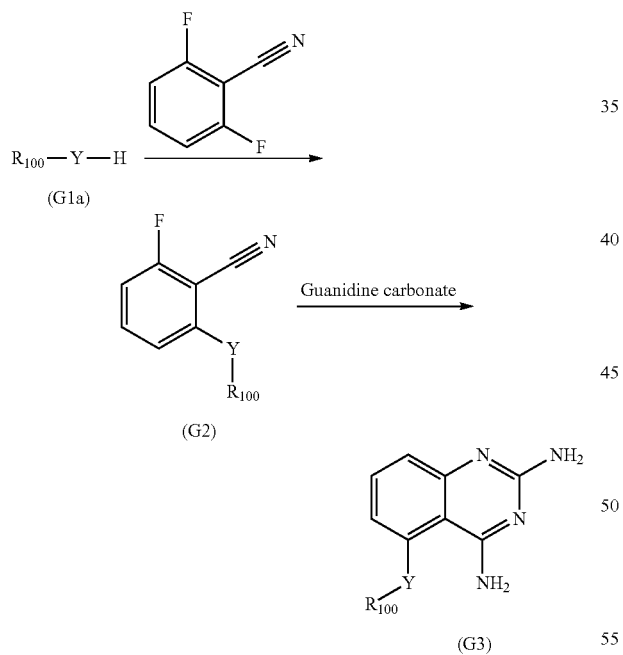

The starting material G1a may either be obtained from commercial sources or may be prepared from numerous procedures outlined in the literature. For example, alcohols may be obtained via reduction of a carboxylic acid (Examples 70 and 89), an ester (Examples 68 and 69), an aldehyde or a ketone (Examples 92, 162 and 164); from olefin via hydroboration or osmylation (Example 131). The reduction of a ketone with a chiral reducing agent either in catalytic mode or with equimolar use of a chiral reagent provides an alcohol of known chirality with very high % ee (see specific examples 92 and 162) [Scheme 2a and 2b].

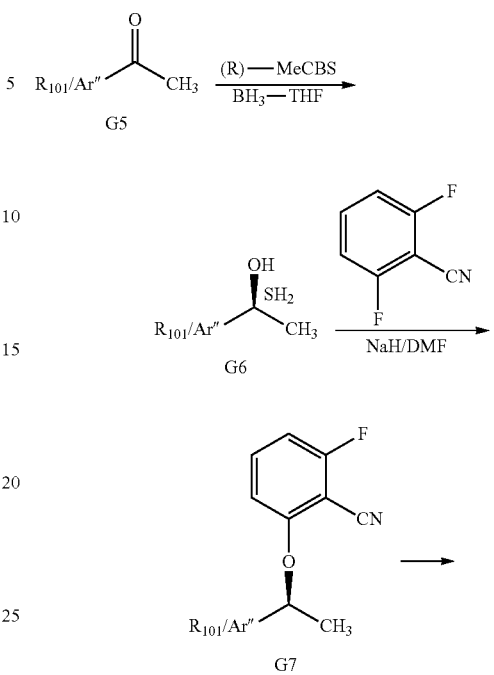

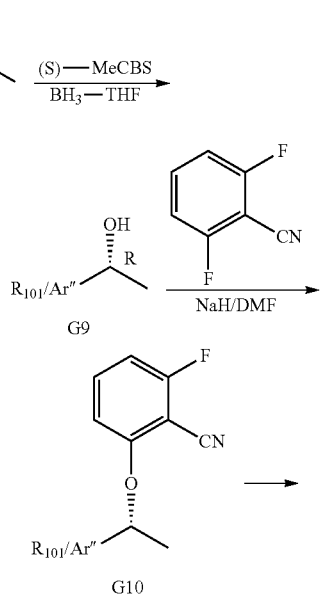

-continued

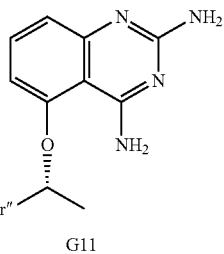
G11

Gem diol synthesis may be carried out via permanganate oxidation of an olefin, as shown in Scheme 3 (and shown by example 161). Alternatively, Sharpless epoxidation followed by subsequent transformation of the chiral epoxide would also provide access to the chiral diols and/or 1,2 amino alcohol. When the synthetic transformation leads to multiple functional groups, e.g. diols, then incorporation of appropriate protecting groups allows access to appropriate intermediates (G2) that could be linked through either the primary or secondary alcohol (for example—specific Examples 68, 69, 155, 156, 169 and 170), and such would lead to ether or amine derived products G3. An alternate approach utilizing alpha-haloketone may allow access to diverse C5 functionalization. Examples of these are shown in Schemes 3-6, below.

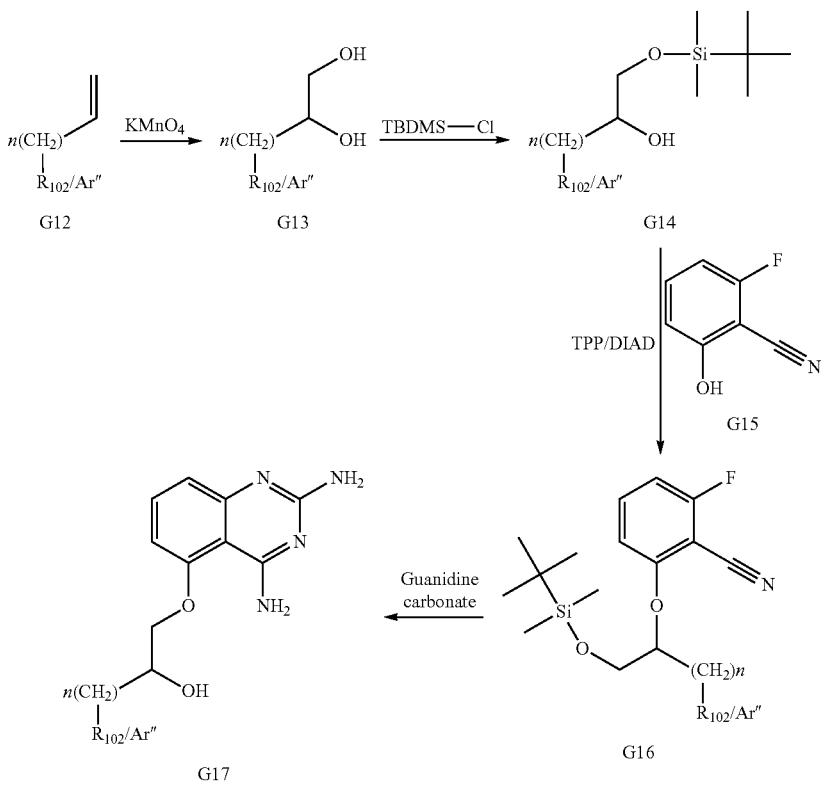

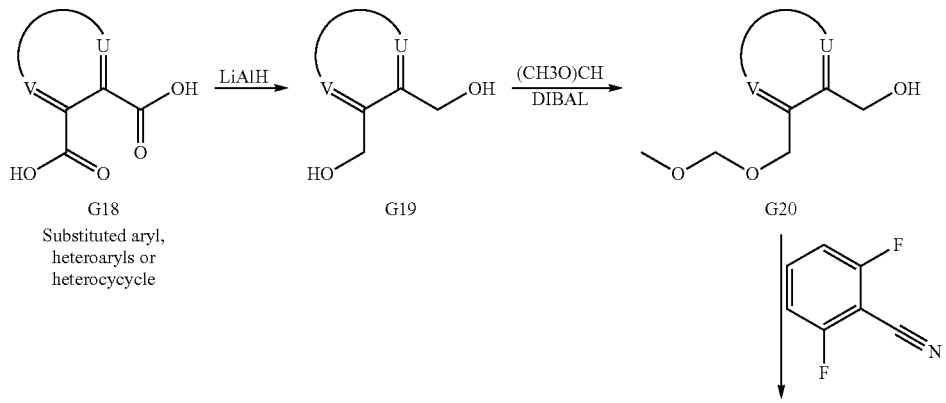

-continued
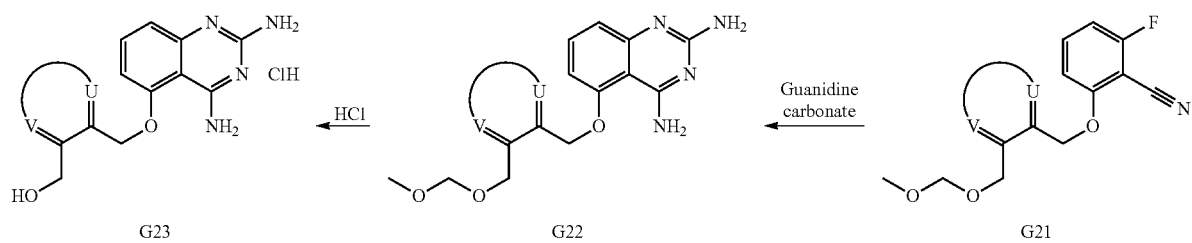
Scheme 5.
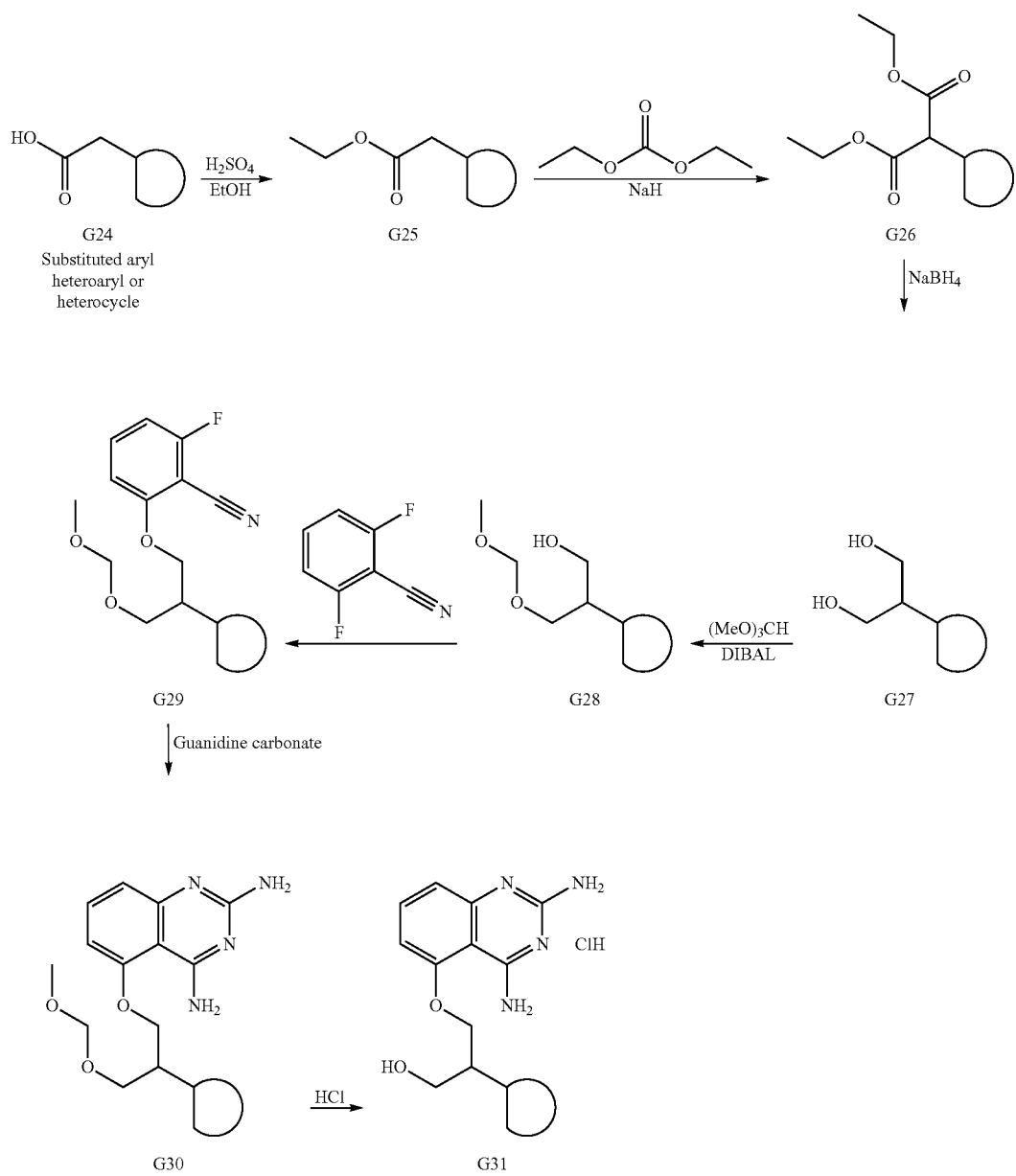

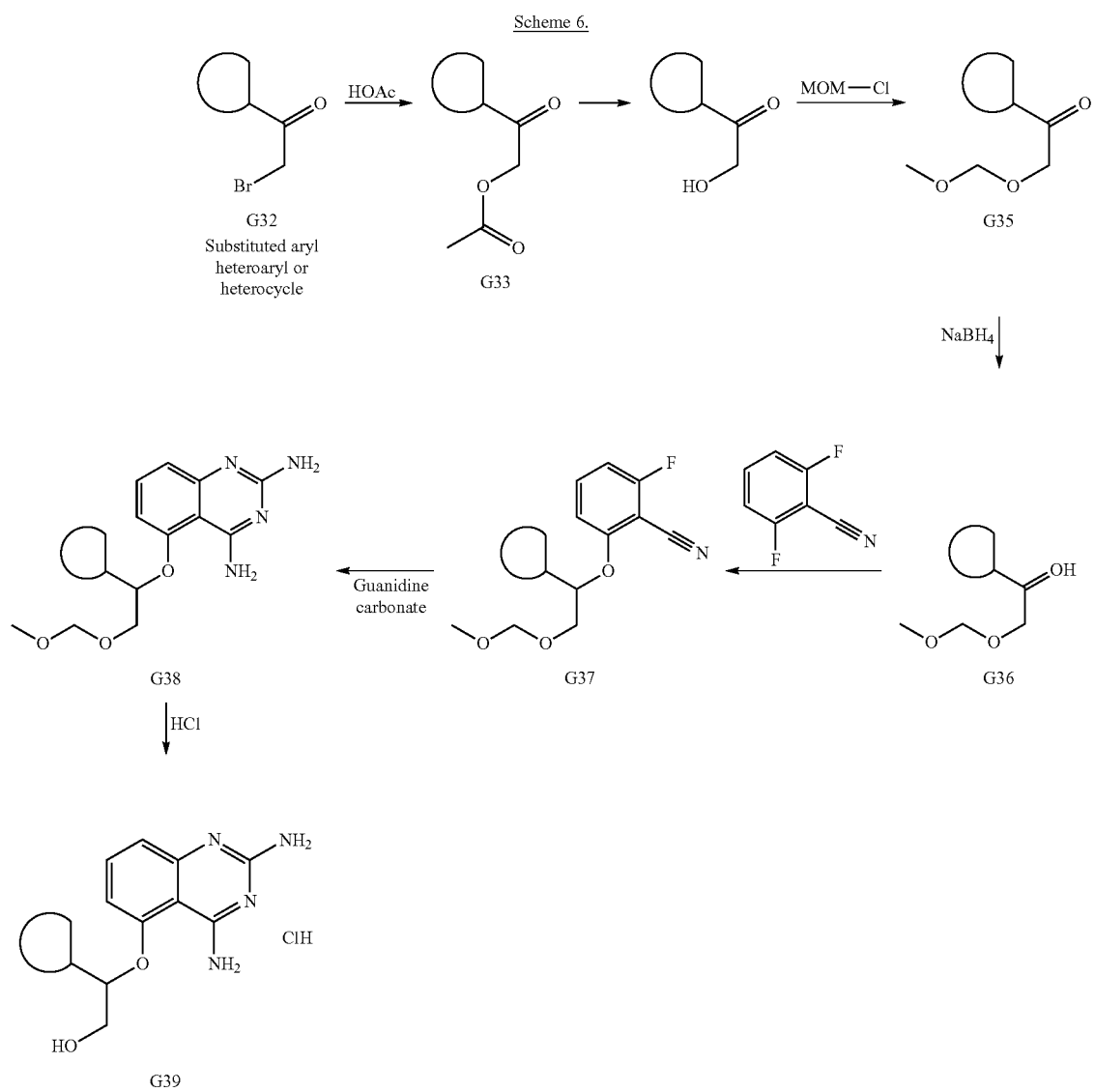
Alternatively, the chiral diols may be obtained from functional group transformation of α-hydroxy acids or esters (examples 153 and 154). As shown in scheme 8, reaction of a Grignard derivative with a lactone provide the α, ω diols (G49) which subsequently are converted to the desired products G51.
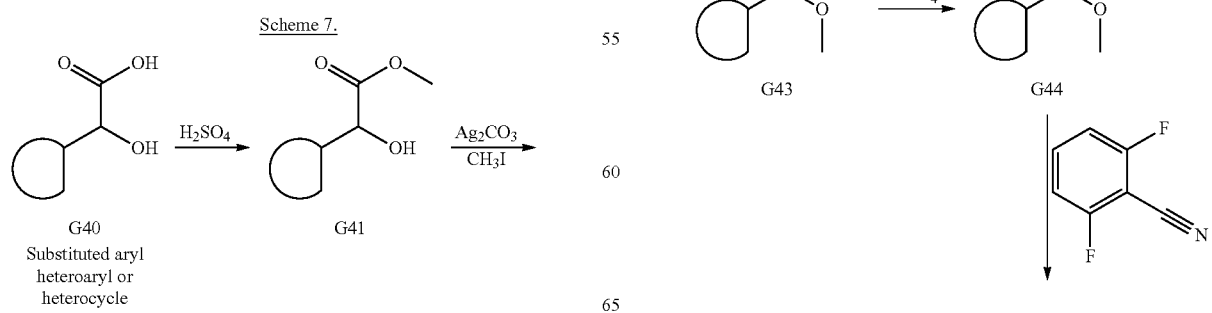

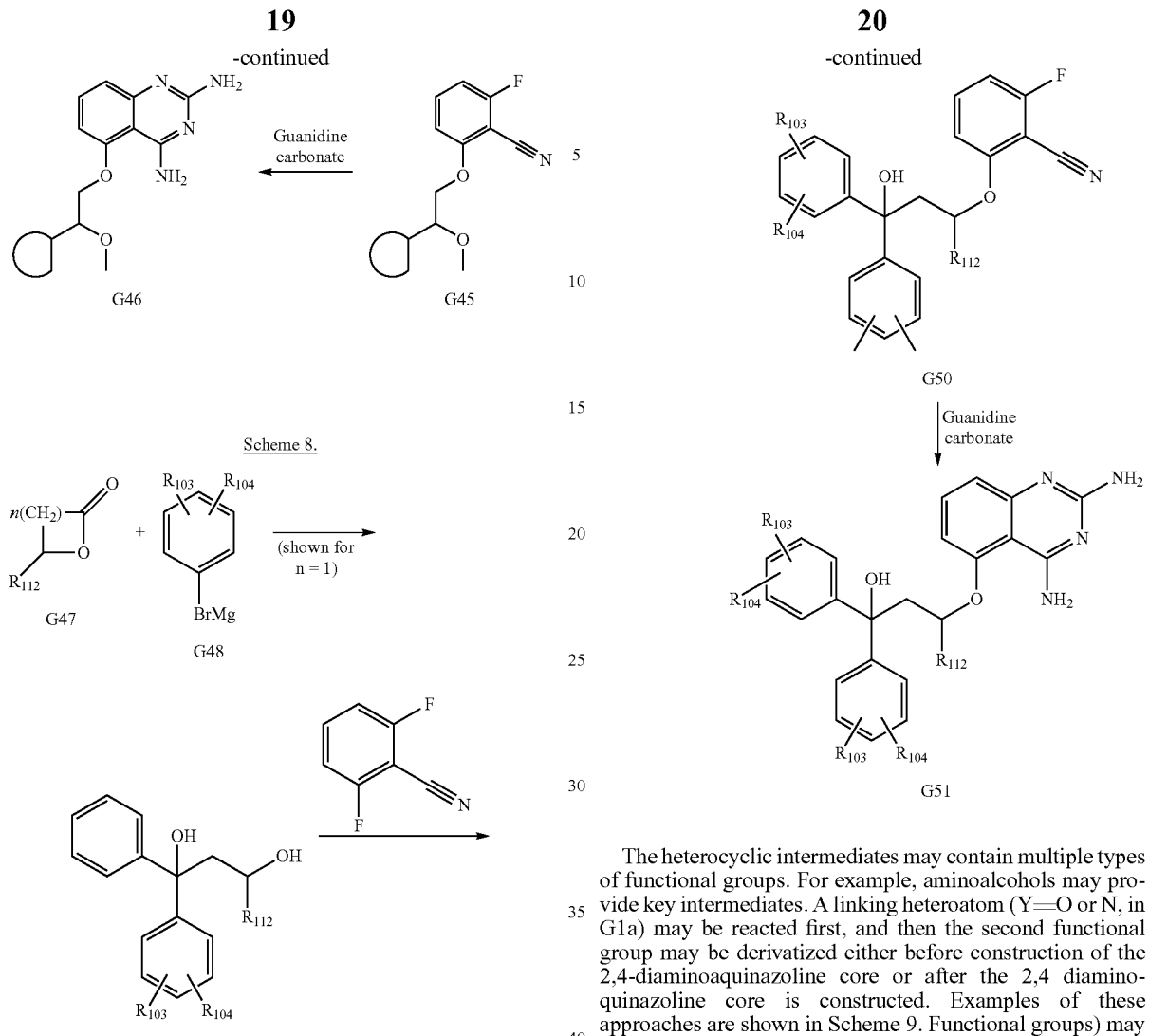

The heterocyclic intermediates may contain multiple types of functional groups. For example, aminoalcohols may provide key intermediates. A linking heteroatom (Y=O or N, in G1a) may be reacted first, and then the second functional group may be derivatized either before construction of the 2,4-diaminoaquinazoline core or after the 2,4 diaminoquinazoline core is constructed. Examples of these approaches are shown in Scheme 9. Functional groups) may also be introduced after the formation of the 2,4 diaminoquinazoline core. An example of conversion of an olefin to diol via osmylation is provided by Example 131.

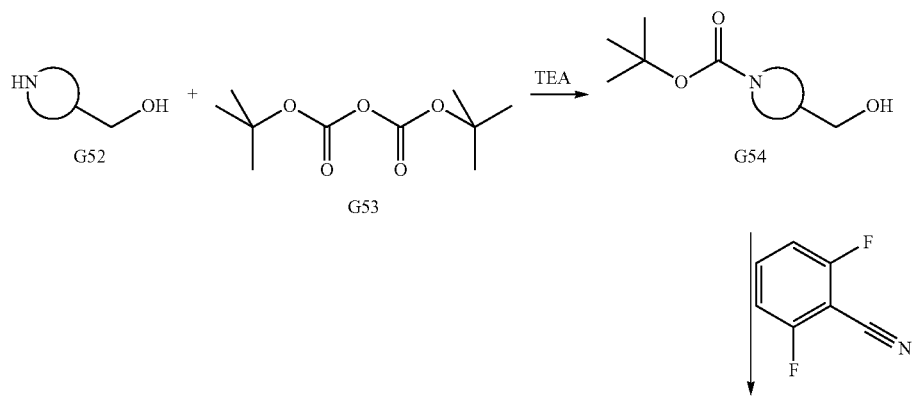

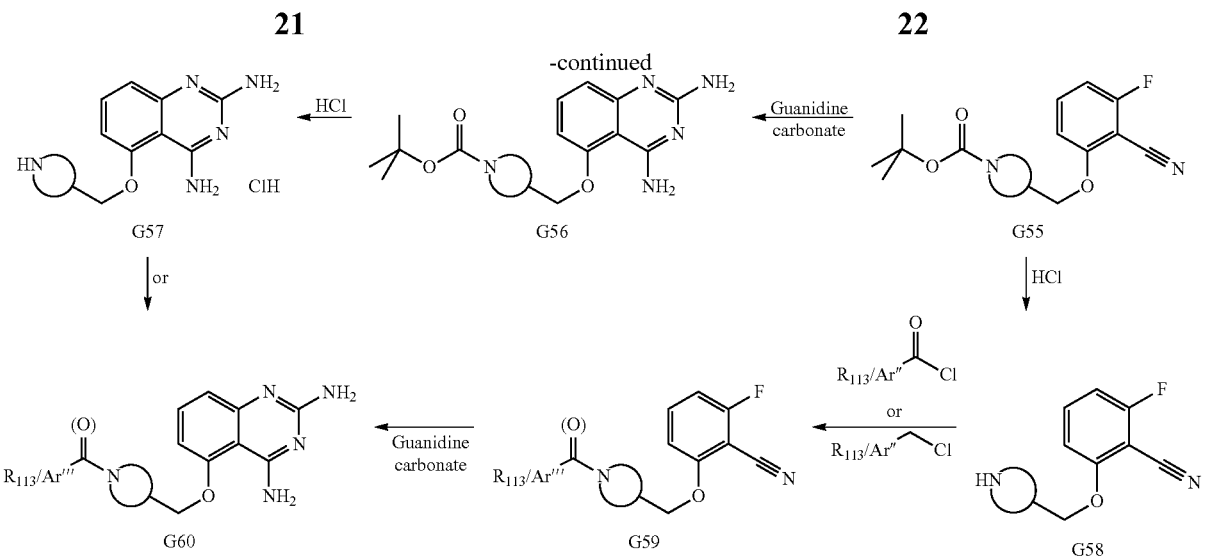

More elaborate groups may be obtained from olefin bearing intermediates, G2, by employing a wide range of dipolar cycloaddition chemistries to provide diverse heterocyclic substituents, which may then be converted to the desired products G3, as shown in Scheme 3.

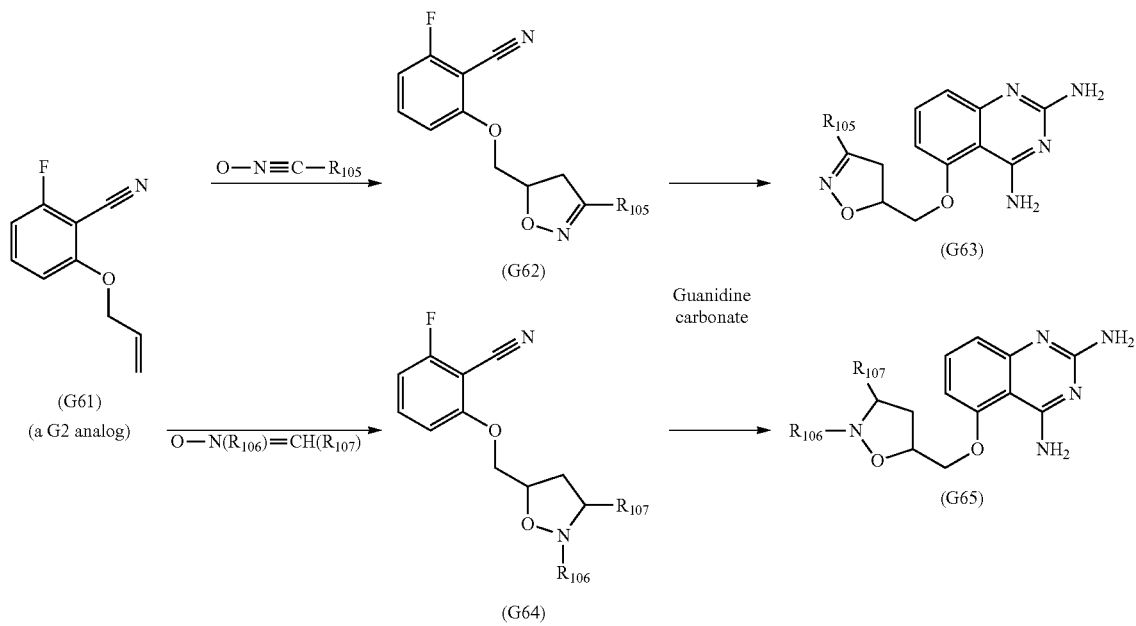

All of the schemes as described above lead to the formation of the 2,4 diaminoquinazoline which bear a heteroatom as an attachment at the C5 position. C5 carbon linked derivatives (Scheme 11) may be obtained by reacting 2-bromomethyl-6-nitro-benzonitrile G66 (prepared as described in J. Med Chem. 1973, 16, 1233) with G1a (shown for Y=O). Alternatively, the 2-bromomethyl derivative G66 may be reacted with a suitable boronic acid derivative to provide a carbon tethered C5 substituent.

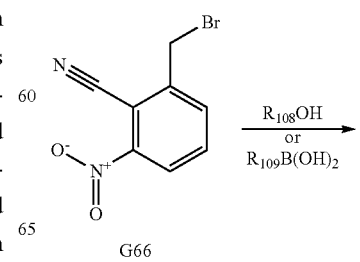

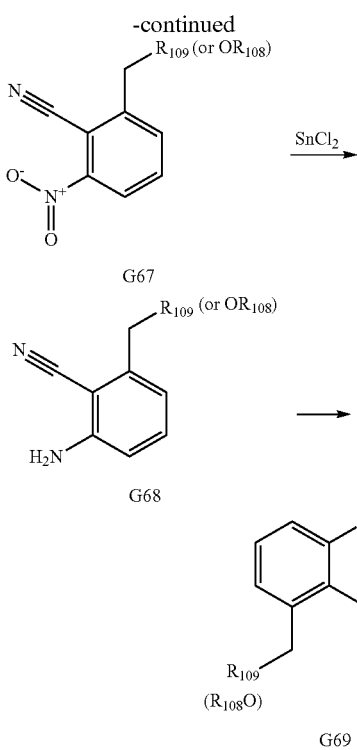

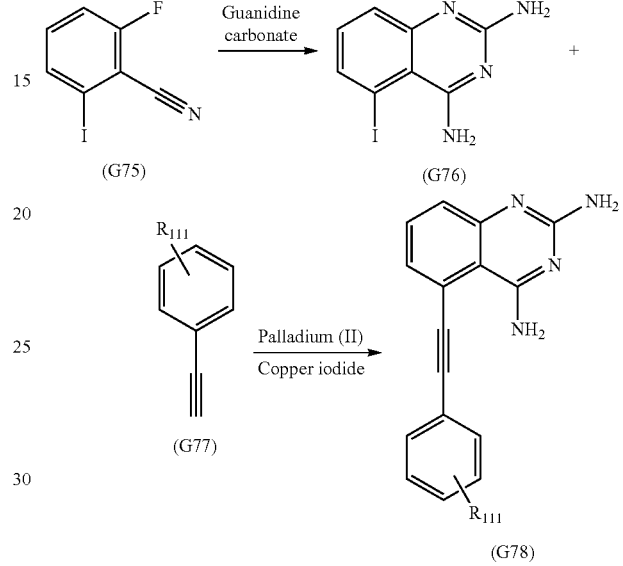

Utilization of enolate (derived from G70) as a nucleophile for displacement of the fluoride from 2,6-difluorobenzonitrile provides another approach to generate carbon linked C5 2,4-diaminoquinazolines (Scheme 12).

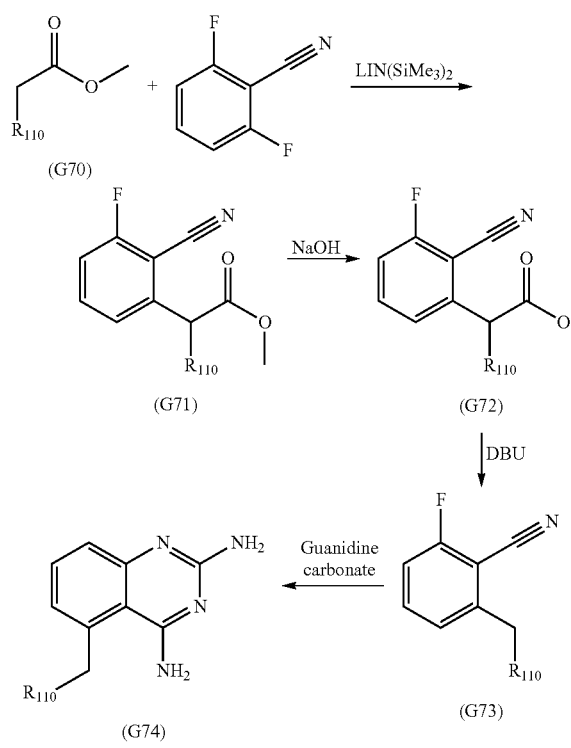

Utilization of 2-bromo or 2-iodo-6-fluorobenzonitirle and palladium based coupling chemistries (Suzuki, Stille, Sonagashira etc. etc.) allow for the introduction of diverse aryl and heteroaromatic groups. These intermediates (G79) are then converted to the desired carbon linked 2,4-diaminoquinazoline analogs, G80. As shown in Schemes 13 and 14, these chemistries may be carried out either prior to or after the synthesis of the 2,4-diaminoquinazoline core ring system.

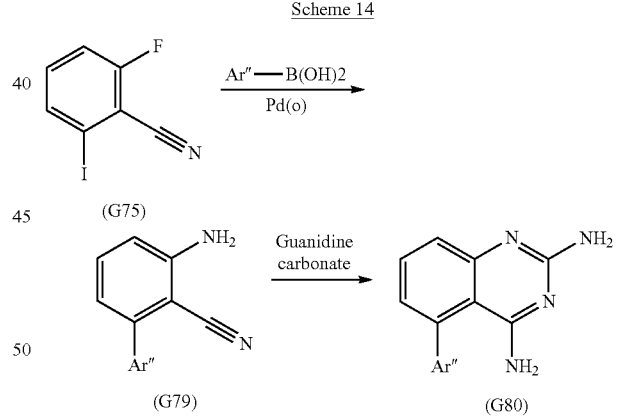

EXAMPLE 1

5-(4-Methylbenzyloxy)quinazoline-2,4-diamine

2-Fluoro-6-(4-methylbenzyloxy)benzonitrile (241.3 mg; 1 mmol) and guanidine carbonate (180.2 mg; 1 mmol) were heated at 145° C. in dimethyl acetamide for 7 hours. The solvent was removed. Purification by recrystallization in hot ethanol/water yielded 106 milligrams of 5-(4-methylbenzyloxy)quinazoline-2,4-diamine.

¹H NMR (500 MHz, DMSO-d₆) δ 7.41 (d, J=7.5 Hz, 2H), 7.35 (t, J=8 Hz, 1H), 7.24 (d, J=8 Hz, 2H), 7.16 (br d, J=28 Hz, 2H), 6.77 (d, J=8.5 Hz, 1H), 6.63 (d, J=8 Hz, 1H), 5.92 (br s, 2H), 5.20 (s, 2H), 2.32 (s, 3H).
MS m/z 281 (M+H)⁺

EXAMPLE 2

5-(4-Chlorobenzyloxy)quinazoline-2,4-diamine

The cyclization reaction of 2-fluoro-6-(4-chlorobenzyloxy)benzonitrile (261 mg, 1 mmol) was done according to example 1 to yield 15 milligrams of 5-(4-chlorobenzyloxy)quinazoline-2,4-diamine.
MS m/z 301 (M+H)⁺
¹H NMR (500 MHz, DMSO-d₆) δ 7.48 (dd, J=9.0, 8.5 Hz, 3H), 7.32 (t, J=8.0, 8.5 Hz, 1H), 7.20 (bd, J=23.5 Hz, 2H), 6.77 (d, J=8.0 Hz, 1H), 6.58 (d, J=8.0 Hz, 1H), 5.95 (s, 2H), 5.27 (s, 2H).

EXAMPLE 3

5-(2,2,2-Trifluoroethoxy)quinazoline-2,4-diamine

The cyclization reaction of 2-fluoro-6-(2,2,2-trifluoroethoxy)benzonitrile (219 mg, 1 mmol) was done according to example 1 to yield 127 milligrams of 5-(2,2,2-trifluoroethoxy)quinazoline-2,4-diamine.
MS m/z 259 (M+H)⁺
¹H NMR (400 MHz, DMSO-d₆) δ 7.40 (t, J=8.4 Hz, 1H), 7.38 (br, 2H), 6.87 (d, J=7.6 Hz, 1H), 6.64 (d, J=7.6 Hz, 1H), 6.08 (br, 2H), 4.97 (q, J=8.8 Hz, 2H).

EXAMPLE 4

5-(4-Iodobenzyloxy)quinazoline-2,4-diamine

Step 1: Sodium hydride (60%; 432 mg; 10.8 mmol) was suspended in DMF (5 mL) and cooled to 0° C. under inert atmosphere. 4-Iodobenzyl alcohol (2.53 g; 10.8 mmol) was dissolved in DMF (5 mL) and added dropwise to the sodium hydride mixture. The solution was allowed to warm to room temperature and stirred for 15 minutes. The solution was then cooled to 0° C. 2,6-Difluorobenzonitrile (1 g; 7.2 mmol) in DMF (20 mL) was added dropwise to the alcohol solution and stirred for 2 hours. The solution was poured over 100 mL of cooled water. The solution was cooled for 1 hour and a precipitate was evident. The solid was collected by vacuum filtration and washed with water. Purification by recrystallization in cyclohexane yielded 1.49 grams of 2-fluoro-6-(4-iodobenzyloxy)benzonitrile.
Step 2: 2-Fluoro-6-(4-iodobenzyloxy)benzonitrile (176.6 mg, 0.5 mmol) and guanidine carbonate (110 mg; 0.6 mmol) were heated at 140° C. in dimethyl acetamide for 7 hours. The mixture was cooled to room temperature and stored in the freezer overnight. The precipitate was collected by filtration and the filtrate was diluted with dichloromethane. The filtrate was stored in the freezer for 3 hours. The resulting precipitate was collected by filtration and all the solids were combined and crystallized from 50% ethanol/water to yield 114 milligrams of 5-(4-iodobenzyloxy)quinazoline-2,4-diamine.
¹H NMR (500 MHz, DMSO-d₆) δ 7.79 (d, J=6.5 Hz, 2H), 7.33 (m, 3H), 7.17 (br s, 2H), 6.77 (d, J=8.5 Hz, 1H), 6.57 (d, J=7.5 Hz, 1H), 5.93 (br s, 2H), 5.23 (s, 2H).
MS m/z (ESI) 391 (M−H)⁺

EXAMPLE 5

5-(3-Chlorobenzyloxy)quinazoline-2,4-diamine

Step 1: The coupling reaction of 3-chlorobenzyl alcohol (1.54 g; 10.8 mmol) was done according to Step 1 of example 4 to yield 1.26 grams of 2-fluoro-6-(3-chlorobenzyloxy)benzonitrile.
Step 2: The cyclization of the previous benzonitrile (131 mg; 0.5 mmol) was done according to Step 2 of example 4 to yield 55 milligrams of 5-(3-chlorobenzyloxy)quinazoline-2,4-diamine.
MS m/z (ESI) 299 (M−H)⁺
¹H NMR (500 MHz, DMSO-d₆) δ 7.60 (s, 1H), 7.45 (m, 3H), 7.33 (t, J=8.0 Hz, 1H), 7.23 (br d, 2H), 6.78 (d, J=8.5 Hz, 1H), 6.58 (d, J=8.0 Hz, 1H), 5.97 (br s, 2H), 5.29 (s, 2H).
¹³CNMR (500 MHz, DMSO-d₆) δ 161.7, 160.7, 155.9, 155.2, 139.0, 133.2, 132.3, 130.6, 128.1, 127.8, 126.6, 117.3, 102.1, 101.4, 69.0.
FTIR 3515, 3397, 3345, 3120, 1652, 1615, 1596, 1575, 1552, 1500, 1479, 1435, 1407, 1371, 1356, 1254, 1178, 1130, 1081, 990, 863, 812, 784, 745, 686.
Elemental Analysis—Calculated: C, 59.91%; H, 4.36%; N, 18.63%. Found: C, 59.93%; H, 4.40%; N, 18.40%.

EXAMPLE 6

5-(2-Chlorobenzyloxy)quinazoline-2,4-diamine

Step 1: The coupling reaction of 2-chlorobenzyl alcohol (1.54 g; 10.8 mmol) was done according to Step 1 of example 4 to yield 1.69 grams of 2-fluoro-6-(2-chlorobenzyloxy)benzonitrile.
Step 2: The cyclization of the previous benzonitrile (131 mg; 0.5 mmol) was done according to Step 2 of example 4 to yield 50 milligrams of 5-(2-chlorobenzyloxy)quinazoline-2,4-diamine.
MS m/z (ESI) 299 (M−H)⁺
¹H NMR (500 MHz, DMSO-d₆) δ 7.63 (dd, J=7.5, 2.5 Hz, 1H), 7.56 (dd, J=7.5, 1.5 Hz, 1H), 7.40 (m, 3H), 7.17 (br d, 2H), 6.81 (d, J=8.5 Hz, 1H), 6.83 (d, J=8.0 Hz, 1H), 6.01 (br s, 2H), 5.33 (s, 2H).
¹³CNMR (500 MHz, DMSO-d₆) δ 161.7, 160.7, 133.5, 133.0, 132.3, 130.9, 130.4, 129.7, 127.6, 117.5, 101.8, 101.3, 67.7.

EXAMPLE 7

5-(2-Methylbenzyloxy)quinazoline-2,4-diamine

Step 1: The coupling reaction of 2-methylbenzyl alcohol (1.32 g; 10.8 mmol) was done according to Step 1 of example 4 to yield 1.64 grams of 2-fluoro-6-(2-methylbenzyloxy)benzonitrile.
Step 2: The cyclization of the previous benzonitrile (121 mg; 0.5 mmol) was done according to Step 2 of example 4 to yield 36 milligrams of 5-(2-methylbenzyloxy)quinazoline-2,4-diamine.
¹H NMR (500 MHz, DMSO-d₆) δ 7.45 (d, J=7.5 Hz, 1H), 7.36 (t, J=8 Hz, 1H), 7.29 (m, 2H), 7.24 (m, 1H), 7.08 (br s, 2H), 6.79 (d, J=8 Hz, 1H), 6.67 (d, J=8 Hz, 1H), 5.94 (s, 2H), 5.24 (s, 2H), 2.36 (s, 3H).
MS m/z (ESI) 281 (M+H)⁺

EXAMPLE 8

5-(2-p-Tolylethoxy)quinazoline-2,4-diamine

Step 1: Sodium hydride (60%; 431 mg; 10.8 mmol) was suspended in DMF and cooled to 0° C. 4-Methylphenethanol (1.5 mL; 10.8 mmol) was added dropwise to the sodium hydride mixture. The solution was allowed to warm to room temperature and stirred for 30 minutes. The solution was then cooled to 0° C. 2,6-Difluorobenzonitrile (1 g; 7.2 mmol) in DMF was cooled to 0° C. and the alcohol mixture was added dropwise to the benzonitrile solution and stirred for 2 hours. The solution was poured into water. The solid was collected by filtration and dried under vacuum to yield 1.52 grams of 2-fluoro-6-(2-p-tolylethoxy)benzonitrile.

Step 2: The cyclization of the previous benzonitrile (128 mg; 0.5 mmol) was done according to Step 2 of example 4. Further purification by recrystallization in ethanol/water yielded 68 milligrams of 5-(2-p-tolylethoxy)quinazoline-2,4-diamine.

$^1$H NMR (500 MHz, DMSO-$d_6$) δ 7.33 (t, J=8 Hz, 1H), 7.24 (d, J=8 Hz, 2H), 7.13 (d, J=7.5 Hz, 2H), 7.04 (m, 2H), 6.75 (d, J=8.5 Hz, 1H), 6.55 (d, J=8 Hz, 1H), 5.89 (s, 2H), 4.32 (m, 2H), 3.11 (m, 2H), 2.27 (s, 3H).

MS m/z (ESI) 295 (M+H)$^+$

EXAMPLE 9

5-[2-(4-Chlorophenyl)ethoxy]quinazoline-2,4-diamine

Step 1: The coupling reaction of 4-chlorophenethyl alcohol (1.69 g; 10.8 mmol) was done according to Step 1 of example 8. The reaction mixture was poured into water and cooled in the refrigerator. The resulting solid was collected by filtration to yield 1.40 grams of 2-fluoro-6-[2-(4-chlorophenyl)ethoxy]benzonitrile.

Step 2: The cyclization of the previous benzonitrile (157 mg; 0.5 mmol) was done according to Step 2 of example 4. Further purification by washing with ethanol/water yielded 44 milligrams of 5-[2-(4-chlorophenyl)ethoxy]quinazoline-2,4-diamine.

MS m/z (ESI) 316 (M+H)$^+$

EXAMPLE 10

5-(3-Methylbenzyloxy)quinazoline-2,4-diamine

Step 1: The coupling reaction of 3-methylbenzyl alcohol (1.32 g; 10.8 mmol) was done according to Step 1 of example 4 to yield 434 milligrams of 2-fluoro-6-(3-methylbenzyloxy)benzonitrile.

Step 2: The cyclization of the previous benzonitrile (121 mg; 0.5 mmol) was done according to Step 2 of example 4. Further purification by recrystallizing with ethanol/water yielded 8 milligrams of 5-(3-methylbenzyloxy)quinazoline-2,4-diamine.

$^1$H NMR (500 MHz, DMSO-$d_6$) δ 7.32 (m, 4H), 7.19 (m, 3H), 6.77 (d, J=8.5 Hz, 1H), 6.62 (d, J=8 Hz, 1H), 5.94 (s, 2H), 5.21 (s, 2H), 2.34 (s, 3H).

MS m/z (ESI) 281 (M+H)$^+$

EXAMPLE 11

5-(Pyridin-3-ylmethoxy)quinazoline-2,4-diamine

Step 1: The coupling reaction of 3-pyridinylcarbinol (1.17 g; 10.8 mmol) was done according to Step 1 of example 4 to yield 1.06 grams of 2-fluoro-6-(pyridin-3-ylmethoxy)benzonitrile.

Step 2: The cyclization of the previous benzonitrile (114 mg; 0.5 mmol) was done according to Step 2 of example 4. After reaction, the mixtures were stored in the refrigerator overnight. The resulting precipitates were collected by filtration and recrystallized from ethanol/water to yield 32 milligrams of 5-(pyridin-3-ylmethoxy)quinazoline-2,4-diamine.

MS m/z (ESI) 268 (M+H)$^+$ $^1$H NMR (500 MHz, DMSO-$d_6$) δ 8.75 (d, J=1.5 Hz, 1H), 8.57 (dd, J=1.0, 1.5 Hz, 1H), 7.94 (d, J=8.0 Hz, 1H), 7.45 (dd, J=5.0, 4.5 Hz, 1H), 7.34 (t, J=8.0 Hz, 1H), 7.17 (bs, 2H), 6.78 (d, J=8.5 Hz, 1H), 6.64 (d, J=8.0 Hz, 1H), 5.95 (s, 2H), 5.33 (s, 2H).

EXAMPLE 12

5-(1-Phenylethoxy)quinazoline-2,4-diamine

Step 1: Sodium hydride (60%; 316 mg; 7.9 mmol) was suspended in DMF and cooled to 0° C. sec-Phenethyl alcohol (966 mg; 7.9 mmol) was dissolved in DMF and added dropwise to the sodium hydride mixture. The solution was allowed to warm to room temperature and stirred for 1 hour. The solution was then cooled to 0° C. 2,6-Difluorobenzonitrile (1 g; 7.2 mmol) in DMF was cooled to 0° C. and the alcohol mixture was added dropwise to the benzonitrile solution and stirred for 2 hours. The solution was poured over 100 mL of cooled water. The solution was stored in the refrigerator for 3 hours and the solid was collected by filtration and dried under vacuum to yield 1.50 grams of 2-fluoro-6-(1-phenylethoxy)benzonitrile.

Step 2: The cyclization of the previous benzonitrile (121 mg; 0.5 mmol) was done according to Step 2 of example 4. Solvent was removed and the residue was recrystallized from ethanol/water to yield 49 milligrams of 541-phenylethoxy)quinazoline-2,4-diamine.

$^1$H NMR (500 MHz, DMSO-$d_6$) δ 7.44 (d, J=7 Hz, 2H), 7.37 (m, 3H), 7.27 (m, 2H), 7.20 (t, J=8.5 Hz, 1H), 6.69 (d, J=8 Hz, 1H), 6.41 (d, J=7.5 Hz, 1H), 5.93 (s, 2H), 5.68 (q, J=6 Hz, 1H), 1.37 (d, J=6.5 Hz, 3H).

MS m/z (ESI) 281 (M+H)$^+$

EXAMPLE 13

5-(Cyclohex-3-enylmethoxy)quinazoline-2,4-diamine

Step 1: The coupling reaction of 3-cyclohexene-1-methanol (888 mg; 7.92 mmol) was done according to Step 1 of example 12 to yield 1.4 grams of 2-fluoro-6-(cyclohex-3-enylmethoxy)benzonitrile.

Step 2: The cyclization of the previous benzonitrile (116 mg; 0.5 mmol) was done according to Step 2 of example 4. The reaction mixture was stored overnight in the freezer and the resulting precipitate was collected by filtration. Purification by recrystallization with ethanol/water yielded 25 milligrams of 5-(cyclohex-3-enylmethoxy)quinazoline-2,4-diamine.

$^1$H NMR (500 MHz, DMSO-$d_6$) δ 7.35 (t, J=8 Hz, 1H), 7.20 (s, 2H), 6.78 (d, J=8.5 Hz, 1H), 6.56 (d, J=7.5 Hz, 1H), 5.94 (s, 2H), 5.71 (s, 2H), 4.04 (m, 2H), 2.18 (m, 2H), 2.09 (m, 2H), 1.88 (m, 2H), 1.38 (m, 1H).

MS m/z (ESI) 271 (M+H)$^+$

EXAMPLE 14

5-(Cyclobutylmethoxy)quinazoline-2,4-diamine

Step 1: The coupling reaction of cyclobutanemethanol (682 mg; 7.92 mmol) was done according to Step 1 of example 12. The mixture was extracted with ethyl acetate and solvent removed to yield 1.33 grams of 2-fluoro-6-(cyclobutylmethoxy)benzonitrile.

Step 2: The cyclization of the previous benzonitrile (103 mg; 0.5 mmol) was done according to Step 2 of example 4. The reaction mixture was stored overnight in the freezer and the resulting precipitate was collected by filtration. Purification by recrystallization with ethanol/water yielded 8 milligrams of 5-(cyclobutylmethoxy)quinazoline-2,4-diamine.

$^1$H NMR (500 MHz, DMSO-$d_6$) δ 7.35 (t, J=8 Hz, 1H), 7.19 (s, 2H), 6.77 (d, J=7.5 Hz, 1H), 6.53 (d, J=8 Hz, 1H), 5.93 (s, 2H), 4.10 (d, J=7 Hz, 2H), 2.85 (m, 1H), 2.11 (m, 2H), 1.90 (m, 4H).

MS m/z (ESI) 245 (M+H)$^+$

EXAMPLE 15

5-(2-Methoxyethoxy)quinazoline-2,4-diamine

Step 1: The coupling reaction of 2-methoxyethanol (605 mg; 7.92 mmol) was done according to Step 1 of example 12. The solid was washed with water and dried under vacuum to yield 837 milligrams of 2-fluoro-6-(2-methoxyethoxy)benzonitrile.

Step 2: The cyclization of the previous benzonitrile (97 mg; 0.5 mmol) was done according to Step 2 of example 4. The solvent was removed and purification by recrystallization with ethanol/water yielded 9 milligrams of 5-(2-methoxyethoxy)quinazoline-2,4-diamine.

$^1$H NMR (500 MHz, DMSO-$d_6$) δ 7.35 (m, 2H), 7.19 (br s, 1H), 6.77 (d, J=7.5 Hz, 1H), 6.54 (d, J=8 Hz, 1H), 5.93 (s, 2H), 4.22 (m, 2H), 3.76 (m, 2H), 3.34 (s, 3H).

MS m/z (BSI) 235 (M+H)$^+$

EXAMPLE 16

5-(Cyclopropylmethoxy)quinazoline-2,4-diamine

Step 1: The coupling reaction of cyclopropylcarbinol (571 mg; 7.92 mmol) was done according to Step 1 of example 12. The mixture was extracted with ethyl acetate and solvent removed to yield 1.41 grams of 2-fluoro-6-(cyclopropylmethoxy)benzonitrile.

Step 2: The cyclization of the previous benzonitrile (96 mg; 0.5 mmol) was done according to Step 2 of example 4. The reaction mixture was stored overnight in the freezer and the resulting precipitate was collected by filtration. Purification by recrystallization with ethanol/water yielded 37 milligrams of 5-(cyclopropylmethoxy)quinazoline-2,4-diamine.

MS m/z (ESI) 231 (M+H)$^+$

EXAMPLE 17

5-(Cyclohexylmethoxy)quinazoline-2,4-diamine

Step 1: The coupling reaction of cyclohexylmethanol (903 mg; 7.9 mmol) was done according to Step 1 of example 12 to yield 1.39 grams of 2-fluoro-6-(cyclohexylmethoxy)benzonitrile.

Step 2: The cyclization of the previous benzonitrile (117 mg; 0.5 mmol) was done according to Step 2 of example 4. The reaction mixture was stored overnight in the freezer and the resulting precipitate was collected by filtration. Purification by recrystallization with ethanol/water yielded 63 milligrams of 5-(cyclohexylmethoxy)quinazoline-2,4-diamine.

MS m/z (ESI) 273 (M+H)$^+$

EXAMPLE 18

5-(Cyclopentylmethoxy)quinazoline-2,4-diamine

Step 1: Sodium hydride (60%; 349 mg; 8.7 mmol) was suspended in DMF (3 mL) and cooled to 0° C. under inert atmosphere. Cyclopentylmethanol (0.79 mL; 7.3 mmol) was added dropwise to the sodium hydride mixture. The solution was allowed to warm to room temperature and stirred for 20 minutes. The solution was then added dropwise to a solution of 2,6-difluorobenzonitrile (1.03 g; 7.4 mmol) in DMF (3 mL) cooled to 0° C. The mixture was allowed to warm to room temperature and stirred for 4 hours. The solution was poured over 50 mL of cooled water and extracted with ethyl acetate and solvent removed. Purification by column chromatography (5% ethyl acetate/hexane) yielded 1.66 grams of 2-fluoro-6-(cyclopentylmethoxy)benzonitrile.

Step 2: The cyclization of the previous benzonitrile (110 mg; 0.5 mmol) was done according to Step 2 of example 4. The reaction mixture was stored overnight in the freezer and the resulting precipitate was collected by filtration. Purification by recrystallization with ethanol/water yielded 42 milligrams of 5-(cyclopentylmethoxy)quinazoline-2,4-diamine.

MS m/z (ESI) 259 (M+H)$^+$

EXAMPLE 19

5-(2-Allyloxyethoxy)quinazoline-2,4-diamine

Step 1: The coupling reaction of 2-allyloxyethanol (807 mg; 7.9 mmol) was done according to Step 1 of example 12 to obtain a quantitative yield of 2-fluoro-6-(2-allyloxyethoxy) benzonitrile.

Step 2: The cyclization of the previous benzonitrile (111 mg; 0.5 mmol) was done according to Step 2 of example 4. The solvent was removed and the product extracted with ethyl acetate. The ethyl acetate was removed to yield 11 milligrams of 5-(2-allyloxyethoxy)quinazoline-2,4-diamine.

$^1$H NMR (400 MHz, DMSO-$d_6$) δ 7.35 (m, 3H), 6.77 (d, J=8.4 Hz, 1H), 6.54 (d, J=8 Hz, 1H), 5.91 (m, 3H), 5.30 (d, J=17.2 Hz, 1H), 5.18 (d, J=10.4 Hz, 1H), 4.24 (m, 2H), 4.05 (d, J=4 Hz, 2H), 3.81 (m, 2H).

MS m/z (ESI) 261 (M+H)$^+$

EXAMPLE 20

5-(1-Methylpiperidin-3-ylmethoxy)quinazoline-2,4-diamine

Step 1: Sodium hydride (60%; 316 mg; 7.9 mmol) was suspended in DMF and cooled to 0° C. 1-Methylpiperidin-3-ylmethanol (998 mg; 7.5 mmol) was added dropwise to the sodium hydride mixture. The solution was allowed to warm to room temperature and stirred for 30 minutes. The solution was then cooled to 0° C. 2,6-Difluorobenzonitrile (1.1 g; 7.9 mmol) in DMF was cooled to 0° C. and the alcohol mixture was added dropwise to the benzonitrile solution and allowed to warm to room temperature overnight. The solution was poured into water and extracted with dichloromethane and solvent removed. Purification by column chromatography (10% ethyl acetate/hexane) to yield 79 milligrams of 2-fluoro-6-(1-methylpiperidin-3-ylmethoxy)benzonitrile.

Step 2: The cyclization of the previous benzonitrile (96 mg; 0.5 mmol) was done according to example 1. After cooling to room temperature and reaction mixtures were stirred for an additional 72 hours. The solvent was removed. Purification by recrystallization with ethanol yielded 83 milligrams of 5-(1-methylpiperidin-3-ylmethoxy)quinazoline-2,4-diamine.

MS m/z (ESI) 288 (M+H)$^+$ $^1$H NMR (500 MHz, DMSO-d$_6$) δ. 7.34 (t, J=8.0 Hz, 1H), 7.24 (br s, 2H), 6.77 (d, J=8.5 Hz, 1H), 6.53 (d, J=8.0 Hz, 1H), 5.93 (br s, 2H), 4.02 (d, J=6.5 Hz, 2H), 2.76 (m, 1H), 2.59 (m, 1H), 2.15 (s, 3H), 2.12 (m, 1H), 2.0-1.82 (m, 2H), 1.77-1.63 (m, 2H), 1.52 (m, 1H), 1.12 (m, 1H).

EXAMPLE 21

5-(Furan-2-ylmethoxy)quinazoline-2,4-diamine

Step 1: The coupling reaction of furfuryl alcohol (777 mg; 7.92 mmol) was done according to Step 1 of example 12 to yield 1.24 grams of 2-fluoro-6-(furan-2-ylmethoxy)benzonitrile.

Step 2: The previous benzonitrile (108.6 mg; 0.5 mmol) and guanidine carbonate (144 mg; 1.6 mmol) were heated at 85-95° C. in dimethyl acetamide for 48 hours. The mixtures were stored in the freezer overnight and the resulting precipitate was collected by filtration. Purification by column chromatography (5% methanol/dichloromethane) to yield 7 milligrams of 5-(furan-2-ylmethoxy)quinazoline-2,4-diamine.

$^1$H NMR (500 MHz, DMSO-d$_6$) δ 7.75 (s, 1H), 7.38 (t, J=8.5 Hz, 1H), 7.17 (br d, 2H), 6.80 (d, J=8 Hz, 1H), 7.72 (d, J=8 Hz, 1H), 6.67 (d, J=3.5 Hz, 1H), 6.51 (m, 1H), 5.97 (s, 2H), 5.24 (s, 2H).

MS m/z 257 (M+H)$^+$

EXAMPLE 22

5-(Thiophen-2-ylmethoxy)quinazoline-2,4-diamine

Step 1: The coupling reaction of 2-thiophene methanol (904 mg; 7.92 mmol) was done according to Step 1 of example 12 to yield 1.42 grams of 2-fluoro-6-(thiophen-2-ylmethoxy)benzonitrile.

Step 2: The cyclization of the previous benzonitrile (117 mg; 0.5 mmol) was done according to Step 2 of example 21 to yield 23 mg of 5-(thiophen-2-ylmethoxy)quinazoline-2,4-diamine.

MS m/z (ESI) 273 (M+H)$^+$ $^1$H NMR (500 MHz, DMSO-d$_6$) δ 7.62 (dd, J=5.3, 1.5 Hz, 1H), 7.37 (t, J=6.5 Hz, 1H), 7.3 (dd, J=3.3, 1.0 Hz, 1H), 7.21 (s, 2H), 7.08 (dd, J=5.3, 4.0 Hz, 1H), 6.8 (d, J=8.5 Hz, 1H), 6.7 (d, J=8.0 Hz, 1H), 5.96 (s, 2H), 5.45 (s, 2H).

EXAMPLE 23

5-(4-Methylbenzyl)quinazoline-2,4-diamine

Step 1: Lithium bis(trimethylsilyl)amide (14 mL; 14 mmol) in tetrahydrofuran was cooled to −40° C. Ethyl-p-tolylacetate (1 g; 5.6 mmol) and 2,6-difluorobenzonitrile (1.4 g; 10.1 mmol) in tetrahydrofuran were added dropwise to the lithium bis(trimethylsilyl)amide solution while keeping the temperature below −25° C. After addition, the solution was warmed to room temperature and stirred for 16 hours. The mixture was added to a cold mixture of aqueous sodium bicarbonate and dichloromethane. The organic layer was separated and the aqueous layer was extracted with dichloromethane. The combined organic layers were washed with brine and dried over magnesium sulfate and solvent removed. Purification by running the material through a pad of alumina (dichloromethane) to yield 1.49 grams of 2-cyano-3-fluorophenyl)-p-tolyl acetic acid ethyl ester.

Step 2: The previous ester (1.0 g; 3.3 mmol) and 1 N sodium hydroxide (7.5 mL) in methanol were shaken at room temperature for 6 hours. The mixture was poured into ice water and washed with ether. The pH of the aqueous layer was adjusted to pH=3 using 6 N HCl and extracted with toluene and solvent removed to yield 790 milligrams of (2-cyano-3-fluorophenyl)-p-tolyl acetic acid.

Step 3: The previous acid (590 mg; 2.2 mmol) and 1,8-diazabicyclo[5.4.0]undec-7-ene (380 mg; 2.5 mmol) in toluene were stirred at 90° C. for 2.5-3 hours. The mixture was cooled and 2 N HCl was added and the mixture was extracted with toluene. The organic layer was washed with water, aqueous sodium bicarbonate, and brine and solvent removed. Purification by running the material through a pad of alumina (dichloromethane) to yield 392 milligrams of 2-fluoro-6-(4-methylbenzyl)benzonitrile.

Step 4: The previous benzonitrile (113 mg; 0.5 mmol) and guanidine carbonate (216 mg; 1.2 mmol) were heated at 150° C. in dimethyl acetamide for 5 hours. The solvent was removed and water added. The resulting solid was filtered and washed with cold water. Purification by recrystallization with methanol to yield 81 milligrams of 5-(4-methylbenzyl)quinazoline-2,4-diamine.

$^1$H NMR (500 MHz, DMSO-d$_6$) δ 7.37 (t, J=7 Hz, 1H), 7.12 (m, 3H), 6.99 (d, J=8 Hz, 2H), 6.72 (d, J=6.5 Hz, 1H), 6.40 (s, 2H), 5.90 (s, 2H), 4.39 (s, 2H), 2.26 (s, 3H).

MS m/z 265 (M+H)$^+$

EXAMPLE 24

5-Benzylquinazoline-2,4-diamine

Step 1: The coupling reaction of methylphenylacetate (1.0 g; 6.6 mmol) was done according to Step 1 of example 23 to yield 1.62 grams of (2-cyano-3-fluorophenyl)phenyl acetic acid ethyl ester.

Step 2: The hydrolysis reaction of the previous ester (1.0 g; 3.7 mmol) was done according to Step 2 of example 23 to yield 860 milligrams of (2-cyano-3-fluorophenyl)phenyl acetic acid.

Step 3: The decarboxylation reaction of the previous acid (630 mg; 2.5 mmol) was done according to Step 3 of example 23 to yield 380 milligrams of 2-benzyl-6-fluorobenzonitrile Step 4: The cyclization reaction of the previous benzonitrile (106 mg; 0.5 mmol) was done according to Step 4 of example 23. Purification by recrystallization with methanol/ethanol to yield 71 milligrams of 5-benzylquinazoline-2,4-diamine.

MS m/z 251 (M+H)$^+$

EXAMPLE 25

5-(4-Chlorobenzyl)Quinazoline-2,4-Diamine

Step 1: The coupling reaction of methyl-4-chlorophenylacetate (1.0 g; 5.4 mmol) was done according to Step 1 of example 23 to yield 1.04 grams of (4-chlorophenyl)(2-cyano-3-fluorophenyl)acetic acid ethyl ester.

Step 2: The hydrolysis reaction of the previous ester (800 mg; 2.63 mmol) was done according to Step 2 of example 23 to yield 720 milligrams of (4-chlorophenyl)(2-cyano-3-fluorophenyl)acetic acid.

Step 3: The decarboxylation reaction of the previous acid (500 mg; 1.73 mmol) was done according to Step 3 of example 23 to yield 392 milligrams of 2-(4-chlorobenzyl)-6-fluorobenzonitrile.

Step 4: The cyclization reaction of the previous benzonitrile (123 mg; 0.5 mmol) was done according to step 4 of example 23 to yield 85 milligrams of 5-(4-chlorobenzyl) quinazoline-2,4-diamine.

MS m/z 286 (M+H)$^+$

EXAMPLE 26

5-(4-Methoxybenzyl)Quinazoline-2,4-Diamine

Step 1: The coupling reaction of methyl-4-methoxyphenylacetate (1.0 g; 5.6 mmol) was done according to Step 1 of example 23 to yield 1.04 grams of (2-cyano-3-fluorophenyl)(4-methoxyphenyl)acetic acid ethyl ester.

Step 2: The hydrolysis reaction of the previous ester (1.0 g; 3.34 mmol) was done according to Step 2 of example 23 to yield 820 milligrams of (2-cyano-3-fluorophenyl)(4-methoxyphenyl)acetic acid.

Step 3: The decarboxylation reaction of the previous acid (600 mg; 2.10 mmol) was done according to Step 3 of example 23 to yield 392 milligrams of 2-(4-methoxybenzyl)-6-fluorobenzonitrile.

Step 4: The cyclization reaction of the previous benzonitrile (121 mg; 0.5 mmol) was done according to Step 4 of example 23 to yield 95 milligrams of 5-(4-methoxybenzyl) quinazoline-2,4-diamine.

MS m/z 281 (M+H)$^+$

EXAMPLE 27

5-[3-(4-Chlorophenyl)propoxy]quinazoline-2,4-diamine

Step 1: The coupling reaction of 3-(4-chlorophenyl)propanol (1.0 g; 5.8 mmol) was done according to Step 1 of example 12 to yield 1.49 grams of 2-fluoro-6-[3-(4-chlorophenyl)propoxy]benzonitrile.

Step 2: The previous benzonitrile (145 mg; 0.5 mmol) and guanidine carbonate (216 mg; 1.2 mmol) were heated at 150° C. in dimethyl acetamide for 6 hours. The reaction mixtures were stored in the refrigerator overnight. The resulting solid was filtered and washed with water to yield 113 milligrams of 5-[3-(4-chlorophenyl)propoxy]quinazoline-2,4-diamine.

$^1$H NMR (500 MHz, DMSO-d$_6$) δ 7.34 (m, 3H), 7.28 (d, J=8 Hz, 2H), 7.21 (br s, 2H), 6.77 (d, J=8.5 Hz, 1H), 6.50 (d, J=8 Hz, 1H), 5.93 (s, 2H), 4.10 (t, J=6.5 Hz, 2H), 2.76 (t, J=8 Hz, 2H), 2.13 (m, 2H).

MS m/z 265 (M+H)$^+$

EXAMPLE 28

5-[1-(3-Chlorophenyl)ethoxy]quinazoline-2,4-diamine

Step 1: The coupling reaction of 1-(3-chlorophenyl)ethanol (1.24 g; 7.92 mmol) was done according to Step 1 of example 12. The mixture was extracted with ethyl acetate and solvent removed to yield 1.94 grams of 2-fluoro-6-[1-(3-chlorophenyl)ethoxy]benzonitrile.

Step 2: The cyclization reaction of the previous benzonitrile (137 mg; 0.5 mmol) was done according to Step 2 of example 27. The solvent was removed and water was added. The resulting solid was filtered and dried to yield 146 milligrams of 5-[3-(4-chlorophenyl)propoxy]quinazoline-2,4-diamine.

MS m/z 316 (M+H)$^+$ $^1$H NMR (500 MHz, DMSO-d$_6$) δ 7.54 (d, J=1.5 Hz, 1H), 7.36 (m, 3H), 7.29 (br s, 2H), 7.22 (t, J=8.5 Hz, 1H), 6.72 (d, J=8.0 Hz, 1H), 6.39 (d, J=7.5 Hz, 1H), 5.99 (br s, 2H), 5.70 (q, J=6.0 Hz, 1H), 1.68 (d, J=6.5 Hz, 3H).

$^{13}$CNMR (500 MHz, DMSO-d$_6$) δ 161.8, 160.6, 155.2, 155.0, 144.7, 133.3, 132.1, 130.6, 127.7, 125.7, 124.4, 117.2, 103.3, 101.6, 75.3.

FTIR 3494, 3471, 3447, 3306, 3098, 2971, 2923, 1650, 1610, 1566, 1507, 1474, 1447, 1432, 1400, 1372, 1352, 1337, 1327, 1245, 1203, 1073, 813, 779, 695.

EXAMPLE 29

5-(4-Chlorobenzylsulfanyl)quinazoline-2,4-diamine

Step 1: The coupling reaction of 4-chlorophenyl methanethiol (1.25 g; 7.9 mmol) was done according to Step 1 of example 12 to yield 1.36 grams of 2-(4-chlorobenzylsulfanyl)-6-fluorobenzonitrile.

Step 2: The cyclization of the previous benzonitrile (139 mg; 0.5 mmol) was done according to Step 2 of example 4. The reaction mixture was stored in the freezer overnight and the resulting solids are collected by filtration, washed with dichloromethane and dried under vacuum. Purification with ethanol/water to yield 14 milligrams of 5-(4-chlorobenzylsulfanyl)quinazoline-2,4-diamine.

MS m/z (ESI) 319 (M+H)$^+$ $^1$H NMR (500 MHz, DMSO-d$_6$) δ 7.76 (br s, 1H), 7.68 (d, J=8 Hz, 1H), 7.62 (d, J=9 Hz, 1H), 7.52 (d, J=8 Hz, 1H), 7.32 (t, J=7 Hz, 1H), 7.29 (d, J=8 Hz, 2H), 7.16 (d, J=8 Hz, 2H), 7.01 (dd, J=7.5, 1.5 Hz, 1H), 6.15 (s, 1H), 5.25 (s, 1H), 4.17 (s, 2H).

EXAMPLE 30

5-p-Tolylethynylquinazoline-2,4-diamine

Step 1: 2-Fluoro-6-iodobenzonitrile (700 mg; 2.83 mmol) is dissolved in dimethylacetamide (5 mL) with guanidine carbonate (766 mg; 4.25 mmol). The vessel is purged with N$_2$, sealed, and heated to 165° C. for 5 hours. After cooling to room temperature, the reaction mixture is placed in the freezer overnight. The precipitate which has formed is removed by filtration and purified by recrystallization from 50% EtOH/water. The resulting solids are filtered and dried at room temperature to yield 158 mg of 5-iodoquinazoline-2,4-diamine.

Step 2: The previous diamine (100 mg; 0.32 mmol), 4-ethynyltoluene (41 uL; 0.326 mmol), copper iodide (6 mg; 0.03 mmol), and dichlorobis(triphenylphoshine) palladium (II) (22 mg; 0.03 mmol) are mixed in anhydrous acetonitrile (4 mL). The reaction vessel is purged with N$_2$, sealed, and heated to 83° C. for 5 hours. After cooling to room temperature, the solids are removed, and the filtrate concentrated to ~⅓. A new crop of solid is removed, combined with the original solid and dried under vacuum at 30° C. overnight. The solid is purified by silica gel chromatography (CH$_2$Cl$_2$: MeOH:NH$_4$OH) to yield 16 milligrams of 5-p-tolylethynylquinazoline-2,4-diamine.

MS m/z (ESI) 275 (M+H)$^+$ $^1$H NMR (500 MHz, DMSO-d$_6$) δ 7.78 (br s, 1H), 7.56 (t, J=8.0 Hz, 1H), 7.52 (d, J=8.0 Hz, 2H), 7.36 (d, J=7.0 Hz, 1H), 7.32 (d, J=6.5 Hz, 1H), 7.31 (d, J=7.5 Hz, 2H), 6.56 (br s, 1H), 6.40 (br s, 1H), 2.37 (s, 3H).

EXAMPLE 31

5-(4-Chlorobenzenesulfonyl)quinazoline-2,4-diamine

Step 1: 4-Chlorobenzenethiol (1.14 g; 7.9 mmol) in anhydrous DMF is added over 1 hour to an ice-cooled suspension of sodium hydride, 60% dispersion in mineral oil (316 mg; 7.9 mmol), in anhydrous DMF. The reaction is allowed to room temperature over 30 minutes. This material is then added over 30 minutes to an ice-cooled solution of 2,6-difluorobenzonitrile (1.0 g; 7.2 mmol) in anhydrous DMF. After the addition the reaction is allowed to room temperature and stirred for 2 hours. The reaction mixture is then poured slowly into vigorously stirred ice water to give a white paste, which becomes solid with continued stirring. The solid is filtered, washed with water, and dried under vacuum at 30° C. overnight to yield 1.66 grams of 2-(4-chlorophenylsulfanyl)-6-fluorobenzonitrile.

Step 2: The previous benzonitrile (1.0 gm; 3.79 mmol) is dissolved in dimethylacetamide (5 mL) with guanidine carbonate (820 mg; 4.55 mmol). The vessel is purged with $N_2$, sealed, and heated to 155° C. for 7 hours. After cooling to room temperature, the reaction mixture is placed in the freezer overnight. The resulting solid is removed by filtration, washed with water, and dried under vacuum at 30° C. overnight. The solid is purified by recrystallization from 50% EtOH/water to yield 1.05 gram of 5-(4-chlorophenylsulfanyl)-quinazoline-2,4-diamine.

Step 3: A solution of $KMnO_4$ (104 mg; 0.66 mmol) in water (2.5 mL) is added at room temperature in four portions to a solution of the previous diamine (100 mg; 0.33 mmol) in glacial acetic acid over 1 hour. The reaction is continued at room temperature overnight. The reaction mixture is passed through a pad of Celite to remove any solids. The filtrate is made basic with concentrated $NH_4OH$ to form a solid precipitate. This precipitate is suspended in boiling dimethylformamide, and passed through a pad of Celite. While still hot, the filtrate is diluted with an additional volume of water and refrigerated for 2 hours. The resulting solid is removed by filtration and dried under vacuum at room temperature overnight to yield 48 milligrams of 5-(4-chlorobenzenesulfonyl)quinazoline-2,4-diamine.

MS m/z (ESI) 335 (M+H)$^+$ $^1$H NMR (400 MHz, DMSO-$d_6$) δ 7.85 (dd, J=7.5, 1.5 Hz, 1H), 7.71 (m, 5H), 7.62 (br s, 2H), 7.57 (dd, J=8.5, 1.5 Hz, 1H), 6.32 (br s, 2H).

FTIR 3453, 3354, 3251, 3169, 3092, 1649, 1623, 1608, 1573, 1549, 1507, 1475, 1459, 1394, 1381, 1345, 1297, 1278, 1152, 1144, 1128, 1091, 1014, 816, 568.

EXAMPLE 32

N-[2-Acetylamino-5-(4-chlorobenzyloxy)quinazolin-4-yl]acetamide 5-(4-Chlorobenzyloxy)-quinazoline-2,4-diamine (Example 2) (75 mg; 0.25 mmol) is dissolved in 1:1 HOAc:acetic anhydride and heated to 130° C. for 5 hours. After allowing the reaction to room temperature, the solvent is removed under $N_2$ purge. The resulting solid is dissolved in minimal hot ethanol and allowed to cool to room temperature and the resulting crystals are filtered and dried under vacuum overnight to yield 20 milligrams of N-[2-acetylamino-5-(4-chlorobenzyloxy)quinazolin-4-yl]acetamide.

MS m/z (ESI) 385 (M+H)$^+$ $^1$H NMR (500 MHz, DMSO-$d_6$) δ 10.44 (s, 1H), 10.37 (s, 1H), 7.77 (t, J=8.5 Hz, 1H), 7.63 (d, J=8.5 Hz, 2H), 7.51 (d, J=8.5 Hz, 2H), 7.29 (d, J=8.5 Hz, 1H), 7.15 (d, J=8.0 Hz, 1H), 5.38 (s, 2H), 2.47 (s, 3H), 2.25 (s, 3H).

EXAMPLE 33

5-(3-Methyl-4,5-dihydroisoxazol-5-ylmethoxy)quinazoline-2,4-diamine

Step 1: The coupling reaction of allyl alcohol (1.09 g, 16 mmol) was done according to Step 1 of example 12 to yield 2.13 grams of 2-[4-(2-cyano-3-fluorophenoxy)phenyl]acetamide.

Step 2: Nitroethane (75.1 mg, 1 mmol) and the previous benzonitrile (358.8 mg, 2 mmol) were stirred in benzene (2 ml) with 2 drops of triethylamine. A solution of phenyl isocyanate (238.2 mg, 2 mmol) in benzene (0.5 ml) was added dropwise to the reaction mixture at ambient temperature. After overnight stirring, the reaction mixture was heated to 50° C. for 1.5 hour. The reaction mixture was washed with water and 5% $NH_4OH$ and dried over $MgSO_4$. The solvent was removed. Purification by column chromatography with hexane/ethyl acetate (4:1) to yield 66 milligrams of 2-fluoro-6-(3-methyl-4,5-dihydroisoxazol-5-ylmethoxy)benzonitrile.

Step 3: The cyclization of the previous benzonitrile (59 mg; 0.22 mmol) was done according to Step 2 of example 4 to yield 37 milligrams of 5-(3-methyl-4,5-dihydroisoxazol-5-ylmethoxy)quinazoline-2,4-diamine.

MS m/z (ESI) 274 (M+H)$^+$ $^1$H NMR (500 MHz, DMSO-$d_6$) δ 7.33 (t, J=8.0, 8.5 Hz, 1H), 7.11 (bs, 2H), 6.78 (d, J=8.0 Hz, 1H), 6.52 (d, J=8.0 Hz, 1H), 5.93 (s, 2H), 4.93 (m, 1H), 4.19 (dd, J=2.5, 3.5 Hz, 1H), 4.05 (dd, J=6.5, 6.0 Hz, 1H), 3.32 (bs, 2H), 3.17 (dd, J=10.5, 11.0 Hz, 1H), 2.85 (dd, J=6.5 Hz, 1H), 1.95 (s, 3H).

EXAMPLE 34

5-(Furan-3-ylmethoxy)quinazoline-2,4-diamine

Step 1: The coupling reaction of 3-furanmethanol (0.7 mL; 8 mmol) was done according to Step 1 of example 12 to yield 0.91 grams of 2-fluoro-6-(furan-3-ylmethoxy)benzonitrile.

Step 2: The cyclization of the previous benzonitrile (217 mg; 1 mmol) was done according to Step 2 of example 4 to yield 16 milligrams of 5-(furan-3-ylmethoxy)quinazoline-2,4-diamine.

MS m/z (ESI) 257 (M+H)$^+$ $^1$H NMR (500 MHz, DMSO-$d_6$) δ 7.88 (s, 1H), 7.72 (s, 1H), 7.37 (t, J=8.0, 8.0 Hz, 1H), 7.23 (s, 2H), 6.79 (d, J=8.0 Hz, 1H), 6.66 (t, J=7.5, 8.0 Hz, 2H), 6.03 (s, 2H), 5.12 (s, 2H).

EXAMPLE 35

5-Benzyloxyquinazoline-2,4-diamine

Step 1: The coupling reaction of benzyl alcohol (1.7 mL; 16 mmol) was done according to Step 1 of example 12 to yield 2.26 grams of 2-fluoro-6-benzyloxybenzonitrile.

Step 2: The cyclization of the previous benzonitrile (228 mg; 1 mmol) was done according to Step 2 of example 4 to yield 11 milligrams of 5-benzyloxyquinazoline-2,4-diamine.

MS m/z (ESI) 267 (M+H)$^+$ $^1$H NMR (500 MHz, DMSO-$d_6$) δ 7.52 (d, J=7.0 Hz, 2H), 7.42 (t, J=8.0, 7.0 Hz, 2H), 7.33 (m, 2H), 7.21 (s, 1H), 7.16 (s, 1H), 6.77 (d, J=8.0 Hz, 1H), 6.20 (d, J=8.0 Hz, 1H), 5.93 (s, 2H), 5.26 (s, 2H).

EXAMPLE 36

5-(Pyridin-2-ylmethoxy)Quinazoline-2,4-diamine

Step 1: The coupling reaction of pyridine-2-methanol (1.0 mL; 10 mmol) was done according to Step 1 of example 12 to yield 2.03 grams of 2-fluoro-6-(pyridin-2-ylmethoxy)benzonitrile.

Step 2: The cyclization of the previous benzonitrile (457 mg; 1 mmol) was done according to Step 2 of example 4 to yield 232 milligrams of 5-benzyloxyquinazoline-2,4-diamine.

MS m/z (ESI) 268 (M+H)$^+$ $^1$H NMR (500 MHz, DMSO-d$_6$) δ 8.62 (d, J=4.5 Hz, 1H), 7.84 (t, J=7.5, 8.0 Hz, 2H), 7.50 (d, J=8.0 Hz, 1H), 7.33 (m, 2H), 7.20 (s, 1H), 6.78 (d, J=8.5 Hz, 1H), 6.58 (d, J=8.5 Hz, 1H), 5.95 (s, 2H), 5.36 (s, 2H).

EXAMPLE 37

5-Phenethyloxyquinazoline-2,4-diamine

Step 1: The coupling reaction of phenethyl alcohol (0.95 mL, 8 mmol) was done according to Step 1 of example 12 to yield 570 milligrams of 2-fluoro-6-phenethyloxy)benzonitrile.

Step 2: The cyclization of the previous benzonitrile (484 mg; 2 mmol) was done according to Step 2 of example 4 to yield 45 milligrams of 5-phenethyloxy-quinazoline-2,4-diamine.

MS m/z (ESI) 281 (M+H)$^+$ $^1$H NMR (500 MHz, DMSO-d$_6$) δ 7.32 (m, 4H), 7.24 (d, J=6.5 Hz, 1H), 7.09 (bs, 1H), 7.02 (bs, 1H), 6.75 (d, J=8.5 Hz, 1H), 6.55 (d, J=8.0 Hz, 1H), 5.89 (s, 2H), 4.35 (t, J=6.0, 6.5 Hz, 2H), 3.15 (t, J=6.5, 6.0 Hz, 2H).

EXAMPLE 38

5-Octyloxyquinazoline-2,4-diamine

Step 1: The coupling reaction of 1-octanol (1.6 mL; 10 mmol) was done according to Step 1 of example 12 to yield 1.68 grams of 2-fluoro-6-octyloxybenzonitrile.

Step 2: The cyclization of the previous benzonitrile (500 mg; 2 mmol) was done according to Step 2 of example 4 to yield 41 milligrams of 5-octyloxyquinazoline-2,4-diamine.

MS m/z (ESI) 289 (M+H)$^+$ $^1$H NMR (500 MHz, DMSO-d$_6$) δ 7.37 (t, J=8.0, 8.0 Hz, 1H), 7.21 (s, 2H), 6.76 (d, J=8.0 Hz, 1H), 6.52 (d, J=8.0 Hz, 1H), 5.92 (s, 2H), 4.10 (t, J=6.0, 6.5 Hz, 2H), 1.80 (t, J=7.5, 7.5 Hz, 2H), 1.40 (dd, J=7.0, 7.5 Hz, 2H), 1.26 (dd, J=10.0, 7.5 Hz, 8H), 0.85 (t, J=7.0, 6.0 Hz, 3H).

EXAMPLE 39

N-5-Cyclooctylquinazoline-2,4,5-triamine

Step 1: Cyclooctylamine (1.4 mL; 10 mmol) was added dropwise to a solution of 2,6-difluorobenzonitrile (1.39 g, 10 mmol) in DMF (6 ml) at 0° C. The reaction mixture was stiffed at room temperature for 4.5 hours. The reaction mixture was added to vigorously stirred ice water (40 ml) and extracted with ethyl acetate. Solvent was removed to yield 1.63 grams of 2-cyclooctylamino-6-fluorobenzonitrile.

Step 2: The cyclization of the previous benzonitrile (494 mg; 2 mmol) was done according to Step 2 of example 4 to yield 137 milligrams of N-5-cyclooctylquinazoline-2,4,5-triamine.

MS m/z (ESI) 286 (M+H)$^+$ $^1$H NMR (500 MHz, DMSO-d$_6$) δ 7.44 (s, 2H), 7.23 (t, J=8.0, 8.0 Hz, 1H), 6.67 (s, 1H), 6.39 (d, J=7.5 Hz, 1H), 4.90 (bs, 1H), 3.32 (s, 1H), 1.45 (m, 1H).

EXAMPLE 40

5-(Indan-2-yloxy)quinazoline-2,4-diamine

Step 1: The coupling reaction of 2-indanol (1.34 mL; 10 mmol) was done according to Step 1 of example 12 to yield 1.69 grams of 2-fluoro-6-(indan-2-yloxybenzonitrile.

Step 2: The cyclization of the previous benzonitrile (507 mg; 2 mmol) was done according to Step 2 of example 4 to yield 467 milligrams of 5-(indan-2-yloxy)quinazoline-2,4-diamine.

MS m/z (ESI) 293 (M+H)$^+$ $^1$H NMR (400 MHz, DMSO-d$_6$) δ 7.72 (dd, J=8.4, 8.4 Hz, 1H), 7.37 (t, J=8.0, 8.0 Hz, 1H), 7.29 (m, 3H), 7.18 (m, 3H), 7.05 (t, J=8.8, 8.8 Hz, 1H), 6.89 (bd, J=33.2 Hz, 2H), 6.77 (d, J=8.4 Hz, 1H), 6.65 (d, J=8.4 Hz, 1H), 5.90 (s, 2H), 5.42 (m, 1H), 3.41 (m, 2H), 3.06 (m, 2H).

EXAMPLE 41

5-((S)-Indan-1-yloxy)quinazoline-2,4-diamine

Step 1: The coupling reaction of (S)-1-indanol (722 mg; 5 mmol) was done according to Step 1 of example 12 to yield 868 milligrams of 2-fluoro-6-((S)-indan-1-yloxybenzonitrile.

Step 2: The cyclization of the previous benzonitrile (507 mg; 2 mmol) was done according to Step 2 of example 4 to yield 450 milligrams of 5-((S)-indan-1-yloxy)quinazoline-2,4-diamine.

MS m/z (ESI) 293 (M+H)$^+$ $^1$H NMR (400 MHz, DMSO-d$_6$) δ 7.76 (m, 2H), 7.49 (d, J=9.5 Hz, 1H), 7.33 (m, 5H), 7.25 (m, 3H), 7.09 (t, J=10.5, 11.0 Hz, 1H), 7.01 (bd, J=12.5 Hz, 2H), 6.77 (m, 2H), 6.09 (m, 1H), 6.01 (m, 1H), 5.93 (s, 1H), 3.05 (m, 2H), 2.88 (m, 2H), 2.60 (m, 2H), 2.04 (m, 1H).

EXAMPLE 42

5-((S)-1-Phenylethoxy)quinazoline-2,4-diamine

Step 1: The coupling reaction of (S)-sec-phenethyl alcohol (611 mg; 5 mmol) was done according to Step 1 of example 12 to yield 494 milligrams of 2-fluoro-6-((S)-phenylethoxy)benzonitrile.

Step 2: The cyclization of the previous benzonitrile (483 mg; 2 mmol) was done according to Step 2 of example 4 to yield 429 milligrams of 5-((S)-1-phenylethoxy)quinazoline-2,4-diamine.

MS m/z (ESI) 281 (M+H)$^+$ $^1$H NMR (400 MHz, DMSO-d$_6$) δ 7.92 (s, 1H), 7.44 (m, 7H), 6.70 (dd, J=8.4, 0.8 Hz, 1H), 6.43 (d, J=7.6 Hz, 1H), 6.03 (br s, 2H), 5.69 (q, J=6.4 Hz, 1H), 1.67 (d, J=6.4 Hz, 3H).

EXAMPLE 43

5-(4-Chlorophenoxymethyl)quinazoline-2,4-diamine

Step 1: 4-Chlorophenol (64.0 mg; 0.5 mmol) and potassium carbonate were added to a cooled (0° C.) and stirred solution of 2-bromomethyl-6-nitrobenzonitrile (120.0 mg; 0.5 mmol) [prepared by the method of Ashton and Hynes, J.

*Med. Chem.* 16, 1233 (1973)] in dimethylformamide under nitrogen atmosphere. The reaction mixture was stirred at 0° C. for 1.5 hours, then diluted with pyridine (1.5 mL), water, stirred for 1 hour, filtered and dried to yield 140 milligrams of 2-(4-chlorophenoxymethyl)-6-nitrobenzonitrile.

Step 2: To a cooled (15° C.) and stirred solution of tin(II) chloride (550.0 mg; 2.43 mmol) and concentrated hydrochloric acid (1.1 mL) was added a solution of the previous benzonitrile (140.0 mg; 0.48 mmol). The reaction mixture was slowly warmed to room temperature and stirred for 3 hours. The reaction mixture was poured on to crushed-ice and potassium hydroxide solution, stirred, filtered and dried to yield 120 milligrams of 2-amino-6-(4-chlorophenoxymethyl)benzonitrile.

Step 3: The previous aminobenzonitrile (40.0 mg; 0.15 mmol) and chloroformamidine hydrochloride (18.0 mg; 0.16 mmol) were heated at 140° C. in diglyme for 3 hours. The reaction mixture was diluted with water, stirred for 2 hours, filtered, washed with water and dried. Purification by silica gel chromatography (5-10% methanol in dichloromethane) to yield 14 milligrams of 5-(4-chlorophenoxymethyl)quinazoline-2,4-diamine.

MS m/z (BSI) 301 (M+H)$^+$ $^1$H NMR (500 MHz, DMSO-d$_6$) δ 7.46 (t, J=8.0 Hz, 1H), 7.39 (d, J=9.0 Hz, 1H), 7.25 (d, J=8.5 Hz, 1H), 7.16 (m, 2H), 6.8 (s, 2H), 6.11 (s, 2H), 5.39 (s, 2H).

EXAMPLE 44

5-p-Tolyloxymethylquinazoline-2,4-diamine

Step 1: The bromide displacement reaction with 4-methylphenol (112.2 mg; 1.04 mmol) was done according to Step 1 of example 43 to yield 226 milligrams of 2-nitro-6-p-tolyloxymethylbenzonitrile.

Step 2: The reduction reaction with the previous nitrobenzonitrile (225.0 mg; 0.83 mmol) was done according to Step 2 of example 43 to yield 176 milligrams of 2-amino-6-p-tolyloxymethylbenzonitrile.

Step 3: The cyclization reaction of the previous benzonitrile (60.0 mg; 0.25 mmol) was done according to Step 3 of example 43 to yield 25 milligrams of 5-p-tolyloxymethylquinazoline-2,4-diamine.

MS m/z (ESI) 281 (M+H)$^+$ $^1$H NMR (500 MHz, DMSO-d$_6$) δ 7.45 (dd, J=8.3, 7.5 Hz, 1H), 7.24 (d, J=8.0 Hz, 1H), 7.14 (m, 3H), 7.01 (d, J=8.5 Hz, 1H), 6.9 (s, 2H), 6.11 (s, 2H), 5.31 (s, 2H), 2.25 (s, 3H).

EXAMPLE 45

5-(4-Fluorophenoxymethyl)quinazoline-2,4-diamine

Step 1: The bromide displacement reaction with 4-fluorophenol (116.3 mg; 1.04 mmol) was done according to Step 1 of example 43 to yield 225 milligrams of 2-(4-fluorophenoxymethyl)-6-nitrobenzonitrile.

Step 2: The reduction reaction with the previous nitrobenzonitrile (225.0 mg; 0.83 mmol) was done according to Step 2 of example 43 to yield 175 milligrams of 2-amino-6-(4-fluorophenoxymethyl)benzonitrile.

Step 3: The cyclization reaction of the previous benzonitrile (100.0 mg; 0.41 mmol) was done according to Step 3 of example 43 to yield 80 milligrams of 5-(4-fluorophenoxymethyl)quinazoline-2,4-diamine.

MS m/z (ESI) 285 (M+H)$^+$ $^1$H NMR (500 MHz, DMSO-d$_6$) δ 7.47 (dd, J=8.3, 7.5 Hz, 1H), 7.26 (dd, J=8.5, 0.5 Hz, 1H), 7.16 (m, 5H), 6.92 (s, 2H), 6.18 (s, 2H), 5.36 (s, 2H).

EXAMPLE 46

5-Thiophen-3-ylmethylquinazoline-2,4-diamine

Step 1: A suspension of 2-bromomethyl-6-nitrobenzonitrilel (100.0 mg, 0.41 mmol), 3-thiopheneboronic acid (110.0 mg, 0.83 mmol), cesium fluoride (190.0 mg, 1.24 mmol) and tetrakis-triphenylphosphenepalladium (0) in anhydrous dimethylformamide was heated at 80° C. for 20 hours. The reaction mixture was cooled, poured in to water, extracted with ethyl acetate, washed with brine, dried and concentrated. Purification by silica gel chromatography (1:1 hexanes in dichloromethane) to yield 40 milligrams of 2-nitro-6-thiophen-3-ylmethylbenzonitrile.

Step 2: The reduction reaction with the previous nitrobenzonitrile (40.0 mg; 0.17 mmol) was done according to Step 2 of example 43 to yield 40 milligrams of 2-amino-6 thiophen-3-ylmethylbenzonitrile.

Step 3: The cyclization reaction of the previous benzonitrile (40.0 mg; 0.19 mmol) was done according to Step 3 of example 43 to yield 30 milligrams of 5-thiophen-3-ylmethylquinazoline-2,4-diamine.

MS m/z (ESI) 257 (M+H)$^+$ $^1$H NMR (500 MHz, DMSO-d$_6$) δ 7.52 (dd, J=5.3, 3.5 Hz, 1H), 7.39 (dd, J=8.3, 7.0 Hz, 1H), 7.13 (dd, J=8.5, 1.0 Hz, 1H), 7.05 (m, 1H), 6.92 (dd, J=4.5, 1.0 Hz, 1H), 6.79 (d, J=6.5 Hz, 1H), 6.5 (s, 2H), 5.98 (s, 2H), 4.4 (s, 2H).

EXAMPLE 47

5-(Thiophen-3-ylmethoxy)quinazoline-2,4-diamine

Step 1: A solution of 3-thiophenemethanol (1.0 g; 8.76 mmol) in dimethylformamide was added to a cooled (0° C.) slurry of sodium hydride (0.42 g; 10.51 mmol) in dimethylformamide under nitrogen atmosphere. The reaction mixture was slowly warmed to room temperature, stirred for 1 hour. Again, cooled (0° C.), then a solution of 2,6-difluorobenzonitrile in dimethylfomamide was added, stirred overnight at room temperature. The reaction mixture was poured on crushed ice-water, stirred, filtered, washed with water and dried to afford 600 milligrams of 2-fluoro-6-(thiophen-3-ylmethoxy)benzonitrile.

Step 2: The previous benzonitrile (200.0 mg; 0.86 mmol) and guanidine carbonate (245 mg; 1.38 mmol) were heated at 145° C. in diglyme for 3 hours. The reaction mixture was diluted with water, stirred for 2 hours, filtered, washed with water and dried. Purification by silica gel chromatography (5-10% methanol in dichloromethane) to yield 143 milligrams of 5-(thiophen-3-ylmethoxy)quinazoline-2,4-diamine.

MS m/z (ESI) 273 (M+H)$^+$ $^1$H NMR (500 MHz, DMSO-d$_6$) δ 7.68 (m, 1H), 7.61 (dd, J=4.0, 3.0 Hz, 1H), 7.37 (t, J=8.0 Hz, 1H), 7.27 (dd, J=5.3, 1.5 Hz, 1H), 7.25 (s, 2H), 6.8 (dd, J=8.5, 0.5 Hz, 1H), 6.68 (d, J=8.0 Hz, 1H), 6.02 (s, 2H), 5.25 (s, 2H).

EXAMPLE 48

5-(1-Pyridin-4-ylethoxy)quinazoline-2,4-diamine

Step 1: Sodium borohydride (310.0 mg; 8.25 mmol) was added portionwise to a cooled (0° C.) solution of 4-acetylpyridine (500.0 mg; 4.13 mmol) in ethanol under argon atmosphere. The reaction mixture was slowly warmed to room temperature, stirred for 4 hours. Quenched with water and solvent removed. Extracted with dichloromethane, washed with water, brine, dried and solvent removed to yield 500 milligrams of 1-(4-pyridyl)ethanol.

Step 2: The coupling reaction of the previous alcohol (230.0 mg; 1.65 mmol) was done according to Step 1 of example 47 to yield 2-fluoro-6-[1-(4-pyridyl)ethoxy]benzonitrile.

Step 3: The cyclization reaction of the previous benzonitrile (170.0 mg; 0.70 mmol) was done according to Step 2 of example 47 to yield 39 milligrams of 5-(1-pyridin-4-ylethoxy)quinazoline-2,4-diamine.

MS m/z (ESI) 282 (M+H)$^+$ $^1$H NMR (500 MHz, DMSO-d$_6$) δ 8.56 (dd, J=4.5, 2.0 Hz, 2H), 7.44 (dd, J=4.5, 1.5 Hz, 2H), 7.33 (brs, 2H), 7.21 (t, J=8.0 Hz, 1H), 6.72 (d, J=8.5 Hz, 1H), 6.33 (d, J=9.5 Hz, 1H), 5.97 (s, 2H), 5.73 (q, J=7.0 Hz, 1H), 1.69 (d, J=7.0 Hz, 3H).

EXAMPLE 49

5-[1-(4-Chlorophenyl)ethoxy]quinazoline-2,4-diamine

Step 1: The reduction reaction of 4-chloroacetophenone (2.0 g; 12.94 mmol) was done according to Step 1 of example 48 to yield 2.0 gams of 1-(4-chlorophenyl)ethanol.

Step 2: The coupling reaction of the previous alcohol (1.0 g; 6.39 mmol) was done according to Step 1 of example 47 to yield 1.12 grains of 2-fluoro-6-[1-(4-chlorophenyl)ethoxy]benzonitrile.

Step 3: The cyclization reaction of the previous benzonitrile (250.0 mg; 0.91 mmol) was done according to Step 2 of example 47 to yield 125 milligrams of 5-[1-(4-chlorophenyl)ethoxy]quinazoline-2,4-diamine.

MS m/z (ESI) 315 (M+H)$^+$ $^1$H NMR (500 MHz, DMSO-d$_6$) δ 7.48 (d, J=8.0 Hz, 2H), 7.43 (d, J=8.5 Hz, 2H), 7.3 (brd, 2H), 7.21 (t, J=8.5 Hz, 1H), 6.7 (d, J=8.0 Hz, 1H), 6.38 (d, J=8.5 Hz, 1H), 5.94 (s, 2H), 5.71 (q, J=6.5 Hz, 1H), 1.67 (d, J=6.5 Hz, 3H).

EXAMPLE 50

5-[1-(4-Chlorophenyl)propoxy]quinazoline-2,4-diamine

Step 1: The reduction reaction of 4-chloropropiophenone (3.0 g; 17.79 mmol) was done according to Step 1 of example 48 to yield 3.0 grams of 1-(4-chlorophenyl)propanol.

Step 2: The coupling reaction of the previous alcohol (1.0 g; 5.86 mmol) was done according to Step 1 of example 47 to yield 1.1 grams of 2-fluoro-6-[1-(4-chlorophenyl)propyloxy]benzonitrile.

Step 3: The cyclization reaction of the previous benzonitrile (250.0 mg; 0.86 mmol) was done according to Step 2 of example 47 to yield 80 milligrams of 5-[1-(4-chlorophenyl)propoxy]quinazoline-2,4-diamine.

MS m/z (EST) 330 (M+H)$^+$ $^1$H NMR (500 MHz, DMSO-d$_6$) δ 7.44 (m, 4H), 7.35 (brd, 2H), 7.2 (t, J=8.0 Hz, 1H), 6.69 (d, J=7.5 Hz, 1H), 6.35 (d, J=7.5 Hz, 1H), 5.99 (s, 2H), 5.48 (t, J=7.0 Hz, 1H), 2.06 (m, 1H), 1.92 (m, 1H), 0.96 (t, J=7.0 Hz, 3H).

EXAMPLE 51

5-[1-(4-Chlorophenyl)-2,2-dimethylpropoxy]quinazoline-2,4-diamine

Step 1: Grignard reaction of trimethylacetaldehyde (240.0 mg; 2.8 mmol) with 4-chlorophenyhnagnesium bromide in anhydrous ether afforded 0.58 grams of 1-(4-chlorophenyl)-2,2-dimethylpropanol.

Step 2: The coupling reaction of the previous alcohol (550.0 mg; 2.77 mmol) was done according to Step 1 of example 47 to yield 720 milligrams of 2-[1-(4-chlorophenyl)-2,2-dimethylpropoxy]-6-fluorobenzonitrile.

Step 3: The cyclization reaction of the previous benzonitrile (360.0 mg; 1.13 mmol) was done according to Step 2 of example 47 except dimethylacetamide was used as solvent to yield 270 milligrams of 5-[1-(4-chlorophenyl)-2,2-dimethylpropoxy]quinazoline-2,4-diamine.

MS m/z (EST) 357 (M+H)$^+$ $^1$H NMR (500 MHz, DMSO-d$_6$) δ 7.5 (brd, 2H), 7.4 (m, 4H), 7.17 (t, J=8.0 Hz, 1H), 6.69 (d, J=8.0 Hz, 1H), 6.31 (d, J=7.5 Hz, 1H), 6.08 (s, 2H), 5.36 (s, 1H), 1.01 (s, 9H).

EXAMPLE 52

5-Benzhydryloxyquinazoline-2,4-diamine

Step 1: Grignard reaction of benzaldehyde (300.0 mg; 2.83 mmol) with phenylmagnesium bromide in anhydrous ether afforded 0.5 grams of diphenylmethanol.

Step 2: The coupling reaction of the previous alcohol (300.0 mg; 1.63 mmol) was done according to Step 1 of example 47 to yield 185 milligrams of 2-benzhydryloxy-6-fluorobenzonitrile.

Step 3: The cyclization reaction of the previous benzonitrile (100.0 mg; 0.33 mmol) was done according to Step 2 of example 47 except dimethylacetamide was used as solvent to yield 48 milligrams of 5-benzhydryloxyquinazoline-2,4-diamine.

MS m/z (ESI) 343 (M+H)$^+$ $^1$H NMR (500 MHz, DMSO-d$_6$) δ 7.3-7.52 (m, 12H), 7.27 (t, J=8.0 Hz, 1H), 6.76 (d, J=7.0 Hz, 1H), 6.51 (d, J=8.0 Hz, 1H), 6.12 (s, 2H).

EXAMPLE 53

5-(5-Methylisoxazol-3-ylmethoxy)quinazoline-2,4-diamine

Step 1: To a mixture of 60% sodium hydride (0.164 g; 4.10 mmol) in DMF (5 mL) at 0° C. was added dropwise (5-methylisoxazol-3-yl)methanol (0.456 g; 4.00 mmol) and stirred at 0° C. for 30 minutes. The mixture was added to a solution of 2,6-difluorobenzonitrile (0.556 g, 4.00 mmol) in DMF (5 mL) at 0° C. and stirred for 18 hours at ambient temperature. The solution was poured into a mixture of ice and water. The solid was collected by filtration and dried in a 40° C. vacuum oven to yield 540 milligrams of (5-methylisoxazole-3-ylmethoxy)benzonitrile.

Step 2: A mixture of the previous benzonitrile (0.498 g; 2.14 mmol) and guanidine carbonate (0.928 g; 5.15 mmol) in DMF (6.3 mL) was heated at 150° C. for 7 hours, cooled to ambient temperature, and stored in a refrigerator for 18 hours. The solid was collected by filtration, stirred in a mixture of water and ethyl acetate, collected by filtration, and dried in a 50° C. vacuum oven to yield 0.292 grams of 5-(5-methylisoxazol-3-ylmethoxy)quinazoline-2,4-diamine.

MS m/z (ESI) 272 (M+H)$^+$ $^1$H NMR (500 MHz, DMSO-d$_6$) δ 7.40-7.20 (m, 3H), 6.81 (d, J=8.0 Hz, 1H), 6.61 (d, J=7.5 Hz, 1H), 6.35 (s, 3H), 5.96 (s, 2H), 5.33 (s, 2H), 2.43 (s, 3H).

EXAMPLE 54

5-(Benzo[1,3]dioxol-5-ylmethoxy)quinazoline-2,4-diamine

Step 1: The coupling reaction of piperonyl alcohol (609 mg; 4.0 mmol) was done according to Step 1 of example 53 to yield 664 milligrams of 2-(benzo[1,3]dioxol-5-ylmethoxy)benzonitrile.

Step 2: The cyclization reaction of the previous benzonitrile (616 mg; 2.27 mmol) was done according to Step 2 of example 53 to yield 224 milligrams of 5-(benzo[1,3]dioxol-5-ylmethoxy)quinazoline-2,4-diamine.

MS m/z (ESI) 311 (M+H)$^+$ $^1$H NMR (500 MHz, DMSO-d$_6$) δ 7.35 (t, 8 Hz, 1H), 7.22-7.10 (m, 3H), 7.02 (dd, J=8.0, 1.5 Hz, 1H), 6.95 (d, J=7.5 Hz, 1H), 6.77 (d, J=8.5 Hz, 1H), 6.63 (d, J=8.0 Hz, 1H), 6.04 (s, 2H), 5.93 (br s, 2H), 5.13 (s, 2H)

EXAMPLE 55

5-(Tetrahydropyran-2-ylmethoxy)quinazoline-2,4-diamine

Step 1: To a mixture of 60% sodium hydride (0.160 g; 4.00 mmol) in DMF (5 mL) at 0° C. was added dropwise (2-hydroxymethyl)tetrahydropyran (0.465 g; 4.00 mmol) and the mixture was stirred at 0° C. for 30 minutes. The mixture was added to a solution of 2,6-difluorobenzonitrile (0.556 g, 4.00 mmol) in DMF (5 mL) at 0° C. and stirred for 18 hours at ambient temperature. The solution was poured into a mixture of ice and water, and extracted with ethyl acetate. The organic layer was washed with water and then brine, dried over magnesium sulfate, and solvent removed. Purification by column chromatography (CH$_2$Cl$_2$) to yield 0.587 grams of 2-(tetrahydropyran-2-ylmethoxy)benzonitrile.

Step 2: The cyclization reaction of the previous benzonitrile (616 mg; 2.27 mmol) was done according to Step 2 of example 53 to yield 362 milligrams of 5-(tetrahydropyran-2-ylmethoxy)quinazoline-2,4-diamine.

MS m/z (ESI) 275 (M+H)$^+$ $^1$H NMR (500 MHz, DMSO-d$_6$) δ 7.46 (s, 1H), 7.34 (t, J=7.5 Hz, 1H), 7.21 (s, 1H), 6.77 (d, J=8 Hz, 1H), 6.52 (d, J=8 Hz, 1H), 5.95 (s, 2H), 4.15 (d, J=9 Hz, 1H), 3.96 (m, 2H), 3.74 (s, 1H), 3.45 (t, J=10 Hz, 1H), 1.82 (m, 1H), 1.51 (m, 5H).

EXAMPLE 56

5-((R)-1-Phenylethoxy)quinazoline-2,4-diamine

Step 1: The coupling reaction of (R)-sec-phenethyl alcohol (0.33 mL; 4.1 mmol) was done according to Step 1 of example 12 to yield 577 milligrams of 2-fluoro-6-((R)-phenylethoxy)benzonitrile.

Step 2: The cyclization of the previous benzonitrile (577 mg; 2 mmol) was done according to Step 2 of example 4 to yield 115 milligrams of 5-((R)-1-phenylethoxy)quinazoline-2,4-diamine.

MS m/z (ESI) 281 (M+H)$^+$ $^1$H NMR (400 MHz, DMSO-d$_6$) δ 7.44 (m, 3H), 7.23 (t, J=8.0 Hz, 2H), 7.02 (dd, J=7.2, 4.2 Hz, 1H), 6.71 (dd, J=7.6, 0.8 Hz, 1H), 6.42 (d, J=7.2 Hz, 1H), 6.19 (bs, 2H), 5.95 (bs, 2H), 5.69 (m, 1H), 1.68 (d, J=6.4 Hz, 3H).

EXAMPLE 57

5-(1-Pyridin-2-ylethoxy)quinazoline-2,4-diamine

Step 1: Sodium borohydride (344 mg; 9.08 mmol) was added portionwise to a solution of 2-acetylpyridine (500.0 mg; 8.25 mmol) in methanol. The reaction mixture was stirred overnight at room temperature. Quenched with water and extracted with ethyl acetate and solvent removed to yield 125 milligrams of 1-(2-pyridyl)ethanol.

Step 2: Sodium hydride (60%; 37 mg; 0.92 mmol) was suspended in DMF and cooled to 0° C. under inert atmosphere. The previous alcohol (113 mg; 0.92 mmol) in DMF was added dropwise to the sodium hydride mixture. The solution was allowed to warm to room temperature and stirred for 30 minutes. The solution was then added dropwise to a solution of 2,6-difluorobenzonitrile (127 mg; 0.92 mmol) in DMF cooled to 0° C. The mixture was allowed to warm to room temperature and stirred for 72 hours. The solution was poured over water and extracted with ethyl acetate and solvent removed. Purification by column chromatography (methanol/dichloromethane) yielded 184 milligrams of 2-fluoro-6-(1-pyridin-2-ylethoxy)benzonitrile.

Step 3: The previous benzonitrile (30.2 mg; 0.12 mmol) and guanidine carbonate (45 mg; 2.5 mmol) were heated at 120° C. in dimethyl acetamide for 4 hours. The reaction mixture was cooled to room temperature and water and ethyl acetate added. Extracted with ethyl acetate and solvent removed to yield 25 milligrams of 5-(1-pyridin-2-ylethoxy)quinazoline-2,4-diamine.

MS m/z 282 (M+H)$^+$ $^1$H NMR (400 MHz, DMSO-d$_6$) δ 8.58 (m, 1H), 7.83 (m, 1H), 7.76 (bs, 2H), 7.48 (m, 1H), 7.34 (m, 1H), 7.25 (t, J=8.4 Hz, 1H), 6.72 (d, J=8.4 Hz, 1H), 6.47 (d, J=8.4 Hz, 1H), 5.95 (bs, 2H), 5.73 (m, 1H), 1.67 (dd, J=5.2, 6.4 Hz, 3H).

EXAMPLE 58

5-(1-Thiazol-2-ylethoxy)quinazoline-2,4-diamine

Step 1: The reduction reaction of 2-acetylthiazole (500 mg; 3.93 mmol) was done according to Step 1 of example 57 to yield 68 milligrams of 1-(2-thiazol)ethanol.

Step 2: The coupling reaction of the previous alcohol (80.5 mg; 0.62 mmol) was done according to Step 2 of example 57 to yield 104 milligrams of 2-fluoro-6-(1-thiazol-2-ylethoxy)benzonitrile.

Step 3: The cyclization reaction of the previous benzonitrile (88 mg; 0.35 mmol) was done according to Step 3 of example 57 to yield 10 milligrams of 5-(1-thiazol-2-ylethoxy)quinazoline-2,4-diamine.

MS m/z (ESI) 288 (M+H)$^+$ $^1$H NMR (400 MHz, DMSO-d$_6$) δ 7.83 (m, 1H), 7.71 (m, 2H), 7.31 (m, 3H), 7.25 (bs, 2H), 6.08 (q, J=2.4 Hz, 1H), 5.98 (bs, 2H), 1.78 (d, J=6.4 Hz, 3H).

EXAMPLE 59

5-(Piperidin-1-yl)quinazoline-2,4-diamine

Step 1: 2,6-Difluorobenzonitrile (250 mg; 1.8 mmol) and piperidine (145 mg; 1.7 mmol) were mixed in DMF (5 mL)

for 3 hours at RT. The solvent is removed under vacuum, and the resulting oil is dried under vacuum at 30° C. overnight to yield 152 milligrams of 2-fluoro-6-(piperidin-1-yl)benzonitrile.

Step 2: The cyclization of the previous benzonitrile (102 mg; 0.5 mmol) was done according to Step 2 of example 4. The reaction mixture was stored overnight in the freezer and the resulting precipitate was collected by filtration. Purification by recrystallization with ethanol/water yielded 38 milligrams of 5-(piperidin-1-yl)quinazoline-2,4-diamine.

MS m/z (ESI) 244 (M+H)$^+$ $^1$H NMR (500 MHz, DMSO-d$_6$) δ 9.04 (br s, 1H), 737 (t, J=8.0 Hz), 7.13 (br s, 1H), 6.94 (d, J=8.5, 1H), 6.82 (d, J=7.5, 1H), 5.87 (br s, 2H), 6.05 (d, J=11.0 Hz, 2H), 2.62 (t, J=12.0, 2.0 Hz, 2H), 1.78 (t, J=13.0 Hz, 3H), 1.63 (m, 2H), 1.31 (m, 1H).

EXAMPLE 60

5-(Toluene-3-sulfonyl)-quinazoline-2,4-diamine

Step 1: To a cold (ice water) suspension of sodium hydride (316 mg; 7.9 mmol) in anhydrous DMF (10 mL) is added a solution of 3-methylbenzenethiol (941 uL; 7.9 mmol) in anhydrous DMF (5 mL) over 10 minutes. After allowing to room temperature over 30 minutes, this solution is added to a cold (ice water) stirred solution of 2,6-difluorobenzonitrile (1 g; 7.2 mmol) in anhydrous DMF (15 mL), and allowed to room temperature over 3 hours. The reaction mixture is poured into ice water with vigorous stirring and the resulting precipitate is removed by filtration and dried under vacuum overnight to give 1.74 grams of 2-fluoro-6-m-tolylsulfanyl-benzonitrile.

Step 2: The previous benzonitrile (363 mg; 1.5 mmol) is heated with guanidine carbonate (648 mg; 3.6 mmol) in dimethylacetamide (4.5 mL) at 150° C. for six hours, cooled to room temperature, and refrigerated overnight. The resulting solid is filtered, washed with water, and dried under vacuum overnight to give 252 milligrams of 5-m-tolylsulfanyl-quinazoline-2,4-diamine.

Step 3: The previous diamine (75 mg; 0.2 mmol) is dissolved in acetic acid (4 mL). Over 1 hour, a solution of potassium permanganate (84 mg; 0.5 mmol) in water (2 mL) is added in four portions, and the reaction is mixed at room temperature overnight. The resulting solids are removed by passing the reaction through a pad of Celite. The filtrate is made basic with concentrated aqueous ammonium hydroxide to give a solid which is filtered and dried at room temperature. The solid is suspended in boiling DMF and passed through a pad of Celite to remove solids. The filtrate is diluted with two volumes of boiling water and refrigerated overnight. The solvents are removed under high vacuum to give 41 milligrams of 5-(toluene-3-sulfanyl)-quinazoline-2,4-diamine.

EXAMPLE 61

5-(6-Chloro-indan-1-yloxy)-quinazoline-2,4-diamine

Step 1: 3-(4-Chlorophenyl)-propionic acid (3.83 g; 20.7 mmol) is dissolved in 50 ml thionyl chloride and stirred at room temperature overnight. The excess thionyl chloride is removed by rotary evaporation to give 3-(4-chlorophenyl)-propionyl chloride as a pale yellow oil, which is used without purification.

Step 2: The previous chloride (4.21 g; 20.7 mmol) dissolved in 25 mL dichloromethane is slowly added to a cold (0° C.), stirred suspension of aluminum chloride (2.77 gm; 20.7 mmol) in 75 mL dichloromethane. After stirring cold for 10 minutes, the reaction mixture is heated to reflux for four hours, and then cooled to RT overnight. The reaction is diluted with 100 mL water and the layers are separated. The organic layer is washed with 0.1 M sodium hydroxide and brine, and then dried over magnesium sulfate. The dried solution is concentrated to give 2.51 grams of 6-chloroindan-1-one.

Step 3: The reduction reaction of 6-chloroindan-1-one (2.51 g; 15 mmol) was done according to Step 1 of example 57 to yield 2.03 grams of 6-chloroindan-1-ol.

Step 4: The coupling reaction of 6-chloroindan-1-ol (2.11 g; 12.5 mmol) was done according to Step 1 of example 12 to yield 2.77 grams of 2-(6-chloroindan-1-yloxy)-6-fluorobenzonitrile.

Step 5: The previous benzonitrile (2.91 g; 10 mmol) is dissolved in dimethylacetamide (100 mL) with guanidine carbonate (3.82 g; 21 mmol). The vessel is purged with N$_2$, sealed, and heated to 150° C. for 8 hours, and cooled to RT overnight. The reaction solution is slowly diluted with 150 mL water and stirred one hour then refrigerated one hour to form a fine brown precipitate which is removed by filtration, washed with ethanol and dried overnight under vacuum at 30° C. The dry solids are slurried in boiling methanol and filtered while hot to give 1.22 grains of 5-(6-chloro-indan-1-yloxy)-quinazoline-2,4-diamine.

MS m/z (ESI) 410 (M+H)$^+$ $^1$H NMR (500 MHz, DMSO-d$_6$) δ 7.55 (s, 1H), 7.41 (t, J=8.0 Hz, 1H), 7.41 (s, 1H), 7.11 (br s, 1H), 6.96 (br s, 1H), 6.82 (d, J=8.5 Hz, 1H), 6.77 (d, J=8.0 Hz, 1H), 6.01 (s, 3H), 3.06 (m, 1H), 2.92 (m, 1H), 2.68 (m, 1H), 2.17 (m, 1H).

$^{13}$CNMR (500 MHz, DMSO-d$_{16}$) δ 161.8, 160.6, 155.5, 155.2, 143.3, 143.0, 132.4, 131.2, 129.1, 126.8, 124.9, 117.3, 103.1, 101.7, 81.6, 31.9, 29.3.

FTIR 3505, 3385, 3306, 3116, 2989, 2955, 2911, 1646, 1613, 1589, 1573, 1558, 1499, 1478, 1442, 1430, 1403, 1354, 1345, 1282, 1247, 1216, 1175, 1062, 813.

EXAMPLE 62

5-(4-Bromobenzyloxy)-quinazoline-2,4-diamine

Step 1: To a cold (ice water) suspension of sodium hydride (316 mg; 7.9 mmol) in anhydrous DMF (10 mL) is added a solution of 4-bromobenzyl alcohol (1.48 g; 7.9 mmol) in anhydrous DMF (5 mL) over 10 minutes. After allowing to room temperature over 30 minutes, this solution is added to a cold (ice water) stirred solution of 2,6-difluorobenzonitrile (1 g; 7.2 mmol) in anhydrous DMF (15 mL), and allowed to room temperature over 3 hours. The reaction mixture is poured into ice water with vigorous stirring and refrigerated overnight. The resulting precipitate is removed by filtration and dried under vacuum at 30° C. overnight to give 1.82 grams 2-(4-bromobenzyloxy)-6-fluorobenzonitrile.

Step 2: The previous benzonitrile (306 mg; 1.0 mmol) is heated with guanidine carbonate (432 mg; 2.4 mmol) in dimethylacetamide (5 mL) at 150° C. overnight. After cooling to room temperature, the solvent is removed under high vacuum. The solid is triturated with hot 25% ethanol in water, filtered and dried under vacuum at 30° C. overnight. The solid is recrystallized from 33% ethanol in water, and again from pure ethanol to give 186 milligrams 5-(4-bromobenzyloxy)-quinazoline-2,4-diamine.

EXAMPLE 63

5-[1-(3-Iodophenyl)-ethoxy]-quinazoline-2,4-diamine

Step 1: To a cold (ice water) solution of 3-iodoacetophenone (2.59 gm; 10.5 mmol) in methanol (10 mL) is added sodium borohydride (395 mg; 10.4 mmol) is stirred for thirty minutes. Water (10 mL) is added to the solution and stirred 15 minutes. Saturated ammonium chloride (40 mL) is added and the solution is extracted with ethyl acetate. The organics are separated and dried over magnesium sulfate. The solvent is removed to give 2.26 grams of 1-(3-iodophenyl)-ethanol.

Step 2: To a cold (ice water) suspension of sodium hydride (216 mg; 5.4 mmol) in anhydrous DMF (3 mL) is added a solution of the previous alcohol (1.25 gm; 5.0 mmol) in anhydrous MT (1 mL) over 10 minutes. After allowing to room temperature over 45 minutes, this solution is added to a cold (ice water) stirred solution of 2,6-difluorobenzonitrile (707 mg; 5.1 mmol) in anhydrous DMF (3 mL), and allowed to room temperature over 3.5 hours. The reaction mixture is poured into ice water with vigorous stirring and extracted with ethyl acetate. The organics are separated and dried over magnesium sulfate. The solvent is removed and the resulting solid is dried under vacuum at 40° C. overnight to give 1.78 grams of 2-fluoro-6-[1-(3-iodophenyl)-ethoxy]-benzonitrile.

Step 3: The previous benzonitrile (754 mg; 2.0 mmol) is heated with guanidine carbonate (359 mg; 2.0 mmol) in dimethylacetamide (2.5 mL) at 150° C. for nine hours, and then allowed to room temperature overnight. The reaction mixture is refrigerated for 1.5 hour and diluted with water (4 mL). The resulting solids are filtered, washed with water and dried 2 hours under vacuum at 40° C. to give 564 milligrams of 5-[1-(3-iodophenyl)-ethoxy]-quinazoline-2,4-diamine.

EXAMPLE 64

5-(1-Benzo[1,3]-dioxol-5-yl-ethoxy)-quinazoline-2,4-diamine

Step 1: To a solution of 1-benzo[1,3]dioxol-5-yl-ethanone (2.5 gm; 15.2 mmol) in methanol (50 mL) is added sodium borohydride (634 mg; 16.7 mmol) in portions allowing for gas evolution. The reaction is stirred at room temperature for 3 hours before additional sodium borohydride is added to give a complete reaction by TLC (20% EA/Hex). The reaction is quenched with saturated ammonium chloride and extracted with ethyl acetate. The organics are separated, washed with water, dried over magnesium sulfate, and the solvent is removed to give 2.18 grams of 1-benzo[1,3]dioxol-5-yl-ethanol.

Step 2: To a cold (ice water) suspension of sodium hydride (316 mg; 7.9 mmol) in anhydrous DMF (10 mL) is added a solution of the previous alcohol (1.31 gm; 7.9 mmol) in anhydrous DMF (5 mL) over 10 minutes. After allowing to room temperature over 30 minutes, this solution is added to a cold (ice water) stirred solution of 2,6-difluorobenzonitrile (1 gm; 7.2 mmol) in anhydrous DMF (15 mL), and allowed to room temperature overnight. The reaction mixture is poured into ice water with vigorous stirring and extracted with ethyl acetate. The organics are separated, washed with brine, dried over magnesium sulfate, and the solvent is removed to give 2.22 grams 2-(1-benzo[1,3]dioxol-5-yl-ethoxy)-6-fluorobenzonitrile.

Step 3: The previous benzonitrile (570 mg; 2 mmol) is heated with guanidine carbonate (864 mg; 4.8 mmol) in dimethylacetamide (4 mL) at 150° C. for five hours, cooled to room temperature, and refrigerated overnight. The resulting solid is filtered to remove unreacted guanidine carbonate and the filtrate is concentrated to an oil. The oil is purified using a strong cation exchange (SCX) column. The resulting semi-solid is triturated with ether, filtered, and dried at room temperature to give 43 milligrams of 5-(1-benzo[1,3]dioxol-5-yl-ethoxy)-quinazoline-2,4-diamine.

EXAMPLE 65

5-(3,4-Dimethoxybenzyloxy)-quinazoline-2,4-diamine

Step 1: To a cold (ice water) suspension of sodium hydride (316 mg; 7.9 mmol) in anhydrous DMF (10 mL) is added a solution of 3,4-dimethoxybenzyl alcohol (1.33 gm; 7.9 mmol) in anhydrous DMF (5 mL) over 10 minutes. After allowing to room temperature over 30 minutes, this solution is added to a cold (ice water) stirred solution of 2,6-difluorobenzonitrile (1 g; 7.2 mmol) in anhydrous DMF (15 mL), and allowed to room temperature over 3 hours. The reaction mixture is poured into ice water with vigorous stirring and refrigerated overnight. The resulting precipitate is removed by filtration and dried under vacuum overnight at 30° C. to give 1.81 grams of 2-(3,4-dimethoxybenzyloxy)-6-fluorobenzonitrile.

Step 2: The previous benzonitrile (500 mg; 1.7 mmol) is heated with guanidine carbonate (752 mg; 4.2 mmol) in dimethylacetamide (20 mL) at 150° C. for eight hours and cooled to room temperature overnight. The reaction mixture is diluted with water (60 mL) and the resulting solid is isolated by filtration. The solid is recrystallized from absolute ethanol and dried under vacuum at 30° C. to give 306 milligrams of 5-(3,4-dimethoxybenzyloxy)-quinazoline-2,4-diamine.

EXAMPLE 66

5-[1-(3-Methoxyphenyl)-ethoxy]-quinazoline-2,4-diamine

Step 1: To a solution of 3-methoxyacetophenone (3 g; 20 mmol) in methanol (60 mL) is added sodium borohydride (1.13 g; 30 mmol) in four portions over one hour. The reaction is stirred at room temperature overnight, neutralized with saturated ammonium chloride, and extracted with ethyl acetate. The organics are separated, washed with water, and dried over magnesium sulfate. The solvent is removed to give 2.62 grams of 1-(3-methoxyphenyl)-ethanol.

Step 2: To a cold (ice water) suspension of sodium hydride (316 mg; 7.9 mmol) in anhydrous DMF (10 mL) is added a solution of the previous alcohol (1.2 g; 7.9 mmol) in anhydrous DMF (5 mL) over 10 minutes. After allowing to room temperature over 30 minutes, this solution is added to a cold (ice water) stirred solution of 2,6-difluorobenzonitrile (1 g; 7.2 mmol) in anhydrous DMF (15 mL), and allowed to room temperature over 3 hours. The reaction mixture is poured into vigorously stirred ice water and stored refrigerated overnight. The mixture is extracted with ethyl acetate. The organics are separated, dried over magnesium sulfate, and the solvent is removed to give 1.55 grams 2-fluoro-6-[1-(3-methoxyphenyl)-ethoxy]-benzonitrile.

Step 3: The previous benzonitrile (500 mg; 1.8 mmol) is heated with guanidine carbonate (797 mg; 4.4 mmol) in dimethylacetamide (20 mL) at 150° C. for seven hours and cooled to room temperature overnight. The reaction mixture is diluted with water (80 mL) and the resulting solid is isolated by filtration. The solid is recrystallized from absolute ethanol and dried under vacuum at 30° C. to give 368 milligrams of 5-[1-(3-methoxyphenyl)-ethoxy]-quinazoline-2,4-diamine.

EXAMPLE 67

5-[1-(3,5-Dimethoxyphenyl)-ethoxy]-quinazoline-2,4-diamine

Step 1: To a solution of 3,5-dimethoxyacetophenone (1 g; 5.5 mmol) in methanol (30 mL) is added sodium borohydride (315 mg; 8.3 mmol) in four portions over one hour. The reaction is stirred at room temperature overnight, neutralized with saturated ammonium chloride, and extracted with ethyl acetate. The organics are separated, washed with water, and dried over magnesium sulfate. The solvent is removed to give 1.12 grams of 1-(3,5-dimethoxyphenyl)-ethanol.

Step 2: To a cold (ice water) suspension of sodium hydride (237 mg; 5.9 mmol) in anhydrous DMF (5 mL) is added a solution of the previous alcohol (1.12 g; 5.9 mmol) in anhydrous DMF (5 mL) over 10 minutes. After allowing to room temperature over 30 minutes, this solution is added to a cold (ice water) stirred solution of 2,6-difluorobenzonitrile (750 mg; 5.4 mmol) in anhydrous DMF (10 mL), and allowed to room temperature over 3 hours. The reaction mixture is poured into vigorously stirred ice water and stored refrigerated overnight. The mixture is extracted with ethyl acetate. The organics are separated, dried over magnesium sulfate, and the solvent is removed to give 1.54 grams 2-[1-(3,5-dimethoxyphenyl)-ethoxy]-6-fluorobenzonitrile.

Step 3: The previous benzonitrile (500 mg; 1.7 mmol) is heated with guanidine carbonate (717 mg; 4.0 mmol) in dimethylacetamide (20 mL) at 150° C. for seven hours and cooled to room temperature overnight. The reaction mixture is diluted with water (80 mL) and the resulting solid is isolated by filtration. The solid is recrystallized from absolute ethanol and dried under vacuum at 30° C. to give 369 milligrams of 5-[1-(3,5-dimethoxyphenyl)-ethoxy]-quinazoline-2,4-diamine.

EXAMPLE 68

5-[2-(4-Chlorophenyl)-3-methoxymethoxypropoxy]-quinazoline-2,4-diamine

Step 1: 4-Chlorophenyl acetic acid (5.0 g; 29.3 mmol) is dissolved in 50 mL absolute ethanol. With stirring, 100 µL sulfuric acid is added to the solution and the reaction is heated to reflux for 2 hours. The ethanol is removed by rotary evaporation and the resulting oil is dissolved in ethyl acetate. The organics are washed successively with saturated sodium bicarbonate, water, and brine, then dried over magnesium sulfate. After removing the ethyl acetate by rotary evaporation, the resulting oil is dried under vacuum at 35° C. for two hours to give 5.60 grams of 4-chlorophenylacetic acid ethyl ester.

Step 2: Sodium hydride (2.38 g @ 60% w/w mineral oil; 59.5 mmol) and diethylcarbonate (16.72 gm; 140.9 mmol) are stirred in 80 mL anhydrous THF. To the cold (ice bath) suspension above is added a solution of the previous ester (5.60 g; 28.2 mmol) in 20 mL anhydrous THF over 30 minutes. The reaction is heated to reflux for two hours, and then allowed to room temperature overnight. The reaction is neutralized slowly with saturated ammonium chloride, then extracted with ethyl acetate. The organics are separated and washed with saturated sodium bicarbonate and brine. After drying over magnesium sulfate, the solvent is removed by rotary evaporation, and the resulting oil is purified by column chromatography (5%-20% EtOAc/Hexane). A total of 7.02 grams of 2-(4-chlorophenyl)-malonic acid diethyl ester is isolated.

Step 3: The previous diethyl ester (7.02 g; 25.9 mmol) is dissolved in 20 mL anhydrous ether, and added dropwise to a cold (<0° C.) suspension of lithium aluminum hydride (1.97 gm; 51.9 mmol) over 30 minutes. The reaction is allowed to room temperature overnight. The reaction is quenched with 200 mL 1M HCl, and the layers separated. The aqueous layer is extracted with fresh ether. The organics are combined, washed with brine, and dried over magnesium sulfate. The solvent is removed by rotary evaporation, and the resulting oil purified by column chromatography (50-80% ether/petroleum ether) to give 1.29 grams of 2-(4-chlorophenyl)-propane-1,3-diol.

Step 4: The previous diol (500 mg; 2.67 mmol) and camphorsulfonic acid (12 mg; 2 mol %) are dissolved in dichloromethane with trimethylorthoformate (1.17 mL; 10.7 mmol). The reaction mixture is heated to 45° C. overnight. After cooling to RT, the solution is further cooled to −78° C. (dry ice/acetone) as diisobutylaluminum hydride (1M in hexane; 26.8 mL; 26.8 mmol) is added drop wise over 30 minutes. The temperature is maintained at −78° C. for 30 minutes, then increased and held at 0° C. for 15 minutes. The reaction is quenched with 3M KOH, and extracted with ether. The organics are separated, dried over magnesium sulfate, and concentrated to give 543 milligrams of 2-(4-chlorophenyl)-3-methoxymethoxypropan-1-ol.

Step 5: Sodium hydride (107 mg; 2.68 mmol) is suspended in cold (ice water) DMF as the previous alcohol (543 mg; 2.68 mmol) is added dropwise over 15 minutes. The reaction is allowed to room temperature over 35 minutes, then added to a cold (ice water) solution of 2,6-difluorobenzonitrile (339 mg; 2.44 mmol) in DMF. The reaction is allowed to room temperature and stirred 2.5 hours. The solution is next added to vigorously stirred ice water, and extracted with ethyl acetate. The organics are separated, dried over magnesium sulfate, and concentrated. The title material is dried under vacuum at 35° C. overnight to give a total of 769 milligrams of 2-[2-(4-chlorophenyl)-3-methoxymethoxypropoxy]-6-fluorobenzonitrile.

Step 6: Guanidine carbonate (792 mg; 4.4 mmol) is suspended in a solution of 2-[2-(4-Chlorophenyl)-3-methoxymethoxypropoxy]-6-fluorobenzonitrile (769 mg; 2.20 mmol) in DMA, and heated to 135° C. for 8 hours. The solution is cooled to RT overnight and placed in a freezer at 4° C. for 24 hours. The resulting black solids are removed by filtration through paper. The filtrate is concentrated under vacuum, and purified by column chromatography (10% MeOH/EtOAc). The collected fractions are dried to give 209 milligrams of 5-[2-(4-chlorophenyl)-3-methoxymethoxypropoxy]-quinazoline-2,4-diamine.

EXAMPLE 69

2-(4-Chlorophenyl)-3-(2,4-diaminoquinazolin-5-yloxy)-propan-1-ol hydrochloride

5-[2-(4-Chlorophenyl)-3-methoxymethoxy-propoxy]-quinazoline-2,4-diamine (Step 6, Example 68) (68 mg; 0.17 mmol) is dissolved in methanol (2 mL), and diluted with 4M HCl in dioxane (1 mL). The reaction is heated in a sealed tube to 60° C. overnight. The solvent is removed under $N_2$ flow. The resulting solid is triturated with 20% MeOH/Ether, and the resulting title compound is filtered and dried under vacuum at 35° C. for 3 hours providing a total of 40 milligrams of 2-(4-chlorophenyl)-3-(2,4-diaminoquinazolin-5-yloxy)-propan-1-ol hydrochloride.

MS m/z (ESI) 345 (M+H)$^+$.

$^1$HNMR (400 MHz, DMSO-d$_6$) δ 12.74 (s, 1H), 8.86 (s, 1H), 8.14 (s, 1H), 7.69 (t, 8.4 Hz, 1H), 7.40 (s, 4H), 7.02 (d,

J=8.0 Hz, 1H), 6.98 (d, J=8.0 Hz, 1H), 4.60 (m, 1H), 4.46 (m, 1H), 3.75 (m, 2H), 3.45 (m, 1H).

EXAMPLE 70

[4,5-Dichloro-2-(2,4-diaminoquinazolin-5-yloxymethyl)phenyl]methanol hydrochloride Step 1: To a suspension of sodium borohydride (454 mg; 12 mmol) in anhydrous THF (20 mL) is added dropwise a solution of 4,5-dichlorophthalic acid (2.35 g; 10 mmol) in THF (20 mL) over 10 minutes. After the gas evolution has ceased, a solution of Iodine (1.27 g; 5 mmol) in THF (20 mL) is added and stirred 1 hour at room temperature. The reaction is quenched with 3M HCl and stirred an additional 1 hour at room temperature. Water is added to dissolve any solids formed and ether is added. The layers are separated and the organics are washed with 3M KOH and brine, then dried over magnesium sulfate. After removing the solvent, the resulting solid is recrystallized from chloroform to give 235 milligrams of (4,5-dichlorophenyl-2-hydroxymethylphenyl)methanol.

Step 2: The previous alcohol (235 mg; 1.13 mmol) and camphorsulfonic acid (5.3 mg; 2 mol %) are dissolved in dichloromethane with trimethylorthoformate (0.5 mL; 4.54 mmol). The reaction is stirred at room temperature overnight, then cooled to −78° C. (dry ice/acetone) while diisobutylaluminum hydride (1M in hexane; 11.35 mL; 11.35 mmol) is added dropwise over 30 minutes. The temperature is maintained at −78° C. for 30 minutes, the allowed to 0° C. for 15 minutes. The reaction is neutralized with 3M KOH and stirred with ether for 2 hours. The aqueous layer is extracted with fresh ether. All organics are combined and dried over magnesium sulfate, then concentrated to give 271 milligrams of (4,5-dichloro-2-methoxy-methoxymethylphenyl)methanol.

Step 3: Sodium hydride (43 mg; 1.08 mmol) is suspended in cold (ice water) DMF as the previous alcohol (271 mg; 1.08 mg) is added dropwise over 15 minutes. The reaction is allowed to room temperature over 30 minutes, then added to a cold (ice water) solution of 2,6-difluorobenzonitrile (136 mg; 0.98 mmol) in DMF. The reaction is stirred at room temperature overnight. The solution is added to vigorously stirred ice water, and allowed to room temperature. The resulting solid is filtered, washed with water, and dried under vacuum at 35° C. overnight to give 274 milligrams of 2-(4,5-dichloro-2-methoxymethoxymethylbenzyloxy)-6-fluorobenzonitrile.

Step 4: Guanidine carbonate (267 mg; 1.48 mmol) is suspended in a solution of the previous benzonitrile (274 mg; 0.74 mmol) in DMA, and heated to 140° C. for 8 hours. The solution is cooled to room temperature overnight and diluted into stirred cold water. The resulting precipitate is removed by filtration and crystallized in a freezer at 4° C. for 24 hours from a 30% water/ethanol solution. The resulting solids are removed by filtration through paper and dried at room temperature overnight to give 153 milligrams of 5-(4,5-dichloro-2-methoxymethoxymethylbenzyloxy)quinazoline-2,4-diamine.

Step 5: The previous diamine is suspended in methanol (2 mL) and diluted with 4M HCl in dioxane (1 mL). The reaction is heated in a sealed tube to 60° C. overnight. The solvent is removed under N2 flow, and the resulting solid is triturated with 10% MeOH/Ether. 5-(4,5-Dichloro-2-methoxy-methoxymethylbenzyloxy)quinazoline-2,4-diamine hydrochloride is isolated by filtration and dried at room temperature to give 79 milligrams.

MS m/z (ESI) 367 (M+H)$^+$.

$^1$HNMR (400 MHz, DMSO-d$_6$) δ 12.81 (s, 1H), 8.92 (s, 1H), 8.39 (s, 1H), 7.69 (m, 4H), 7.00 (t, J=8.0 Hz, 2H), 5.47 (s, 2H), 4.62 (s, 2H).

EXAMPLE 71

5-(4-Chloro-2-methoxyphenoxy)-quinazoline-2,4-diamine

Step 1: To a solution of 2,6-difluorobenzonitrile (100 mg; 0.72 mmol) and 4-chloro-2-methoxyphenol (114 mg; 0.72 mmol) in anhydrous DMF (5 mL) is added potassium carbonate (50 mg; 0.36 mmol). The reaction mixture is heated to 70° C. overnight. After allowing to room temperature, the solvent is removed under vacuum and the resulting solid is partitioned between ethyl acetate and water. The organics are separated and dried over magnesium sulfate. The solvent is removed to give 145 milligrams of 2-(4-chloro-2-methoxyphenoxy)-6-fluorobenzonitrile.

Step 2: The previous benzonitrile (145 mg; 0.52 mmol) is heated with guanidine carbonate (188 mg; 1.04 mmol) in dimethylacetamide (5 mL) at 140° C. for eight hours and cooled to room temperature overnight. The reaction mixture is diluted with water (10 mL) and refrigerated overnight. The resulting solid is isolated by filtration and triturated with absolute ethanol, filtered and dried under vacuum at 30° C. to give 136 milligrams of 5-(4-chloro-2-methoxyphenoxy)-quinazoline-2,4-diamine.

MS m/z (ESI) 317 (M+H)$^+$ $^1$HNMR (400 MHz, DMSO-d$_6$) δ 7.31 (d, J=2.4 Hz, 1H), 7.26 (t, J=8.0 Hz, 1H), 7.21 (d, J=8.0 Hz, 1H), 7.18 (br s, 2H), 7.08 (dd, J=8.8, 2.4 Hz, 1H), 6.86 (d, J=8.4 Hz, 1H), 6.07 (br s, 2H), 6.04 (d, J=8.0 Hz, 1H), 3.77 (s, 3H).

EXAMPLE 72

5-(7-Methoxy-2,3-dihydrobenzofuran-3-yoloxy)-quinazoline-2.4-diamine

Step 1: To a cold (ice water) solution of 7-methoxy-3-(2H)-benzofuranone (846 mg; 5.0 mmol) in methanol (5 mL) is added sodium borohydride (179 mg; 5.0 mmol) is stirred for 15 minutes. Water (5 mL) is added to the solution and stirred 15 minutes. Saturated ammonium chloride (20 mL) is added and the solution is extracted with ethyl acetate. The organics are separated and dried over magnesium sulfate. The solvent is removed to give 831 milligrams of 7-methoxy-2,3-dihydrobenzofuran-3-ol.

Step 2: To a cold (ice water) suspension of sodium hydride (168 mg; 4.0 mmol) in anhydrous DMF (4 mL) is added a solution of the previous alcohol (672 mg; 4.0 mmol) in anhydrous DMF (5 mL) over 10 minutes. After allowing to room temperature over 1.5 hours, this solution is added to a cold (ice water) stirred solution of 2,6-difluorobenzonitrile (557 mg; 4.0 mmol) in anhydrous DMF (3 mL), and allowed to room temperature over 4 hours. After a TLC of the reaction mixture (25% EtOAc/Hexanes) the reaction is warmed to 40° C. for thirty minutes. The reaction mixture is poured into ice water with vigorous stirring and stored refrigerated overnight. The resulting solid is filtered, washed with water, and dried under vacuum at 40° C. for 3 hours to give 699 mg 2-fluoro-6-(7-methoxy-2,3-dihydrobenzofuran-3-yloxy)-benzonitrile.

Step 3: The previous benzonitrile (570 mg; 2.0 mmol) is heated with guanidine carbonate (343 mg; 1.9 mmol) in dimethylacetamide (2.5 mL) at 135° C. for seven hours, and then allowed to room temperature overnight. The reaction mixture is diluted with water (4 mL), stirred for one hour, and extracted with ethyl acetate. The organics are separated and dried with magnesium sulfate. The solvent is removed and the resulting solids are dried overnight under vacuum to give 269 milligrams of 5-(7-methoxy-2,3-dihydrobenzofuran-3-yoloxy)-quinazoline-2,4-diamine.

EXAMPLE 73

5-(Adamantan-1-ylmethoxy)-quinazoline-2,4-diamine

Step 1: To a cold (ice water) suspension of sodium hydride (206 mg; 5.0 mmol) in anhydrous DMF (4 mL) is added a solution of 1-adamantane methanol (830 mg; 4.9 mmol) in anhydrous DMF (5 mL) over 10 minutes. After allowing to room temperature over 40 minutes, this solution is added to a cold (ice water) stirred solution of 2,6-difluorobenzonitrile (702 mg; 5.0 mmol) in anhydrous DMF (3 mL), and allowed to room temperature over 3 hours. The reaction mixture is poured into ice water with vigorous stirring and extracted with ethyl acetate. The organics are separated and dried over magnesium sulfate. The solvent is removed and the resulting solid is dried under vacuum at 40° C. for 3 hours to give 1.32 grams of 2-(adamantan-1-ylmethoxy)-6-fluorobenzonitrile.

Step 2: The previous benzonitrile (546 mg; 2.0 mmol) is heated with guanidine carbonate (356 mg; 2.0 mmol) in dimethylacetamide (2.5 mL) at 150° C. for eight hours, and then allowed to room temperature overnight. The reaction mixture is refrigerated for 1 hour and diluted with water (4 mL). The resulting solids are dried 2 hours under vacuum at 40° C. and purified by column chromatography (10% MeOH/DCM) to give 141 milligrams of 5-(adamantan-1-ylmethoxy)-quinazoline-2,4-diamine.

EXAMPLE 74

5-(2-Bromo-benzyloxy)-quinazoline-2,4-diamine

Step 1: To a cold (ice water) suspension of sodium hydride (222 mg; 5.0 mmol) in anhydrous DMF (4 mL) is added a solution of 2-bromobenzyl alcohol (941 mg; 5.0 mmol) in anhydrous DMF (5 mL) over 10 minutes. After allowing to room temperature over 45 minutes, this solution is added to a cold (ice water) stirred solution of 2,6-difluorobenzonitrile (703 mg; 5.0 mmol) in anhydrous DMF (3 mL), and allowed to room temperature over 4 hours. The reaction mixture is poured into ice water with vigorous stirring and the resulting solid is filtered, washed with water, and dried under vacuum at 40° C. for 3 hours to give 1.27 grams of 2-fluoro-6-(2-bromobenzyloxy)-benzonitrile.

Step 2: The previous benzonitrile (574.5 mg; 2.0 mmol) and guanidine carbonate (360 mg; ~2 mmol) were heated at 150° C. in dimethylacetamide for 8 hours. The reaction mixture was diluted with water, stirred for 1 hour, filtered, washed with water and dried to yield 650 milligrams of 5-(2-bromobenzyloxy)-quinazoline-2,4-diamine.

EXAMPLE 75

5-(2-Iodo-benzyloxy)-quinazoline-2,4-diamine

Step 1: To a cold (ice water) suspension of sodium hydride (216 mg; 5.0 mmol) in anhydrous DMF (4 mL) is added a solution of 2-iodobenzyl alcohol (1.17 gm; 5.0 mmol) in anhydrous DMF (5 mL) over 10 minutes. After allowing to room temperature over 45 minutes, this solution is added to a cold (ice water) stirred solution of 2,6-difluorobenzonitrile (702 mg; 5.0 mmol) in anhydrous DMF (3 mL), and allowed to room temperature over 4 hours. The reaction mixture is poured into ice water with vigorous stirring and the resulting solid is filtered, washed with water, and dried under vacuum at 40° C. for 3 hours to give 1.40 grams of 2-fluoro-6-(2-iodobenzyloxy)-benzonitrile.

Step 2: Same as Example 74, Step 2 with 669 milligrams of previous benzonitrile to give 597 milligrams of 5-(3-iodo-benzyloxy)-quinazoline-2,4-diamine.

EXAMPLE 76

5-(3-Bromobenzyloxy)quinazoline-2,4-diamine

Step 1: 3-Bromobenzyl alcohol (1.45 mg; 7.9 mmol) in dimethylformamide was added to a cooled (0° C.) slurry of sodium hydride (316 mg; 7.9 mmol) in dimethylformamide under nitrogen atmosphere. The reaction mixture was slowly warmed to room temperature, stirred for 30 min. The reaction mixture was then added to a cooled (0° C.) solution of 2,6-difluorobenzonitrile in dimethylformamide, stirred for 2 hours at room temperature. The reaction mixture was poured on crushed ice-water, stirred, filtered, washed with water and dried to afford 1.81 grams of 2-fluoro-6-(3-bromophenyl-methoxy)benzonitrile.

Step 2: The previous benzonitrile (574.5 mg; 2.0 mmol) and guanidine carbonate (342.6 mg; ~2 mmol) were heated at 150° C. in dimethylacetamide for 8 hours. The reaction mixture was diluted with water, stirred for 1 hour, filtered, washed with water and dried to yield 579.8 milligrams of 5-(3-bromophenyl-methoxy)quinazoline-2,4-diamine.

$^1$H NMR (400 MHz, DMSO-$d_6$) δ 7.74 (t, J=1.6, 1.6 Hz, 1H), 7.52 (m, 2H), 7.32 (m, 2H), 7.20 (bs, 2H), 6.77 (dd, J=0.8, 8.4 Hz, 1H), 6.57 (dd, J=0.8, 8.0 Hz, 1H), 5.96 (s, 2H), 5.29 (s, 2H).

MS m/z 343 (M−H)$^+$

EXAMPLE 77

5-(3-Iodo-benzyloxy)-quinazoline-2,4-diamine

Step 1: To a cold (ice water) suspension of sodium hydride (316 mg; 7.9 mmol) in anhydrous DMF (10 mL) is added a solution of 3-iodobenzyl alcohol (1.85 g; 7.9 mmol) in anhydrous DMF (5 mL) over 30 minutes. After allowing to room temperature over 30 minutes, this solution is added to a cold (ice water) stirred solution of 2,6-difluorobenzonitrile (1.0 g; 7.2 mmol) in anhydrous DMF (15 mL), and allowed to room temperature over 2 hours. The reaction mixture is poured into ice water with vigorous stirring and refrigerated overnight. The resulting solid is filtered, washed with water, and dried under vacuum at 30° C. overnight to give 1.86 grams of 2-fluoro-6-(3-iodobenzyloxy)-benzonitrile.

Step 2: The previous benzonitrile (669 mg; 2.0 mmol) is heated with guanidine carbonate (352 mg; 2.0 mmol) in dimethylacetamide (2.5 mL) at 150° C. for eight hours, and then allowed to room temperature overnight. The reaction mixture is refrigerated for 1 hour and diluted with water (4 mL). The resulting solids are dried 2 hours under vacuum at 40° C. to give 740 milligrams of 5-(3-iodo-benzyloxy)-quinazoline-2,4-diamine.

EXAMPLE 78

5-[1-(3,4-Dichlorophenyl)-ethoxy]-quinazoline-2,4-diamine

Step 1: To a cold (ice water) suspension of sodium hydride (316 mg; 7.9 mmol) in anhydrous DMF (10 mL) is added a solution of 1-(3,4-dichlorophenyl)-ethanol (1.40 g; 7.3 mmol) in anhydrous DMF (5 mL) over 30 minutes. After allowing to room temperature over 30 minutes, this solution is added to a cold (ice water) stirred solution of 2,6-difluorobenzonitrile (1.0 g; 7.2 mmol) in anhydrous DMF (15 mL), and allowed to room temperature over 2 hours. The reaction mixture is poured into ice water with vigorous stirring and extracted with ethyl acetate. The organics are separated and dried over magnesium sulfate. The solvent is removed and the resulting oil is dried under vacuum at 30° C. overnight to give 1.93 gm of 2-[1-(3,4-dichlorophenyl)-ethoxy]-6-fluorobenzonitrile.

Step 2: The previous benzonitrile (623 mg; 2.0 mmol) is heated with guanidine carbonate (360 mg; 2.0 mmol) in dimethylacetamide (2.5 mL) at 150° C. for eight hours, and then allowed to room temperature overnight. The reaction mixture is refrigerated for 1.5 hour and diluted with water (4 mL). The resulting solids are filtered, washed with water, recrystallized from 50% ethanol/water (16 mL), and dried 1 hour under vacuum at 50° C. to give 696 milligrams of 5-[1-(3,4-dichlorophenyl)-ethoxy]-quinazoline-2,4-diamine.

EXAMPLE 79

5-(3,5-Difluorobenzyloxy)quinazoline-2,4-diamine

Step 1: 3,5-Difluorobenzyl alcohol (595.2 mg; 4 mmol) was added to a cooled (0° C.) slurry of sodium hydride (172.5 mg; 4.3 mmol) in dimethylformamide under nitrogen atmosphere. The reaction mixture was slowly warmed to room temperature, stirred for 1 hour. The reaction mixture was then added to a cooled (0° C.) solution of 2,6-difluorobenzonitrile in dimethylformamide, stirred for 4 hours at room temperature. The reaction mixture was poured on crushed ice-water, stirred, filtered, washed with water and dried to afford 547.3 milligrams of 2-fluoro-6-(3,5-difluorophenylmethoxy)benzonitrile.

Step 2: The previous benzonitrile (267.8 mg; 1.0 mmol) and guanidine carbonate (180.5 mg; 1 mmol) were heated at 150° C. in dimethylacetamide for 10 hours. The reaction mixture was diluted with water, stirred for ½ hour, filtered, washed with water and dried to yield 278.6 milligrams of 5-(3,5-difluorophenyl-methoxy)quinazoline-2,4-diamine.
$^1$H NMR (400 MHz, DMSO-$d_6$) δ 7.21 (m, 6H), 6.78 (d, J=8.4 Hz, 1H), 6.56 (d, J=8.0 Hz, 1H), 5.97 (s, 2H), 5.31 (s, 2H).
MS m/z 304 (M+H)$^+$

EXAMPLE 80

5-(4-Fluoroindan-1-yloxy)-quinazoline-2,4-diamine

Step 1: A solution of 3-(2-fluorophenyl)propionic acid (1.72 g; 10 mmol) in thionyl chloride (7.5 mL; 103 mmol) is stirred at room temperature for 72 hours under a nitrogen atmosphere. The excess thionyl chloride is removed under high vacuum to give 1.80 grams 3-(4-fluorophenyl)propionyl chloride.

Step 2: To a cold (ice water) suspension of aluminum chloride (1.29 g; 9.6 mmol) in dichloromethane (7 mL) is added a solution of the previous propionyl chloride (1.80 g; 9.6 mmol) in dichloromethane (3 mL). The reaction mixture is heated to reflux for 3.5 hours and cooled to room temperature overnight. The reaction is poured into ice water and extracted with dichloromethane. The organics are separated, washed with 0.1 M sodium hydroxide and brine, and dried over magnesium sulfate. The solvent is removed to give 871 milligrams of 4-fluoroindan-1-one.

Step 3: To a cold (ice water) solution of the previous ketone (791 mg; 5.3 mmol) in methanol (5 mL) is added sodium borohydride (203 mg; 5.3 mmol) and stirred thirty minutes. Water (5 mL) is added to the solution and stirred 15 minutes. Saturated ammonium chloride (14 mL) is added and the solution is extracted with ethyl acetate. The organics are separated and dried over magnesium sulfate. The solvent is removed to give 407 milligrams of 4-fluoroindan-1-ol.

Step 4: To a cold (ice water) suspension of sodium hydride (89 mg; 2.2 mmol) in anhydrous DMF (2 mL) is added a solution of the previous alcohol (391 mg; 2.6 mmol) in anhydrous DMF (2 mL) over 10 minutes. After allowing to room temperature over 1 hour, this solution is added to a cold (ice water) stirred solution of 2,6-difluorobenzonitrile (371 mg; 2.4 mmol) in anhydrous DMF (2 mL), and allowed to room temperature overnight. The reaction mixture is poured into ice water with vigorous stirring and refrigerated for 1 hour. The resulting solid is filtered, washed with water, and dried under vacuum at 40° C. for 2.5 hours to give 369 milligrams of 2-fluoro-6-(4-fluoroindan-1-yloxy)-benzonitrile.

Step 5: The previous benzonitrile (273 mg; 1.0 mmol) is heated with guanidine carbonate (178 mg; 1.0 mmol) in dimethylacetamide (2 mL) at 140° C. for nine hours, and then allowed to room temperature overnight. The reaction mixture is refrigerated for 1 hour and diluted with water (3 mL). The resulting solids are filtered, washed with water and dried 3 hours under vacuum at 40° C. to give 89 milligrams of 5-(4-fluoroindan-1-yloxy)-quinazoline-2,4-diamine.
MS m/z (ESI) 311 (M+H)$^+$
1HNMR (400 MHz, DMSO-$d_6$) δ 7.41 (t, J=8.0 Hz, 1H), 7.35 (s, 1H), 7.20 (t, J=9.2 Hz, 1H), 7.04 (br s, 1H), 6.95 (br s, 1H), 6.81 (d, J=8.4 Hz, 1H), 6.77 (d, J=8.0 Hz, 1H), 6.06 (t, J=5.2 Hz, 1H), 5.94 (br s, 2H), 3.09 (m, 1H), 2.97 (m, 1H), 2.73 (m, 2H), 2.20 (m, 1H).

EXAMPLE 81

5-(6-Fluoroindan-1-yloxy)-quinazoline-2,4-diamine

Step 1: Same as Example 80, Step 1 with 3-(4-fluorophenyl)propionic acid (1.69 g; 10 mmol) to give 1.76 gram of 3-(4-fluorophenyl)propionyl chloride.

Step 2: Same as Example 80, Step 2 with previous chloride (1.76 g; 9.4 mmol) to give 816 milligrams of 6-fluoroindan-1-one.

Step 3: Same as Example 80, Step 3 with previous ketone (770 mg; 5.1 mmol) to give 301 milligrams of 6-fluoroindan-1-ol.

Step 4: Same as Example 80, Step 4 with previous alcohol (314 mg; 2 mmol) to give 425 milligrams of 2-fluoro-6-(6-fluoroindan-1-yloxy)-benzonitrile.

Step 5: Same as Example 80, Step 5 with previous benzonitrile (272 mg; 1.00 mmol) to give 247 milligrams of 5-(6-fluoroindan-1-yloxy)-quinazoline-2,4-diamine.

EXAMPLE 82

5-[1-(2,6-Difluorophenyl)-ethoxy]-quinazoline-2,4-diamine

Step 1: To a cold (ice water) suspension of sodium hydride (409 mg; 10 mmol) in anhydrous DMF (4 mL) is added a solution of 2,6-difluoro-alpha-methylbenzyl alcohol (1.63 g; 10 mmol) in anhydrous DMF (5 mL) over 10 minutes. After allowing to room temperature over 1 hour, this solution is added to a cold (ice water) stirred solution of 2,6-difluorobenzonitrile (1.53 g; 11 mmol) in anhydrous DMF (6 mL), and allowed to room temperature over 2.5 hours. The reaction mixture is poured into ice water with vigorous stirring and the resulting solid is filtered, washed with water, and dried under vacuum at 40° C. overnight to give 1.92 grams of 2-[1-(2,6-difluorophenyl)-ethoxy]-6-fluorobenzonitrile.

Step 2: The previous benzonitrile (277 mg; 1.0 mmol) is heated with guanidine carbonate (180 mg; 1.0 mmol) in dimethylacetamide (2 mL) at 140° C. for eight hours, and then allowed to room temperature overnight. The reaction mixture is refrigerated and diluted with water (4 mL). The resulting solids are filtered, washed with water and dried 3 hours under vacuum at 40° C. to give 270 milligrams of 5-[1-(2,6-difluorophenyl)-ethoxy]-quinazoline-2,4-diamine.

EXAMPLE 83

5-(2,3,5-Trifluorobenzyloxy)-quinazoline-2,4-diamine

Step 1: To a cold (ice water) suspension of sodium hydride (407 mg; 10 mmol) in anhydrous DMF (4 is added a solution of 2,3,5-trifluorobenzyl alcohol (1.62 g; 10 mmol) in anhydrous DMF (5 mL) over 10 minutes. After allowing to room temperature over 1 hour, this solution is added to a cold (ice water) stirred solution of 2,6-difluorobenzonitrile (1.56 gm; 11 mmol) in anhydrous DMF (5 mL), and allowed to room temperature over 3 hours. TLC (25% EA/Hex) was incomplete so the reaction was continued at room temperature for an additional 2 hours. The reaction mixture is poured into ice water with vigorous stirring and the resulting solid is filtered, washed with water, and dried under vacuum at 40° C. for 4.5 hours to give 2.05 grams of 2-fluoro-6-(2,3,5-trifluorobenzyloxy)-benzonitrile.

Step 2: The previous benzonitrile (287 mg; 1.0 mmol) is heated with guanidine carbonate (181 mg; 1.0 mmol) in dimethylacetamide (2 mL) at 140° C. for nine hours, and then allowed to room temperature overnight. The reaction mixture is refrigerated and diluted with water (4 mL). The resulting solids are filtered, washed with water and dichloromethane, and dried 2.5 hours under vacuum at 40° C. to give 141 milligrams of 5-(2,3,5-trifluorobenzyloxy)-quinazoline-2,4-diamine.

EXAMPLE 84

5-(2,5-Difluorobenzyloxy)-quinazoline-2,4-diamine

Step 1: Same as Example 83, Step 1 with 1.46 g of 2,5-difluorobenzyl alcohol to give 1.84 grams of 2-(2,5-difluorobenzyloxy)-6-fluorobenzonitrile.

Step 2: Same as Example 83, Step 1 with 264 mg of previous benzonitrile to give 143 milligrams of 5-(2,5-difluorobenzyloxy)-quinazoline-2,4-diamine.

EXAMPLE 85

5-(2,4-Difluorobenzyloxy)-quinazoline-2,4-diamine

Step 1: Same as Example 83, Step 1 with 1.44 g g 2,4-difluorobenzyl alcohol to give 2.04 grams of 2-(2,4-difluorobenzyloxy)-6-fluorobenzonitrile.

Step 2: Same as Example 83, Step 1 with 265 mg of previous benzonitrile to give 147 milligrams of 5-(2,4-difluorobenzyloxy)-quinazoline-2,4-diamine.

EXAMPLE 86

5-(2,6-Difluorobenzyloxy)-quinazoline-2,4-diamine

Step 1: Same as Example 83, Step 1 with 1.48 grams of 2,6-difluorobenzonitrile to give 2.04 grams of 2-(2,4-difluorobenzyloxy)-6-fluorobenzonitrile.

Step 2: Same as Example 83 Step 2 with 264 mg of the previous benzonitrile to give 147 milligrams of 5-(2,4-difluorobenzyloxy)-quinazoline-2,4-diamine.

EXAMPLE 87

5-(3,4-Difluorobenzyloxy)quinazoline-2,4-diamine

Step 1: 3,4-Difluorobenzyl alcohol (1.47 g; 10.1 mmol) was added to a cooled (0° C.) slurry of sodium hydride (0.414 g; 10.3 mmol) in dimethylformamide under nitrogen atmosphere. The reaction mixture was slowly warmed to room temperature, stirred for 1 hour. The reaction mixture was then added to a cooled (0° C.) solution of 2,6-difluorobenzonitrile in dimethylformamide, stirred for 3 hours at room temperature. The reaction mixture was poured on crushed ice-water, stirred, filtered, washed with water and dried to afford 1.47 grams of 2-fluoro-6-(3,4-difluorophenylmethoxy)benzonitrile.

Step 2: The previous benzonitrile (263.8 mg; 1.0 mmol) and guanidine carbonate (181.9 mg; ~1 mmol) were heated at 140° C. in dimethylacetamide for 8 hours. The reaction mixture was diluted with water, stirred for 1 hour, filtered, washed with water and dried to yield 95.4 milligrams of 5-(3,4-difluorophen-3-ylmethoxy)quinazoline-2,4-diamine.

$^1$H NMR (400 MHz, DMSO-d$_6$) δ 7.62 (m, 1H), 7.32 (m, 3H), 7.19 (bs, 2H), 6.77 (dd, J=0.2, 8.4 Hz, 1H), 6.59 (d, J=9.5 Hz, 1H), 5.95 (s, 2H), 5.26 (s, 2H).

MS m/z 303.6 (M+H)$^+$

EXAMPLE 88

5-(5-Chloro-2-methoxybenzyloxy)quinazoline-2,4-diamine

Step 1: To a cold (ice water) suspension of sodium hydride (472 mg; 11.8 mmol) in anhydrous DMF (5 mL) is added a solution of 5-chloro-2-methoxybenzyl alcohol (1.72 g; 9.7 mmol) in anhydrous DMF (5 mL) over 15 minutes. After allowing to room temperature over 1 hour, this solution is added to a cold (ice water) stirred solution of 2,6-difluorobenzonitrile (1.63 g; 11.3 mmol) in anhydrous DMF (8 mL), and allowed to room temperature over 3 hours. The reaction mixture is poured into ice water with vigorous stirring and the resulting solid is filtered, washed with water, and dried under vacuum at 45° C. overnight to give 2.28 grams of 2-(5-chloro-2-methoxybenzyloxy)-6-fluorobenzonitrile.

Step 2: The previous benzonitrile (585 mg; 2.0 mmol) is heated with guanidine carbonate (361 mg; 2.0 mmol) in dimethylacetamide (3 mL) at 160° C. for eleven hours, and then allowed to room temperature overnight. The reaction mixture is diluted with water (10 mL). The resulting solids are filtered, washed with water and hexanes, and dried five hours under vacuum at 40° C. to give 532 milligrams of 5-(5-chloro-2-methoxybenzyl)-quinazoline-2,4-diamine.

EXAMPLE 89

[4-Chloro-2-(2,4-diamino-quinazolin-5-yloxymethyl)-phenyl]-methanol hydrochloride Step 1: 4-Chlorophthalic acid, monosodium salt (1.11 g; 5 mmol) and 1.0 M hydrochloride acid (5 ml, 5 mmol) was stirred at room temperature for 18 hours. The reaction mixture was then extracted with ethyl acetate (5 ml×3). The combined organic layers were dried to afford 892.3 milligrams of beige solid as 4-chlorophthalic acid.

Step 2: A solution of the previous acid (802.9 mg, 4 mmol) in tetrahydrofuran was added to a cooled (−75° C.) slurry of lithium aluminum hydride, 95% (320.6 mg, 8 mmol) in tetrahydrofuran over 25 min. period. The reaction mixture was allowed to warm up to room temperature then heated to reflux for 18 hours. The reaction mixture was quenched with water, 15% sodium hydroxide, and water in ice bath. The separated organic layer was dried to yield 607.8 milligrams of 4-chlorobenzen-1,2-dimethanol.

Step 3: The previous diol (345.2 mg; 2.0 mmol), trimethyl orthoformate (0.41 ml, 4 mmol) and a catalytic amount of (1S)-(+)-10-camphorsulfonic acid (4.6 mg; ~1% mol) were stirred at room temperature for 22 hours. The reaction mixture was cooled to −75° C. Diisobutylaluminum hydride 1.0 M solution in hexane (20 ml, 20 mmol) was added dropwise over 20 min. period at −75° C., stirred for 30 min. at −75° C., then stirred at 0° C. for 15 min. The reaction mixture was poured into 2N sodium hydroxide and extracted the aqueous solution with ethyl acetate. The combined organic layers washed with brine, dried (MgSO$_4$), filtered and dried to yield 410.1 milligrams of (5-chloro-2-methoxymethoxymethylphenyl)methanol as a purple oil.

Step 4: The previous protected diol (334.3 mg; 1.5 mmol) was added dropwise to a cooled (0° C.) slurry of sodium hydride (69.1 mg; 1.7 mmol) in dimethylformamide under nitrogen atmosphere. The reaction mixture was stirred at room temperature for 1.5 hours. The reaction mixture was added to a cooled (0° C.) solution of 2,6-difluorobenzonitrile (273.8 mg, 1.8 mmol) in dimethylformamide. The reaction mixture was stirred at room temperature for 2.75 hours. The reaction mixture was poured on crushed ice-water. After stored in refrigerator for 16 hours, the aqueous solution was filtered, washed with water and dried to yield 241.9 milligrams of 2-(5-chloro-2-methoxymethoxymethylbenzyloxy)-6-fluorobenzonitrile.

Step 5: The previous benzonitrile (230.5 mg; 0.68 mmol) and guanidine carbonate (126.7 mg; ~1 mmol) were heated at 120° C. in dimethylacetamide for 12 hours. The reaction mixture was diluted with water, stirred for 15 min., filtered, washed with hexane and dried to yield crude residue. Purification by silica gel chromatography and preparative layer chromatography plate yield 12.7 milligrams of [4-chloro-2-(2,4-diamino-quinazolin-5-yloxymethyl)-phenyl]-methanol.

Step 6: Hydrogen chloride 2.0 M solution in diethyl ether (0.1 ml, 0.2 mmol) was added to a solution of the previous diamine in ethanol and stirred at room temperature for 86 hours. Filtered to yield 4.6 milligrams of [4-chloro-2-(2,4-diamino-quinazolin-5-yloxymethyl)-phenyl]-methanol hydrochloride.

$^1$H NMR (400 MHz, DMSO-d) δ 12.66 (s, 1H), 8.92 (d, J=9.6 Hz, 1H), 8.42 (t, J=8.8, 13.6 Hz, 1H), 7.42 (m, 4H), 7.06 (s, 1H), 6.99 (t, J=4.0, 4.4 Hz, 1H), 5.47 (dd, J=8.0, 46.4 Hz, 2H), 4.61 (d, J=7.2 Hz, 1H), 3.38 (t, J=6.8, 7.2 Hz, 2H).

MS m/z 331 (M+H)$^+$

EXAMPLE 90

5-Thiophen-3-yl-quinazoline-2,4-diamine

Step 1: In a dry round bottom flask were added 2-fluoro-6-iodobenzonitrile (500 mg; 2.02 mmol), 3-thiophene boronic acid (311 mg; 2.43 mmol), sodium carbonate (2.32 g; 21.86 mmol), tetrakis(triphenylphosphine)palladium(0) (77 mg; 0.07 mmol), DME (20 mL) and water (20 mL) and heated to reflux for 5 hours. The reaction mixture was cooled to room temperature and extracted with ethyl acetate (3×), washed with brine (1×) and water (1×). Organic layers were combined and dried over sodium sulfate and then filtered and solvent removed to yield crude material which was purified by column chromatography (4% ethyl acetate/hexane) to obtain 150 milligrams of 2-fluoro-6-thiophen-3-yl-benzonitrile.

Step 2: The previous benzonitrile (150 mg; 0.74 mmol) and guanidine carbonate (266 mg; 1.48 mmol) were heated at 130° C. in dimethyl acetamide for 7 hours. The reaction mixture was cooled to room temperature and filtered. The solid was recrystallized in 50% ethanol/water to yield 2.7 milligrams of 5-thiophen-3-yl-quinazoline-2,4-diamine.

EXAMPLE 91

5-(3-Chlorophenyl)-quinazoline-2,4-diamine

Step 1: In a dry round bottom flask were added 2-fluoro-6-iodobenzonitrile (500 mg; 2.02 mmol), 3-chlorophenyl boronic acid (380 mg; 2.43 mmol), sodium carbonate (2.32 g; 21.86 mmol), tetrakis(triphenylphosphine)palladium(0) (77 mg; 0.07 mmol), DME (20 mL) and water (20 mL) and heated to reflux for 8 hours. The reaction mixture was cooled to room temperature and extracted with ethyl acetate (3×), washed with brine (1×) and water (1×). Organic layers were combined and dried over sodium sulfate and then filtered and solvent removed to yield crude material which was purified by column chromatography (4% ethyl acetate/hexane) to obtain 150 milligrams of 3'-chloro-3-fluorobiphenyl-2-carbonitrile.

Step 2: The previous carbonitrile (150 mg; 0.65 mmol) and guanidine carbonate (233 mg; 1.30 mmol) were heated at 130° C. in dimethyl acetamide for 7 hours. The reaction mixture was cooled to room temperature and filtered. The solid was recrystallized in 50% ethanol/water to yield 58 milligrams of 5-(3-chlorophenyl)-quinazoline-2,4-diamine.

EXAMPLE 92

5-[(R)-1-(3-Chlorophenyl)ethoxyl]quinazolin-2,4-diamine

Step 1: To a solution of borane-tetrahydrofuran (0.647 mL, 0.647 mmol, Aldrich, 1 M solution in THF) and (S)-MeCBS (0.647 mL, 0.647 mmol, Aldrich, 1M solution in toluene) was added simultaneously a solution of 3-chloroacetophenone (1.00 g, 6.47 mmol) in anhydrous tetrahydrofuran (2.42 mL) and a solution of borane-tetrahydrofuran (3.24 mL, 3.24 mmol, Aldrich, 1 M solution in THF) over 30 min at ambient temperature. After complete addition, the reaction mixture was stirred for 10 min, quenched slowly at 0° C. with methanol (0.94 mL) and then saturated HCl in ether (0.12 mL). After stirring at 0° C. for 5 min and ambient temperature for 30 min, the solution was concentrated in vacuo to an oil. The oil was twice diluted with benzene and concentrated in vacuo, diluted with ether, and concentrated in vacuo to an oil. The oil was purified by flash chromatography(silica gel, 20% EA in hexane) to give (R)-1-(3-chlorophenyl)ethanol as a clear colorless oil (0.784 g, 78%). Optical rotation in CHCl$_3$ at 20° C. at concentration 0.220 was +40.9° (Literature, Bull. Chem. Soc. Jpn. 1996, 69(4), 1079-1085, optical rotation in CHCl$_3$ at 21° C. at concentration 0.220 was +44°).

Step 2: A solution of (R)-1-(3-chlorophenyl)ethanol (0.730 g, 4.66 mmol) in dimethylformamide (5 mL) was added to a 0° C. slurry of sodium hydride (0.207 g, 5.18 mmol) in dimethylformamide (5 mL) under nitrogen atmosphere. The reaction mixture was warmed to room temperature, stirred for 3 hour, and then cooled with an ice bath. The cold orange solution was added dropwise to a 0° C. solution of 2,6-difluorobenzonitrile (0.720 g, 5.18 mmol) in dimethylfomamide (5 mL). After the reaction was stirred at ambient temperature for around 18 hours, the reaction was diluted with water and extracted with EA. The organic layer was washed with water and brine, dried over $MgSO_4$, and concentrated in vacuo to a yellow semi-solid. Flash chromatography purification (silica gel, 50% hexane in DCM) afforded the 2-fluoro-5-[(R)-1-(3-chlorophenyl)ethoxy]benzonitrile as a pale yellow oil (0.645 g, 50%).

Step 3: To a mixture of the previous benzonitrile (0.630 g, 2.29 mmol) and guanidine carbonate (0.988 g, 5.48 mmol) in dimethylacetamide (4.0 mL) was heated at 145° C. for 7 hours. The mixture was concentrated in vacuo to a black solid. The solid was stirred in a mixture of water and EA; and then the tan solid was collected. Flash chromatography purification (silica gel, 10% methanol in DCM) afforded 5-(R)-1-(3-chloro-phenyl)-ethoxy-quinazoline-2,4-diamine as an off white solid (0.357 g, 49%).

$^1$H NMR (400 MHz, DMSO-$d_6$) δ 7.54 (d, J=1.6 Hz, 1H), 7.32-7.44 (m, 5H), 7.23 (t, J=8.4 Hz), 6.72 (dd, J=8.4, 0.8 Hz, 1H), 6.41 (d, J=8.0 Hz, 1H), 6.03 (s, 2H), 5.71 (q, J=6.4 Hz, 1H), 1.68 (d, J=6.4 Hz, 3H).

MS (ESI) m/z 315 (M+H)$^+$

HPLC 96.8% pure (99.0% ee).

EXAMPLE 93

5-[1-(3-Fluorophenyl)-ethoxy]-quinazoline-2,4-diamine

Step 1: A solution of 1-(3-fluorophenyl)ethanol (0.7 ml; 5.6 mmol) in dimethylformamide was added to a cooled (0° C.) slurry of sodium hydride (224 mg; 5.6 mmol) in dimethylformamide under nitrogen atmosphere. The reaction mixture was slowly warmed to room temperature, and stirred for 45 minutes. In another vessel, a solution of 2,6-difluorobenzonitrile (780 mg, 5.6 mmol) in dimethylformamide was chilled to 0° C., and activiated anion was added over 20 minutes. Mixture was then stirred 2 hours at room temperature. The reaction mixture was poured on crushed ice-water, stirred, filtered, washed with water and dried to afford g of solid (yield) of 2-fluoro-6-[1-(3-fluorophenyl)-ethoxy]-benzonitrile.

Step 2: The previous benzonitrile (420 mg; 1.4 mmol) and guanidine carbonate (252 mg; 1.4 mmol) were heated at 133° C. in dimethylacetamide for 6 hours, then cooled back to room temperature over night. The reaction mixture was diluted with water, stirred for 45 minutes, filtered, triturated with ethanol, and filtered. Ethanol mother-liquor set idle for 2 hours, filtered, and dried solids to afford 5-[1-(3-fluorophenyl)-ethoxy]-quinazoline-2,4-diamine. (191 mg, 43% yield).

$^1$H NMR (400 MHz, DMSO-$d_6$) δ 7.42 (m, 3H), 7.31 (m, 2H), 7.22 (t, J=8.4, 8 Hz, 1H), 7.11 (m, 1H), 6.72 (dd, J=0.8 Hz, 1H), 6.41 (d, J=7.6 Hz, 1H), 5.96 (bs, 2H), 5.72 (q, J=6.4 Hz, 1H), 1.69 (d, J=6.4 Hz, 3H).

MS (ESI) m/z 300 (M+H)$^+$

EXAMPLE 94

5-[1-(2-Trifluoromethylphenyl)-ethoxy]-quinazoline-2,4-diamine

Step 1: A solution of alpha-methyl-2-(trifluoromethyl)benzyl alcohol (750 mg; 3.9 mmol) in dimethylformamide was added to a cooled (0° C.) slurry of sodium hydride (156 mg; 3.9 mmol) in dimethylformamide under nitrogen atmosphere. The reaction mixture was slowly warmed to room temperature, and stirred for 45 minutes. In another vessel, a solution of 2,6-difluorobenzonitrile (543 mg, 3.9 mmol) in dimethylfomamide was chilled to 0° C., and activiated anion was added over 20 minutes. Mixture was then stirred 2 hours at room temperature. The reaction mixture was poured on crushed ice-water, stirred, filtered, washed with water and dried to afford 1.2 g of solid (99% yield) of 2-fluoro-6-[1-(2-trifluoromethylphenyl)-ethoxy]-benzonitrile.

Step 2: The previous benzonitrile (420 mg; 1.4 mmol) and guanidine carbonate (252 mg; 1.4 mmol) were heated at 133° C. in dimethylacetamide for 6 hours, then cooled back to room temperature over night. The reaction mixture was diluted with water, stirred for 45 minutes, filtered, triturated with ethanol, and filtered. Solids were dried to afford title compound. (234 mg, 48% yield).

$^1$H NMR (400 MHz, DMSO-$d_6$) δ 7.80 (d, J=8.0 Hz, 1H), 7.73 (m, 2H), 7.52 (t, J=7.6, 7.2 Hz, 1H), 7.34 (bs, 2H), 7.19 (t, J=8.4, 8.0 Hz, 1H), 6.72 (d, J=7.6 Hz, 1H), 6.18 (d, J=7.6 Hz, 1H), 6.0 (bs, 2H), 5.83 (q, J=6.0 Hz, 1H), 1.75 (d, J=6.4 Hz, 3H).

EXAMPLE 95

5-[1-(3-Trifluoromethylphenyl)-ethoxy]-quinazoline-2,4-diamine

Step 1: A solution of alpha-methyl-3-(trifluoromethyl)benzyl alcohol (0.6 ml; 3.9 mmol) in dimethylformamide was added to a cooled (0° C.) slurry of sodium hydride (156 mg; 3.9 mmol) in dimethylformamide under nitrogen atmosphere. The reaction mixture was slowly warmed to room temperature, and stirred for 45 minutes. In another vessel, a solution of 2,6-difluorobenzonitrile (543 mg, 3.9 mmol) in dimethylformamide was chilled to 0° C., and activiated anion was added over 20 minutes. Mixture was then stirred 2 hours at room temperature. The reaction mixture was poured on crushed ice-water, stirred, filtered, washed with water and dried to afford 1.2 grams of 2-fluoro-6-[1-3-trifluoromethylphenyl)-ethoxy]-benzonitrile.

Step 2: The previous benzonitrile (420 mg; 1.4 mmol) and guanidine carbonate (252 mg; 1.4 mmol) were heated at 133° C. in dimethylacetamide for 6 hours, then cooled back to room temperature over night. The reaction mixture was diluted with water, stirred for 45 minutes, filtered, triturated with ethanol, filtered, and dried to obtain 65 milligrams of 5-[1-(3-trifluoromethylphenyl)-ethoxy]-quinazoline-2,4-diamine.

$^1$H NM (400 MHz, DMSO-$d_6$) δ 7.85 (s, 1H), 7.76 (d, J=7.2 Hz, 1H), 7.65 (m, 2H), 7.38 (bs, 1H), 7.3 (bs, 1H), 7.21 (t, J=8.4 Hz, 1H), 6.72 (dd, J=0.8, 8.4 Hz, 1H), 6.41 (d, J=7.6 Hz, 1H), 5.97 (bs, 2H), 5.83 (m, 1H), 1.72 (d, J=6.4 Hz, 3H).

MS m/z (ESI) 350 (M+H)$^+$.

EXAMPLE 96

5-(2-Fluorobenzyloxy)-quinazoline-2,4-diamine

Step 1: A solution of 2-fluorobenzyl alcohol (0.7 ml; 6.5 mmol) in dimethylformamide was added to a cooled (0° C.) slurry of sodium hydride (260 mg; 6.5 mmol) in dimethylformamide under nitrogen atmosphere. The reaction mixture was slowly warmed to room temperature, and stirred for 45 minutes. In another vessel, a solution of 2,6-difluorobenzonitrile (900 mg, 6.5 mmol) in dimethylfomamide was chilled to 0° C., and activated anion was added over 20 minutes. Mixture was then stirred 2 hours at room temperature. The reaction mixture was poured on crushed ice-water, stirred, filtered, washed with water and dried to afford 1.3 g of solid (82% yield) of 2-fluoro-6-(2-fluorobenzyloxy)-benzonitrile.

Step 2: The previous benzonitrile (400 mg; 1.6 mmol) and guanidine carbonate (288 mg; 1.6 mmol) were heated at 133° C. in dimethylacetamide for 6 hours, then cooled back to room temperature over night. The reaction mixture was diluted with water, stirred for 45 minutes, filtered, triturated with ethanol twice, and filtered. Solids were dried to afford 5-(2-fluorobenzyloxy)-quinazoline-2,4-diamine. (98 mg, 22% yield).

EXAMPLE 97

5-(4-Fluorobenzyloxy)-quinazoline-2,4-diamine

Step 1: A solution of 4-fluorobenzyl alcohol (0.7 ml; 6.5 mmol) in dimethylformamide was added to a cooled (0° C.) slurry of sodium hydride (260 mg; 6.5 mmol) in dimethylformamide under nitrogen atmosphere. The reaction mixture was slowly warmed to room temperature, and stirred for 45 minutes. In another vessel, a solution of 2,6-difluorobenzonitrile (900 mg, 6.5 mmol) in dimethylformamide was chilled to 0° C., and activated anion was added over 20 minutes. Mixture was then stirred 2 hours at room temperature. The reaction mixture was poured on crushed ice-water, stirred, filtered, washed with water and dried to afford 1.3 g of solid (82% yield) of 2-Fluoro-6-(4-fluorobenzyloxy)-benzonitrile.

Step 2: The previous benzonitrile (400 mg; 1.6 mmol) and guanidine carbonate (288 mg; 1.6 mmol) were heated at 133° C. in dimethylacetamide for 6 hours, then cooled back to room temperature over night. The reaction mixture was diluted with water, stirred for 45 minutes, filtered, triturated with ethanol twice, and filtered. Solids were dried to afford 5-(4-fluorobenzyloxy)-quinazoline-2,4-diamine. (174 mg, 38% yield).

EXAMPLE 98

5-(3-Trifluoromethylbenzyloxy)-quinazoline-2,4-diamine

Step 1: Same as Example 83, Step 1 with 1.13 g of 3-(trifluoromethylbenzyl alcohol to give 1.14 grams of 2-(3-trifluoromethylbenzyloxy)-6-fluorobenzonitrile.

Step 2: The previous benzonitrile (300 mg; 1.01 mmol) and guanidine carbonate (183 mg; 1.01 mmol) were heated at 150° C. in dimethylacetamide for 5 hours, then cooled back to room temperature over night. The reaction mixture was diluted with water, stirred for 45 minutes, filtered, triturated with ethanol, and filtered. Solids were dried to afford 5-(3-trifluoromethylbenzyloxy)-quinazoline-2,4-diamine. (235 mg, 70% yield).

EXAMPLE 99

5-(2-Trifluoromethylbenzyloxy)-quinazoline-2,4-diamine

Step 1: 2-(Trifluoromethyl)benzyl alcohol (1.15 g; 6.3 mmol) was added to a cooled (0° C.) slurry of sodium hydride (243.7 mg; 6 mmol) in dimethylformamide under nitrogen atmosphere. The reaction mixture was slowly warmed to room temperature, stirred for 45 min. The reaction mixture was then added to a cooled (0° C.) solution of 2,6-difluorobenzonitrile in dimethylformamide, stirred for 3 hours at room temperature. The reaction mixture was poured on crushed ice-water, stirred, filtered, washed with water and dried to afford 1.39 grams of 2-fluoro-6-(2-trifluoro-methylphenyl-methoxy)benzonitrile as a white solid.

Step 2: The previous benzonitrile (300 mg; 1.0 mmol) and guanidine carbonate (183 mg; 1.0 mmol) were heated at 150° C. in dimethylacetamide for 5 hours, then cooled back to room temperature overnight. The reaction mixture was diluted with water, stirred for 45 minutes, filtered, triturated with ethanol, filtered, and dried to obtain 250 milligrams of 5-(2-trifluoromethylbenzyloxy)-quinazoline-2,4-diamine.

$^1$H NMR (400 MHz, DMSO-d$_6$) δ 7.86 (d, J=6.6, 1H), 7.77 (m, 2H), 7.63 (t, J=7.6, 6.4 Hz, 1H), 7.35 (t, J=8.0, 8.4 Hz, 1H), 7.15 (bs, 1H), 7.09 (bs, 1H), 6.82 (d, J=8.4 Hz, 1H), 6.57 (d, J=8.0 Hz, 1H), 5.99 (bs, 2H), 5.41 (s, 2H).

MS m/z (ESI) 334 (M−H)$^+$.

EXAMPLE 100

5-(4-Trifluoromethylbenzyloxy)-quinazoline-2,4-diamine

Step 1: 4-(Trifluoromethyl)benzyl alcohol (1.15 g; 6.3 mmol) was added to a cooled (0° C.) slurry of sodium hydride (249.7 mg; 6.2 mmol) in dimethylformamide under nitrogen atmosphere. The reaction mixture was slowly warmed to room temperature overnight. The reaction mixture was then added to a cooled (0° C.) solution of 2,6-difluorobenzonitrile in dimethylfomamide, stirred for 6 hours at room temperature. The reaction mixture was poured on crushed ice-water, stirred, filtered, washed with water and dried to afford 804.4 milligrams of 2-fluoro-6-(4-trifluoromethylphenyl-methoxy)-benzonitrile as waxy yellow solid. Yield 45%.

Step 2: The previous benzonitrile (300 mg; 1.0 mmol) and guanidine carbonate (183 mg; 1.0 mmol) were heated at 150° C. in dimethylacetamide for 5 hours, then cooled back to room temperature over night. The reaction mixture was diluted with water, stirred for 45 minutes, filtered, triturated with ethanol, filtered, and dried. 5-(4-Trifluoromethylbenzyloxy)-quinazoline-2,4-diamine was obtained at a 70% yield (236 mg).

$^1$H NMR (400 MHz, DMSO-d$_6$) δ 7.81 (d, J=8.4 Hz, 2H), 7.74 (d, J=8.4 Hz, 2H), 7.32 (t, J=8.4, 8.0 Hz, 1H), 7.25 (bs, 1H), 7.2 (bs, 1H), 6.82 (dd, J=8.4, 0.8 Hz, 1H), 6.58 (d, J=8.0, 0.8 Hz, 1H), 5.97 (bs, 2H), 5.40 (s, 2H).

MS m/z (ESI) 333 (M−H)$^+$.

EXAMPLE 101

5-[1-(4-fluorophenyl)-1-methyl-ethoxy]-quinazoline-2,4-diamine

Step 1: A solution of alpha-methyl-4-fluorobenzyl alcohol (0.7 ml; 5.5 mmol) in dimethylformamide was added to a cooled (0° C.) slurry of sodium hydride (220 mg; 5.5 mmol) in dimethylformamide under nitrogen atmosphere. The reaction mixture was slowly warmed to room temperature, and stirred for 45 minutes. In another vessel, a solution of 2,6-difluorobenzonitrile (765 mg, 5.5 mmol) in dimethylformamide was chilled to 0° C., and activated anion was added over 20 minutes. Mixture was then stirred 2 hours at room temperature. The reaction mixture was poured on crushed ice-water, stirred, filtered, washed with water and dried to afford 1.1 g of 2-fluoro-6-[1-(4-fluorophenyl)-ethoxy]-benzonitrile (78% yield).

Step 2: The previous benzonitrile (300 mg; 1.2 mmol) and guanidine carbonate (216 mg; 1.2 mmol) were heated at 150° C. in dimethylacetamide for 5 hours, then cooled back to room temperature over night. The reaction mixture was diluted with water, stirred for 45 minutes, aqueous mixture was then extracted EA (6×8 mls). Combine EA was then washed with water (3×5 mls), brine and dried over MgSO$_4$. Upon filtration and concentration yellow oil was purified by flash silica gel and eluted with 5-10% MeOH/DCM gradient. 5-[1-(4-Fluorophenyl)-1-methyl-ethoxy]-quinazoline-2,4-diamine was obtained at a 77% yield (275 mg).

$^1$H NMR (400 MHz, DMSO-d$_6$) δ 7.51 (m, 2H), 7.4 (bs, 1H), 7.3 (bs, 1H), 7.19 (m, 3H), 7.2 (bs, 1H), 6.72 (dd, J=8.4, 0.8 Hz, 1H), 6.43 (d, J=7.6 Hz, 1H), 5.99 (bs, 2H), 5.72 (q, J=6.4 Hz, 1H), 1.68 (d, J=6.4 Hz, 3H).

MS m/z (ESI) 297 (M−H)$^+$.

EXAMPLE 102

5-(3-Fluorobenzyloxy)quinazoline-2,4-diamine

Step 1: Same as Example 101, Step 1 with 3-fluorobenzyl alcohol (0.7 ml; 6.5 mmol) to afford 2-fluoro-6-(3-fluorobenzyloxy)benzonitrile. (1.4 g, 88% yield).

Step 2: Same as Example 101, Step 2 with the previous benzonitrile (400 mg; 1.6 mmol) to obtain 68 milligrams of 5-[1-(3-Fluorophenyl)-ethoxy]-quinazoline-2,4-diamine.

$^1$H NMR (400 MHz, DMSO-d$_6$) δ 7.51 (m, 2H), 7.36 (m, 2H), 7.31 (m, 2H), 7.22 (t, J=8.4, 0.8 Hz, 1H), 7.10 (m, 1H), 6.72 (dd, J=8.4, 0.8 Hz, 1H), 6.41 (d, J=7.6 Hz, 1H), 5.96 (bs, 2H), 5.72 (q, J=6.4 Hz, 1H), 1.69 (d, J=6.4 Hz, 3H)

MS m/z (ESI) 290 (M−H)$^+$.

EXAMPLE 103

5-[1-(2-Fluorophenyl)-ethoxy]-quinazoline-2,4-diamine

Step 1: Same as Example 101, Step 1 with 1-(2-fluorophenyl)ethanol (0.7 ml; 5.6 mmol) to give 794 milligram of 2-fluoro-6-[1-(2-fluorophenyl)-ethoxy]-benzonitrile.

Step 2: Same as Example 101, Step 2 with the previous benzonitrile (300 mg; 1.2 mmol) to obtain 191 milligrams of 5-[1-(2-fluorophenyl)-ethoxy]-quinazoline-2,4-diamine.

EXAMPLE 104

5-[1-(2-Chlorophenyl)ethoxy]-quinazoline-2,4-diamine

Step 1: Same as Example 101, Step 1 with 1-(2-chlorophenyl)ethanol (1.43 grams) to afford 872 milligrams of 2-[1-(2-chlorophenyl)-ethoxy]-6-fluorobenzonitrile.

Step 2: Same as Example 101, Step 2 with previous benzonitrile (300 mg; 1.1 mmol) to afford 5-[1-(2-Chlorophenyl)-ethoxy]-quinazoline-2,4-diamine (106 mg).

$^1$H NMR (400 MHz, DMSO-d$_6$) δ 7.80 (d, J=8.0 Hz, 1H), 7.73 (m, 2H), 7.52 (t, J=7.6, 7.2 Hz, 1H), 7.34 (bs, 2H), 7.19 (t, J=8.4, 8.0 Hz, 1H), 6.72 (d, J=7.6 Hz, 1H), 6.18 (d, J=7.6 Hz, 1H), 6.0 (bs, 2H), 5.83 (q, J=6.0 Hz, 1H), 1.75 (d, J=6.4 Hz, 3H).

EXAMPLE 105

5-[1-(4-Trifluoromethylphenyl)ethoxy]quinazoline-2,4-diamine

Step 1: Same as Example 101, Step 1 with alpha-methyl-4-trifluoromethylbenzyl alcohol (320 mg; 1.7 mmol) to afford 450 milligrams of 2-fluoro-6-[1-(4-trifluoromethylphenyl)-ethoxy]-benzonitrile.

Step 2: Same as Example 101, Step 2 with previous benzonitrile (450 mg; 1.5 mmol) to afford 177 milligrams of 5-[1-methyl-1-(4-trifluoromethylphenyl)-ethoxy]-quinazoline-2,4-diamine.

$^1$H NMR (400 MHz, DMSO-d$_6$) δ 7.76 (d, J=8.4 Hz, 2H), 7.68 (d, J=8.4 Hz, 2H), 7.37 (bs, 1H), 7.3 (bs, 1H), 7.2 (t, J=8.4, 8.0 Hz, 1H), 6.72 (dd, J=8.4, 0.8 Hz, 1H), 6.36 (d, J=7.2 Hz, 1H), 5.97 (bs, 2H), 5.72 (q, J=6.0 Hz, 1H), 1.71 (d, J=6.4 Hz, 3H).

MS m/z (ESI) 347 (M−H)$^+$.

EXAMPLE 106

5-(3,5-Dichlorobenzyloxy)quinazoline-2,4-diamine

Step 1: Same as Example 101, Step 1 with 3,5-dichlorobenzyl alcohol (1 g; 5.6 mmol) to afford 2-fluoro-6-(3,5-dichlorobenzyloxy)-benzonitrile (1.4 grams).

Step 2: Same as Example 101, Step 2 with the previous benzonitrile (300 mg; 1.0 mmol) to afford 230 milligrams of 5-[1-(3,5-dichlorophenyl)-ethoxy]-quinazoline-2,4-diamine.

$^1$H NMR (400 MHz, DMSO-d$_6$) δ 7.6 (s, 3H), 7.33 (t, J=8.4, 8.0 Hz, 1H), 7.26 (bs, 1H), 7.22 (bs, 1H), 6.97 (d, J=8.0 Hz, 1H), 6.57 (d, J=8.0 Hz, 1H), 5.96 (bs, 2H), 5.31 (s, 2H).

MS m/z (ESI) 337 (M+H)$^+$.

EXAMPLE 107

5-[1-(3,5-Difluorophenyl)ethoxy]quinazoline-2,4-diamine

Step 1: Sodium borohydride (267 mg, 7.0 mmol) was added in portions to a solution of 3-5-difluoroacetophenone (1 g, 6.4 mmol) in methanol at room temperature. Reaction was quenched after 3 hours stirring with 10 mls (aq) sat. NH$_4$Cl. Mixture was extracted with ethyl acetate (3×30 ml). Combined organics were washed with brine and dried over MgSO$_4$. Crude 3,5-difluorophenylethanol was obtained upon filtration and concentration to a colorless oil. (960 mg; 95% yield).

Step 2: Same as Example 101, Step 1 with 3,5-difluorophenylethanol (960 mg; 6.1 mmol to afford 2-fluoro-6-[1-(3,5-difluorophenyl)-ethoxy]-benzonitrile. (1.6 g, 94% yield).

Step 3: Same as Example 101, Step 2 with the previous benzonitrile (300 mg; 1.1 mmol) to afford 145 milligrams of 5-[1-(3,5-difluorophenyl)-1-methyl-ethoxy]-quinazoline-2,4-diamine.

$^1$H NMR (400 MHz, DMSO-d$_6$) δ 7.31 (bs, 2H), 7.24 (m, 2H), 7.15 (m, 1H), 6.74 (dd, J=8.0, 7.6 Hz, 1H), 6.40 (d, J=7.6 Hz, 1H), 5.97 (bs, 2H), 5.72 (q, J=6.4 Hz, 1H), 1.69 (d, J=6.4 Hz, 3H).

MS m/z (ESI) 315 (M−H)$^+$.

EXAMPLE 108

5-((S)-1-Naphthalen-1-yl-ethoxy)-quinazoline-2,4-diamine

Step 1: Same as Example 101, Step 1 with (S)-(−)-alpha-methyl-1-naphthalene methanol (1 g; 5.8 mmol) to obtain 1.53 grams 2-fluoro-6-((S)-1-naphthalen-1-yl-ethoxy)-benzonitrile.

Step 2: Same as Example 101, Step 2 with the previous benzonitrile (582 mg; 2.0 mmol to afford 257 milligrams 5-((S)-1-naphthalen-1-yl-ethoxy)-quinazoline-2,4-diamine.

EXAMPLE 109

5-((S)-1-Naphthalen-2-yl-ethoxy)-quinazoline-2,4-diamine

Step 1: Same as Example 101, Step 1 with (S)-(−)-alpha-methyl-2-naphthalene methanol (796 mg; 4.6 mmol) to afford 2-fluoro-6-((S)-1-naphthalen-2-yl-ethoxy)-benzonitrile was obtained as a colorless oil. (892 mg; 67% yield).

Step 2: Same as Example 101, Step 2 with the previous benzonitrile (730 mg; 2.51 mmol) to afford 310 milligrams of 5-((S)-1-naphthalen-2-yl-ethoxy)-quinazoline-2,4-diamine.

$^1$H NMR (500 MHz, DMSO-$d_6$) δ 7.97 (s, 1H), 7.94 (d, J=8.0 Hz, 1H), 7.89 (m, 2H), 7.61 (m, 1H), 7.51 (m, 3H), 7.29 (bs, 1H), 7.18 (t, J=8.5, 8.0 Hz, 1H), 6.69 (d, J=8.5 Hz, 1H), 6.47 (d, J=8.0 Hz, 1H), 5.95 (bs, 2H), 5.85 (q, J=6.5 Hz, 1H), 1.78 (d, J=6.5 Hz, 3H).

$^{13}$C NMR (500 MHz, DMSO-$d_6$) δ 161.9, 160.6, 155.3, 155.1, 139.5, 132.7, 132.5, 132.1, 128.5, 127.8, 127.6, 126.4, 126.1, 124.6, 123.6, 117.0, 103.5, 101.7, 76.4, 23.7.

MS m/z (ESI) 332 (M+H)$^+$

EXAMPLE 110

5-((R)-1-Naphthalen-1-yl-ethoxy)-quinazoline-2,4-diamine

Step 1: Same as Example 101, Step 1 with (R)-(+)-alpha-methyl-1-naphthalene methanol (990 mg; 5.75 mmol) to afford 1.6 grams of 2-fluoro-6-((R)-1-naphthalen-1-yl-ethoxy)-benzonitrile.

Step 2: Same as Example 101, Step 2 with the previous benzonitrile (425 mg; 1.4 mmol) to afford 137 milligrams of 5-((R)-1-naphthalen-1-yl-ethoxy)-quinazoline-2,4-diamine.

$^1$H NMR (500 MHz, DMSO-$d_6$) δ 8.32 (d, J=8.5 Hz, 1H), 8.0 (d, J=8.0 Hz, 1H), 7.87 (d, J=8.0 Hz, 1H), 7.63 (t, J=8.5, 7.0 Hz, 1H), 7.58 (t, J=8.0, 7.0 Hz, 1H), 7.48 (m, 2H), 7.34 (bs, 1H), 7.11 (d, J=8.5, 8.0 Hz, 1H), 6.70 (d, J=8.5 Hz, 1H), 6.46 (q, J=6.5, 6.0 Hz, 1H), 6.23 (d, J=8.0 Hz, 1H), 6.01 (bs, 2H), 1.83 (d, J=6.0 Hz, 3H).

MS m/z (ESI) 332 (M+H)$^+$

EXAMPLE 111

5-(1-Naphthalen-1-yl-ethoxy)-quinazoline-2,4-diamine

Step 1: Same as Example 101, Step 1 with alpha-methyl-1-naphthalene methanol (1.0 g; 5.8 mmol) to afford 1.3 grams 2-fluoro-6-(1-naphthalen-1-yl-ethoxy)-benzonitrile.

Step 2: Same as Example 101, Step 2 with the previous benzonitrile (330 mg; 1.13 mmol) to obtain 65 milligrams of 5-(1-naphthalen-1-yl-ethoxy)-quinazoline-2,4-diamine.

EXAMPLE 112

5-(Quinolin-3-ylmethoxy)-quinazoline-2,4-diamine

Step 1: Sodium borohydride (240 mg; 6.4 mmol) was added in portions to a solution of 3-Quinoline-carboxaldehyde (910 mg, 5.8 mmol) in methanol at room temperature. Reaction was quenched after 3 hours stirring with 10 mls (aq) sat. NH$_4$Cl. Mixture was extracted with ethyl acetate (3×30 ml). Combined organics were washed with brine and dried over MgSO$_4$. Crude Quinolin-3-ylmethanol was obtained upon filtration and concentration (795 mg; 86% yield).

Step 2: Same as Example 101, Step 1 with quinolin-3-ylmethanol (785 mg; 4.9 mmol) to afford 2-fluoro-6-(quinolin-3-ylmethoxy)-benzonitrile (1.1 g; 81% yield).

Step 3: Same as Example 101, Step 2 with the previous benzonitrile (300 mg; 1.1 mmol) to afford 162 mg of 5-(quinolin-3-ylmethoxy)-quinazoline-2,4-diamine. (46% yield).

$^1$H NMR (400 MHz, DMSO-$d_6$) δ 9.09 (d, J=2.4 Hz, 1H), 8.51 (d, J=2.4 Hz, 1H), 8.03 (m, 2H), 7.80 (m, 1H), 7.65 (m, 1H), 7.36 (t, J=8.4, 8.0 Hz, 1H), 7.21 (bs, 1H), 7.13 (bs, 1H), 6.80 (dd, J=0.8 Hz, 1H), 6.72 (dd, J=0.8 Hz, 1H), 5.95 (bs, 2H), 5.51 (s, 2H).

MS m/z (ESI) 319 (M+H)$^+$

EXAMPLE 113

5-(Quinolin-8-ylmethoxy)-quinazoline-2,4-diamine

Step 1: Sodium borohydride (280 mg, 7.4 mmol) was added in portions to a solution of 3-quinoline-carboxaldehyde (1.06 g, 6.7 mmol) in methanol at room temperature. Reaction was quenched after 3 hours stirring with 10 mL (aq) sat. NH$_4$Cl. Mixture was extracted with ethyl acetate (3×30 ml). Combined organics were washed with brine and dried over MgSO$_4$. Crude material was purified by chromatography using (20-40% EA/Hex gradient) to afford quinolin-8-yl-methanol as an off white solid (800 mg; 75% yield).

Step 2: Same as Example 101, Step 1 with quinolin-8-yl-methanol (785 mg; 4.9 mmol) to afford 2-Fluoro-6-(quinolin-8-ylmethoxy)-benzonitrile (485 mg; 36% yield).

Step 3: The previous benzonitrile (150 mg; 0.5 mmol) and guanidine carbonate (97 mg; 0.5 mmol) were heated at 115° C. in dimethylacetamide for 18 hours, then cooled back to room temperature over night. The reaction mixture was diluted with water, stirred for 45 minutes, filtered, recrystallized with hot ethanol to afford 75 mg of crude material. Material was further purified on flash silica with 5% MeOH/DCM isocratic to afford 5-(quinolin-8-ylmethoxy)-quinazoline-2,4-diamine. (12 mg, 7% yield).

$^1$H NMR (400 MHz, DMSO-$d_6$) δ 9.01 (dd, J=2.0, 1.6 Hz, 1H), 8.46 (dd, J=1.6 Hz, 1H), 8.04 (dd, J=1.2 Hz, 1H), 7.95 (dd, J=1.2 Hz, 1H), 7.65 (m, 2H), 7.58 (bs, 1H), 7.37 (t, J=8.4, 8.0 Hz, 1H), 7.25 (bs, 1H), 6.80 (m, 2H), 6.09 (bs, 2H), 5.89 (s, 2H).

MS m/z (ESI) 318 (M+H)$^+$

EXAMPLE 114

5-[1-(4-Chlorophenyl)-2-methoxyethoxy]-quinazoline-2,4-diamine

Step 1: Equipped with magnetic stirring, (methoxymethyl)-triphenylphosphonium chloride (5.2 g, 15.2 mmol) was suspended in anhydrous tetrahydrofuran at 0° C. under N$_2$ flow. Phenyl lithium, in 1.8 M in di-n-butyl ether (8.4 mL, 15.2 mmol), was added such that the temperature did not exceed 4° C. Mixture remained at 0° C. for 15 minutes, and a solution of 4-chlorobenzonitrile (0.56 g, 4.07 mmol) dissolved in 10 mls of anhydrous tetrahydrofuran was added over 15 minutes. Reaction was warmed to room temperature and continued for another 2 hours. Reaction was quenched with 50 ml of water and mixture was extracted (3×100 mls) with ether. Combined ethers were washed (2×20 mls) brine, and dried over MgSO$_4$. Organics were filtered and concentrated to an amber oil. Oil was loaded on a flash silica gel column and eluted with 10-40% EA/Hex gradient to afford 382 mg of 1-(4-chlorophenyl)-2-methoxy-ethanone. (51% yield).

Step 2: Sodium borohydride (111 mg, 2.9 mmol) was added in portions to a solution of 1-(4-chlorophenyl)-2-methoxy-ethanone (1 g, 6.4 mmol) in methanol at room temperature. After 1 hour, reaction was quenched with 3 mls (aq) sat. $NH_4Cl$. Water was added to dissolve the inorganic and mixture was extracted with ethyl acetate 3×5 ml. Combined organics were washed with brine (2×3 ml) and dried over $MgSO_4$. Crude material was obtained upon filtration and concentration to an amber oil which was purified by flash silica gel and eluted with 10-17% EA/Hex gradient. 1-(4-chlorophenyl)-2-methoxy-ethan-1-ol was obtained as an amber oil (370 mg, 68% yield).

Step 3: A solution of 1-(4-chlorophenyl)-2-methoxy-ethan-1-ol (0.364 g; 1.95 mmol) in dimethylformamide was added to a cooled (0° C.) slurry of sodium hydride (101 mg; 2.54 mmol) in dimethylformamide under nitrogen atmosphere. The reaction mixture was slowly warmed to room temperature, and stirred for 45 minutes. In another vessel, a solution of 2,6-difluorobenzonitrile (271 mg. 1.95 mmol) in dimethylfomamide was chilled to 0° C., and activiated anion was added over 20 minutes. Mixture was then warmed to room temperature over 16 hours. The reaction mixture was poured on crushed ice-water, and mixture was extracted with ethyl acetate (4×75 mls). Combined organics was washed with water (10×20 mls), once with brine, and over $MgSO_4$. The dried organic layer was filtered and concentrated to a yellow oil, which was loaded onto a flash silica gel column. Column was eluted with 10-20% EA/Hex gradient to affored 2-[1-(4-Chlorophenyl)-2-methoxy-ethoxy]-6-fluoro-benzonitrile. (437 mg, 73% yield).

Step 4: The previous benzonitrile (427 mg; 1.4 mmol) and guanidine carbonate (250 mg; 1.4 mmol) were heated at 135° C. in dimethylacetamide for 5 hours, then cooled back to room temperature over night. The reaction mixture was diluted with water, stirred for 30 minutes and filtered. Solids were then triturated with hot ethanol for 45 minutes and cooled back to room temperature with no stirring. Solids filtered and dried to afford 230 milligrams of 5-[1-(4-chlorophenyl)-2-methoxyethoxy]-quinazoline-2,4-diamine.

$^1$H NMR (400 MHz, DMSO-$d_6$) δ 7.58 (bs, 1H), 7.47 (m, 4H), 7.30 (bs, 1H), 7.18 (t, J=8.4, 8.0 Hz, 1H), 6.72 (dd, J=8.0, 7.6 Hz, 1H), 6.28 (d, J=7.6 Hz, 1H), 5.97 (bs, 2H), 5.72 (q, J=3.6 Hz, 1H), 3.77 (m, 2H), 3.33 (s, 3H).

MS m/z (ESI) 346 (M+H)$^+$

EXAMPLE 115

(4-Chlorophenyl)-(2,4-diamino-quinazolin-5-yloxy)-acetic acid

Step 1: Same as Example 101, Step 1 with 4-chloromandelic acid (350 mg; 1.9 mmol) to afford (4-chlorophenyl)-(2-cyano-3-fluorophenoxy)-acetic upon reverse phase chromatography 0-100% acetonitrile/water gradient. (380 mg; 65% yield).

Step 2: Same as Example 101, Step 2 with the previous benzonitrile (190 mg; 0.6 mmol) to afford 35 mg of (4-chlorophenyl)-(2,4-diamino-quinazolin-5-yloxy)-acetic acid. (17% yield).

$^1$H NMR (400 MHz, DMSO-$d_6$) δ 8.79 (s, 1H), 7.69 (m, 2H), 7.47 (m, 3H), 7.40 (m, 2H), 7.00 (s, 2H), 6.86 (d, J=7.6 Hz, 1H), 6.58 (d, J=8.8 Hz, 1H), 5.66 (s, 1H).

MS m/z (ESI) 345 (M+H)$^+$

EXAMPLE 116

5-(Piperidin-4-ylmethoxy)-quinazoline-2,4-diamine hydrochloride

Step 1: 4-Piperidinemethanol (1.5 g; 13.0 mmol) was dissolved in a mixture of dichloromethane and triethylamine (2.7 mL; 19.5 mmol). Di-tert-butyl dicarbonate (3.1 g; 14.3 mmol) was added such that no bumping occurred. After 2.5 hours reaction was poured over dilute acetic acid and organic layer separated. Organics were washed with water, saturated sodium bicarbonate, brine, and dried over $MgSO_4$. Crude material was purified by flash chromatography using 1-5% methanol/DCM gradient to afford 4-hydroxymethyl-piperidine-1-carboxylic acid tert-butyl ester. (2.5 g; 89% yield)

Step 2: Same as Example 101, Step 1 with 4-hydroxymethylpiperidine-1-carboxylic acid tert-butyl ester (1 g; 4.6 mmol) to afford 4-(2-Cyano-3-fluorophenoxymethyl)-piperidine-1-carboxylic acid tert-butyl ester upon chromatography 15-20% ethyl acetate/hexanes gradient. (1.22 g; 81%)

Step 3: Same as Example 101, Step 2 with previous benzonitrile (300 mg; 0.9 mmol) to afford 4-(2,4-diamino-quinazolin-5-yloxymethyl)-piperidine-1-carboxylic acid tert-butyl ester (267 mg; 80% yield).

Step 4: The previous diamino-quinazoline (167 mg; 0.4 mmol) was suspended in dioxane and at room temperature 4M HCl/Dioxane (3 eq.) was added in one. Mixture stirred 6 hours and acidic mixture decanted off. Residue was triturated once with dioxane and twice with diethyl ether. Solids dried to afford 5-(piperidin-4-ylmethoxy)-quinazoline-2,4-diamine hydrochloride as a white solids. (120 mg; 39% yield).

$^1$H NMR (400 MHz, DMSO-$d_6$) δ 12.8 (s, 1H), 9.0 (m, 2H), 8.24 (s, 1H), 7.72 (m, 2H), 7.04 (m, 2H), 4.21 (d, J=6.8 Hz, 2H), 3.8 (bs, 1H), 3.30 (d, 2H), 2.88 (d, 2H), 2.27 (m, 1H), 1.90 (d, 2H), 1.55 (d, 2H).

MS m/z (ESI) 318 (M+H)$^+$

EXAMPLE 117

5-(1-Methyl-piperidin-2-ylmethoxy)-quinazoline-2,4-diamine

Step 1: Same as Example 101, Step 1 with quinolin-3-ylmethanol (785 mg; 4.9 mmol) to afford 2-fluoro-6-(quinolin-3-ylmethoxy)-benzonitrile (1.1 g; 81% yield).

Step 2: The previous benzonitrile (300 mg; 1.2 mmol) and guanidine carbonate (218 mg; 1.2 mmol) were heated at 135° C. in dimethylacetamide for 5 hours, then cooled back to room temperature over night. The reaction mixture was diluted with water, stirred for 30 minutes, and filtered. Mother liquor was extracted with ethyl acetate (6×5 mL), and combined organics washed with water, brine and dried over $MgSO_4$. Crude material was purified by flash chromatography 5-10% methanol/DCM gradient to afford title compound as a foam solid. (95 mg, 28% yield).

$^1$H NMR (400 MHz, DMSO-$d_6$) δ 7.90 (bs, 1H), 7.34 (t, J=8.4, 8.0 Hz, 1H), 7.16 (bs, 1H), 6.77 (dd, J=1.2, 0.8 Hz, 1H), 6.5 (dd, J=0.8 Hz, 1H), 5.91 (bs, 2H), 4.23 (dd, J=3.6 Hz, 1H), 4.04 (dd, J=1.6 Hz, 1H), 2.86 (d, J=10.8 Hz, 1H), 2.21 (s, 3H), 2.16 (m, 1H), 2.09 (m, 1H), 1.75 (s, 1H), 1.72 (s, 1H), 1.62 (m, 2H), 1.48 (m, 1H), 1.28 (m, 1H).

MS m/z (ESI) 288 (M+H)$^+$

EXAMPLE 118

5-((1R,2R,4S)-Bicyclo[2.2.1]hept-2-yloxy)quinazoline-2,4-diamine

Step 1: Same as Example 101, Step 1 with exo-Norborneol (0.6 g; 5.3 mmol) to afford 2-((2R),4S)-bicyclo[2.2.1]hept- 2-yloxy)-6-fluoro-benzonitrile upon chromatography 2.5% ethyl acetate/hexanes isocratic. (1.2 g; 98%)

Step 2: Same as Example 101, Step 2 with the previous benzonitrile (300 mg; 1.3 mmol) to afford 129 milligrams of 5-((2R,4S)-bicyclo[2.2.1]hept-2-yloxy)-quinazoline-2,4-diamine. (37% yield).

$^1$H NMR (400 MHz, DMSO-d$_6$) δ 7.33 (t, J=8.4, 8.0 Hz, 1H), 7.18 (bs, 2H), 6.74 (dd, J=0.8 Hz, 1H), 6.46 (d, J=7.2 Hz, 1H), 5.92 (bs, 2H), 4.42 (d, J=6.4 Hz, 1H), 2.5 (m, 1H), 2.33 (m, 1H), 1.88 (m, 1H), 1.54 (m, 4H), 1.23 (m, 2H), 1.14 (m, 1H).

MS m/z (ESI) 271 (M+H)$^+$

EXAMPLE 119

5-(Adamanta-2-yloxy)quiazoline-2,4-diamine

Step 1: Same as Example 101, Step 1 with 2-adamantanol (0.6 g; 3.4 mmol) to afford 2-(adamantan-2-yloxy)-6-fluoro-benzonitrile as a white solid. (1.0 g; 96%)

Step 2: Same as Example 101, Step 2 with the previous benzonitrile (300 mg; 1.3 mmol) to afford 129 mg of 5-(adamanta-2-yloxy)quiazoline-2,4-diamine. (52% yield).

EXAMPLE 120

5-(1-Cyclopentyl-ethoxy)-quinazoline-2,4-diamine

Step 1: Same as Example 101, Step 1 with 1-cyclopentyl ethanol (0.8 g; 7.0 mmol) to afford 2-(1-cyclopentyl-ethoxy)-6-fluoro-benzonitrile upon chromatography 5% ethyl acetate/hexanes isocratic as a colorless oil. (1.4 g; 88%)

Step 2: Same as Example 101, Step 2 with the previous benzonitrile (300 mg; 1.3 mmol) to afford 100 mg of 5-(1-cyclopentyl-ethoxy)-quinazoline-2,4-diamine. (28% yield).

$^1$H NMR (400 MHz, DMSO-d$_6$) δ 7.33 (t, J=8.4, 8.0 Hz, 1H), 7.28 (bs, 1H), 7.20 (bs, 1H), 6.73 (dd, J=1.2, 0.8 Hz, 1H), 6.56 (d, J=8 Hz, 1H), 5.91 (bs, 2H), 4.5 (m, 1H), 2.22 (m, 1H), 1.82 (m, 1H), 1.72 (m, 1H), 1.58 (m, 4H), 1.32 (m, 5H).

MS m/z (ESI) 273 (M+H)$^+$

EXAMPLE 121

4-(2,4-Diamino-quinazolin-5-yloxymethyl)-piperidin-1-carboxylic acid tert-butyl ester Step 1: 4-Piperidinemethanol (1.5 g; 13.0 mmol) was dissolved in a mixture of dichloromethane and triethylamine (2.7 mL; 19.5 mmol). Di-tert-butyl dicarbonate (3.1 g; 14.3 mmol) was added such that no bumping occurred. After 2.5 hours reaction was poured over dilute acetic acid and organic layer separated. Organics were washed with water, saturated sodium bicarbonate, brine, and dried over MgSO$_4$. Crude material was purified by flash chromatography using 1-5% methanol/DCM gradient to afford 4-hydroxymethyl-piperidine-1-carboxylic acid tert-butyl ester. (2.5 g; 89% yield)

Step 2: Same as Example 101, Step 1 with 4-hydroxymethylpiperidine-1-carboxylic acid tert-butyl ester (1 g; 4.6 mmol) to afford 4-(2-Cyano-3-fluorophenoxymethyl)-piperidine-1-carboxylic acid tert-butyl ester upon chromatography 15-20% ethyl acetate/hexanes gradient. (1.22 g; 81%)

Step 3: Same as Example 101, Step 2 with previous benzonitrile (300 mg; 0.9 mmol) to afford 4-(2,4-diamino-quinazoline-5-yloxymethyl)-piperidin-1-carboxylic acid tert-butyl ester. (267 mg; 80% yield).

$^1$H NMR (400 MHz, DMSO-d$_6$) δ 7.34 (t, J=8.4, 8.0, 1H), 7.17 (bs, 2H), 6.77 (dd, J=0.8, 1H), 6.54 (d, J=8.0, 1H), 5.95 (bs, 2H), 4.00 (d, J=6.4 Hz, 2H), 3.98 (s, 2H), 2.77 (bs, 2H), 2.08 (m, 1H), 1.77 (s, 1H), 1.75 (s, 1H), 1.40 (s, 9H), 1.18 (m, 2H).

MS m/z (ESI) 374 (M+H)$^+$

EXAMPLE 122

5-(Bicyclo[2.2.1]hept-5-en-2-ylmethoxy)-quinazoline-2,4-diamine

Step 1: Same as Example 101, Step 1 with 5-norbornene-2-methanol (0.6 g; 4.8 mmol) to afford 2-(bicyclo[2.2.1]hept-5-en-2-ylmethoxy)-6-fluoro-benzonitrile upon chromatography 2-5% ethyl acetate/hexanes gradient. (950 mg; 81%)

Step 2: Same as Example 101, Step 2 with previous benzonitrile (300 mg; 1.29 mmol) to afford 5-(bicyclo[2.2.1]hept-5-en-2-ylmethoxy)-quinazoline-2,4-diamine. (140 mg; 41% yield).

EXAMPLE 123

(4-Chlorophenyl)-[4-(2,4-diamino-quinazolin-5-yloxymethyl)-piperidin-1-yl]-methanone Step 1: 4-Piperidinemethanol (1.5 g; 13.0 mmol) was dissolved in a mixture of dichloromethane and triethylamine (2.7 mL; 19.5 mmol). Di-tert-butyl dicarbonate (3.1 g; 14.3 mmol) was added such that no bumping occurred. After 2.5 hours reaction was poured over dilute acetic acid and organic layer separated. Organics were washed with water, saturated sodium bicarbonate, brine, and dried over MgSO$_4$. Crude material was purified by flash chromatography using 1-5% methanol/DCM gradient to afford 4-hydroxymethyl-piperidine-1-carboxylic acid tert-butyl ester. (2.5 g; 89% yield).

Step 2: Same as Example 101, Step 1 with 4-hydroxyethylpiperidine-1-carboxylic acid tert-butyl ester (1 g; 4.6 mmol) to afford 4-(2-cyano-3-fluorophenoxymethyl)-piperidine-1-carboxylic acid tert-butyl ester upon chromatography 15-20% ethyl acetate/hexanes gradient. (1.22 g; 81%)

Step 3: Previous benzonitrile (920 mg; 2.8 mmol) was suspended in dioxane and 4M HCl/dioxane (4 eq) at room temperature for 5 hours. Solids were filtered and rinsed twice with dioxane and twice with diethyl ether to afford 2-fluoro-6-(piperidin-4-ylmethoxy)-benzonitrile hydrochloride. (500 mg; 66% yield).

Step 4: Previous benzonitrile (122 mg; 0.5 mmol) and triethylamine (0.2 mL; 1.4 mmol) were stirred at room temperature in the presence of 4-chlorobenzoyl chloride (0.06 mL; 0.5 mmol) for 4 days. Material was quenched with water and adjusted to pH8. Mixture was extracted with ethyl acetate (2×10 mL). Combined organics were washed with brine and dried over MgSO$_4$. Material was purified by flash chromatography using 0.5-2% methanol/DCM gradient to afford 2-[1-(4-chlorobenzoyl)-piperidin-4-ylmethoxy]-6-fluoro-benzonitrile. (116 mg; 69% yield).

Step 5: Same as Example 101, Step 2 with previous benzonitrile (110 mg; 0.3 mmol) to afford (4-chlorophenyl)-[4-(2,4-diamino-quinazolin-5-yloxymethyl)-piperidin-1-yl]-methanone. (75 mg; 59% yield).

$^1$H NMR (400 MHz, DMSO-d$_6$) δ 7.52 (m, 2H), 7.43 (m, 2H), 7.35 (t, J=8.4, 8.0 Hz, 1H), 7.21 (bs, 1H), 7.17 (bs, 1H), 6.77 (dd, J=0.8 Hz, 1H), 6.55 (d, J=7.2 Hz, 1H), 5.95 (bs, 2H), 4.51 (bs, 1H), 4.03 (d, J=6.4 Hz, 2H), 3.59 (bs, 1H), 3.11 (bs,

1H), 2.84 (bs, 1H), 2.22 (m, 1H), 1.87 (bs, 1H), 1.76 (bs, 1H), 1.33 (bs, 1H), 1.30 (bs, 1H).
MS m/z (ESI) 412 (M+H)+

EXAMPLE 124

5-(Bicyclo[2.2.1]hept-2-yloxy)-quinazoline-2,4-diamine

Step 1: Same as Example 101, Step 1 with alpha-Norborneol (0.6 g; 5.3 mmol) to afford 2-(bicyclo[2.2.1]hept-2-yloxy)-6-fluoro-benzonitrile as a crude oil. (1.2 g; 98%)
Step 2: Same as Example 101, Step 2 with previous benzonitrile (300 mg; 1.3 mmol) to afford 5-(bicyclo[2.2.1]hept-2-yloxy)-quinazoline-2,4-diamine. (75 mg; 21% yield).

EXAMPLE 125

5-(1-Cyclohexyl-butoxy)-quinazoline-2,4-diamine

Step 1: Same as Example 101, Step 1 with 1-cyclohexyl-1-butanol (0.6 g; 3.8 mmol) to afford 2-(1-cyclohexyl-butoxy)-6-fluoro-benzonitrile upon flash chromatography (5% diethyl ether/hexanes) as a colorless oil. (0.9 g; 85% yield).
Step 2: Same as Example 101, Step 2 with previous benzonitrile (300 mg; 1.3 mmol) to afford 5-(1-cyclohexyl-butoxy)-quinazoline-2,4-diamine. (115 mg; 33% yield).
$^1$H NMR (400 MHz, DMSO-$d_6$) δ 7.32 (t, J=8.4, 8.0 Hz, 1H), 7.29 (bs, 1H), 7.19 (bs, 1H), 6.72 (dd, J=0.8, 0.4 Hz, 1H), 6.58 (d, J=7.6 Hz, 1H), 5.93 (bs, 2H), 4.46 (q, J=5.6 Hz, 1H), 1.83 (d, 1H), 1.68 (m, 7H), 1.34 (m, 7H), 0.85, (t, J=7.2 Hz, 3H).
MS m/z (ESI) 316 (M+H)+

EXAMPLE 126

5-(1-Cyclohexyl-ethoxy)-quinazoline-2,4-diamine

Step 1: Same as Example 101, Step 1 with quinolin-3-ylmethanol (0.6 g; 4.7 mmol) to afford 2-(1-cyclohexyl-ethoxy)-6-fluoro-benzonitrile as a crude colorless oil. (1.0 g; 83% yield).
Step 2: The previous benzonitrile (300 mg; 1.2 mmol) and guanidine carbonate (218 mg; 1.2 mmol) were heated at 135° C. in dimethylacetamide for 5 hours, then cooled back to room temperature over night. The reaction mixture was diluted with water, stirred for 30 minutes, and decanted. Residue taken up in ethanol and purified by flash chromatography 2-10% methanol/DCM gradient to afford 5-(1-cyclohexyl-ethoxy)-quinazoline-2,4-diamine as a foam solid. (140 mg, 40% yield).

EXAMPLE 127

5-(3-Methyl-oxetan-3-ylmethoxy)-quinazoline-2,4-diamine

Step 1: Same as Example 101, Step 1 with 3-methyl-3-oxetanemethanol (0.6 g; 5.9 mmol) to afford 2-fluoro-6-(3-methyl-oxetan-3-ylmethoxy)-benzonitrile as a white solid. (1.06 g; 81% yield).
Step 2: Same as Example 101, Step 2 with previous benzonitrile (300 mg; 1.4 mmol) to afford 5-(3-methyl-oxetan-3-ylmethoxy)-quinazoline-2,4-diamine. (211 mg; 58% yield).
$^1$H NMR (400 MHz, DMSO-$d_6$) δ 7.54 (bs, 1H), 7.37 (t, J=8.4, 8.0, Hz, 1H), 7.15 (bs, 1H), 6.81 (dd, J=0.8, 0.4 Hz, 1H), 6.58 (d, J=7.2 Hz, 1H), 5.92 (bs, 2H), 4.57 (d, J=6.0 Hz, 2H), 4.48 (d, J=6.0 Hz, 2H), 4.10 (s, 2H), 1.32 (s, 3H).
MS m/z (ESI) 261 (M+H)+

EXAMPLE 128

5-(5-Chloro-2,3-dihydro-benzofuran-3-yloxy)-quinazoline-2,4-diamine

Step 1: (Ref: *J. Org. Chem.* 1955; 20; 813-818) A mixture of 4-chlorophenol (5 g; 39.0 mmol) and chloroacetyl chloride (3.41 mL; 42.8 mmol) was heated to 80° C. for 2.5 hours. Mixture cooled to 30° C. and aluminum chloride (5.2 g; 39.0 mmol) was added over 30 minutes. Mixture heated to 130° C. for 15 hours. Mixture cooled under N2 flow and reaction was quenched with 0.5 g of ice chuncks over 5 minutes. Mixture was treated with 12 mLs of 20% HCl and heated to 60° C. for 15 minutes (fumes generated). Mixture cooled back room temperature and after 30 minutes 2 phases observed. Aqueous phase was extracted, and oil organic layer was triturated with petroleum ether. Petroleum ether was decanted off. Mixture was then heated to 60° C. in 100 mL of benzene and charcoal. Mixture filtered and filtrate was concentrated to a third volume. Another 40 mLs of petroleum ether added and allowed to stand overnight. Mixture was decanted and mother liquor was evaporated to afford 2-chloro-1-(5-chloro-2-hydroxy-phenyl)-ethanone. (5 g; 63% yield).
Step 2: (Ref: *J. Org. Chem.* 1955; 20; 813-818) A solution of 2-chloro-1-(5-chloro-2-hydroxy-phenyl)-ethanone (5 g; 24.4 mmol) in ethanol was heated to reflux for 10 minutes and sodium acetate (2 g; 24.4 mmol) was added to the hot mixture. Mixture continued to reflux an additional 10 minutes, and reaction was stopped and chilled to 0° C. for 20 minutes. Mixture was quenched with water and mixture extracted with ethyl acetate (3×75 mL). Combined organics was washed with brine and dried over MgSO$_4$. Crude material was purified by chromatography using 0-1% methanol/DCM to afford 5-chlorobenzofuran-3-one as a oily solid. (3.0 g; 75% yield).
Step 3: Sodium borohydride (779 mg, 20.6 mmol) was added in portions to a solution of 5-chlorobenzofuran-3-one (2.9 g, 17.2 mmol) in methanol at room temperature. Reaction was quenched after 3 hours stirring with 10 mL (aq) sat. NH$_4$Cl. Mixture was extracted with ethyl acetate (3×30 ml). Combined organics were washed with brine and dried over MgSO$_4$, Crude material was purified by chromatography using (5-20% EA/Hex gradient) to afford 5-chloro-2-hydroxy-benzofuranone. (1.1 g; 38% yield).
Step 4: Same as Example 101, Step 1 with 5-chloro-2-hydroxy-benzofuranone (1.1 g; 6.4 mmol) to afford 2-(5-chloro-2,3-dihydro-benzofuran-3-yloxy)-6-fluoro-benzonitrile as a yellow solid. (1.0 g; 96% yield).
Step 5: The previous benzonitrile (120 mg; 0.4 mmol) and guanidine carbonate (60 mg; 1.2 mmol) were heated at 135° C. in dimethylacetamide for 2.5 hours, then cooled back to room temperature over night. The reaction mixture was loaded onto a flash silica column and eluted with 2-10% methanol/DCM gradient to afford 5-(5-Chloro-2,3-dihydro-benzofuran-3-yloxy)-quinazoline-2,4-diamine as a yellow solid. (33 mg, 25% yield).
$^1$H NMR (400 MHz, DMSO-$d_6$) δ 7.65 (d, J=2.5 Hz, 1H), 7.42 (m, 2H), 7.18 (bs, 1H), 7.03 (d, J=8.8 Hz, 1H), 6.85 (m, 2H), 6.69 (d, J=7.6 Hz, 1H), 6.23 (dd, 2.0 Hz, 1H), 6.08 (bs, 2H), 4.88 (m, 1H), 4.72 (m, 1H).
MS m/z (ESI) 327 (M−H)+

EXAMPLE 129

5-(1-Cyclohexylpropoxy)-quinazoline-2,4-diamine

Step 1: Same as Example 101, Step 1 with 1-cyclohexyl-1-propanol (0.61 g; 4.3 mmol) to afford 2-(1-cyclohexylpropoxy)-6-fluoro-benzonitrile (1 gram) as a colorless oil.

Step 2: Same as Example 101, Step 2 with the previous benzonitrile (303 mg; 1.16 mmol) to afford 74 milligrams of 5-(1-cyclohexylpropoxy)-quinazoline-2,4-diamine.

$^1$H NMR (400 MHz, DMSO-$d_6$) δ 7.32 (m, 2H), 7.22 (bs, 1H), 6.74 (dd, J=8.0, 7.6 Hz, 1H), 6.59 (d, J=8.0 Hz, 1H), 5.94 (bs, 2H), 4.40 (q, J=6.4 Hz, 1H), 1.86 (bd, J=12 Hz, 1H), 1.72 (m, 7H), 1.16 (m, 5H), 0.90 (t, J=7.6 Hz, 3H).

MS m/z (ESI) 301 (M+H)$^+$

EXAMPLE 130

5-((1S,2R,5S)-6,6-Dimethylbicyclo[3.1.1]hept-2-ylmethoxy)quinazoline-2,4-diamine Step 1: Same as Example 101, Step 1 with (−)-cis-Myrtanol (0.6 g; 3.95 mmol) to afford 2-((R)-6,6-Dimethyl-bicyclo[3.1.1]hept-2-ylmethoxy)-6-fluorobenzonitrile as a white solid. (1.0 g; 93% yield).

Step 2: Same as Example 101, Step 2 with previous benzonitrile (301 mg; 1.1 mmol) to afford 5-((R)-6,6-dimethylbicyclo[3.1.1]hept-2-ylmethoxy)-quinazoline-2,4-diamine. (236 mg; 69% yield).

EXAMPLE 131

5-(2,4-Diamino-quinazolin-5-yloxymethyl)-bicyclo[2.2.1]heptane-2,3-diol

4-Methylmorpholine N-oxide (50 mg; 0.42 mmol) was added to a chilled (5° C.) solution of 5-(bicyclo[2.2.1]hept-5-en-2-ylmethoxy)-quinazoline-2,4-diamine (60 mg; 0.21 mmol) (Example 122) in 1/1/1 mixture of methanol/acetone/water over 2 minutes, and Osmium tetroxide (4% aq) was added in one portion. Mixture remained at 5° C. for 45 minutes, and allowed to warm to room temperature then continued for 88 hours. Reaction was quenched with sodium metabisulfite (3 eq) and after 2.5 hours reaction was extracted with ethyl acetate (3×20 mL). Combined organics was washed with water, brine and dried over MgSO$_4$. 5-(2,4-Diamino-quinazolin-5-yloxymethyl)-bicyclo[2.2.1]heptane-2,3-diol was obtained as a white solid. (23 mg; 35% yield).

$^1$H NMR (400 MHz, DMSO-$d_6$) δ 7.35 (m, 1H), 7.25 (bs, 2H), 6.78 (m, 1H), 6.55 (m, 1H), 5.99 (bs, 2H), 4.62 (bs, 2H), 4.01 (m, 2H), 3.83 (m, 1H), 3.54 (bs, 1H), 2.34 (m, 1H), 1.99 (m, 2H), 1.18 (m, 3H), 0.76 (m, 1H).

MS m/z (ESI) 317 (M+H)$^+$

EXAMPLE 132

5-[1-(3,4-Dichlorobenzyl)-piperidin-4-ylmethoxy]-quinazoline-2,4-diamine

Step 1: A mixture of 2-fluoro-6-(piperidin-4-ylmethoxy)-benzonitrile hydrochloride (240 mg; 0.89 mmol) (Example 126, Step 3) was heated with 3,4-dichlorobenzyl chloride (0.15 mL; 2.0 mmol) and triethylamine (0.3 mL; 2.0 mmol) to 50° C. for 16 hours. Reaction was cooled and quenched with dilute HCl and mixture extracted with ethyl acetate (2×20 mL). Combined organics washed with water, saturated sodium bicarbonate, brine and dried over Na$_2$SO$_4$. Crude material was purified by chromatography using 0.5-2% methanol/DCM gradient to afford 2-[1-(3,4-dichloro-benzyl)-piperidin-4-ylmethoxy]-6-fluoro-benzonitrile as a yellow oil. (280 mg; 73% yield).

Step 2: Same as Example 101, Step 2 with previous benzonitrile (273 mg; 0.69 mmol) to afford 5-[1-(3,4-dichlorobenzyl)-piperidin-4-ylmethoxy]-quinazoline-2,4-diamine. (249 mg; 83% yield).

EXAMPLE 133

(2-Chlorophenyl)-[4-(2,4-diamino-quinazolin-5-yloxymethyl)-piperidin-1-yl]-methanone Step 1: A mixture of 2-fluoro-6-(piperidin-4-ylmethoxy)-benzonitrile hydrochloride (200 mg; 0.7 mmol) (Example 126, Step 3) was stirred at room temperature with 2-chlorobenzoyl chloride (129 mg; 0.7 mmol) and triethylamine (0.3 mL; 2.1 mmol) for 16 hours. Reaction was cooled and quenched with dilute HCl and mixture extracted with ethyl acetate (2×20 mL). Combined organics washed with water, saturated sodium bicarbonate, brine and dried over Na$_2$SO$_4$. Crude material was purified by chromatography using 0.5-2% methanol/DCM gradient to afford 2-[1-(2-chloro-benzoyl)-piperidin-4-ylmethoxy]-6-fluoro-benzonitrile as a white solid. (225 mg; 86% yield).

Step 2: Same as Example 101, Step 2 with previous benzonitrile (219 mg; 0.6 mmol) to afford (2-chlorophenyl)-[4-(2,4-diamino-quinazolin-5-yloxymethyl)-piperidin-1-yl]-methanone. (70.6 mg; 29% yield).

EXAMPLE 134

(3-Chlorophenyl)-[4-(2,4-diamino-quinazolin-5-yloxymethyl)-piperidin-1-yl]-methanone Step 1: A mixture of 2-fluoro-6-(piperidin-4-ylmethoxy)-benzonitrile hydrochloride (200 mg; 0.7 mmol) (Example 123, Step 3) was stirred at room temperature with 3-chlorobenzoyl chloride (129 mg; 0.7 mmol) and triethylamine (0.3 mL; 2.1 mmol) for 16 hours. Reaction was cooled and quenched with dilute HCl and mixture extracted with ethyl acetate (2×20 mL). Combined organics washed with water, saturated sodium bicarbonate, brine and dried over Na$_2$SO$_4$. Crude material was purified by chromatography using 0.5-2% methanol/DCM gradient to afford 2-[1-(3-chloro-benzoyl)-piperidin-4-ylmethoxy]-6-fluoro-benzonitrile as a white solid. (200 mg; 77% yield).

Step 2: Same as Example 101, Step 2 with previous benzonitrile (194 mg; 0.5 mmol) to afford (3-chlorophenyl)-[4-(2,4-diamino-quinazolin-5-yloxymethyl)-piperidin-1-yl]-methanone as an off white solid. (169 mg; 82% yield).

EXAMPLE 135

[4-(2,4-Diaminoquinzolin-5-yloxymethyl)piperidin-1-yl]-(3-iodophenyl)methanone

Step 1: A mixture of 2-fluoro-6-(piperidin-4-ylmethoxy)-benzonitrile hydrochloride (200 mg; 0.7 mmol) (Example 123, Step 3) was stirred at room temperature with 3-iodobenzoyl chloride (187 mg; 0.7 mmol) and triethylamine (0.3 mL; 2.1 mmol) for 16 hours. Reaction was cooled and quenched with dilute HCl and mixture extracted with ethyl acetate (2×20 mL). Combined organics washed with water, saturated sodium bicarbonate, brine and dried over Na$_2$SO$_4$. Crude solid was obtained as 2-[1-(3-iodo-benzoyl)-piperidin-4-ylmethoxy]-6-fluoro-benzonitrile. (310 mg; 95% yield).

Step 2: Same as Example 101, Step 2 with previous benzonitrile (296 mg; 0.6 mmol) to afford (3-iodophenyl)-[4-(2,4-diamino-quinazolin-5-yloxymethyl)-piperidin-1-yl]-methanone as an off white solid. (235 mg; 78% yield).

$^1$HNMR (400 MHz, DMSO-$d_6$) δ 7.82 (d, J=7.6 Hz, 1H), 7.73 (s, 1H), 7.40 (d, J=6.4 Hz, 1H), 7.35 (t, J=8.0 Hz, 1H), 7.25 (t, J=8.0 Hz, 1H), 7.18 (br s, 2H), 6.77 (d, J=8.4 Hz, 1H), 6.54 (d, J=8.0 Hz, 1H), 5.94 (br s, 2H), 4.49 (m, 1H), 4.03 (d, J=6.4 Hz, 2H), 3.57 (m, 1H), 3.11 (m, 1H), 2.82 (m, HA 2.21 (m, 1H), 1.87 (m, 1H), 1.75 (m, 1H), 1.32 (m, 2H).

MS m/z (ESI) 505 (M+H)$^+$

EXAMPLE 136

[4-(2,4-Diaminoquinzolin-5-yloxymethyl)piperidin-1-yl]-(4-iodophenyl)methanone

Step 1: A mixture of 2-fluoro-6-(piperidin-4-ylmethoxy)-benzonitrile hydrochloride (200 mg; 0.7 mmol) (Example 123, Step 3) was stirred at room temperature with 4-iodobenzoyl chloride (187 mg; 0.7 mmol) and triethylamine (0.3 mL; 2.1 mmol) for 16 hours. Reaction was cooled and quenched with dilute HCl and mixture extracted with ethyl acetate (2×20 mL). Combined organics washed with water, saturated sodium bicarbonate, brine and dried over $Na_2SO_4$. Crude material was purified by chromatography using 0.5-1% methanol/DCM gradient to afford 2-[1-(4-iodo-benzoyl)-piperidin-4-ylmethoxy]-6-fluoro-benzonitrile as a white solid. (273 mg; 84% yield).

Step 2: Same as Example 101, Step 2 with previous benzonitrile (265 mg; 0.6 mmol) to afford (4-iodophenyl)-[4-(2,4-diamino-quinazolin-5-yloxymethyl)-piperidin-1-yl]-methanone as an off white solid. (238 mg; 79% yield).

$^1$HNMR (400 MHz, DMSO-$d_6$) δ 7.82 (dd, J=8.4, 2 Hz, 2H), 7.34 (t, J=8.0 Hz, 1H), 7.19 (dd, J=6.8, 2 Hz, 2H), 7.18 (br s, 2H), 6.77 (dd, J=8.4, 0.8 Hz, 1H), 6.54 (d, J=7.2 Hz, 1H), 5.94 (br s, 2H), 4.50 (m, 1H), 4.03 (d, J=6.4 Hz, 2H), 3.59 (m, 1H), 3.09 (m, 1H), 2.83 (m, 1H), 2.21 (m, 1H), 1.87 (m, 1H), 1.74 (m, 1H), 1.32 (m, 2H).

MS m/z (ESI) 505 (M+H)$^+$

EXAMPLE 137

[4-(2,4-Diaminoquinzolin-5-yloxymethyl)piperidin-1-yl]-(2-iodophenyl)methanone

Step 1: A mixture of 2-fluoro-6-(piperidin-4-ylmethoxy)-benzonitrile hydrochloride (200 mg; 0.7 mmol) (Example 123, Step 3) was stirred at room temperature with 2-iodobenzoyl chloride (200 mg; 0.7 mmol) and triethylamine (0.3 mL; 2.1 mmol) for 16 hours. Reaction was cooled and quenched with dilute HCl and mixture extracted with ethyl acetate (2×20 mL). Combined organics washed with water, saturated sodium bicarbonate, brine and dried over $Na_2SO_4$. Crude 2-[1-(2-iodo-benzoyl)-piperidin-4-ylmethoxy]-6-fluoro-benzonitrile was obtained as a solid. (320 mg; 98% yield).

Step 2: Same as Example 101, Step 2 with previous benzonitrile (330 mg; 0.71 mmol) to afford (2-iodophenyl)-[4-(2,4-diamino-quinazolin-5-yloxymethyl)-piperidin-1-yl]-methanone as an off white solid. (135 mg; 38% yield).

$^1$HNMR (400 MHz, DMSO-$d_6$) δ 7.88 (dd, J=7.2, 4 Hz, 1H), 7.46 (q, J=7.6 Hz, 1H), 7.35 (t, J=8.4 Hz, 1H), 7.29 (dd, J=7.2, 1.6 Hz, 1H), 7.21 (dd, J=7.2, 1.6 Hz, 1H), 7.16 (m, 2H), 6.77 (d, J=8.4 Hz, 1H), 6.55 (t, J=7.2 Hz, 1H), 5.94 (d, J=7.2 Hz, 2H), 4.59 (t, J=14.0 Hz, 1H), 4.04 (t, J=6.8 Hz, 2H), 3.27 (t, J=12.4 Hz, 1H), 3.06 (m, 1H), 2.83 (m, 1H), 2.02 (m, 1H), 1.91 (d, J=12.8 Hz, 1H), 1.71 (m, 1H), 1.37 (m, 2H).

MS m/z (ESI) 505 (M+H)$^+$

EXAMPLE 138

5-(2-Chlorophenoxymethyl)quinazoline-2,4-diamine

Step 1: 2-Iodophenol (0.11 g, 0.83 mmol) and potassium carbonate were added to a cooled (0° C.) and stirred solution of 2-bromomethyl-6-nitrobenzonitrile [W. T. Ashton and J. B. Hynes, J. Med. Chem, 16, 1233 (1973)] (0.2 g, 0.83 mmol) in dimethylformamide under nitrogen atmosphere. The reaction mixture was stirred at 0° C. for 1.5 hours, then diluted with pyridine (1.5 mL), water, stirred for 1 hour, filtered and dried to yield 210 mg of 2-(2-chlorophenoxymethyl)-6-nitrobenzonitrile.

Step 2: To a cooled (15° C.) and stirred solution of tin (II) chloride (0.78 g, 3.46 mmol) and con. hydrochloric acid (1.5 mL) was added a solution of 2-(2-chlorophenoxymethyl)-6-nitrobenzonitrile (200.0 mg, 0.69 mmol). The reaction mixture was slowly warmed to room temperature and stirred for 3 hours. The reaction mixture was poured on to crushed-ice and potassium hydroxide solution, stirred, filtered and dried to yield 140 mg of 2-amino-6-(2-chlorophenoxymethyl)benzonitrile.

Step 3: 2-Amino-6-(2-chlorophenoxymethyl)benzonitrile (80.0 mg; 0.31 mmol) and chloroformamidine hydrochloride (53.0 mg, 0.46 mmol) were heated at 140° C. in diglyme for 3 hours. The reaction mixture was diluted with water, stirred for 2 hours, filtered, washed with water and dried. Purification by silica gel chromatography (5% methanol in dichloromethane) yielded 50 mg of 5-(2-chlorophenoxymethyl)quinazoline-2,4-diamine.

$^1$H NMR (400 MHz, DMSO-$d_6$) δ 7.44-7.5 (m, 3H), 7.36 (ddd, J=8.0, 8.0, 1.6 Hz, 1H), 7.26 (dd, J=8.4, 1.2 Hz, 1H), 7.21 (dd, J=8.4, 1.2 Hz, 1H), 7.04 (ddd, J=7.6, 7.6, 1.6 Hz, 1H), 6.93 (s, 2H), 6.14 (s, 2H), 5.51 (s, 2H).

MS m/z (ESI) 301 (M+H)$^+$

EXAMPLE 139

5-(4-Chloro-2-methylphenoxymethyl)quinazoline-2,4-diamine

Step 1: 4-Chloro-2-methylphenol (0.12 g, 0.83 mmol) and potassium carbonate were added to a cooled (0° C.) and stirred solution of 2-bromomethyl-6-nitrobenzonitrile [W. T. Ashton and J. B. Hynes, J. Med. Chem, 16, 1233 (1973)] (0.2 g, 0.83 mmol) in dimethylformamide under nitrogen atmosphere. The reaction mixture was stirred at 0° C. for 1.5 hours, then diluted with pyridine (1.5 mL), water, stirred for 1 hour, filtered and dried to yield 155 mg of 2-(4-chloro-2-methylphenoxymethyl)-6-nitrobenzonitrile.

Step 2: To a cooled (15° C.) and stirred solution of tin (II) chloride (0.56 g, 2.48 mmol) and con. hydrochloric acid (2.0 mL) was added a solution of 2-(4-chloro-2-methylphenoxymethyl)-6-nitrobenzonitrile (150.0 mg, 0.5 mmol). The reaction mixture was slowly warmed to room temperature and stirred for 3 hours. The reaction mixture was poured on to crushed-ice and potassium hydroxide solution, stirred, extracted with dichloromethane, filtered and dried to yield 120 mg of 2-amino-6-(4-chloro-2-methylphenoxymethyl)benzonitrile.

Step 3: 2-Amino-6-(4-chloro-2-methylphenoxymethyl)benzonitrile (80.0 mg; 0.29 mmol) and chloroformamidine hydrochloride (51.0 mg, 0.44 mmol) were heated at 140° C. in diglyme for 3 hours. The reaction mixture was diluted with water, stirred for 2 hours, filtered, washed with water and dried. Purification by silica gel chromatography (5% methanol in dichloromethane) yielded 55 mg of the 5-(4-chloro-2-methylphenoxymethyl)quinazoline-2,4-diamine.

$^1$H NMR. (400 MHz, DMSO-d$_6$) δ 7.47 (dd, J=8.6, 6.8 Hz, 1H), 7.16-7.29 (m, 5H), 6.88 (s, 2H), 6.16 (s, 2H), 5.41 (s, 2H), 2.15 (s, 3H).

MS m/z (ESI) 315 (M+H)$^+$

EXAMPLE 140

5-[1-(3-Chlorophenyl)-1-methylethoxy]quinazoline-2,4-diamine

Step 1: Methylmagnesium bromide (3.6 mL, 10.67 mmol, Aldrich, 3 M solution in ether) was added to a cooled (−10° C.) solution of 3-chloroacetophenone (1.5 g, 9.7 mmol) in anhydrous ether slowly over 30 min. After complete addition, the reaction mixture was slowly warmed to room temperature, stirred for 18 hours. Again cooled (−5° C.), than quenched with sat. ammonium chloride solution over 30 min. The reaction mixture was extracted with ether, dried, filtered and concentrated to afford 1.55 g of 2-(3-chlorophenyl)propan-2-ol.

Step 2: A solution of previous alcohol (0.8 g, 4.69 mmol) in dimethylformamide was added to a cooled (0° C.) slurry of sodium hydride (206 mg, 5.16 mmol) in dimethylformamide under nitrogen atmosphere. The reaction mixture was slowly warmed to room temperature, stirred for 1 hour. Again, cooled (0° C.), then a solution of 2,6-difluorobenzonitrile (0.65 g, 4.69 mmol) in dimethylfomamide was added, stirred overnight at room temperature. The reaction mixture was poured on crushed-ice water, stirred, filtered, and dried to yield 490 mg of 2-fluoro-5-[1-(3-chlorophenyl)-1-methylethoxy]benzonitrile.

Step 3: The previous benzonitrile (0.3 g, 1.04 mmol) and guanidine carbonate (0.28 g, 1.55 mmol) were heated at 145° C. in dimethylacetamide for 5 hours. The reaction mixture was diluted with water, stirred for 2 hours, filtered, washed with water and dried. Purification by silica gel chromatography (5-10% methanol in dichloromethane) yielded 88 mg of 5-[1-(3-chlorophenyl)-1-methylethoxy]quinazoline-2,4-diamine.

$^1$H NMR (400 MHz, DMSO-d$_6$) δ 7.52 (d, J=1.2 Hz, 1H), 7.36-7.48 (m, 5H), 7.08 (t, J=8.8 Hz, 1H), 6.7 (d, J=9.6 Hz, 1H), 6.05 (s, 2H), 5.8 (d, J=8.4 Hz, 1H), 1.81 (s, 6H).

MS m/z (ESI) 329 (M+H)$^+$

EXAMPLE 141

5-(4-Chloro-3-methylphenoxymethyl)quinazoline-2,4-diamine

Step 1: 4-Chloro-3-methylphenol (0.12 g, 0.83 mmol) and potassium carbonate were added to a cooled (0° C.) and stirred solution of 2-bromomethyl-6-nitrobenzonitrile [W. T. Ashton and J. B. Hynes, J. Med. Chem, 16, 1233 (1973)] (0.2 g, 0.83 mmol) in dimethylformamide under nitrogen atmosphere. The reaction mixture was stirred at 0° C. for 1.5 hours, then diluted with pyridine (1.5 mL), water, stirred for 1 hour, filtered and dried to yield 145 mg of 2-(4-chloro-3-methylphenoxymethyl)-6-nitrobenzonitrile.

Step 2: To a cooled (15° C.) and stirred solution of tin (II) chloride (0.37 g, 1.65 mmol) and con. hydrochloric acid (2.0 mL) was added a solution of 2-(4-chloro-3-methylphenoxymethyl)-6-nitrobenzonitrile (100.0 mg, 0.33 mmol). The reaction mixture was slowly warmed to room temperature and stirred for 3 hours. The reaction mixture was poured on to crushed-ice and potassium hydroxide solution, stirred, extracted with dichloromethane, filtered and dried to yield 80 mg of 2-amino-6-(4-chloro-3-methylphenoxymethyl)benzonitrile.

Step 3: 2-Amino-6-(4-chloro-3-methylphenoxymethyl) benzonilrile (80.0 mg; 0.29 mmol) and chloroformamidine hydrochloride (51.0 mg, 0.44 mmol) were heated at 140° C. in diglyme for 3 hours. The reaction mixture was diluted with water, stirred for 2 hours, filtered, washed with water and dried. Purification by silica gel chromatography (5% methanol in dichloromethane) yielded 60 mg of 5-(4-chloro-3-methylphenoxymethyl)quinazoline-2,4-diamine.

EXAMPLE 142

5-(2-Methoxybenzyloxy)quinazoline-2,4-diamine

Step 1: To a solution of 2-methoxybenzyl alcohol (1.0 g, 7.2 mmol) in dimethylformamide was added to a cooled (0° C.) slurry of sodium hydride (0.32 g, 7.91 mmol) in dimethylformamide under nitrogen atmosphere. The reaction mixture was slowly warmed to room temperature, stirred for 1 hour. Again, cooled (0° C.), then a solution of 2,6-difluorobenzonitrile (1.0 g, 7.2 mmol) in dimethylfomamide was added, stirred overnight at room temperature. The reaction mixture was poured on crushed ice-water, stirred, filtered and dried to afford 1.55 g of 2-fluoro-5-(2-methoxybenzyloxy) benzonitrile.

Step 2: The previous benzonitrile (0.5 g, 1.94 mmol) and guanidine carbonate (0.53 g, 2.92 mmol) were heated at 145° C. in dimethylacetamide for 5 hours. The reaction mixture was diluted with water, stirred for 2 hours, filtered, washed with water and dried. Purification by silica gel chromatography (5% methanol in dichloromethane) yielded 160 mg of 5-(2-Methoxybenzyloxy)quinazoline-2,4-diamine.

$^1$H NMR (400 MHz, DMSO-d$_6$) δ 7.44 (dd, J=7.2, 1.6 Hz, 1H), 7.31-7.41 (m, 2H), 7.31 (brs, 1H), 7.19 (brs, 1H), 7.10 (dd, J=8.4, 0.8 Hz, 1H), 6.98 (ddd, J=7.6, 7.6, 1.2 Hz, 1H), 6.78 (dd, J=8.4, 0.8 Hz, 1H), 6.68 (dd, J=7.6, 0.8 Hz, 1H), 5.97 (s, 2H), 5.22 (s 2H), 3.85 (s, 3H).

MS m/z (ESI) 298 (M+H)$^+$

EXAMPLE 143

5-(3-Methoxybenzyloxy)quinazoline-2,4-diamine

Step 1: To a solution of 3-methoxybenzyl alcohol (1.0 g, 7.2 mmol) in dimethylformamide was added to a cooled (0° C.) slurry of sodium hydride (0.32 g, 7.91 mmol) in dimethylformamide under nitrogen atmosphere. The reaction mixture was slowly warmed to room temperature, stirred for 1 hour. Again, cooled (0° C.), then a solution of 2,6-difluorobenzonitrile (1.0 g, 7.2 mmol) in dimethylfomamide was added, stirred overnight at room temperature. The reaction mixture was poured on crushed ice-water, stirred, filtered and dried to afford 1.6 g of 2-fluoro-5-(3-methoxybenzyloxy) benzonitrile.

Step 2: The previous benzonitrile (0.5 g, 1.94 mmol) and guanidine carbonate (0.53 g, 2.92 mmol) were heated at 145° C. in dimethylacetamide for 5 hours. The reaction mixture was diluted with water, stirred for 2 hours, filtered, washed with water and dried. Purification by silica gel chromatography (5% methanol in dichloromethane) yielded 110 mg of 5-(3-methoxybenzyloxy)quinazoline-2,4-diamine.

EXAMPLE 144

5-(4-Methoxybenzyloxy)quinazoline-2,4-diamine

Step 1: To a solution of 4-methoxybenzyl alcohol (1.0 g, 7.2 mmol) in dimethylformamide was added to a cooled (0° C.) slurry of sodium hydride (0.32 g, 7.91 mmol) in dimethylformamide under nitrogen atmosphere. The reaction mixture was slowly warmed to room temperature, stirred for 1 hour. Again, cooled (0° C.), then a solution of 2,6-difluorobenzonitrile (1.0 g, 7.2 mmol) in dimethylfomamide was added, stirred overnight at room temperature. The reaction mixture was poured on crushed ice-water, stirred, filtered and dried to afford 1.58 g of 2-fluoro-5-(4-methoxybenzyloxy)benzonitrile.

Step 2: The previous benzonitrile (0.5 g, 1.94 mmol) and guanidine carbonate (0.53 g, 2.92 mmol) were heated at 145° C. in dimethylacetamide for 5 hours. The reaction mixture was diluted with water, stirred for 2 hours, filtered, washed with water and dried. Purification by silica gel chromatography (5% methanol in dichloromethane) yielded 195 mg of 5-(4-Methoxybenzyloxy)quinazoline-2,4-diamine.

EXAMPLE 145

5-[1-(3-Chlorophenyl)cyclohexyloxy]quinazoline-2,4-diamine

Step 1: 3-Chlorophenylmagnesium bromide (3.4 mL, 3.4 mmol) was added to a cooled (−10° C.) solution of cyclohexanone (0.3 g, 3.1 mmol) in anhydrous tetrahydrofuran slowly over 30 min. After complete addition, the reaction mixture was slowly warmed to room temperature, stirred for 18 hours. Again cooled (−5° C.), than quenched with sat. ammonium chloride solution over 30 min. The reaction mixture was extracted with ethyl acetate, dried, filtered and concentrated to afford 550 mg of 1-(3-chlorophenyl)cyclohexanol.

Step 2: A solution of previous alcohol (0.5 g, 2.84 mmol) in dimethylformamide was added to a cooled (0° C.) slurry of sodium hydride (125 mg, 3.12 mmol) in dimethylformamide under nitrogen atmosphere. The reaction mixture was slowly warmed to room temperature, stirred for 1 hour. Again, cooled (0° C.), then a solution of 2,6-difluorobenzonitrile (0.43 g, 3.12 mmol) in dimethylfomamide was added, stirred overnight at room temperature. The reaction mixture was poured on crushed-ice water, stirred. The reaction mixture was extracted with ethyl acetate, dried, filtered and concentrated to afford 720 mg of 2-fluoro-5-[1-(3-chlorophenyl)-cyclohexyloxy]benzonitrile.

Step 3: The previous benzonitrile (0.18 g, 0.55 mmol) and guanidine carbonate (0.15 g, 0.82 mmol) were heated at 145° C. in dimethylacetamide for 6 hours. The reaction mixture was diluted with water, stirred for 2 hours, filtered, washed with water and dried. Purification by silica gel chromatography (5-10% methanol in dichloromethane) followed by recrystallization from ethanol-water yielded 38 mg of 5-[1-(3-chlorophenyl)cyclohexyloxy]quinazoline-2,4-diamine.

$^1$H NMR (400 MHz, DMSO-d$_6$) δ 7.56 (brs, 1H), 7.53 (m, 1H), 7.34-7.47 (m, 4H), 7.02 (t, J=8.0 Hz, 1H), 6.66 (dd, J=8.4, 0.8 Hz, 1H), 5.94 (s, 2H), 5.76 (dd, J=8.4, 0.8 Hz, 1H), 2.45 (m, 1H), 1.85 (m, 2H), 1.5-1.74 (m, 6H), 1.36 (m, 1H).

MS m/z (ESI) 369 (M+H)$^+$

EXAMPLE 146

5-[1-(3-Chlorophenyl)cyclopropoxy]quinazoline-2,4-diamine

Step 1: A solution of methyl 3-chlorobenzoate (0.27 g, 1.58 mmol) and diiodomethane) in anhydrous tetrahydrofuran was added slowly to a vigorously stirred and heated (50° C.) slurry of samarium powder (1.0 g, 6.65 mmol) in tetrahydrofuran over 1.5 hours. After complete addition, the reaction mixture was stirred for 1 hour, than cooled (−10° C.), quenched with 1 N hydrochloric acid over 30 min. The reaction mixture was extracted with ether, dried, filtered and concentrated. Purification by silica gel chromatography (1:1 hexanes in dichloromethane) afford 100 mg of 1-(3-chlorophenyl)cyclopropanol.

Step 2: A solution of previous alcohol (0.09 g, 0.53 mmol) in dimethylformamide was added to a cooled (0° C.) slurry of sodium hydride (23 mg, 0.59 mmol) in dimethylformamide under nitrogen atmosphere. The reaction mixture was slowly warmed to room temperature, stirred for 1 hour. Again, cooled (0° C.), then a solution of 2,6-difluorobenzonitrile (0.11 g, 0.8 mmol) in dimethylfomamide was added, stirred overnight at room temperature. The reaction mixture was poured on crushed-ice water, stirred. The reaction mixture was extracted with ethyl acetate, dried, filtered and concentrated. Purification by silica gel chromatography (20% ethyl acetate in hexanes) yielded 55 mg of 2-fluoro-5-[1-(3-chlorophenyl)cyclopropoxy]benzonitrile.

Step 3: The previous benzonitrile (0.05 g, 0.17 mmol) and guanidine carbonate (0.047 g, 0.26 mmol) were heated at 145° C. in dimethylacetamide for 4 hours. The reaction mixture was diluted with water, stirred for 2 hours, filtered, washed with water and dried. Purification by silica gel chromatography (5-10% methanol in dichloromethane) yielded 30 mg of 5-[1-(3-chlorophenyl)cyclopropoxy]quinazoline-2,4-diamine.

$^1$H NMR (400 MHz, DMSO-d$_6$) δ 7.67 (brs, 2H), 7.55 (m, 1H), 7.26-7.46 (m, 3H), 6.84 (dd, J=8.2, 0.8 Hz, 1H), 6.4 (brs, 2H), 6.35 (m 2H), 1.72 (d, J=7.2 Hz, 4H).

MS m/z (ESI) 327 (M+H)$^+$

EXAMPLE 147

5-(2,4-Difluorophenoxymethyl)quinazoline-2,4-diamine

Step 1: 2,4-Difluorophenol (0.11 g, 0.83 mmol) and potassium carbonate were added to a cooled (0° C.) and stirred solution of 2-bromomethyl-6-nitrobenzonitrile [W. T. Ashton and J. B. Hynes, J. Med. Chem, 16, 1233 (1973)] (0.2 g, 0.83 mmol) in dimethylformamide under nitrogen atmosphere. The reaction mixture was stirred at 0° C. for 1.5 hours, then diluted with pyridine (1.5 mL), water, stirred for 1 hour, filtered and dried. Purification by silica gel chromatography (50% hexanes in dichloromethane) yielded 165 mg of 2-(2,4-difluorophenoxymethyl)-6-nitrobenzonitrile.

Step 2: To a cooled (15° C.) and stirred solution of tin (II) chloride (0.37 g, 1.65 mmol) and con. hydrochloric acid (2.0 mL) was added a solution of 2-(2,4-difluorophemoxymethyl)-6-nitrobenzonitrile (160.0 mg, 0.55 mmol). The reaction mixture was slowly warmed to room temperature and stirred for 3 hours. The reaction mixture was poured on to crushed-ice and potassium hydroxide solution, stirred, extracted with dichloromethane, filtered and dried to yield 131 mg of 2-amino-6-(2,4-difluorophenoxymethyl)benzonitrile.

Step 3: 2-Amino-6-(2,4-difluorophenoxymethyl)benzonitrile (120.0 mg; 0.46 mmol) and chloroformamidine hydrochloride (80.0 mg, 0.70 mmol) were heated at 140° C. in diglyme for 3 hours. The reaction mixture was diluted with water, stirred for 2 hours, filtered, washed with water and dried. Purification by silica gel chromatography (5% methanol in dichloromethane) yielded 72 mg of 5-(2,4-difluorophenoxymethyl)quinazoline-2,4-diamine.

EXAMPLE 148

5-(4-Methoxyphenoxymethyl)quinazoline-2,4-diamine

Step 1: 4-Methoxyphenol (0.1 g, 0.83 mmol) and potassium carbonate were added to a cooled (0° C.) and stirred solution of 2-bromomethyl-6-nitrobenzonitrile [W. T. Ashton and J. B. Hynes, J. Med. Chem, 16, 1233 (1973)] (0.2 g, 0.83 mmol) in dimethylformamide under nitrogen atmosphere. The reaction mixture was stirred at 0° C. for 1.5 hours, then diluted with pyridine (1.5 mL), water, stirred for 1 hour, filtered and dried. Purification by silica gel chromatography (50% hexanes in dichloromethane) yielded 100 mg of 2-(4-methoxyphenoxymethyl)-6-nitrobenzonitrile.

Step 2: To a cooled (15° C.) and stirred solution of tin (II) chloride (0.37 g, 1.65 mmol) and con. hydrochloric acid (2.0 mL) was added a solution of 2-(4-methoxyphenoxymethyl)-6-nitrobenzonitrile (100.0 mg, 0.35 mmol). The reaction mixture was slowly warmed to room temperature and stirred for 3 hours. The reaction mixture was poured on to crushed-ice and potassium hydroxide solution, stirred, extracted with dichloromethane, filtered and dried. Purification by silica gel chromatography (1% methanol in dichloromethane) yielded 65 mg of 2-amino-6-(4-methoxyphenoxymethyl)benzonitrile.

Step 3: 2-Amino-6-(4-methoxyphenoxymethyl)benzonitrile (50.0 mg; 0.2 mmol) and chloroformamidine hydrochloride (34.0 mg, 0.30 mmol) were heated at 140° C. in diglyme for 3 hours. The reaction mixture was diluted with water, stirred for 2 hours, filtered, washed with water and dried. Purification by silica gel chromatography (5% methanol in dichloromethane) yielded 30 mg of 5-(4-methoxyphenoxymethyl)quinazoline-2,4-diamine.

EXAMPLE 149

5-((S)-6-Chloroindan-1-yloxy)quinazoline-2,4-diamine

Step 1: Thionyl chloride (16.31 g, 137.09 mmol) was added to 3-(4-chlorophenyl)propionic acid (3.0 g, 16.25 mmol) at room temperature. The reaction mixture was stirred for 20 hours, then concentrated to afford 3.3 g of 3-(4-chlorophenyl)propionyl chloride.

Step 2: To a cooled (0° C.) slurry of aluminum chloride (2.17 g, 16.25 mmol) in dichloromethane was added dropwise a solution of previous acid chloride (3.3 g, 16.25 mmol) under nitrogen atmosphere. The reaction mixture was slowly warmed to room temperature, than refluxed for 3 hours. Cooled to room temperature, than poured on to crushed-ice water, extracted with dichloromethane, filtered and dried to yield 2.56 g of 6-chloro-1-indanone.

Step 3: To a solution of borane-tetrahydrofuran (1.8 mL, 1.8 mmol, Aldrich, 1 M solution in THF) and (R)-MeCBS (0.3 mL, 0.3 mmol, Aldrich, 1 M solution in toluene) was added a solution of previous indanone (0.5 g, 3.0 mmol) in anhydrous tetrahydrofuran slowly over 30 min at room temperature. After complete addition, the reaction mixture was stirred for 10 min, quenched with 2N hydrochloric acid over 30 min. The reaction mixture was extracted with ether, dried, filtered and concentrated to afford 498 mg of (S)-6-chloroindan-1-ol.

Step 4: A solution of (S)-6-chloroindan-1-ol (0.45 g, 2.67 mmol) in dimethylformamide was added to a cooled (0° C.) slurry of sodium hydride (112 mg, 2.8 mmol) in dimethylformamide under nitrogen atmosphere. The reaction mixture was slowly warmed to room temperature, stirred for 1 hour. Again, cooled (0° C.), then a solution of 2,6-difluorobenzonitrile (0.41 g, 2.94 mmol) in dimethylfomamide was added, stirred overnight at room temperature. The reaction mixture was poured on crushed-ice water, stirred, filtered, and dried. Purification by silica gel chromatography (dichloromethane) yielded 365 mg of 2-fluoro-5-((S)-6-chloroindan-1-yloxy) benzonitrile.

Step 5: The previous benzonitrile (0.34 g, 1.18 mmol) and guanidine carbonate (0.43 g, 2.366 mmol) were heated at 145° C. in dimethylacetamide for 5 hours. The reaction mixture was diluted with water, stirred for 2 hours, filtered, washed with water and dried. Purification by silica gel chromatography (5-10% methanol in dichloromethane) yielded 237 mg of 5-((S)-6-chloroindan-1-yloxy)quinazoline-2,4-diamine.

EXAMPLE 150

5-((R)-6-Chloroindan-1-yloxy)quinazoline-2,4-diamine

Step 1: To a solution of borane-tetrahydrofuran (1.8 mL, 1.8 mmol, Aldrich, 1 M solution in THF) and (S)-MeCBS (0.3 mL, 0.3 mmol, Aldrich, 1 M solution in toluene) was added a solution of 6-chloro-1-indanone (0.5 g, 3.0 mmol) in anhydrous tetrahydrofuran slowly over 30 min at room temperature. After complete addition, the reaction mixture was stirred for 10 min, quenched with 2N hydrochloric acid over 30 min. The reaction mixture was extracted with ether, dried, filtered and concentrated to afford 500 mg of (R)-6-chloroindan-1-ol.

Step 2: A solution of (R)-6-chloroindan-1-ol (0.45 g, 2.67 mmol) in dimethylformamide was added to a cooled (0° C.) slurry of sodium hydride (112 mg, 2.8 mmol) in dimethylformamide under nitrogen atmosphere. The reaction mixture was slowly warmed to room temperature, stirred for 1 hour. Again, cooled (0° C.), then a solution of 2,6-difluorobenzonitrile (0.41 g, 2.94 mmol) in dimethylfomamide was added, stirred overnight at room temperature. The reaction mixture was poured on crushed-ice water, stirred, filtered, and dried to yield 450 mg of 2-fluoro-5-((R)-6-chloroindan-1-yloxy)benzonitrile.

Step 3: The previous benzonitrile (0.36 g, 1.25 mmol) and guanidine carbonate (0.45 g, 2.5 mmol) were heated at 145° C. in dimethylacetamide for 5 hours. The reaction mixture was diluted with water, stirred for 2 hours, filtered, washed with water and dried. Purification by silica gel chromatography (5-10% methanol in dichloromethane) yielded 248 mg of 5-((R)-6-chloroindan-1-yloxy)quinazoline-2,4-diamine.

EXAMPLE 151

5-(Bicyclo[2.2.1]hept-2-ylmethoxy)quinazoline-2,4-diamine

Step 1: A solution of 2-norbornane methanol (1.3 g, 10.3 mmol) in dimethylformamide was added to a cooled (0° C.) slurry of sodium hydride (450 mg, 11.33 mmol) in dimethylformamide under nitrogen atmosphere. The reaction mixture was slowly warned to room temperature, stirred for 1 hour. Again, cooled (0° C.), then a solution of 2,6-difluorobenzonitrile (1.58 g, 11.33 mmol) in dimethylfomamide was added, stirred overnight at room temperature. The reaction mixture was poured on crushed-ice water, stirred, filtered. The reaction mixture was extracted with ethyl acetate, dried, filtered and concentrated. Purification by silica gel chromatography (1:1 hexanes in dichloromethane) yielded 986 mg of 2-fluoro-5-(bicyclo[2.2.1]hept-2-ylmethoxy)benzonitrile.

Step 2: The previous benzonitrile (0.9 g, 3.67 mmol) and guanidine carbonate (1.32 g, 7.34 mmol) were heated at 145° C. in dimethylacetamide for 4.5 hours. The reaction mixture was diluted with water, stirred for 2 hours, filtered, washed with water and dried. Purification by silica gel chromatography (5-10% methanol in dichloromethane) yielded 330 mg of 5-(bicyclo[2.2.1]hept-2-ylmethoxy)quinazoline-2,4-diamine.

$^1$H NMR (400 MHz, DMSO-d$_6$) δ 7.37 (m, 1H), 7.23 (s, 2H), 6.76 (m, 1H), 6.59 (m, 1H), 5.96 (s, 2H), 3.78-4.1 (m, 2H), 0.9-2.4 (m, 11H).

MS m/z (ESI) 285 (M+H)$^+$

EXAMPLE 152

5-((1S,2S,5S)-6,6-Dimethylbicyclo[3.1.1]hept-2-ylmethoxy) quinazoline-2,4-diamine Step 1: A solution of (1S,2S,5S)-(−)-myrtanol (1.0 g, 6.48 mmol) in dimethylformamide was added to a cooled (0° C.) slurry of sodium hydride (310 mg, 7.78 mmol) in dimethylformamide under nitrogen atmosphere. The reaction mixture was slowly warmed to room temperature, stirred for 1 hour. Again, cooled (0° C.), then a solution of 2,6-difluorobenzonitrile (1.08 g, 7.78 mmol) in dimethylfomamide was added, Stirred overnight at room temperature. The reaction mixture was poured on crushed-ice water, stirred. The reaction mixture was extracted with ethyl acetate, dried, filtered and concentrated. Purification by silica gel chromatography (1:1 hexanes in dichloromethane) yielded 1.36 g of 2-fluoro-5-((1S,2S,5S)-6,6-dimethylbicyclo[3.1.1]hept-2-ylmethoxy) benzonitrile.

Step 2: The previous benzonitrile (1.1 g, 4.03 mmol) and guanidine carbonate (1.45 g, 8.05 mmol) were heated at 145° C. in dimethylacetamide for 6 hours. The reaction mixture was diluted with water, stirred for 2 hours, filtered, washed with water and dried. Recrystallization from ethanol-water yielded 995 mg of 5-((1S,2S,5S)-6,6-dimethylbicyclo [3.1.1] hept-2-ylmethoxy)quinazoline-2,4-diamine $^1$H NMR (400 MHz, DMSO-d$_6$) δ 7.33 (t, J=7.6 Hz, 1H), 7.18 (s, 2H), 6.76 (dd, J=8.4, 0.8 Hz, 1H), 6.53 (dd, J=7.2, 0.8 Hz, 1H), 5.93 (s, 2H), 3.91 (m, 2H), 2.52 (m, 1H), 2.07 (m, 1H), 1.7-1.93 (m, 5H), 1.43 (m, 2H), 1.23 (s, 3H), 0.87 (s, 3H).

MS m/z (ESI) 314 (M+H)$^+$

EXAMPLE 153

5-[1-(4-Fluorophenyl)-2-methoxymethoxyethoxy] quinazoline-2,4-diamine

Step 1: To a stirred solution of 4-fluoromandelic acid (1.0 g, 5.88 mmol) in tetrahydrofuran was added lithium aluminum hydride (0.47 g, 12.34 mmol). The reaction mixture was refluxed for 1.5 hours. The reaction mixture was cooled (0° C.), quenched with sat. ammonium chloride solution, filtered, concentrated to yield 0.87 g of 1-(4-fluorophenyl)ethane-1,2-diol.

Step 2: To a stirred solution of previous diol (0.62 g, 4.0 mmol) and trimethyl orthoformate (0.85 g, 8.0 mmol) in dichloromethane was added camphorsulfonic acid. The reaction mixture was stirred for 20 hours, cooled (−78° C.), than diisobutylaluminum hydride (27.0 mL, 40 mmol) was slowly added over 10 min. The reaction mixture was stirred at −78° C. for 30 minutes, warmed to 0° C., poured on to 2N sodium hydroxide solution. Extracted with ether, washed with brine, dried, and concentrated. Purification by silica gel chromatography (5-10% acetone in dichloromethane) yielded 0.38 g of 1-(4-fluorophenyl)-2-methoxymethoxyethanol.

Step 3: A solution of previous alcohol (0.37 g, 1.85 mmol) in dimethylformamide was added to a cooled (0° C.) slurry of sodium hydride (81 mg, 2.03 mmol) in dimethylformamide under nitrogen atmosphere. The reaction mixture was slowly warmed to room temperature, stirred for 1 hour. Again, cooled (0° C.), then a solution of 2,6-difluorobenzonitrile (0.26 g, 1.85 mmol) in dimethylfomamide was added, stirred overnight at room temperature. The reaction mixture was poured on crushed ice-water, stirred for 4 hours. Extracted with ether, washed with brine, dried, and concentrated Purification by silica gel chromatography (1-5% acetone in dichloromethane) yielded 0.25 g of 2-fluoro-6-[1-(4-fluorophenyl)-2-methoxymethoxyethoxy]benzonitrile.

Step 4: The previous benzonitrile (0.24 g, 0.75 mmol) and guanidine carbonate (0.27 g, 1.5 mmol) were heated at 145° C. in dimethylacetamide for 6 hours. The reaction mixture was cooled, diluted with water, stirred for 1.5 h, filtered, dried. Purification by silica gel chromatography (5-10% methanol in dichloromethane) yielded 24 mg of 5-[1-(4-fluorophenyl)-2-methoxymethoxyethoxy]quinazoline-2,4-diamine.

$^1$H NMR (400 MHz, DMSO-d$_6$) δ 7.58 (brs, 1H), 7.51 (m, 2H), 7.33 (brs, 1H), 7.2 (m, 3H), 6.7 (dd, J=8.8, 0.8 Hz, 2H), 6.32 (d, J=8.0 Hz, 1H), 5.94 (s, 2H), 5.75 (m, 1H), 4.63 (m, 2H), 3.89 (m, 2H), 3.19 (s, 3H).

MS m/z (ESI) 359 (M+H)$^+$

EXAMPLE 154

2-(2,4-Diaminoquinazolin-5-yloxy)-2-(4-fluorophenyl)ethanol hydrochloride

Step 1: To a stirred solution of 4-fluoromandelic acid (1.0 g, 5.88 mmol) in tetrahydrofuran was added lithium aluminum hydride (0.47 g, 12.34 mmol). The reaction mixture was refluxed for 1.5 hours. The reaction mixture was cooled (0° C.), quenched with sat. ammonium chloride solution, filtered, concentrated to yield 0.87 g of 1-(4-fluorophenyl)ethane-1, 2-diol.

Step 2: To a stirred solution of previous diol (0.62 g, 4.0 mmol) and trimethyl orthoformate (0.85 g, 8.0 mmol) in dichloromethane was added camphorsulfonic acid. The reaction mixture was stirred for 20 hours, cooled (−78° C.), than diisobutylaluminum hydride (27.0 mL, 40 mmol) was slowly added over 10 min. The reaction mixture was stirred at −78° C. for 30 minutes, warmed to 0° C., poured on to 2N sodium hydroxide solution. Extracted with ether, washed with brine, dried, and concentrated. Purification by silica gel chromatography (5-10% acetone in dichloromethane) yielded 0.38 g of 1-(4-fluorophenyl)-2-methoxymethoxyethanol.

Step 3: A solution of previous alcohol (0.37 g, 1.85 mmol) in dimethylformamide was added to a cooled (0° C.) slurry of sodium hydride (81 mg, 2.03 mmol) in dimethylformamide under nitrogen atmosphere. The reaction mixture was slowly warmed to room temperature, stirred for 1 hour. Again, cooled (0° C.), then a solution of 2,6-difluorobenzonitrile (0.26 g, 1.85 mmol) in dimethylfomamide was added, stirred overnight at room temperature. The reaction mixture was poured on crushed ice-water, stirred for 4 hours. Extracted with ether, washed with brine, dried, and concentrated Purification by silica gel chromatography (1-5% acetone in dichloromethane) yielded 0.25 g of 2-fluoro-6-[1-(4-fluorophenyl)-2-methoxymethoxyethoxy]benzonitrile.

Step 4: The previous benzonitrile (0.24 g, 0.75 mmol) and guanidine carbonate (0.27 g, 1.5 mmol) were heated at 145° C. in dimethylacetamide for 6 hours. The reaction mixture was cooled, diluted with water, stirred for 1.5 h, filtered, dried. Purification by silica gel chromatography (5-10% methanol in dichloromethane) yielded 230 mg of 2-(2,4-diaminoquinazolin-5-yloxy)-2-(4-fluorophenyl)ethanol.

Step 5: To a stirred solution of previous diamine (0.06 g, 0.17 mmol) in methanol was added 4N hydrochloric acid in dioxane (0.6 mL, 2.4 mmol). The reaction mixture was heated at 60° C. for 2 hours. The reaction mixture was concentrated, recrystallized from methanol-ether to yield 30.3 mg of 2-(2, 4-diaminoquinazolin-5-yloxy)-2-(4-fluorophenyl)ethanol hydrochloride.

$^1$H NMR (400 MHz, DMSO-d$_6$) δ 12.54 (s, 1H), 9.11 (s, 1H), 8.76 (s, 1H), 7.7 (brs, 1H), 7.5 (m, 3H), 7.21 (t, J=8.8 Hz, 2H), 6.94 (d, J=8.0 Hz, 1H), 6.74 (d, J=8.0 Hz, 1H), 5.69 (m, 1H), 5.57 (s, 1H), 3.84 (m, 2H).

MS m/z (ESI) 315 (M+H)$^+$

EXAMPLE 155

5-(2-Benzo[1,3]dioxol-5-yl-2-methoxymethoxyethoxy)quinazoline-2,4-diamine

Step 1: To a stirred solution of 3,4-(methylenedioxy)mandelic acid (1.5 g, 7.65 mmol) in tetrahydrofuran was added lithium aluminum hydride (0.58 g, 15.29 mmol). The reaction mixture was refluxed for 1.5 hours. The reaction mixture was cooled (0° C.), quenched with sat. ammonium chloride solution, filtered, concentrated to yield 1.3 g of 1-benzo[1,3]dioxol-5-yl-ethane-1,2-diol Step 2: To a stirred solution of previous diol (1.05 g, 5.76 mmol) and trimethyl orthoformate (1.22 g, 11.53 mmol) in dichloromethane was added camphorsulfonic acid. The reaction mixture was stirred for 20 hours, concentrated. Again dissolved in dichloromethane, cooled (−78° C.), than diisobutylaluminum hydride (11.5 mL, 17.3 mmol) was slowly added over 10 min. The reaction mixture was stirred at −78° C. for 30 minutes, warmed to 0° C., poured on to 2N sodium hydroxide solution. Extracted with ether, washed with brine, dried, and concentrated.

Purification by silica gel chromatography (3-10% acetone in dichloromethane) yielded 0.27 g of 2-benzo[1,3]dioxol-5-yl-2-methoxymethoxyethanol.

Step 3: A solution of previous alcohol (0.26 g, 1.15 mmol) in dimethylformamide was added to a cooled (0° C.) slurry of sodium hydride (51 mg, 1.26 mmol) in dimethylformamide under nitrogen atmosphere. The reaction mixture was slowly warmed to room temperature, stirred for 1 hour. Again, cooled (0° C.), then a solution of 2,6-difluorobenzonitrile (0.18 g, 1.26 mmol) in dimethylfomamide was added, stirred overnight at room temperature. The reaction mixture was poured on crushed ice-water, stirred for 4 hours. Extracted with ether, washed with brine, dried, and concentrated. Purification by silica gel chromatography (1-3% acetone in dichloromethane) yielded 0.36 g of 2-(2-benzo[1,3]dioxol-5-yl-2-methoxymethoxyethoxy)-6-fluorobenzonitrile.

Step 4: The previous benzonitrile (0.35 g, 1.01 mmol) and guanidine carbonate (0.4 g, 2.23 mmol) were heated at 150° C. in dimethylacetamide for 6 hours. The reaction mixture was cooled, diluted with water, stirred for 1.5 h, filtered, dried. Purification by silica gel chromatography (5-10% methanol in dichloromethane) yielded 310 mg of 5-(2-benzo[1,3]dioxol-5-yl-2-methoxymethoxyethoxy)quinazoline-2, 4-diamine.

$^1$H NMR (400 MHz, DMSO-d$_6$) δ 7.3 (m, 3H), 7.05 (d, J=1.6 Hz, 1H), 6.95 (m, 2H), 6.77 (dd, J=8.4, 0.8 Hz, 1H), 6.55 (d, J=7.6 Hz, 1H), 6.03 (m, 2H), 5.92 (s, 2H), 5.03 (dd, J=7.2, 4.0 Hz, 1H), 4.6 (m, 2H), 4.26 (m, 2H), 3.27 (s, 3H).

MS m/z (ESI) 385 (M+H)$^+$

EXAMPLE 156

5-(1-Benzo[1,3]dioxol-5-yl-2-methoxymethoxyethoxy)quinazoline-2,4-diamine

Step 1: To a stirred solution of 3,4-(methylenedioxy)mandelic acid (1.5 g, 7.65 mmol) in tetrahydrofuran was added lithium aluminum hydride (0.58 g, 15.29 mmol). The reaction mixture was refluxed for 1.5 hours. The reaction mixture was cooled (0° C.), quenched with sat, ammonium chloride solution, filtered, concentrated to yield 1.3 g of 1-benzo[1,3]dioxol-5-yl-ethane-1,2-diol.

Step 2: To a stirred solution of previous diol (1.05 g, 5.76 mmol) and trimethyl orthoformate (1.22 g, 11.53 mmol) in dichloromethane was added camphorsulfonic acid. The reaction mixture was stirred for 20 hours, concentrated. Again dissolved in dichloromethane, cooled (−78° C.), than diisobutylaluminum hydride (11.5 mL, 17.3 mmol) was slowly added over 10 min. The reaction mixture was stirred at −78° C. for 30 minutes, warmed to 0° C., poured on to 2N sodium hydroxide solution. Extracted with ether, washed with brine, dried, and concentrated. Purification by silica gel chromatography (3-10% acetone in dichloromethane) yielded 0.4 g of 1-benzo[1,3]dioxol-5-yl-2-methoxymethoxyethanol.

Step 3: A solution of previous alcohol (0.19 g, 0.84 mmol) in dimethylformamide was added to a cooled (0° C.) slurry of sodium hydride (37 mg, 0.92 mmol) in dimethylformamide under nitrogen atmosphere. The reaction mixture was slowly warmed to room temperature, stirred for 1 hour. Again, cooled (0° C.), then a solution of 2,6-difluorobenzonitrile (0.13 g, 0.92 mmol) in dimethylfomamide was added, stirred overnight at room temperature. The reaction mixture was poured on crushed ice-water, stirred for 4 hours. Extracted with ether, washed with brine, dried, and concentrated Purification by silica gel chromatography (1-3% acetone in dichloromethane) yielded 0.27 g of 2-fluoro-5-(1-benzo[1,3]dioxol-5-yl-2-methoxymethoxyethoxy)benzonitrile.

Step 4: The previous benzonitrile (0.27 g, 0.77 mmol) and guanidine carbonate (0.3 g, 1.69 mmol) were heated at 150° C. in dimethylacetamide for 6 hours. The reaction mixture was cooled, diluted with water, stirred for 1.5 h, filtered, dried. Purification by silica gel chromatography (5-10% methanol in dichloromethane) yielded 210 mg of the 5-(1-benzo[1,3]dioxol-5-yl-2-methoxymethoxyethoxy) quinazoline-2,4-diamine.

$^1$H NMR (400 MHz, DMSO-d$_6$) δ 7.61 (brs, 1H), 7.37 (brs, 1H), 7.22 (t, J=8.0 Hz, 1H) 7.04 (d, J=1.6 Hz, 1H), 6.97 (dd, J=8.0, 1.6 Hz, 1H), 6.89 (d, J=7.6 Hz, 1H), 6.71 (dd, J=8.4, 0.8 Hz, 1H), 6.39 (d, J=7.6 Hz, 1H), 6.0 (m, 2H), 5.92 (s, 4H), 5.63 (dd, J=6.8, 3.6 Hz, 1H), 4.64 (m, 2H), 3.85 (m, 2H), 3.22 (s, 3H).

MS m/z (ESI) 385 (M+H)$^+$

EXAMPLE 157

2-(2,4-Diaminoquinazolin-5-yloxy)-1-phenyl-ethanol

Step 1: To a cooled (0° C.) and stirred solution of 1-phenylethane-1,2-diol (1.0 g, 7.24 mmol) and tert-butyldimethylsilyl chloride (1.1 g, 7.24 mmol) in dichloromethane was added imidazole (0.74 g, 10.86 mmol). The reaction mixture was slowly warmed to room temperature and stirred for 20 hours. The reaction mixture was washed with water, dried, and concentrated to yield 1.8 g of 2-(tert-butyldimethylsilanyloxy)-1-phenylethanol.

Step 2: The previous alcohol (0.55 g, 2.19 mmol), 2-fluoro-6-hydmxybenzonitrile (0.55 g, 2.19 mmol) and triphenylphosphene (0.61 g, 2.33 mmol) in tetrahydrofuran was added diisopropylazodicarbxylate (0.47 g, 2.33 mmol). The reaction mixture was stirred at room temperature for 20 hours, concentrated. Purification by silica gel chromatography (1:1 dichloromethane in hexanes) yielded 290 mg of 2-[2-(tert-butyldimethylsilanyloxy)-1-phenylethoxy]-6-fluorobenzonitrile.

Step 3: The previous benzonitrile (0.15 g, 0.4 mmol) and guanidine carbonate (0.11 g, 0.61 mmol) were heated at 145° C. in dimethylacetamide for 4 hours. The reaction mixture was diluted with water, stirred for 2 hours, extracted with ethyl acetate, washed with brine and dried gave 135.0 mg of light yellow solid. Recrystallization from dichloromethane gave 19 mg of 2-(2,4-diaminoquinazolin-5-yloxy)-1-phenylethanol.

$^1$H NMR (400 MHz, DMSO-$d_6$) δ 7.49 (d, J=7.2 Hz, 2H), 7.14-7.41 (m, 6H), 6.76 (dd, J=8.4, 0.8 Hz, 1H), 6.52 (d, J=7.2 Hz, 1H), 5.89 (s, 2H), 5.06 (m, 1H), 4.25 (dd, J=9.8, 3.6 Hz, 1H), 4.1 (dd, J=9.6, 7.2 Hz, 1H).

MS m/z (ESI) 298 (M+H)$^+$

EXAMPLE 158

5-(3-Chlorophenoxymethyl)quinazoline-2,4-diamine

Step 1: 3-Chlorophenol (0.27 g, 2.07 mmol) and potassium carbonate were added to a cooled (0° C.) and stirred solution of 2-bromomethyl-6-nitrobenzonitrile [W. T. Ashton and J. B. Hynes, J. Med. Chem, 16, 1233 (1973)] (0.5 g, 2.07 mmol) in dimethylformamide under nitrogen atmosphere. The reaction mixture was stirred at 0° C. for 1.5 hours, then diluted with pyridine (1.5 mL), water, stirred for 1 hour, filtered and dried. Purification by silica gel chromatography (1:1 dichloromethane in hexanes) yielded 185 mg of 2-(3-chlorophenoxymethyl)-6-nitrobenzonitrile.

Step 2: To a cooled (15° C.) and stirred solution of tin (II) chloride (0.4 g, 1.73 mmol) and conc. hydrochloric acid (1.2 mL) was added a solution of 2-(3-chlorophenoxymethyl)-6-nitrobenzonitrile (100.0 mg, 0.35 mmol). The reaction mixture was slowly warmed to room temperature and stirred for 3 hours. The reaction mixture was poured on to crushed-ice and potassium hydroxide solution, stirred, extracted with dichloromethane, filtered and dried. Purification by silica gel chromatography (dichloromethane) yielded 38 mg of 2-amino-6-(3-chlorophenoxymethyl)benzonitrile.

Step 3: 2-Amino-6-(3-chlorophenoxymethyl)benzonitrile (35.0 mg; 0.14 mmol) and chloroformamidine hydrochloride (23.0 mg, 0.2 mmol) were heated at 140° C. in diglyme for 3 hours. The reaction mixture was diluted with water, stirred for 2 hours, filtered, washed with water and dried. Purification by silica gel chromatography (5-10% methanol in dichloromethane) yielded 20 mg of 5-(3-chlorophenoxymethyl)quinazoline-2,4-diamine.

$^1$H NMR (400 MHz, DMSO-$d_6$) δ 7.5 (dd, J=8.6, 7.2 Hz, 1H), 7.37 (t, J=8.4 Hz, 1H), 7.27 (m, 2H), 7.21 (d, J=6.0 Hz, 1H), 7.07-7.12 (m, 2H), 6.91 (s, 2H), 6.27 (s, 2H), 5.44 (s, 2H).

MS m/z (ESI) 301 (M+H)$^+$

EXAMPLE 159

5-(2-Iodophenoxymethyl)quinazoline-2,4-diamine

Step 1: 2-Iodophenol (0.18 g, 0.87 mmol) and potassium carbonate were added to a cooled (0° C.) and stirred solution of 2-bromomethyl-6-nitrobenzonitrile [W. T. Ashton and J. B. Hynes, J. Med. Chem, 16, 1233 (1973)] (0.2 g, 0.83 mmol) in dimethylformamide under nitrogen atmosphere. The reaction mixture was stirred at 0° C. for 1.5 hours, then diluted with pyridine (1.5 mL), water, stirred for 1 hour, filtered and dried to yield 280 mg of 2-(2-iodophenoxymethyl)-6-nitrobenzonitrile.

Step 2: To a cooled (15° C.) and stirred solution of tin (II) chloride (0.74 g, 3.29 mmol) and con. hydrochloric acid (2.0 mL) was added a solution of 2-(2-iodophenoxymethyl)-6-nitrobenzonitrile (250.0 mg, 0.66 mmol). The reaction mixture was slowly warmed to room temperature and stirred for 3 hours. The reaction mixture was poured on to crushed-ice and potassium hydroxide solution, stirred, extracted with dichloromethane, filtered and dried. Purification by silica gel chromatography (dichloromethane) yielded 80 mg of 2-amino-6-(2-iodophenoxymethyl)benzonitrile.

Step 3: 2-Amino-6-(2-iodophenoxymethyl)benzonitrile (120.0 mg; 0.34 mmol) and chloroformamidine hydrochloride (59.0 mg, 0.51 mmol) were heated at 140° C. in diglyme for 3 hours. The reaction mixture was diluted with water, stirred for 2 hours, filtered, washed with water and dried. Purification by silica gel chromatography (5% methanol in dichloromethane) yielded 65 mg of 5-(2-Iodophenoxymethyl)quinazoline-2,4-diamine.

$^1$H NMR (400 MHz, DMSO-$d_6$) δ 7.82 (d, J=7.6 Hz, 1H), 7.49 (t, J=7.6 Hz, 1H), 7.42 (t, J=7.2 Hz, 1H), 7.27 (m, 3H), 6.86 (m, 3H), 6.16 (s, 2H), 5.47 (s, 2H).

MS m/z (ESI) 393 (M+H)$^+$

EXAMPLE 160

1-(4-Chlorophenyl)-2-(2,4-diaminoquinazolin-5-yloxy)ethanol

Step 1: To a stirred solution of 4-chloromandelic acid (10.0 g, 53.6 mmol) in methanol was added sulfuric acid (3.1 mL, 58.9 mmol). The reaction mixture was refluxed for 6 hours. The reaction mixture was concentrated, neutralized with sat. sodium carbonate solution, extracted with ether, washed with brine, dried, and concentrated. Purification by silica gel chromatography (40% ethyl acetate in hexanes) yielded 10.0 g of (4-chlorophenyl)hydroxyacetic acid methyl ester.

Step 2: To a cooled (10° C.) and stirred solution of previous ester (10.0 g, 49.8 mmol) in methanol-water (9:1) was added sodium borohydride (2.45 g, 65.0 mmol). The reaction mixture was slowly warmed to room temperature and stirred for 1.5 hours. The reaction mixture was quenched with sat. ammonium chloride solution, concentrated. Extracted with ethyl acetate, washed with brine, dried, and concentrated to yield 8.0 g of 1-(4-chlorophenyl)ethane-1,2-diol.

Step 3: To a cooled (0° C.) and stirred solution of previous diol (7.9 g, 45.77 mmol) and tert-butyldimethylsilyl chloride (7.24 g, 48.06 mmol) in dichloromethane was added imidazole (4.53 g, 68.65 mmol). The reaction mixture was slowly warmed to room temperature and stirred for 20 hours. The reaction mixture was washed with water, dried, and concentrated to yield 11.8 g of 2-(tert-butyldimethylsilanyloxy)-1-(4-chlorophenyl)ethanol.

Step 4: To a stirred solution of previous alcohol (7.5 g, 26.14 mmol), 2-fluoro-6-hydroxybenzonitrile (3.41 g, 24.84 mmol) and triphenylphosphine (8.91 g, 33.99 mmol) in tetrahydrofuran was added diisopropylazodicarbxylate (6.87 g, 33.99 mmol). The reaction mixture was stirred at room temperature for 20 hours, concentrated. Purification by silica gel chromatography (1:1 dichloromethane in hexanes) yielded 8.8 g of 2-[2-(tert-butyldimethylsilanyloxy)-1-(4-chlorophenyl)ethoxy]-6-fluorobenzonitrile.

Step 5: The previous benzonitrile (5.0 g, 12.32 mmol) and guanidine carbonate (5.55 g, 30.79 mmol) were heated at. 150° C. in dimethylacetamide for 7 hours. The reaction mixture was diluted with dichloromethane, filtered. The filtrte was purified by silica gel chromatography (10% methanol in dichloromethane) yielded 1.12 g. Recrystallization of the solid in hot ethanol-water (1:1) solution gave 680.0 mg of 1-(4-chlorophenyl)-2-(2,4-diaminoquinazolin-5-yloxy)ethanol.

$^1$H NMR (400 MHz, DMSO-$d_6$) δ 7.52 (d, J=8.4 Hz, 2H), 7.44 (m, 3H), 7.32 (t, J=8.4 Hz, 1H), 7.24 (s, 1H), 6.76 (dd, J=8.4, 0.8 Hz, 1H), 6.53 (dd, J=8.0, 0.8 Hz, 1H), 5.99 (d, J=4.8 Hz, 1H), 5.92 (s, 2H), 5.08 (m, 1H), 4.25 (dd, J=9.6, 3.6 Hz, 1H), 4.11 (dd, J=9.6, 7.2 Hz, 1H).

MS m/z (EST) 331 (M+H)$^+$

HPLC 99.9% pure.

Anal. Calcd for $C_{16}H_{15}ClN_4O_2$: C, 58.10; H, 4.57; N, 16.94. Found: C, 56.24; H, 4.79; N, 16.20 (Anal. Calcd for $C_{16}H_{15}ClN_4O_2$ with 0.6% $H_2O$: C, 56.26; H, 4.78; N, 16.40).

EXAMPLE 161

1-(3-Chlorophenyl)-2-(2,4-diaminoquinazolin-5-yloxy)ethanol

Step 1: To a stirred solution of 1-chloro-3-vinyl-benzene (1.0 g, 7.2 mmol) and potassium permanganate (1.14 g, 7.2 mmol) in methanol was added 1N sodium hydroxide. The reaction mixture was stirred at room temperature for 1.5 hours. Filtered, extracted with dichloromethane, washed with sodium bicarbonate, brine, dried. Purification by silica gel chromatography (5% methanol in dichloromethane) yielded 250.0 mg of 1-(3-chlorophenyl)ethane-1,2-diol.

Step 2: To a cooled (0° C.) and stirred solution of previous diol (0.25 g, 1.45 mmol) and tert-butyldimethylsilyl chloride (0.22 g, 1.45 mmol) in dichloromethane was added imidazole (0.15 g, 2.17 mmol). The reaction mixture was slowly warmed to room temperature and stirred for 20 hours. The reaction mixture was washed with water, dried, and concentrated to yield 0.4 g of 2-(tert-butyldimethylsilanyloxy)-1-(3-chlorophenyl)ethanol.

Step 3: To a stirred solution of previous alcohol (0.38 g, 1.32 mmol), 2-fluoro-6-hydroxybenzonitrile (0.15 g, 1.06 mmol) and triphenylphosphene (0.45 g, 1.72 mmol) in tetrahydrofuran was added diisopropylazodicarbxylate (0.35 g, 1.72 mmol). The reaction mixture was stirred at room temperature for 20 hours, concentrated. Purification by silica gel chromatography (1:1 dichloromethane in hexanes) yielded 0.45 g of 2-[2-(tert-butyldimethylsilanyloxy)-1-(3-chlorophenyl)ethoxy]-6-fluorobenzonitrile.

Step 4: The previous benzonitrile (0.43 g, 1.06 mmol) and guanidine carbonate (0.29 g, 1.59 mmol) were heated at 145° C. in dimethylacetamide for 6 hours. The reaction mixture was concentrated, purified by silica gel chromatography (5-10% methanol in dichloromethane) yielded 0.1 g. Recrystallization of the solid in methanol-dichloromethane solution gave 12.0 mg of 1-(3-chlorophenyl)-2-(2,4-diaminoquinazolin-5-yloxy)ethanol.

$^1$H NMR (400 MHz, DMSO-$d_6$) δ 7.56 (d, J=1.6 Hz, 1H), 7.46 (dd, J=7.2, 1.2 Hz, 1H), 7.18-7.42 (m, 5H), 6.76 (dd, J=8.2, 0.8 Hz, 1H), 6.54 (dd, J=7.8, 0.8 Hz, 1H), 6.03 (d, J=4.8 Hz, 1H), 5.89 (s, 2H), 5.09 (m, 1H), 4.27 (dd, J=9.8, 3.6 Hz, 1H), 4.11 (dd, J=9.8, 7.6 Hz, 1H).

MS m/z (ESI) 331 (M+H)$^+$

EXAMPLE 162

5-[(S)-1-(3-Chlorophenyl)ethoxy]quinazolin-2,4-diamine

Step 1: To a solution of borane-tetrahydrofuran (77.6 mL, 77.62 mmol, Aldrich, 1 M solution in THF) and (R)-MeCBS (12.9 mL, 12.9 mmol, Aldrich, 1M solution in toluene) was added a solution of 3-chloroacetophenone (20.0 g, 129.37 mmol) in anhydrous tetrahydrofuran slowly over 30 min at room temperature. After complete addition, the reaction mixture was stirred for 10 min, quenched with 2N hydrochloric acid over 30 min. The reaction mixture was extracted with ether, dried, filtered and concentrated to afford 20.8 g of (S)-1-(3-chlorophenyl)ethanol as a viscous liquid.

Step 2: A solution of (S)-1-(3-chlorophenyl)ethanol (20.4 g, 130.26 mmol) in dimethylformamide was added to a cooled (0° C.) slurry of sodium hydride (5.73 g, 143.29 mmol) in dimethylformamide under nitrogen atmosphere. The reaction mixture was slowly warmed to room temperature, stirred for 1 hour. Again, cooled (0° C.), then a solution of 2,6-difluorobenzonitrile (19.93 g, 143.29 mmol) in dimethylfomamide was added, stirred overnight at room temperature. The reaction mixture was poured on crushed ice-water, stirred, extracted with ether, dried, filtered and concentrated to afford 30.0 g of 2-fluoro-5-[(S)-1-(3-chlorophenyl)ethoxy]benzonitrile.

Step 3: The previous benzonitrile (29.15 g, 105.73 mmol) and guanidine carbonate (41.91 g, 232.6 mmol) were heated at 150° C. in dimethylacetamide for 8 hours. The reaction mixture was diluted with water, stirred for 2 hours, filtered, washed with water and dried. The white solid was recrystallized from methanol-water to yield 24.9 g of 5-(S)-1-(3-chloro-phenyl)-ethoxy-quinazoline-2,4-diamine. M.p. 224-225° C.

$^1$H NMR (400 MHz, DMSO-$d_6$) δ 7.55 (d, J=1.6 Hz, 1H), 7.31-7.43 (m, 5H), 7.23 (t, J=7.2 Hz), 6.74 (dd, J=8.4, 0.8 Hz, 1H), 6.39 (d, J=8.0 Hz, 1H), 6.05 (s, 2H), 5.7 (q, J=6.4 Hz, 1H), 1.69 (d, J=6.4 Hz, 3H).

$^{13}$C NMR (100.5 MHz, DMSO-$d_6$) δ 161.87, 160.62, 155.17, 155.03, 144.7, 133.31, 132.18, 130.64, 127.68, 125.72, 124.42, 117.16, 103.33, 101.62, 75.37, 23.68.

MS m/z (ESI) 315 (M+H)$^+$

FT-IR 3509, 3392, 3350, 3308, 3164, 3134, 1642, 1590, 1569, 1550, 1499, 1443, 1252, 1075, 814 cm$^{-1}$.

HPLC 99.9% pure (99.0% ee).

Axial. Calcd for $C_{16}H_{15}ClN_4O$: C, 61.05; H, 4.80; N, 17.80. Found: C, 60.94; H, 5.06; N, 17.57.

EXAMPLE 163

2-(2,4-Diaminoquinazolin-5-yloxy)-1-(4-trifluoromethylphenyl)ethanol

Step 1: To a stirred solution of 4-trifluoromethylmandelic acid (1.0 g, 4.54 mmol) in tetrahydrofuran was added lithium aluminum hydride (0.36 g, 9.54 mmol). The reaction mixture was refluxed for 1.5 hours. The reaction mixture was quenched with sat. ammonium chloride solution, filtered, concentrated to yield 0.8 g of 1-(4-trifluoromethylphenyl)ethane-1,2-diol.

Step 2: To a cooled (0° C.) and stirred solution of previous diol (0.4 g, 1.94 mmol) and tert-butyldimethylsilyl chloride (0.32 g, 2.13 mmol) in dichloromethane was added imidazole (0.19 g, 2.91 mmol). The reaction mixture was slowly warmed to room temperature and stirred for 20 hours. The reaction mixture was washed with water, dried, and concentrated to yield 0.62 g of 2-(tert-butyldimethylsilanyloxy)-1-(4-trifluoromethylphenyl)ethanol.

Step 3: To a stirred solution of previous alcohol (0.62 g, 1.93 mmol), 2-fluoro-6-hydroxybenzonitrile (0.21 g, 1.55 mmol) and triphenylphosphene (0.66 g, 2.52 mmol) in tetrahydrofuran was added diisopropylazodicarbxylate (0.51 g, 2.52 mmol). The reaction mixture was stirred at room temperature for 20 hours, concentrated. Purification by silica gel chromatography (1:1 dichloromethane in hexanes) yielded 0.73 g of 2-[2-(tert-butyldimethylsilanyloxy)-1-(4-trifluoromethylphenyl)ethoxy]-6-fluorobenzonitrile.

Step 4: The previous benzonitrile (0.5 g, 1.14 mmol) and guanidine carbonate (0.31 g, 1.71 mmol) were heated at 120° C. in dimethylacetamide for 4 hours than at 145° C. for 1 hour. The reaction mixture was cooled, diluted with water, extracted with ethyl acetate, washed with brine, dried and concentrated. Purification by silica gel chromatography (10% methanol in dichloromethane) yielded 0.13 g. Recrystallization of the solid in hot ethanol-water (1:1) solution gave 34.0 mg of 1-(4-trifluoromethylphenyl)-2-(2,4-diaminoquinazolin-5-yloxy)ethanol.

$^1$H NMR (400 MHz, DMSO-d$_6$) δ 7.74 (m, 4H), 7.43 (s, 1H), 7.31 (t, J=8.0 Hz, 1H), 7.21 (s, 1H), 6.76 (dd, J=8.4, 1.2 Hz, 1H), 6.53 (dd, J=8.0, 0.8 Hz, 1H), 6.11 (d, J=4.8 Hz, 1H), 5.9 (s, 2H), 5.18 (m, 1H), 4.3 (dd, J=9.6, 3.6 Hz, 1H), 4.15 (dd, J=9.8, 7.2 Hz, 1H).

MS m/z (ESI) 366 (M+H)$^+$

EXAMPLE 164

2-(4-Chlorophenyl)-2-(2,4-diaminoquinazolin-5-yloxy)ethanol hydrochloride

Step 1: To a cooled (4° C.) and stirred solution of 2-bromo-4-chloroacetophenone (5.0 g, 21.41 mmol) and glacial acetic acid (2.8 mL, 49.25 mmol) in acetonitrile was added triethylamine (6.1 mL, 44.97 mmol). The reaction mixture was warmed to room temperature, than refluxed for 3 hours. The reaction mixture was extracted with ether, acetate, washed with 1N hydrochloric acid, brine, dried, and concentrated to yield 4.1 g of acetic acid 2-(4-chlorophenyl)-2-oxo-ethyl ester.

Step 2: To a cooled (5° C.) and stirred solution of previous ester (1.4 g, 6.58 mmol) in methanol-water (3:1) was added potassium carbonate (0.46 g, 3.3 mmol). The reaction mixture was slowly warmed to room temperature, stirred for 0.5 hours. Extracted with ethyl acetate, washed with brine, dried to yield 1.0 g of 1-(4-chlorophenyl)-2-hydroxyethanone.

Step 3: To a cooled (0° C.) and stirred solution of previous alcohol (0.95 g, 5.57 mmol) and diisopropylethylamine (1.44 g, 11.14 mmol) in dichloromethane was added chloromethyl methyl ether (2.24 g, 27.8 mmol). The reaction mixture was slowly warmed to room temperature, stirred for 20 hours. Extracted with dichloromethane, washed with water, brine, dried. Purification by silica gel chromatography (15-20% ethyl acetate in hexanes) yielded 0.96 g of 1-(4-chlorophenyl)-2-methoxymethoxyethanone.

Step 4: To a cooled (0° C.) and stirred solution of previous ketone (0.2 g, 0.92 mmol) in methanol-water (9:1) was added sodium borohydride (0.052 g, 1.38 mmol). The reaction mixture was stirred for 0.5 hours. The reaction mixture was quenched with sat. ammonium chloride solution, concentrated. Extracted with ether, washed with brine, dried, and concentrated to yield 0.2 g of 1-(4-chlorophenyl)-2-methoxymethoxyethanol.

Step 5: A solution of previous alcohol (0.17 g, 0.78 mmol) in dimethylformamide was added to a cooled (0° C.) slurry of sodium hydride (35 mg, 0.86 mmol) in dimethylformamide under nitrogen atmosphere. The reaction mixture was slowly warmed to room temperature, stirred for 1 hour. Again, cooled (0° C.), then a solution of 2,6-difluorobenzonitrile (0.12 g, 0.86 mmol) in dimethylfomamide was added, stirred overnight at room temperature. The reaction mixture was poured on crushed ice-water, stirred for 4 hours. Extracted with ether, washed with brine, dried, and concentrated Purification by silica gel chromatography (1% acetone in dichloromethane) yielded 0.2 g of 2-[1-(4-chlorophenyl)-2-methoxymethoxyethoxy]-6-fluorobenzonitrile.

Step 6: The previous benzonitrile (0.2 g, 0.58 mmol) and guanidine carbonate (0.23 g, 1.28 mmol) were heated at 150° C. in dimethylacetamide for 6 hours. The reaction mixture was cooled, diluted with water, stirred for 1.5 h, filtered, dried. Purification by silica gel chromatography (10% methanol in dichloromethane) yielded 167 mg of 5-[1-(4-chlorophenyl)-2-methoxymethoxyethoxy]quinazoline-2,4-diamine.

Step 7: To a stirred solution of previous diamine (0.08 g, 0.21 mmol) in methanol was added 4N hydrochloric acid in dioxane (0.27 mL, 1.1 mmol). The reaction mixture was stirred at room temperature for 1 hour, than heated at 50° C. for 0.5 hours. The reaction mixture was concentrated, recrystallized from methanol-ether to yield 68.2 mg of 2-(2,4-diaminoquinazolin-5-yloxy)-2-(4-chlorophenyl)ethanol hydrochloride.

$^1$H NMR (400 MHz, DMSO-d$_6$) δ 12.44 (s, 1H), 9.1 (s, 1H), 8.75 (s, 1H), 7.7 (brs, 1H), 7.54 (t, J=8.0 Hz, 1H), 7.45 (m, 3H), 6.94 (d, J=8.0 Hz, 1H), 6.82 (t, J=7.6 Hz, 1H), 6.72 (d, J=8.4 Hz, 1H), 6.69 (m, 1H), 5.57 (m, 1H), 3.77-3.92 (m, 2H).

MS m/z (ESI) 333 (M+H)$^+$

EXAMPLE 165

5-[2-(4-Chlorophenyl)-2-methoxyethoxy]quinazoline-2,4-diamine

Step 1: To a stirred solution of 4-chloromandelic acid (10.7 g, 57.3 mmol) in methanol was added sulfuric acid (3.3 mL, 63.1 mmol). The reaction mixture was refluxed for 6 hours. The reaction mixture was concentrated, neutralized with sat. sodium carbonate solution, extracted with ether, washed with brine, dried, and concentrated. Purification by silica gel chromatography (40% ethyl acetate in hexanes) yielded 10.3 g of (4-chlorophenyl)hydroxyacetic acid methyl ester.

Step 2: To a stirred solution of previous methyl ester (1.0 g, 4.98 mmol) and silver carbonate (2.74 g, 9.96 mmol) in acetone was added methyl iodide (2.12 g, 14.95 mmol). The reaction mixture was stirred for 72 hours. The reaction mixture was filtered, concentrated to yield 0.82 g of (4-chlorophenyl)methoxyacetic acid methyl ester.

Step 3: To a stirred solution of previous ester (0.8 g, 3.73 mmol) in methanol-water (9:1) was added sodium borohydride (0.28 g, 7.45 mmol). The reaction mixture was stirred at room temperature and stirred for 4 hours. The reaction mixture was quenched with sat. ammonium chloride solution, concentrated. Extracted with ethyl acetate, washed with brine, dried, and concentrated. Purification by silica gel chromatography (10% acetone in dichloromethane) yielded 0.32 g of 2-(4-chlorophenyl)-2-methoxyethanol.

Step 4: A solution of previous alcohol (0.32 g, 1.71 mmol) in dimethylformamide was added to a cooled (0° C.) slurry of sodium hydride (75 mg, 1.88 mmol) in dimethylformamide under nitrogen atmosphere. The reaction mixture was slowly warmed to room temperature, stirred for 1 hour. Again, cooled (0° C.), then a solution of 2,6-difluorobenzonitrile (2.57 g, 1.5 mmol) in dimethylfomamide was added, stirred overnight at room temperature. The reaction mixture was poured on crushed ice-water, stirred for 2 hours, filtered, washed with water, dried to afford 0.28 g of 2-(4-chlorophenyl)-2-methoxyethoxy-6-fluorobenzonitrile.

Step 5: The previous benzonitrile (0.27 g, 0.88 mmol) and guanidine carbonate (0.32 g, 1.77 mmol) were heated at 145° C. in dimethylacetamide for 5 hours. The reaction mixture was cooled, diluted with water, stirred for 1.5 h, filtered, dried. Purification by silica gel chromatography (10% methanol in dichloromethane) yielded 225 mg of 5-[2-(4-chlorophenyl)-2-methoxyethoxy]quinazoline-2,4-diamine.

$^1$H NMR (400 MHz, DMSO-$d_6$) δ 7.49 (s, 4H), 7.37 (s, 1H), 7.32 (1, J=8.4 Hz, 1H), 6.77 (dd, J=8.4, 0.8 Hz, 1H), 6.55 (d, J=7.2 Hz, 1H), 5.98 (s, 2H), 4.8 (dd, J=7.4, 3.6 Hz, 1H), 4.3 (dd, J=10.2, 3.6 Hz, 1H), 4.19 (dd, J=10.2, 7.2 Hz, 1H), 3.28 (s, 3H).

MS m/z (ESI) 345 (M+H)$^+$

EXAMPLE 166

5-(2-Methoxy-1-phenylethoxy)quinazoline-2,4-diamine

Step 1: To a stirred solution of 2-methoxy-1-phenylethanone (1.0 g, 6.66 mmol) in ethanol was added sodium borohydride (0.28 g, 7.32 mmol). The reaction mixture was stirred at room temperature for 1 hour. The reaction mixture was quenched with sat. ammonium chloride solution, concentrated. Extracted with ethyl acetate, washed with brine, dried, and concentrated to yield 0.8 g of 2-methoxy-1-phenylethanol.

Step 2: A solution of previous alcohol (0.6 g, 3.94 mmol) in dimethylformamide was added to a cooled (0° C.) slurry of sodium hydride (0.16 g, 3.94 mmol) in dimethylformamide under nitrogen atmosphere. The reaction mixture was slowly warmed to room temperature, stirred for 1 hour. Again, cooled (0° C.), then a solution of 2,6-difluorobenzonitrile (0.60 g, 4.34 mmol) in dimethylfomamide was added, stirred overnight at room temperature. The reaction mixture was poured on crushed ice-water, stirred for 2 hours. Extracted with ethyl acetate, washed with water, dried. Purification by silica gel chromatography (dichloromethane) yielded 290 mg of 2-methoxy-1-phenylethoxy-6-fluorobenzonitrile.

Step 3: The previous benzonitrile (0.29 g, 1.07 mmol) and guanidine carbonate (0.39 g, 2.14 mmol) were heated at 145° C. in dimethylacetamide for 5 hours. The reaction mixture was cooled, diluted with water, stirred for 1.5 h, filtered, dried. Recrystallization from hot ethanol-water yielded 260 mg of 5-(2-Methoxy-2-phenylethoxy)quinazoline-2,4-diamine.

$^1$H NMR (400 MHz, DMSO-$d_6$) δ 7.61 (s, 1H), 7.45 (d, J=7.6 Hz, 2H), 7.26-7.4 (m, 4H), 7.16 (t, J=8.0 Hz, 1H), 6.69 (dd, J=8.4, 0.8 Hz, 1H), 6.29 (d, J=8.0 Hz, 1H), 5.94 (s, 2H), 5.68 (dd, J=6.8, 3.2 Hz, 1H), 3.73-3.81 (m, 2H), 3.34 (s, 3H).

MS m/z (ESI) 312 (M+H)$^+$

EXAMPLE 167

2-(2,4-Diaminoquinazolin-5-yloxy)-1-(4-fluorophenyl)ethanol

Step 1: To a stirred solution of 4-fluoromandelic acid (1.0 g, 5.88 mmol) in tetrahydrofuran was added lithium aluminum hydride (0.47 g, 12.34 mmol). The reaction mixture was refluxed for 1.5 hours. The reaction mixture was quenched with sat. ammonium chloride solution, filtered, concentrated to yield 0.87 g of 1-(4-fluorophenyl)ethane-1,2-diol.

Step 2: To a cooled (0° C.) and stirred solution of previous diol (0.3 g, 1.92 mmol) and tert-butyldimethylsilyl chloride (0.32 g, 2.13 mmol) in dichloromethane was added imidazole (0.19 g, 2.9 mmol). The reaction mixture was slowly warmed to room temperature and stirred for 20 hours. The reaction mixture was washed with water, dried, and concentrated to yield 0.48 g of 2-(tert-butyldimethylsilanyloxy)-1-(4-fluorophenyl)ethanol.

Step 3: To a stirred solution of previous alcohol (0.47 g, 1.74 mmol), 2-fluoro-6-hydroxybenzonitrile (0.19 g, 1.39 mmol) and triphenylphosphene (0.59 g, 2.26 mmol) in tetrahydrofuran was added diisopropylazodicarbxylate (0.46 g, 2.26 mmol). The reaction mixture was stirred at room temperature for 20 hours, concentrated. Purification by silica gel chromatography (1:1 dichloromethane in hexanes) yielded 0.52 g of 2-[2-(tert-butyldimethylsilanyloxy)-1-(4-fluorophenyl)ethoxy]-6-fluorobenzonitrile.

Step 4: The previous benzonitrile (0.3 g, 0.77 mmol) and guanidine carbonate (0.28 g, 1.54 mmol) were heated at 145° C. in dimethylacetamide for 5 hours. The reaction mixture was cooled, diluted with water, stirred for 1.5 h, filtered, dried. Purification by silica gel chromatography (10% methanol in dichloromethane) yielded 0.11 g. Recrystallization of the solid in hot ethanol-water (1:1) solution gave 42.0 mg of 1-(4-fluorophenyl)-2-(2,4-diaminoquiriazolin-5-yloxy)ethanol.

$^1$H NMR (400 MHz, DMSO-$d_6$) δ 7.54 (dd, J=7.8, 6.0 Hz, 2H), 7.44 (m, 1H), 7.31 (t, J=8.4 Hz, 1H), 7.2 (m, 3H), 6.76 (dd, J=8.4, 0.8 Hz, 1H), 6.52 (dd, J=8.0, 0.8 Hz, 1H), 5.93 (m, 1H), 5.9 (s, 2H), 5.07 (m, 1H), 4.24 (dd, J=9.8, 4.0 Hz, 1H), 4.1 (dd, J=9.6, 7.2 Hz, 1H).

MS m/z (ESI) 316 (M+H)$^+$

EXAMPLE 168

1,1-Bis-(4-chlorophenyl)-3-(2,4-diaminoquinazolin-5-yloxy)butan-1-ol

Step 1: To a cooled (−5° C.) and stirred solution of 4-methyloxetan-2-one (0.5 g, 5.81 mmol) in anhydrous tetrahydrofuran was added a solution of 4-chlorophenylmagnesium bromide (5.8 mL, 5.8 mmol) slowly over 10 min. After complete addition, the reaction mixture was warmed to room temperature, stirred for 1 hour. Again cooled to (0° C.), quenched with sat. ammonium chloride solution. The reaction mixture was extracted with ether, dried, filtered and concentrated. Purification by silica gel chromatography (30% ethyl acetate in hexanes) yielded 320 mg of 1,1-bis-(4-chlorophenyl)butane-1,3-diol.

Step 2: A solution of previous diol (0.3 g, 0.96 mmol) in dimethylformamide was added to a cooled (0° C.) slurry of sodium hydride (0.06 g, 1.51 mmol) in dimethylformamide under nitrogen atmosphere. The reaction mixture was slowly warmed to room temperature, stirred for 1 hour. Again, cooled (0° C.), then a solution of 2,6-difluorobenzonitrile (0.21 g, 1.51 mmol) in dimethylformamide was added, stirred overnight at room temperature. The reaction mixture was poured on crushed ice-water, stirred, extracted with ethyl acetate, dried, filtered and concentrated. Purification by silica gel chromatography (1:1 dichloromethane in hexanes) yielded 118 mg of 3-(2-cyano-3-fluoro-phenoxy)-1,1-bis-(4-chloro-phenyl)-butan-1-ol.

Step 3: The previous benzonitrile (011 g, 0.26 mmol) and guanidine carbonate (0.09 g, 0.51 mmol) were heated at 145° C. in dimethylacetamide for 5 hours. The reaction mixture was diluted with water, stirred for 2 hours, filtered, washed with water and dried. Purification by silica gel chromatography (5-10% methanol in dichloromethane) yielded 70.1 mg of 1,1-bis-(4-chlorophenyl)-3-(2,4-diaminoquinazolin-5-yloxy)butan-1-ol.

$^1$H NMR (400 MHz, DMSO-d$_6$) δ 7.33-7.5 (m, 6H), 7.18-7.32 (m, 4H), 7.07 (brs, 1H), 6.68 (dd, J=8.4, 0.8 Hz, 1H), 6.2 (d, J=7.6 Hz, 1H), 6.09 (s, 1H), 5.9 (s, 2H), 4.64 (m, 1H), 2.93 (dd, J=14.2, 5.2 Hz, 1H), 2.67 (dd, J=14.2, 6.0 Hz, 1H), 1.19 (d, J=6.0 Hz, 1H).

MS m/z (ESI) 471 (M+H)$^+$

EXAMPLE 169

5-(2-Benzo[1,3]dioxol-5-yl-2-methoxyethoxy)quinazoline-2,4-diamine hydrochloride Step 1: To a stirred solution of 3,4-(methylenedioxy)mandelic acid (1.5 g, 7.65 mmol) in tetrahydrofuran was added lithium aluminum hydride (0.58 g, 15.29 mmol). The reaction mixture was refluxed for 1.5 hours. The reaction mixture was cooled (0° C.), quenched with sat. ammonium chloride solution, filtered, concentrated to yield 1.3 g of 1-benzo[1,3]dioxol-5-yl-ethane-1,2-diol Step 2: To a stirred solution of previous diol (1.05 g, 5.76 mmol) and trimethyl orthoformate (1.22 g, 11.53 mmol) in dichloromethane was added camphorsulfonic acid. The reaction mixture was stirred for 20 hours, concentrated. Again dissolved in dichloromethane, cooled (−78° C.), than diisobutylaluminum hydride (11.5 mL, 17.3 mmol) was slowly added over 10 min. The reaction mixture was stirred at −78° C. for 30 minutes, warmed to 0° C., poured on to 2N sodium hydroxide solution. Extracted with ether, washed with brine, dried, and concentrated. Purification by silica gel chromatography (3-10% acetone in dichloromethane) yielded 0.27 g of 2-benzo[1,3]dioxol-5-yl-2-methoxymethoxyethanol.

Step 3: A solution of previous alcohol (0.26 g, 1.15 mmol) in dimethylformamide was added to a cooled (0° C.) slurry of sodium hydride (51 mg, 1.26 mmol) in dimethylformamide under nitrogen atmosphere. The reaction mixture was slowly warmed to room temperature, stirred for 1 hour. Again, cooled (0° C.), then a solution of 2,6-difluorobenzonitrile (0.18 g, 1.26 mmol) in dimethylfomamide was added, stirred overnight at room temperature. The reaction mixture was poured on crushed ice-water, stirred for 4 hours. Extracted with ether, washed with brine, dried, and concentrated Purification by silica gel chromatography (1-3% acetone in dichloromethane) yielded 0.36 g of 2-(2-benzo[1,3]dioxol-5-yl-2-methoxymethoxyethoxy)-6-fluorobenzonitrile.

Step 4: The previous benzonitrile (0.35 g, 1.01 mmol) and guanidine carbonate (0.4 g, 2.23 mmol) were heated at 150° C. in dimethylacetamide for 6 hours. The reaction mixture was cooled, diluted with water, stirred for 1.5 h, filtered, dried. Purification by silica gel chromatography (5-10% methanol in dichloromethane) yielded 310 mg of 1-benzo[1,3]dioxol-5-yl-2-(2,4-diaminoquinazolin-5-yloxy)ethanol.

Step 5: To a stirred solution of previous diamine (0.15 g, 0.39 mmol) in methanol was added 4N hydrochloric acid in dioxane (1.0 mL, 4.0 mmol). The reaction mixture was heated at 60° C. for 2 hours. The reaction mixture was concentrated, recrystallized from methanol-ether to yield 131 mg of 1-benzo[1,3]dioxol-5-yl-2-(2,4-diaminoquinazolin-5-yloxy)ethanol hydrochloride.

$^1$H NMR (400 MHz, DMSO-d$_6$) δ 12.56 (s, 1H), 9.02 (s, 1H), 8.41 (s, 1H), 7.8 (brs, 1H), 7.68 (t, J=8.0 Hz, 2H), 6.87-7.1 (m, 4H), 6.04 (m, 2H), 4.74 (dd, J=8.0, 4.0 Hz, 1H), 4.41 (dd, J=10.4, 4.0 Hz, 1H), 4.3 (dd, J=10.2, 8.0 Hz, 1H), 3.24 (s, 3H).

MS m/z (ESI) 355 (M+H)$^+$

EXAMPLE 170

2-Benzo[1,3]dioxol-5-yl-2-(2,4-diaminoquinazolin-5-yloxy)ethanol hydrochloride

Step 1: To a stirred solution of 3,4-(methylenedioxy)mandelic acid (1.5 g, 7.65 mmol) in tetrahydrofuran was added lithium aluminum hydride (0.58 g, 15.29 mmol). The reaction mixture was refluxed for 1.5 hours. The reaction mixture was cooled (0° C.), quenched with sat. ammonium chloride solution, filtered, concentrated to yield 1.3 g of 1-benzo[1,3]dioxol-5-yl-ethane-1,2-diol Step 2: To a stirred solution of previous diol (1.05 g, 5.76 mmol) and trimethyl orthoformate (1.22 g, 11.53 mmol) in dichloromethane was added camphorsulfonic acid. The reaction mixture was stirred for 20 hours, concentrated. Again dissolved in dichloromethane, cooled (−78° C.), than diisobutylaluminum hydride (11.5 mL, 17.3 mmol) was slowly added over 10 min. The reaction mixture was stirred at −78° C. for 30 minutes, warmed to 0° C., poured on to 2N sodium hydroxide solution. Extracted with ether, washed with brine, dried, and concentrated. Purification by silica gel chromatography (3-10% acetone in dichloromethane) yielded 0.4 g of 1-benzo[1,3]dioxol-5-yl-2-methoxymethoxyethanol.

Step 3: A solution of previous alcohol (0.19 g, 0.84 mmol) in dimethylformamide was added to a cooled (0° C.) slurry of sodium hydride (37 mg, 0.92 mmol) in dimethylformamide under nitrogen atmosphere. The reaction mixture was slowly warmed to room temperature, stirred for 1 hour. Again, cooled (0° C.), then a solution of 2,6-difluorobenzonitrile (0.13 g, 0.92 mmol) in dimethylfomamide was added, stirred overnight at room temperature. The reaction mixture was poured on crushed ice-water, stirred for 4 hours. Extracted with ether, washed with brine, dried, and concentrated Purification by silica gel chromatography (1-3% acetone in dichloromethane) yielded 0.27 g of 2-(1-benzo[1,3]dioxol-5-yl-2-methoxymethoxyethoxy)-6-fluorobenzonitrile.

Step 4: The previous benzonitrile (0.27 g, 0.77 mmol) and guanidine carbonate (0.3 g, 1.69 mmol) were heated at 150° C. in dimethylacetamide for 6 hours. The reaction mixture was cooled, diluted with water, stirred for 1.5 h, filtered, dried. Purification by silica gel chromatography (5-10% methanol in dichloromethane) yielded 210 mg of 5-(1-benzo[1,3]dioxol-5-yl-2-methoxymethoxyethoxy)quinazoline-2,4-diamine.

Step 5: To a stirred solution of previous diamine (0.04 g, 0.1 mmol) in methanol was added 4N hydrochloric acid in dioxane (0.1 mL, 0.42 mmol). The reaction mixture was heated at 50° C. for 0.5 hours. The reaction mixture was concentrated, recrystallized from methanol-ether, dissolved in water, concentrated to yield 36.0 mg of 2-benzo[1,3]dioxol-5-yl-2-(2,4-diaminoquinazolin-5-yloxy)ethanol hydrochloride.

¹H NMR (400 MHz, DMSO-d₆) δ 12.46 (s, 1H), 9.08 (s, 1H), 8.75 (s, 1H), 7.8 (brs, 1H), 7.55 (t, J=8.4 Hz, 1H), 7.03 (d, J=1.2, Hz, 1H), 6.93 (m, 3H), 6.78 (d, J=8.4 Hz, 1H), 5.99 (dd, J=6.6, 0.8 Hz, 1H), 5.55 (m, 1H), 3.81 (s, 1H).

MS m/z (ESI) 341 (M+H)⁺

The structures of each of the compounds of Examples 1-170 were confirmed by proton NMR and by mass spectrometry. Table 1 provides the nomenclature for these compounds. All names were derived from Autonom 2000, ISIS Draw version 2.5, MDL Information Systems, Inc.

TABLE 1

| Example No. | Compound Name |
|---|---|
| 1 | 5-(4-Methylbenzyloxy)quinazoline-2,4-diamine |
| 2 | 5-(4-Chlorobenzyloxy)quinazoline-2,4-diamine |
| 3 | 5-(2,2,2-Trifluoroethoxy)quinazoline-2,4-diamine |
| 4 | 5-(4-Iodobenzyloxy)quinazoline-2,4-diamine |
| 5 | 5-(3-Chlorobenzyloxy)quinazoline-2,4-diamine |
| 6 | 5-(2-Chlorobenzyloxy)quinazoline-2,4-diamine |
| 7 | 5-(2-Methylbenzyloxy)quinazoline-2,4-diamine |
| 8 | 5-(2-p-Tolylethoxy)quinazoline-2,4-diamine |
| 9 | 5-[2-(4-Chlorophenyl)ethoxy]quinazoline-2,4-diamine |
| 10 | 5-(3-Methylbenzyloxy)quinazoline-2,4-diamine |
| 11 | 5-(Pyridin-3-ylmethoxy)quinazoline-2,4-diamine |
| 12 | 5-(1-Phenylethoxy)quinazoline-2,4-diamine |
| 13 | 5-(Cyclohex-3-enylmethoxy)quinazoline-2,4-diamine |
| 14 | 5-(Cyclobutylmethoxy)quinazoline-2,4-diamine |
| 15 | 5-(2-Methoxyethoxy)quinazoline-2,4-diamine |
| 16 | 5-(Cyclopropylmethoxy)quinazoline-2,4-diamine |
| 17 | 5-(Cyclohexylmethoxy)quinazoline-2,4-diamine |
| 18 | 5-(Cyclopentylmethoxy)quinazoline-2,4-diamine |
| 19 | 5-(2-Allyloxyethoxy)quinazoline-2,4-diamine |
| 20 | 5-(1-Methylpiperidin-3-ylmethoxy)quinazoline-2,4-diamine |
| 21 | 5-(Furan-2-ylmethoxy)quinazoline-2,4-diamine |
| 22 | 5-(Thiophen-2-ylmethoxy)quinazoline-2,4-diamine |
| 23 | 5-(4-Methylbenzyl)quinazoline-2,4-diamine |
| 24 | 5-Benzylquinazoline-2,4-diamine |
| 25 | 5-(4-Chlorobenzyl)quinazoline-2,4-diamine |
| 26 | 5-(4-Methoxybenzyl)quinazoline-2,4-diamine |
| 27 | 5-[3-(4-Chlorophenyl)propoxy]quinazoline-2,4-diamine I |
| 28 | 5-[1-(3-Chlorophenyl)ethoxy]quinazoline-2,4-diamine |
| 29 | 5-(4-Chlorobenzylsulfanyl)quinazoline-2,4-diamine |
| 30 | 5-p-Tolylethynylquinazoline-2,4-diamine |
| 31 | 5-(4-Chlorobenzenesulfonyl)quinazoline-2,4-diamine |
| 32 | N-[2-Acetylamino-5-(4-chlorobenzyloxy)quinazolin-4-yl]acetamide |
| 33 | 5-(3-Methyl-4,5-dihydroisoxazol-5-ylmethoxy)quinazoline-2,4-diamine |
| 34 | 5-(Furan-3-ylmethoxy)quinazoline-2,4-diamine |
| 35 | 5-Benzyloxyquinazoline-2,4-diamine |
| 36 | 5-(Pyridin-2-ylmethoxy)quinazoline-2,4-diamine |
| 37 | 5-Phenethyloxyquinazoline-2,4-diamine |
| 38 | 5-Octyloxyquinazoline-2,4-diamine |
| 39 | N-5-Cyclooctylquinazoline-2,4,5-triamine |
| 40 | 5-(Indan-2-yloxy)quinazoline-2,4-diamine |
| 41 | 5-((S)-Indan-1-yloxy)quinazoline-2,4-diamine |
| 42 | 5-((S)-1-Phenylethoxy)quinazoline-2,4-diamine |
| 43 | 5-(4-Chlorophenoxymethyl)quinazoline-2,4-diamine |
| 44 | 5-p-Tolyloxymethylquinazoline-2,4-diamine |
| 45 | 5-(4-Fluorophenoxymethyl)quinazoline-2,4-diamine |
| 46 | 5-Thiophen-3-ylmethylquinazoline-2,4-diamine |
| 47 | 5-(Thiophen-3-ylmethoxy)quinazoline-2,4-diamine |
| 48 | 5-(1-Pyridin-4-ylethoxy)quinazoline-2,4-diamine |
| 49 | 5-[1-(4-Chlorophenyl)ethoxy]quinazoline-2,4-diamine |
| 50 | 5-[1-(4-Chlorophenyl)propoxy]quinazoline-2,4-diamine |
| 51 | 5-[1-(4-Chlorophenyl)-2,2-dimethylpropoxy]quinazoline-2,4-diamine |
| 52 | 5-Benzhydryloxyquinazoline-2,4-diamine |
| 53 | 5-(5-Methylisoxazol-3-ylmethoxy)quinazoline-2,4-diamine |
| 54 | 5-(Benzo[1,3]dioxol-5-ylmethoxy)quinazoline-2,4-diamine |
| 55 | 5-(Tetrahydropyran-2-ylmethoxy)quinazoline-2,4-diamine |
| 56 | 5-((R)-1-Phenylethoxy)quinazoline-2,4-diamine |
| 57 | 5-(1-Pyridin-2-ylethoxy)quinazoline-2,4-diamine |
| 58 | 5-(1-Thiazol-2-ylethoxy)quinazoline-2,4-diamine |
| 59 | 5-(Piperidin-1-yl)quinazoline-2,4-diamine |
| 60 | 5-(Toluene-3-sulfonyl)-quinazoline-2,4-diamine |
| 61 | 5-(6-Chloro-indan-1-yloxy)-quinazoline-2,4-diamine |
| 62 | 5-(4-Bromobenzyloxy)-quinazoline-2,4-diamine |
| 63 | 5-[1-(3-Iodophenyl)-ethoxy]-quinazoline-2,4-diamine |
| 64 | 5-(1-Benzo[1,3]dioxol-5-yl-ethoxy)-quinazoline-2,4-diamine |
| 65 | 5-(3,4-Dimethoxybenzyloxy)-quinazoline-2,4-diamine |
| 66 | 5-[1-(3-Methoxyphenyl)-ethoxy]-quinazoline-2,4-diamine |
| 67 | 5-[1-(3,5-Dimethoxyphenyl)-ethoxy]-quinazoline-2,4-diamine |
| 68 | 5-[2-(4-Chlorophenyl)-3-methoxymethoxypropoxy]-quinazoline-2,4-diamine |
| 69 | 2-(4-Chlorophenyl)-3-(2,4-diaminoquinazolin-5-yloxy)-propan-1-ol |

TABLE 1-continued

| Example No. | Compound Name |
|---|---|
| 70 | [4,5-Dichloro-2-(2,4-diaminoquinazolin-5-yloxymethyl)phenyl]methanol |
| 71 | 5-(4-Chloro-2-methoxyphenoxy)-quinazoline-2,4-diamine |
| 72 | 5-(7-Methoxy-2,3-dihydrobenzofuran-3-yoloxy)-quinazoline-2,4-diamine |
| 73 | 5-(Adamantan-1-ylmethoxy)-quinazoline-2,4-diamine |
| 74 | 5-(2-Bromo-benzyloxy)-quinazoline-2,4-diamine |
| 75 | 5-(2-Iodo-benzyloxy)-quinazoline-2,4-diamine |
| 76 | 5-(3-Bromobenzyloxy)quinazoline-2,4-diamine |
| 77 | 5-(3-Iodo-benzyloxy)-quinazoline-2,4-diamine |
| 78 | 5-[1-(3,4-Dichlorophenyl)-ethoxy]-quinazoline-2,4-diamine |
| 79 | 5-(3,5-Difluorobenzyloxy)quinazoline-2,4-diamine |
| 80 | 5-(4-Fluoroindan-1-yloxy)-quinazoline-2,4-diamine |
| 81 | 5-(6-Fluoroindan-1-yloxy)-quinazoline-2,4-diamine |
| 82 | 5-[1-(2,6-Difluorophenyl)-ethoxy]-quinazoline-2,4-diamine |
| 83 | 5-(2,3,5-Trifluorobenzyloxy)-quinazoline-2,4-diamine |
| 84 | 5-(2,5-Difluorobenzyloxy)-quinazoline-2,4-diamine |
| 85 | 5-(2,4-Difluorobenzyloxy)-quinazoline-2,4-diamine |
| 86 | 5-(2,6-Difluorobenzyloxy)-quinazoline-2,4-diamine |
| 87 | 5-(3,4-Difluorobenzyloxy)quinazoline-2,4-diamine |
| 88 | 5-(5-Chloro-2-methoxybenzyloxy)quinazoline-2,4-diamine |
| 89 | [4-Chloro-2-(2,4-diamino-quinazolin-5-yloxymethyl)-phenyl]-methanol |
| 90 | 5-Thiophen-3-yl-quinazoline-2,4-diamine |
| 91 | 5-(3-Chlorophenyl)-quinazoline-2,4-diamine |
| 92 | 5-[(R)-1-(3-Chlorophenyl)ethoxy]quinazolin-2,4-diamine |
| 93 | 5-[1-(3-Fluorophenyl)-ethoxy]-quinazoline-2,4-diamine |
| 94 | 5-[1-(2-Trifluoromethylphenyl)-ethoxy]-quinazoline-2,4-diamine |
| 95 | 5-[1-(3-Trifluoromethylphenyl)-ethoxy]-quinazoline-2,4-diamine |
| 96 | 5-(2-Fluorobenzyloxy)-quinazoline-2,4-diamine |
| 97 | 5-(4-Fluorobenzyloxy)-quinazoline-2,4-diamine |
| 98 | 5-(3-Trifluoromethylbenzyloxy)-quinazoline-2,4-diamine |
| 99 | 5-(2-Trifluoromethylbenzyloxy)-quinazoline-2,4-diamine |
| 100 | 5-(4-Trifluoromethylbenzyloxy)-quinazoline-2,4-diamine |
| 101 | 5-[1-(4-fluorophenyl)-1-methyl-ethoxy]-quinazoline-2,4-diamine |
| 102 | 5-(3-Fluorobenzyloxy)quinazoline-2,4-diamine |
| 103 | 5-[1-(2-Fluorophenyl)-ethoxy]-quinazoline-2,4-diamine |
| 104 | 5-[1-(2-Chlorophenyl)-ethoxy]-quinazoline-2,4-diamine |
| 105 | 5-[1-(4-Trifluoromethylphenyl)ethoxy]quinazoline-2,4-diamine |
| 106 | 5-(3,5-Dichlorobenzyloxy)quinazoline-2,4-diamine |
| 107 | 5-[1-(3,5-Difluorophenyl)ethoxy]quinazoline-2,4-diamine |
| 108 | 5-((S)-1-Naphthalen-1-yl-ethoxy)-quinazoline-2,4-diamine |
| 109 | 5-((S)-1-Naphthalen-2-yl-ethoxy)-quinazoline-2,4-diamine |
| 110 | 5-((R)-1-Naphthalen-1-yl-ethoxy)-quinazoline-2,4-diamine |
| 111 | 5-(1-Naphthalen-1-yl-ethoxy)-quinazoline-2,4-diamine |
| 112 | 5-(Quinolin-3-ylmethoxy)-quinazoline-2,4-diamine |
| 113 | 5-(Quinolin-8-ylmethoxy)-quinazoline-2,4-diamine |
| 114 | 5-[1-(4-Chlorophenyl)-2-methoxyethoxy]-quinazoline-2,4-diamine |
| 115 | (4-Chlorophenyl)-(2,4-diamino-quinazolin-5-yloxy)-acetic acid |
| 116 | 5-(Piperidin-4-ylmethoxy)-quinazoline-2,4-diamine |
| 117 | 5-(1-Methyl-piperidin-2-ylmethoxy)-quinazoline-2,4-diamine |
| 118 | 5-((1R,2R,4S)-Bicyclo[2.2.1]hept-2-yloxy)quinazoline-2,4-diamine |
| 119 | 5-(Adamanta-2-yloxy)quiazoline-2,4-diamine |
| 120 | 5-(1-Cyclopentyl-ethoxy)-quinazoline-2,4-diamine |
| 121 | 4-(2,4-Diamino-quinzaolin-5-yloxymethyl)-piperidin-1-carboxylic acid tert-butyl ester |
| 122 | 5-(Bicyclo[2.2.1]hept-5-en-2-ylmethoxy)-quinazoline-2,4-diamine |
| 123 | (4-Chlorophenyl)-[4-(2,4-diamino-quinazolin-5-yloxymethyl)-piperidin-1-yl]-methanone |
| 124 | 5-(Bicyclo[2.2.1]hept-2-yloxy)-quinazoline-2,4-diamine |
| 125 | 5-(1-Cyclohexyl-butoxy)-quinazoline-2,4-diamine |
| 126 | 5-(1-Cyclohexyl-ethoxy)-quinazoline-2,4-diamine |
| 127 | 5-(3-Methyl-oxetan-3-ylmethoxy)-quinazoline-2,4-diamine |
| 128 | 5-(5-Chloro-2,3-dihydro-benzofuran-3-yloxy)-quinazoline-2,4-diamine |
| 129 | 5-(1-Cyclohexylpropoxy)-quinazoline-2,4-diamine |
| 130 | 5-((1S,2R,5S)-6,6-Dimethylbicyclo[3.1.1]hept-2-ylmethoxy)quinazoline-2,4-diamine |
| 131 | 5-(2,4-Diamino-quinazolin-5-yloxymethyl)-bicyclo[2.2.1]heptane-2,3-diol |
| 132 | 5-[1-(3,4-Dichlorobenzyl)-piperidin-4-ylmethoxy]-quinazoline-2,4-diamine |
| 133 | (2-Chlorophenyl)-[4-(2,4-diamino-quinazolin-5-yloxymethyl)-piperidin-1-yl]-methanone |
| 134 | (3-Chlorophenyl)-[4-(2,4-diamino-quinazolin-5-yloxymethyl)-piperidin-1-yl]-methanone |
| 135 | [4-(2,4-Diaminoquinzolin-5-yloxymethyl)piperidin-1-yl]-(3-iodophenyl)methanone |
| 136 | [4-(2,4-Diaminoquinzolin-5-yloxymethyl)piperidin-1-yl]-(4-iodophenyl)methanone |

TABLE 1-continued

| Example No. | Compound Name |
|---|---|
| 137 | [4-(2,4-Diaminoquinzolin-5-yloxymethyl)piperidin-1-yl]-(2-iodophenyl)methanone |
| 138 | 5-(2-Chlorophenoxymethyl)quinazoline-2,4-diamine |
| 139 | 5-(4-Chloro-2-methylphenoxymethyl)quinazoline-2,4-diamine |
| 140 | 5-[1-(3-Chlorophenyl)-1-methylethoxy]quinazoline-2,4-diamine |
| 141 | 5-(4-Chloro-3-methylphenoxymethyl)quinazoline-2,4-diamine |
| 142 | 5-(2-Methoxybenzyloxy)quinazoline-2,4-diamine |
| 143 | 5-(3-Methoxybenzyloxy)quinazoline-2,4-diamine |
| 144 | 5-(4-Methoxybenzyloxy)quinazoline-2,4-diamine |
| 145 | 5-[1-(3-Chlorophenyl)cyclohexyloxy]quinazoline-2,4-diamine |
| 146 | 5-[1-(3-Chlorophenyl)cyclopropoxy]quinazoline-2,4-diamine |
| 147 | 5-(2,4-Difluorophenoxymethyl)quinazoline-2,4-diamine |
| 148 | 5-(4-Methoxyphenoxymethyl)quinazoline-2,4-diamine |
| 149 | 5-((S)-6-Chloroindan-1-yloxy)quinazoline-2,4-diamine |
| 150 | 5-((R)-6-Chloroindan-1-yloxy)quinazoline-2,4-diamine |
| 151 | 5-(Bicyclo[2.2.1]hept-2-ylmethoxy)quinazoline-2,4-diamine |
| 152 | 5-((1S,2S,5S)-6,6-Dimethylbicyclo[3.1.1]hept-2-ylmethoxy)quinazoline-2,4-diamine |
| 153 | 5-[1-(4-Fluorophenyl)-2-methoxymethoxyethoxy]quinazoline-2,4-diamine |
| 154 | 2-(2,4-Diaminoquinazolin-5-yloxy)-2-(4-fluorophenyl)ethanol |
| 155 | 5-(2-Benzo[1,3]dioxol-5-yl-2-methoxymethoxyethoxy)quinazoline-2,4-diamine |
| 156 | 5-(1-Benzo[1,3]dioxol-5-yl-2-methoxymethoxyethoxy)quinazoline-2,4-diamine |
| 157 | 2-(2,4-Diaminoquinazolin-5-yloxy)-1-phenyl-ethanol |
| 158 | 5-(3-Chlorophenoxymethyl)quinazoline-2,4-diamine |
| 159 | 5-(2-Iodophenoxymethyl)quinazoline-2,4-diamine |
| 160 | 1-(4-Chlorophenyl)-2-(2,4-diaminoquinazolin-5-yloxy)ethanol |
| 161 | 1-(3-Chlorophenyl)-2-(2,4-diaminoquinazolin-5-yloxy)ethanol |
| 162 | 5-[(S)-1-(3-Chlorophenyl)ethoxy]quinazolin-2,4-diamine |
| 163 | 2-(2,4-Diaminoquinazolin-5-yloxy)-1-(4-trifluoromethylphenyl)ethanol |
| 164 | 2-(4-Chlorophenyl)-2-(2,4-diaminoquinazolin-5-yloxy)ethanol |
| 165 | 5-[2-(4-Chlorophenyl)-2-methoxyethoxy]quinazoline-2,4-diamine |
| 166 | 5-(2-Methoxy-1-phenylethoxy)quinazoline-2,4-diamine |
| 167 | 2-(2,4-Diaminoquinazolin-5-yloxy)-1-(4-fluorophenyl)ethanol |
| 168 | 1,1-Bis-(4-chlorophenyl)-3-(2,4-diaminoquinazolin-5-yloxy)butan-1-ol |
| 169 | 5-(2-Benzo[1,3]dioxol-5-yl-2-methoxyethoxy)quinazoline-2,4-diamine |
| 170 | 2-Benzo[1,3]dioxol-5-yl-2-(2,4-diaminoquinazolin-5-yloxy)ethanol |

All compounds were screened using an in vitro based SMN2 promoter assay. We used NSC-34 cells, a hybrid cell line between mouse spinal cord cells and mouse neuroblastoma cells. NSC-34 cells harbor an expression plasmid containing a 3.4 kb promoter fragment of the SMN2 gene driving β-lactamase expression.

For biological evaluation the NSC-34 cells are incubated (60,000 cells/well) with 10 and 50 µM of compound for 19 hours. Following the incubation, the cells are further incubated for three hours with the β-lactamase substrate CCF2-AM (Invitrogen) (Zlokarnik et, al., 1998. Science vol. 279, pp. 84). CCF2-AM diffuses across the plasma membrane and is converted into an active β-lactamase substrate by cytoplasmic esterase. Excitation at 409 nM leads to fluorescence resonance energy transfer and reemission of green light at 520 nM. Hydrolysis by the β-lactamase of the active substrate leads to emission at 447 nM following excitation at 409 nM. Fold induction is therefore determined by comparing the 447/520 ratios for a compound versus DMSO control (negative control). The fold induction is proportional to the extent of β-lactamase produced and in turn proportional to SMN2 promoter activation for a given compound relative to vehicle (DMSO) control. Compounds that give 1.2 to 2-fold induction at 10 uM are further tested using 12 point dose curve to obtain a $EC_{50}$ value using the NSC-34 promoter assay as described above—(dose range ~30 uM to 0.0002 µM). Average of 3-6 different dose curve experiments are used to obtain an average $EC_{50}$ value and the fold induction at maximum stimulation. These values are used to rank activities of the compounds and derive structure activity relationship. The promoter assay data for these examples is shown in Table 2.

TABLE 2

| Example No. | EC50 [1 < 1 uM; 2 = 1-5 uM; 3 = 5-10 uM; 4 = 10-20 uM |
|---|---|
| 1 | 1 |
| 2 | 1 |
| 3 | 2 |
| 4 | 1 |
| 5 | 1 |
| 6 | 1 |
| 7 | 1 |
| 8 | 1 |
| 9 | 1 |
| 10 | 1 |
| 11 | 1 |
| 12 | 1 |
| 13 | 1 |
| 14 | 1 |
| 15 | 1 |
| 16 | 1 |
| 17 | 2 |
| 18 | 1 |
| 19 | 1 |
| 20 | 1 |
| 21 | 1 |
| 22 | 1 |
| 23 | 2 |
| 24 | 1 |
| 25 | 1 |

TABLE 2-continued

| Example No. | EC50 [1 < 1 uM; 2 = 1-5 uM; 3 = 5-10 uM; 4 = 10-20 uM |
|---|---|
| 26 | 1 |
| 27 | 1 |
| 28 | 1 |
| 29 | 1 |
| 30 | 1 |
| 31 | 2 |
| 32 | 3 |
| 33 | 2 |
| 34 | 1 |
| 35 | 1 |
| 36 | 1 |
| 37 | 1 |
| 38 | 1 |
| 39 | 2 |
| 40 | 1 |
| 41 | 3 |
| 42 | 1 |
| 43 | 1 |
| 44 | 1 |
| 45 | 1 |
| 46 | 1 |
| 47 | 1 |
| 48 | 1 |
| 49 | 1 |
| 50 | 1 |
| 51 | 3 |
| 52 | 1 |
| 53 | 1 |
| 54 | 1 |
| 55 | 1 |
| 56 | 1 |
| 57 | 1 |
| 58 | 1 |
| 59 | 1 |
| 60 | 2 |
| 61 | 1 |
| 62 | 1 |
| 63 | 1 |
| 64 | 1 |
| 65 | 1 |
| 66 | 1 |
| 67 | 1 |
| 68 | 1 |
| 69 | 1 |
| 70 | 1 |
| 71 | 1 |
| 72 | 2 |
| 73 | 1 |
| 74 | 1 |
| 75 | 1 |
| 76 | 1 |
| 77 | 1 |
| 78 | 1 |
| 79 | 1 |
| 80 | 1 |
| 81 | 1 |
| 82 | 1 |
| 83 | 1 |
| 84 | 1 |
| 85 | 1 |
| 86 | 1 |
| 87 | 1 |
| 88 | 1 |
| 89 | 1 |
| 90 | 2 |
| 91 | 1 |
| 92 | 1 |
| 93 | 1 |
| 94 | 4 |
| 95 | 1 |
| 96 | 1 |
| 97 | 1 |
| 98 | 1 |
| 99 | 1 |
| 100 | 1 |
| 101 | 1 |
| 102 | 1 |
| 103 | 1 |
| 104 | 1 |
| 105 | 1 |
| 106 | 1 |
| 107 | 1 |
| 108 | 2 |
| 109 | 1 |
| 110 | 2 |
| 111 | 2 |
| 112 | 1 |
| 113 | 1 |
| 114 | 1 |
| 115 | 1 |
| 116 | 1 |
| 117 | 1 |
| 118 | 1 |
| 119 | 1 |
| 120 | 1 |
| 121 | 1 |
| 122 | 1 |
| 123 | 1 |
| 124 | 1 |
| 125 | 1 |
| 126 | 1 |
| 127 | 1 |
| 128 | 1 |
| 129 | 1 |
| 130 | 1 |
| 131 | 1 |
| 132 | 1 |
| 133 | 1 |
| 134 | 1 |
| 135 | 1 |
| 136 | 1 |
| 137 | 1 |
| 138 | 1 |
| 139 | 1 |
| 140 | 2 |
| 141 | 1 |
| 142 | 1 |
| 143 | 1 |
| 144 | 1 |
| 145 | 2 |
| 146 | 1 |
| 147 | 1 |
| 148 | 2 |
| 149 | 1 |
| 150 | 1 |
| 151 | 1 |
| 152 | 1 |
| 153 | 1 |
| 154 | 1 |
| 155 | 1 |
| 156 | 1 |
| 157 | 1 |
| 158 | 1 |
| 159 | 1 |
| 160 | 1 |
| 161 | 1 |
| 162 | 1 |
| 163 | 1 |
| 164 | 1 |
| 165 | 1 |
| 166 | 1 |
| 167 | 1 |
| 168 | 2 |
| 169 | 1 |
| 170 | 1 |

The present invention includes compounds of formulae I-VI in the form of salts, in particular acid addition salts. Suitable salts include those formed with both organic and inorganic acids. Such acid addition salts will normally be pharmaceutically acceptable, although non-pharmaceutically acceptable salts may be of utility in the preparation and purification of the compound in question. Thus, preferred salts include those formed from hydrochloric, hydrobromic, sulphuric, citric, tartaric, phosphoric, lactic, pyruvic, acetic, succinic, oxalic, fumaric, maleic, oxaloacetic, methanesulphonic, ethanesulphonic, p-toluenesulphonic, benzenesulphonic and isethionic acids. Salts of the compounds of the invention can be made by reacting the appropriate compound in the form of the free base with the appropriate acid.

While it may be possible for the compounds of formulae I-VI to be administered as the raw chemical, it is preferable to present them as a pharmaceutical composition. According to a further aspect, the present invention provides a pharmaceutical composition comprising a compound of formula I, II, III, N, or VI, or a pharmaceutically acceptable salt or solvate thereof, together with one or more pharmaceutically carriers thereof and optionally one or more other therapeutic ingredients. The carrier(s) must be "acceptable" in the sense of being compatible with the other ingredients of the formulation and not deleterious to the recipient thereof.

The formulations include those suitable for oral, parenteral (including subcutaneous, intradermal, intramuscular, intravenous and intraarticular), rectal and topical (including dermal, buccal, sublingual and intraocular) administration. The most suitable route may depend upon the condition and disorder of the recipient. The formulations may conveniently be presented in unit dosage form and may be prepared by any of the methods well known in the art of pharmacy. All methods include the step of bringing into association a compound of the invention or a pharmaceutically acceptable salt or solvate thereof ("active ingredient") with the carrier, which constitutes one or more accessory ingredients. In general, the formulations are prepared by uniformly and intimately bringing into association the active ingredient with liquid carriers or finely divided solid carriers or both and then, if necessary, shaping the product into the desired formulation.

Formulations of the present invention suitable for oral administration may be presented as discrete units such as capsules, cachets or tablets each containing a predetermined amount of the active ingredient; as a powder or granules; as a solution or a suspension in an aqueous liquid or a non-aqueous liquid; or as an oil-in-water liquid emulsion or a water-in-oil liquid emulsion. The active ingredient may also be presented as a bolus, electuary or paste.

A tablet may be made by compression or molding, optionally with one or more accessory ingredients. Compressed tablets may be prepared by compressing in a suitable machine the active ingredient in a free-flowing form such as a powder or granules, optionally mixed with a binder, lubricant, inert diluent, lubricating, surface active or dispersing agent. Molded tablets may be made by molding in a suitable machine a mixture of the powdered compound moistened with an inert liquid diluent. The tablets may optionally be coated or scored and may be formulated so as to provide sustained, delayed or controlled release of the active ingredient therein.

Formulations for parenteral administration include aqueous and non-aqueous sterile injection solutions, which may contain anti-oxidants, buffers, bacteriostats and solutes which render the formulation isotonic with the blood of the intended recipient. Formulations for parenteral administration also include aqueous and non-aqueous sterile suspensions, which may include suspending agents and thickening agents. The formulations may be presented in unit-dose of multi-dose containers, for example sealed ampoules and vials, and may be stored in a freeze-dried (lyophilized) condition requiring only the addition of a sterile liquid carrier, for example saline, phosphate-buffered saline (PBS) or the like, immediately prior to use. Extemporaneous injection solutions and suspensions may be prepared from sterile powders, granules and tablets of the kind previously described.

Formulations for rectal administration may be presented as a suppository with the usual carriers such as cocoa butter or polyethylene glycol.

Formulations for topical administration in the mouth, for example buccally or sublingually, include lozenges comprising the active ingredient in a flavoured basis such as sucrose and acacia or tragacanth, and pastilles comprising the active ingredient in a basis such as gelatin and glycerin or sucrose and acacia.

Preferred unit dosage formulations are those containing an effective dose, as hereinbelow recited, or an appropriate fraction thereof, of the active ingredient.

It should be understood that in addition to the ingredients particularly mentioned above, the formulations of this invention may include other agents conventional in the art having regard to the type of formulation in question, for example those suitable for oral administration may include flavoring agents.

The compounds of the invention may be administered at a dose from 0.01 to 250 mg/kg per day. The dose range for adult humans is generally from 0.05 mg to 10 g/day. Tablets or other forms of presentation provided in discrete units may conveniently contain an amount of compound of the invention which is effective at such dosage or as a multiple of the same, for instance, units containing 5 mg to 500 mg, usually around 10 mg to 200 mg. The precise amount of compound administered to a patient will be the responsibility of the attendant physician. The dose employed will depend on a number of factors, including the age and sex of the patient and the severity of the disorder. Also, the route of administration may vary depending on the condition and its severity.

Combination therapy is possible with any combination of agents that improve SMA; those that operate by a mechanism independent of promotion of SMN2 may offer additional advantages. Combination therapy can be achieved by administering two or more agents, each of which is formulated and administered separately, or by administering two or more agents in a single formulation. Other combinations are also encompassed by combination therapy. For example, two agents can be formulated together and administered in conjunction with a separate formulation containing a third agent. While the two or more agents in the combination therapy can be administered simultaneously, they need not be. For example, administration of a first agent (or combination of agents) can precede administration of a second agent (or combination of agents) by minutes, hours, days, or weeks. While in many cases it is desirable that the two or more agents used in a combination therapy be present in within the patient's body at the same time, this need not be so. Combination therapy can also include two or more administrations of one or more of the agents used in the combination. For example, if agent X and agent Y are used in a combination, one could administer them sequentially in any combination one or more times, e.g., in the order X-Y-X, X-X-Y, Y-X-Y, Y-Y-X, X-X-Y-Y, etc.

Examples of drugs that improve SMA include, but are not limited to valproic acid, hydroxybutyrate, phenylbutyrate, phenylbutyrate derivatives, histone deacetylase (HDAC) inhibitors and methylase inhibitors. Exemplary HDAC inhibitors include, but are not limited to, valproic acid, hydroxybutyrate, phenylbutyrate, phenylbutyrate derivatives, trichostatin A (TSA) and suberoylanilide hydroxamic acid (SAHA). An exemplary methylase inhibitor is 5-azacytidine. Other HDAC and methylase inhibitors would be obvious to one of ordinary skill. Effects of the quinazoline derivatives of formulae I-IV and VI on SMN2 promoter induction are additive and/or synergistic with HDAC inhibitors and with methylese inhibitors.

Each of the patents, patent applications, patent publications, and references mentioned herein is hereby incorporated by reference in its entirety.

We claim:

1. A 2,4-diaminoquinazoline compound selected from:
(A) 2,4-diaminoquinazoline compounds selected from the group consisting of formula II:

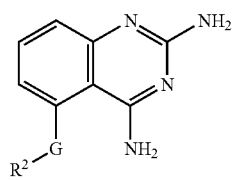

II wherein
G is selected from the group consisting of —NR$^6$—, —CH$_2$—, and —CH$_2$O—;
R$^2$ is selected from the group consisting of cycloalkyl, fused cycloalkylaryl, heterocyclyl, heteroaryl; substituted cycloalkyl, substituted aryl, substituted fused cycloalkylaryl, substituted heterocyclyl, and substituted heteroaryl with the proviso that when G is —CH$_2$— then R$^2$ is other than phenyl or substituted phenyl, wherein said aryl is selected from phenyl, naphthalenyl, indanyl, tetralinyl, and fluorenyl and said heterocyclyl or heteroaryl is selected from imidazolyl, pyridinyl, indolyl, thiophenyl, benzopyranonyl, thiazolyl, furanyl, benzimidazolyl, quinolinyl, isoquinolinyl, quinoxalinyl, pyrimidinyl, pyrazinyl, tetrazolyl, and pyrazolyl, and wherein substituents are selected from alkyl, aryl, halogen, hydroxy, lower alkoxy, carboxy, carboxamido, cyano, nitro, amino, dialkylamino, and alkylthio;

and, (B) 2,4-diaminoquinazoline compounds of formula IV:

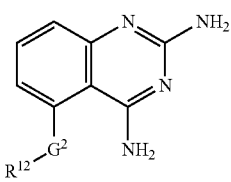

IV wherein G$^2$ is selected from the group consisting of —O—, —S—, and NH—; and
R$^{12}$ is selected from the group consisting of C$_7$-C$_{10}$ polycyclic hydrocarbon, substituted C$_7$-C$_{10}$ polycyclic hydrocarbon, and

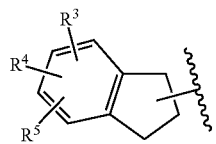

wherein the wavy line indicates the point of attachment; and
wherein one or more carbon atoms in the cyclopentyl ring is optionally replaced by a heteroatom independently selected from the group consisting of N, O, and S; and
R$^3$, R$^4$ and R$^5$ are independently selected from the group consisting of hydrogen, halogen, C$_1$-C$_6$ alkyl, C$_1$-C$_6$ alkoxy, haloalkyl, hydroxy, carboxy, C$_1$-C$_6$ alkoxycarbonyl, carboxamido, cyano, formyl, nitro, amino, C$_1$-C$_6$ alkylamino, C$_1$-C$_6$ dialkylamino, mercapto, C$_1$-C$_6$ alkylthio, C$_1$-C$_6$ alkylsulfoxide, C$_1$-C$_6$ alkylsulfone, C$_1$-C$_6$ acylamino, amidino, phenyl, benzyl, phenoxy and benzyloxy, with the proviso that at least one of R$^3$, R$^4$ and R$^5$ must be other than hydrogen or a pharmaceutically acceptable salt of such a compound, in any stereoisomeric or tautomeric form, or a mixture of any such compounds in any ratio.

2. A compound according to claim 1 of formula II:

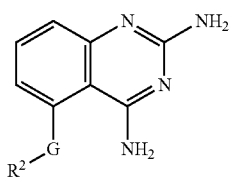

II wherein
G is —CH$_2$O—; and
R$^2$ is selected from the group consisting of cycloalkyl, fused cycloalkylaryl, heterocyclyl, heteroaryl, substituted cycloalkyl, substituted aryl, substituted fused cycloalkylaryl, substituted heterocyclyl, and substituted heteroaryl.

3. A compound according to claim 1 selected from the group consisting of
5-(2-p-Tolylethoxy)quinazoline-2,4-diamine;
5-[2-(4-Chlorophenyl)ethoxy]quinazoline-2,4-diamine;
5-[3-(4-Chlorophenyl)propoxy]quinazoline-2,4-diamine;
5-[1-(3-Chlorophenyl)ethoxy]quinazoline-2,4-diamine;
5-(1-Pyridim-4-ylethoxy)quinazoline-2,4-diamine;
5-[1-(4-Chlorophenyl)ethoxy]quinazoline-2,4-diamine;
5-[1-(4-Chlorophenyl)propoxy]quinazoline-2,4-diamine;
5-Benzhydryloxyquinazoline-2,4-diamine;
5-(1-Pyridin-2-ylethoxy)quinazoline-2,4-diamine;
5-(1-Thiazol-2-ylethoxy)quinazoline-2,4-diamine;
5-(1-Benzo[1,3]dioxol-5-ylethoxy)quinazoline-2,4-diamine;
5-[1-(3-Methoxyphenyl)ethoxy]quinazoline-2,4-diamine;
5-[1-(3,5-Dimethoxyphenyl)ethoxy]quinazoline-2,4-diamine;
5-[2-(4-Chlorophenyl)-3-methoxymethoxypropoxy]quinazoline-2,4-diamine;
2-(4-Chlorophenyl)-3-(2,4-diaminoquinazolin-5-yloxy)propan-1-ol;
5-[1-(3,4-Dichlorophenyl)ethoxy]quinazoline-2,4-diamine;

5-[1-(2,6-Difluorophenyl)ethoxy]quinazoline-2,4-diamine;
5-[(R)-1-(3-Chlorophenyl)ethoxy]quinazolin-2,4-diamine;
5-[1-(3-Fluorophenyl)ethoxy]quinazoline-2,4-diamine;
5-[1-(3-Trifluoromethylphenyl)ethoxy]quinazoline-2,4-diamine;
5-[1-(4-fluorophenyl)-1-methylethoxy]quinazoline-2,4-diamine;
5-[1-(2-Fluorophenyl)ethoxy]quinazoline-2,4-diamine;
5-[1-(2-Chlorophenyl)ethoxy]quinazoline-2,4-diamine;
5-[1-(4-Trifluoromethylphenyl)ethoxy]quinazoline-2,4-diamine;
5-[1-(3,5-Difluorophenyl)ethoxy]quinazoline-2,4-diamine;
5-[1-(4-Chlorophenyl)-2-methoxyethoxy]quinazoline-2,4-diamine;
(4-Chlorophenyl)(2,4-diaminoquinazolin-5-yloxy)acetic acid;
5-(1-Cyclopentylethoxy)quinazoline-2,4-diamine;
5-(1-Cyclohexylbutoxy)quinazoline-2,4-diamine;
5-(1-Cyclohexylethoxy)quinazoline-2,4-diamine;
5-(1-Cyclohexylpropoxy)quinazoline-2,4-diamine;
5-[1-(3-Chlorophenyl)cyclopropoxy]quinazoline-2,4-diamine;
5-[1-(4-Fluorophenyl)-2-methoxymethoxyethoxy]quinazoline-2,4-diamine;
2-(2,4-Diaminoquinazolin-5-yloxy)-2-(4-fluorophenyl)ethanol;
5-(2-Benzo[1,3]dioxol-5-yl-2-methoxymethoxyethoxy)quinazoline-2,4-diamine;
5-(1-Benzo[1,3]dioxol-5-yl-2-methoxymethoxyethoxy)quinazoline-2,4-diamine;
2-(2,4-Diaminoquinazolin-5-yloxy)-1-phenyl-ethanol;
1-(4-Chlorophenyl)-2-(2,4-diaminoquinazolin-5-yloxy)ethanol;
1-(3-Chlorophenyl)-2-(2,4-diaminoquinazolin-5-yloxy)ethanol;
5-[(S)-1-(3-Chlorophenyl)ethoxy]quinazolin-2,4-diamine;
2-(2,4-Diaminoquinazolin-5-yloxy)-1-(4-trifluoromethylphenyl)ethanol;
2-(4-Chlorophenyl)-2-(2,4-diaminoquinazolin-5-yloxy)ethanol;
5-[2-(4-Chlorophenyl)-2-methoxyethoxy]quinazoline-2,4-diamine;
5-(2-Methoxy-1-phenylethoxy)quinazoline-2,4-diamine;
2-(2,4-Diaminoquinazolin-5-yloxy)-1-(4-fluorophenyl)ethanol;
5-(2-Benzo[1,3]dioxol-5-yl-2-methoxyethoxy)quinazoline-2,4-diamine;
2-Benzo[1,3]dioxol-5-yl-2-(2,4-diaminoquinazolin-5-yloxy)ethanol;
5-[1-(3-Chlorophenyl)-1-methylethoxy]quinazoline-2,4-diamine;
5-[1-(3-Chlorophenyl)cyclohexyloxy]quinazoline-2,4-diamine;
5-[1-(4-Chlorophenyl)-2,2-dimethylpropoxy]quinazoline-2,4-diamine;
5-[1-(2-Trifluoromethylphenyl)ethoxy]quinazoline-2,4-diamine;
5-Thiophen-3-ylquinazoline-2,4-diamine;
5-(4-Chlorophenoxymethyl)quinazoline-2,4-diamine;
5-p-Tolyloxymethylquinazoline-2,4-diamine;
5-(4-Fluorophenoxymethyl)quinazoline-2,4-diamine;
5-Thiophen-3-ylmethylquinazoline-2,4-diamine;
5-[1-(3-Iodophenyl)ethoxy]quinazoline-2,4-diamine;
5-((1R,2R,4S)-Bicyclo[2.2.1]hept-2-yloxy)quinazoline-2,4-diamine;
5-(Adamantan-2-yloxy)quinazoline-2,4-diamine;
5-(Bicyclo[2.2.1]hept-2-yloxy)quinazoline-2,4-diamine;
5-(2-Chlorophenoxymethyl)quinazoline-2,4-diamine;
5-(4-Chloro-2-methylphenoxymethyl)quinazoline-2,4-diamine;
5-(4-Chloro-3-methylphenoxymethyl)quinazoline-2,4-diamine;
5-(2,4-Difluorophenoxymethyl)quinazoline-2,4-diamine;
5-(3-Chlorophenoxymethyl)quinazoline-2,4-diamine;
5-(2-Iodophenoxymethyl)quinazoline-2,4-diamine;
5-(4-Chlorobenzenesulfonyl)quinazoline-2,4-diamine;
5-(Toluene-3-sulfonyl)quinazoline-2,4-diamine;
5-(4-Methoxyphenoxymethyl)quinazoline-2,4-diamine;
5-(4-Methylbenzyloxy)quinazoline-2,4-diamine;
5-(4-Chlorobenzyloxy)quinazoline-2,4-diamine;
5-(4-Iodobenzyloxy)quinazoline-2,4-diamine;
5-(3-Chlorobenzyloxy)quinazoline-2,4-diamine;
5-(2-Chlorobenzyloxy)quinazoline-2,4-diamine;
5-(2-Methylbenzyloxy)quinazoline-2,4-diamine;
5-(3-Methylbenzyloxy)quinazoline-2,4-diamine;
5-(Pyridin-3-ylmethoxy)quinazoline-2,4-diamine;
5-(Cyclohex-3-enylmethoxy)quinazoline-2,4-diamine;
5-(Cyclobutylmethoxy)quinazoline-2,4-diamine;
5-(2-Methoxyethoxy)quinazoline-2,4-diamine;
5-(Cyclopropylmethoxy)quinazoline-2,4-diamine;
5-(Cyclopentylmethoxy)quinazoline-2,4-diamine;
5-(2-Allyloxyethoxy)quinazoline-2,4-diamine;
5-(1-Methylpiperidin-3-ylmethoxy)quinazoline-2,4-diamine;
5-(Furan-2-ylmethoxy)quinazoline-2,4-diamine;
5-(Thiophen-2-ylmethoxy)quinazoline-2,4-diamine;
5-(Furan-3-ylmethoxy)quinazoline-2,4-diamine;
5-Benzyloxyquinazoline-2,4-diamine;
5-(Pyridin-2-ylmethoxy)quinazoline-2,4-diamine;
5-Octyloxyquinazoline-2,4-diamine;
5-(Thiophen-3-ylmethoxy)quinazoline-2,4-diamine;
5-(5-Methylisoxazol-3-ylmethoxy)quinazoline-2,4-diamine;
5-(Benzo[1,3]dioxol-5-ylmethoxy)quinazoline-2,4-diamine;
5-(Tetrahydropyran-2-ylmethoxy)quinazoline-2,4-diamine;
5-(4-Bromobenzyloxy)quinazoline-2,4-diamine;
5-(3,4-Dimethoxybenzyloxy)quinazoline-2,4-diamine;
[4,5-Dichloro-2-(2,4-diaminoquinazolin-5-yloxymethyl)phenyl]methanol;
5-(Adamantan-1-ylmethoxy)quinazoline-2,4-diamine;
5-(2-Bromo-benzyloxy)quinazoline-2,4-diamine;
5-(2-Iodo-benzyloxy)quinazoline-2,4-diamine;
5-(3-Bromobenzyloxy)quinazoline-2,4-diamine;
5-(3-Iodo-benzyloxy)quinazoline-2,4-diamine;
5-(3,5-Difluorobenzyloxy)quinazoline-2,4-diamine;
5-(2,3,5-Trifluorobenzyloxy)quinazoline-2,4-diamine;
5-(2,5-Difluorobenzyloxy)quinazoline-2,4-diamine;
5-(2,4-Difluorobenzyloxy)quinazoline-2,4-diamine;
5-(2,6-Difluorobenzyloxy)quinazoline-2,4-diamine;
5-(3,4-Difluorobenzyloxy)quinazoline-2,4-diamine;
5-(5-Chloro-2-methoxybenzyloxy)quinazoline-2,4-diamine;
[4-Chloro-2-(2,4-diaminoquinazolin-5-yloxymethyl)phenyl]methanol;
5-(2-Fluorobenzyloxy)quinazoline-2,4-diamine;
5-(4-Fluorobenzyloxy)quinazoline-2,4-diamine;
5-(3-Trifluoromethylbenzyloxy)quinazoline-2,4-diamine;
5-(2-Trifluoromethylbenzyloxy)quinazoline-2,4-diamine;

5-(4-Trifluoromethylbenzyloxy)quinazoline-2,4-diamine;
5-(3-Fluorobenzyloxy)quinazoline-2,4-diamine;
5-(3,5-Dichlorobenzyloxy)quinazoline-2,4-diamine;
5-(Quinolin-3-ylmethoxy)quinazoline-2,4-diamine;
5-(Quinolin-8-ylmethoxy)quinazoline-2,4-diamine;
5-(Piperidin-4-ylmethoxy)quinazoline-2,4-diamine;
5-(1-Methyl-piperidin-2-ylmethoxy)quinazoline-2,4-diamine;
4-(2,4-Diaminoquinazolin-5-yloxymethyl)piperidin-1-carboxylic acid tert-butyl ester;
5-(Bicyclo[2.2.1]hept-5-en-2-ylmethoxy)quinazoline-2,4-diamine;
(4-Chlorophenyl)[4-(2,4-diaminoquinazolin-5-yloxymethyl)piperidin-1-yl]methanone;
5-(3-Methyl-oxetan-3-ylmethoxy)quinazoline-2,4-diamine;
5-((1S,2R,5S)-6,6-Dimethylbicyclo[3.1.1]hept-2-ylmethoxy)quinazoline-2,4-diamine;
5-(2,4-Diaminoquinazolin-5-yloxymethyl)bicyclo[2.2.1]heptane-2,3-diol;
5-[1-(3,4-Dichlorobenzyl)piperidin-4-ylmethoxy]quinazoline-2,4-diamine;
(2-Chlorophenyl)[4-(2,4-diaminoquinazolin-5-yloxymethyl)piperidin-1-yl-]methanone;
(3-Chlorophenyl)[4-(2,4-diaminoquinazolin-5-yloxymethyl)piperidin-1-yl]methanone;
[4-(2,4-Diaminoquinzolin-5-yloxymethyl)piperidin-1-yl](3-iodophen-yl)methanone;
[4-(2,4-Diaminoquinzolin-5-yloxymethyl)piperidin-1-yl](4-iodophenyl)methanone;
[4-(2,4-Diaminoquinzolin-5-yloxymethyl)piperidin-1-yl](2-iodophenyl)-methanone;
5-(2-Methoxybenzyloxy)quinazoline-2,4-diamine;
5-(3-Methoxybenzyloxy)quinazoline-2,4-diamine;
5-(4-Methoxybenzyloxy)quinazoline-2,4-diamine;
5-(Bicyclo[2.2.1]hept-2-ylmethoxy)quinazoline-2,4-diamine;
5-((1S,2S,5S)-6,6-Dimethylbicyclo[3.1.1]hept-2-ylmethoxy)quinazoline-2,4-diamine;
5-(Cyclohexylmethoxy)quinazoline-2,4-diamine;
5-(3-Methyl-4,5-dihydroisoxazol-5-ylmethoxy)quinazoline-2,4-diamine; and
1,1-Bis-(4-chlorophenyl)-3-(2,4-diaminoquinazolin-5-yloxy)butan-1-ol.

4. A compound according to claim 3 selected from the group consisting of
5-(2-p-Tolylethoxy)quinazoline-2,4-diamine;
5-[2-(4-Chlorophenyl)ethoxy]quinazoline-2,4-diamine;
5-[3-(4-Chlorophenyl)propoxy]quinazoline-2,4-diamine;
5-[1-(3-Chlorophenyl)ethoxy]quinazoline-2,4-diamine;
5-(1-Pyridin-4-ylethoxy)quinazoline-2,4-diamine;
5-[1-(4-Chlorophenyl)ethoxy]quinazoline-2,4-diamine;
5-[1-(4-Chlorophenyl)propoxy]quinazoline-2,4-diamine;
5-Benzhydryloxyquinazoline-2,4-diamine;
5-(1-Pyridin-2-ylethoxy)quinazoline-2,4-diamine;
5-(1-Thiazol-2-ylethoxy)quinazoline-2,4-diamine;
5-(1-Benzo[1,3]dioxol-5-ylethoxy)quinazoline-2,4-diamine;
5-[1-(3-Methoxyphenyl)ethoxy]quinazoline-2,4-diamine;
5-[1-(3,5-Dimethoxyphenyl)ethoxy]quinazoline-2,4-diamine;
5-[2-(4-Chlorophenyl)-3-methoxymethoxypropoxy]quinazoline-2,4-diamine;
2-(4-Chlorophenyl)-3-(2,4-diaminoquinazolin-5-yloxy)propan-1-ol;
5-[1-(3,4-Dichlorophenyl)ethoxy]quinazoline-2,4-diamine;
5-[1-(2,6-Difluorophenyl)ethoxy]quinazoline-2,4-diamine;
5-(3-Chlorophenyl)quinazoline-2,4-diamine;
5-[(R)-1-(3-Chlorophenyl)ethoxy]quinazolin-2,4-diamine;
5-[1-(3-Fluorophenyl)ethoxy]quinazoline-2,4-diamine;
5-[1-(3-Trifluoromethylphenyl)ethoxy]quinazoline-2,4-diamine;
5-[1-(4-fluorophenyl)-1-methylethoxy]quinazoline-2,4-diamine;
5-[1-(2-Fluorophenyl)ethoxy]quinazoline-2,4-diamine;
5-[1-(2-Chlorophenyl)ethoxy]quinazoline-2,4-diamine;
5-[1-(4-Trifluoromethylphenyl)ethoxy]quinazoline-2,4-diamine;
5-[1-(3,5-Difluorophenyl)ethoxy]quinazoline-2,4-diamine;
5-((S)-1-Naphthalen-2-ylethoxy)quinazoline-2,4-diamine;
5-[1-(4-Chlorophenyl)-2-methoxyethoxy]quinazoline-2,4-diamine;
(4-Chlorophenyl)(2,4-diaminoquinazolin-5-yloxy)acetic acid;
5-(1-Cyclopentylethoxy)quinazoline-2,4-diamine;
5-(1-Cyclohexyl-butoxy)quinazoline-2,4-diamine;
5-(1-Cyclohexylethoxy)quinazoline-2,4-diamine;
5-(1-Cyclohexylpropoxy)quinazoline-2,4-diamine;
5-[1-(3-Chlorophenyl)cyclopropoxy]quinazoline-2,4-diamine;
5-[1-(4-Fluorophenyl)-2-methoxymethoxyethoxy]quinazoline-2,4-diamine;
2-(2,4-Diaminoquinazolin-5-yloxy)-2-(4-fluorophenyl)ethanol;
5-(2-Benzo[1,3]dioxol-5-yl-2-methoxymethoxyethoxy)quinazoline-2,4-diamine;
5-(1-Benzo[1,3]dioxol-5-yl-2-methoxymethoxyethoxy)quinazoline-2,4-diamine;
2-(2,4-Diaminoquinazolin-5-yloxy)-1-phenyl-ethanol;
1-(4-Chlorophenyl)-2-(2,4-diaminoquinazolin-5-yloxy)ethanol;
1-(3-Chlorophenyl)-2-(2,4-diaminoquinazolin-5-yloxy)ethanol;
5-[(S)-1-(3-Chlorophenyl)ethoxy]quinazolin-2,4-diamine;
2-(2,4-Diaminoquinazolin-5-yloxy)-1-(4-trifluoromethylphenyl)ethanol;
2-(4-Chlorophenyl)-2-(2,4-diaminoquinazolin-5-yloxy)ethanol;
5-[2-(4-Chlorophenyl)-2-methoxyethoxy]quinazoline-2,4-diamine;
5-(2-Methoxy-1-phenylethoxy)quinazoline-2,4-diamine;
2-(2,4-Diaminoquinazolin-5-yloxy)-1-(4-fluorophenyl)ethanol;
5-(2-Benzo[1,3]dioxol-5-yl-2-methoxyethoxy)quinazoline-2,4-diamine;
2-Benzo[1,3]dioxol-5-yl-2-(2,4-diaminoquinazolin-5-yloxy)ethanol;
5-(4-Chlorophenoxymethyl)quinazoline-2,4-diamine;
5-p-Tolyloxymethylquinazoline-2,4-diamine;
5-(4-Fluorophenoxymethyl)quinazoline-2,4-diamine;
5-Thiophen-3-ylmethylquinazoline-2,4-diamine;
5-[1-(3-Iodophenyl)ethoxy]quinazoline-2,4-diamine;
5-((1R,2R,4S)-Bicyclo[2.2.1]hept-2-yloxy)quinazoline-2,4-diamine;
5-(Adamantan-2-yloxy)quinazoline-2,4-diamine;
5-(Bicyclo[2.2.1]hept-2-yloxy)quinazoline-2,4-diamine;
5-(2-Chlorophenoxymethyl)quinazoline-2,4-diamine;

5-(4-Chloro-2-methylphenoxymethyl)quinazoline-2,4-diamine;
5-(4-Chloro-3-methylphenoxymethyl)quinazoline-2,4-diamine;
5-(2,4-Difluorophenoxymethyl)quinazoline-2,4-diamine;
5-(3-Chlorophenoxymethyl)quinazoline-2,4-diamine;
5-(2-Iodophenoxymethyl)quinazoline-2,4-diamine;
5-(4-Methylbenzyloxy)quinazoline-2,4-diamine;
5-(4-Chlorobenzyloxy)quinazoline-2,4-diamine;
5-(4-Iodobenzyloxy)quinazoline-2,4-diamine;
5-(3-Chlorobenzyloxy)quinazoline-2,4-diamine;
5-(2-Chlorobenzyloxy)quinazoline-2,4-diamine;
5-(2-Methylbenzyloxy)quinazoline-2,4-diamine;
5-(3-Methylbenzyloxy)quinazoline-2,4-diamine;
5-(Pyridin-3-ylmethoxy)quinazoline-2,4-diamine;
5-(Cyclohex-3-enylmethoxy)quinazoline-2,4-diamine;
5-(Cyclobutylmethoxy)quinazoline-2,4-diamine;
5-(2-Methoxyethoxy)quinazoline-2,4-diamine;
5-(Cyclopropylmethoxy)quinazoline-2,4-diamine;
5-(Cyclopentylmethoxy)quinazoline-2,4-diamine;
5-(2-Allyloxyethoxy)quinazoline-2,4-diamine;
5-(1-Methylpiperidin-3-ylmethoxy)quinazoline-2,4-diamine;
5-(Furan-2-ylmethoxy)quinazoline-2,4-diamine;
5-(Thiophen-2-ylmethoxy)quinazoline-2,4-diamine;
5-(Furan-3-ylmethoxy)quinazoline-2,4-diamine;
5-(Pyridin-2-ylmethoxy)quinazoline-2,4-diamine;
5-Octyloxyquinazoline-2,4-diamine;
5-(Thiophen-3-ylmethoxy)quinazoline-2,4-diamine;
5-(5-Methylisoxazol-3-ylmethoxy)quinazoline-2,4-diamine;
5-(Benzo[1,3]dioxol-5-ylmethoxy)quinazoline-2,4-diamine;
5-(Tetrahydropyran-2-ylmethoxy)quinazoline-2,4-diamine;
5-(4-Bromobenzyloxy)quinazoline-2,4-diamine;
5-(3,4-Dimethoxybenzyloxy)quinazoline-2,4-diamine;
[4,5-Dichloro-2-(2,4-diaminoquinazolin-5-yloxymethyl)phenyl]methanol;
5-(Adamantan-1-ylmethoxy)quinazoline-2,4-diamine;
5-(2-Bromo-benzyloxy)quinazoline-2,4-diamine;
5-(2-Iodo-benzyloxy)quinazoline-2,4-diamine;
5-(3-Bromobenzyloxy)quinazoline-2,4-diamine;
5-(3-Iodo-benzyloxy)quinazoline-2,4-diamine;
5-(3,5-Difluorobenzyloxy)quinazoline-2,4-diamine;
5-(2,3,5-Trifluorobenzyloxy)quinazoline-2,4-diamine;
5-(2,5-Difluorobenzyloxy)quinazoline-2,4-diamine;
5-(2,4-Difluorobenzyloxy)quinazoline-2,4-diamine;
5-(2,6-Difluorobenzyloxy)quinazoline-2,4-diamine;
5-(3,4-Difluorobenzyloxy)quinazoline-2,4-diamine;
5-(5-Chloro-2-methoxybenzyloxy)quinazoline-2,4-diamine;
[4-Chloro-2-(2,4-diaminoquinazolin-5-yloxymethyl)phenyl]methanol;
5-(2-Fluorobenzyloxy)quinazoline-2,4-diamine;
5-(4-Fluorobenzyloxy)quinazoline-2,4-diamine;
5-(3-Trifluoromethylbenzyloxy)quinazoline-2,4-diamine;
5-(2-Trifluoromethylbenzyloxy)quinazoline-2,4-diamine;
5-(4-Trifluoromethylbenzyloxy)quinazoline-2,4-diamine;
5-(3-Fluorobenzyloxy)quinazoline-2,4-diamine;
5-(3,5-Dichlorobenzyloxy)quinazoline-2,4-diamine;
5-(Quinolin-3-ylmethoxy)quinazoline-2,4-diamine;
5-(Quinolin-8-ylmethoxy)quinazoline-2,4-diamine;
5-(Piperidin-4-ylmethoxy)quinazoline-2,4-diamine;
5-(1-Methyl-piperidin-2-ylmethoxy)quinazoline-2,4-diamine;
4-(2,4-Diamino-quinzaolin-5-yloxymethyl)piperidin-1-carboxylic acid tert-butyl ester;
5-(Bicyclo[2.2.1]hept-5-en-2-ylmethoxy)quinazoline-2,4-diamine;
(4-Chlorophenyl)[4-(2,4-diaminoquinazolin-5-yloxymethyl)piperidin-1-yl]methanone;
5-(3-Methyl-oxetan-3-ylmethoxy)quinazoline-2,4-diamine;
5-((1S,2R,5S)-6,6-Dimethylbicyclo[3.1.1]hept-2-ylmethoxy)quinazoline-2,4-diamine;
5-(2,4-Diaminoquinazolin-5-yloxymethyl)bicyclo[2.2.1]heptane-2,3-diol;
5-[1-(3,4-Dichlorobenzyl)piperidin-4-ylmethoxy]quinazoline-2,4-diamine;
(2-Chlorophenyl)[4-(2,4-diaminoquinazolin-5-yloxymethyl)piperidin-1-yl]methanone;
(3-Chlorophenyl)[4-(2,4-diaminoquinazolin-5-yloxymethyl)piperidin-1-yl]methanone;
[4-(2,4-Diaminoquinzolin-5-yloxymethyl)piperidin-1-yl](3-iodophen-yl)methanone;
[4-(2,4-Diaminoquinzolin-5-yloxymethyl)piperidin-1-yl](4-iodophenyl)methanone;
[4-(2,4-Diaminoquinzolin-5-yloxymethyl)pipendin-1-yl](2-iodophenyl)-methanone;
5-(2-Methoxybenzyloxy)quinazoline-2,4-diamine;
5-(3-Methoxybenzyloxy)quinazoline-2,4-diamine;
5-(4-Methoxybenzyloxy)quinazoline-2,4-diamine;
5-(Bicyclo[2.2.1]hept-2-ylmethoxy)quinazoline-2,4-diamine; and
5-((1S,2S,5S)-6,6-Dimethylbicyclo[3.1.1]hept-2-ylmethoxy)quinazoline-2,4-diamine.

5. A 2,4-diaminoquinazoline compound according to claim 1 of formula IV

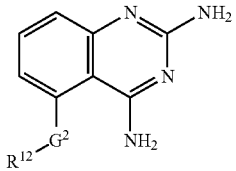

IV wherein $G^2$ is selected from the group consisting of —O—, —S—, and —NH—; and $R^{12}$ is selected from the group consisting of $C_7$-$C_{10}$ polycyclic hydrocarbon, substituted $C_7$-$C_{10}$ polycyclic hydrocarbon, and

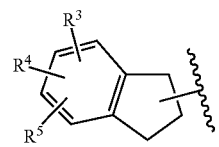

wherein the wavy line indicates the point of attachment; and wherein one or more carbon atoms in the cyclopentyl ring is optionally replaced by a heteroatom independently selected from the group consisting of N, O, and S; and $R^3$, $R^4$ and $R^5$ are independently selected from the group consisting of hydrogen, halogen, $C_1$-$C_6$ alkyl, $C_1$-$C_6$ alkoxy, haloalkyl, hydroxy, carboxy, $C_1$-$C_6$ alkoxycarbonyl, carboxamido, cyano, formyl, nitro, amino, $C_1$-$C_6$ alkylamino, $C_1$-$C_6$ dialkylamino, mercapto, $C_1$-$C_6$ alkylthio, $C_1$-$C_6$ alkylsulfoxide, $C_1$-$C_6$ alkylsulfone, $C_1$-$C_6$ acylamino, amidino, phenyl, benzyl, phenoxy and benzyloxy, with the proviso that at least one of $R^3$, $R^4$ and $R^5$ must be other than hydrogen;

or a pharmaceutically acceptable salt thereof, in any stereoisomeric or tautomeric form, or a mixture of any such compounds in any ratio.

6. A compound according to claim 5 wherein $R^3$, $R^4$ and $R^5$ are independently selected from the group consisting of hydrogen, halogen, $C_1$-$C_6$ alkoxy, $C_1$-$C_6$ alkoxy, and haloalkyl.

7. A compound according to claim 5 selected from the group consisting of 5-(6-Chloro-indan-1-yloxy)quinazoline-2,4-diamine;
5-(4-Fluoroindan-1-yloxy)quinazoline-2,4-diamine;
5-(6-Fluoroindan-1-yloxy)quinazoline-2,4-diamine;
5-(5-Chloro-2,3-dihydro-benzofuran-3-yloxy)quinazoline-2,4-diamine;
5-((S)-6-Chloroindan-1-yloxy)quinazoline-2,4-diamine;
5-((R)-6-Chloroindan-1-yloxy)quinazoline-2,4-diamine; and
5-(7-Methoxy-2,3-dihydrobenzofuran-3-yoloxy)quinazoline-2.4-diamine.

8. A method for treating spinal muscular atrophy comprising administering to a patient suffering from or disposed to SMA a therapeutically effective amount of a 2,4-diaminoquinazoline compound according to claim 1.

* * * * *